US011897930B2

(12) United States Patent
Ye et al.

(10) Patent No.: US 11,897,930 B2
(45) Date of Patent: Feb. 13, 2024

(54) INTERLEUKIN-2 POLYPEPTIDES AND FUSION PROTEINS THEREOF, AND THEIR PHARMACEUTICAL COMPOSITIONS AND THERAPEUTIC APPLICATIONS

(71) Applicant: Anwita Biosciences, Inc., San Carlos, CA (US)

(72) Inventors: Fan Ye, Mountain View, CA (US); Eric Liao, San Francisco, CA (US); Ella Li, San Francisco, CA (US); Matthew Siegel, Menlo Park, CA (US); Jianing Huang, San Mateo, CA (US); Ziyang Zhong, Belmont, CA (US)

(73) Assignee: Anwita Biosciences, Inc., San Carlos, CA (US)

( * ) Notice: Subject to any disclaimer, the term of this patent is extended or adjusted under 35 U.S.C. 154(b) by 108 days.

(21) Appl. No.: 17/241,074

(22) Filed: Apr. 27, 2021

(65) Prior Publication Data

US 2021/0340208 A1    Nov. 4, 2021

Related U.S. Application Data

(60) Provisional application No. 63/047,867, filed on Jul. 2, 2020, provisional application No. 63/027,929, filed on May 20, 2020, provisional application No. 63/016,289, filed on Apr. 28, 2020.

(51) Int. Cl.
  *C07K 14/55* (2006.01)
  *A61K 38/00* (2006.01)

(52) U.S. Cl.
  CPC .............. *C07K 14/55* (2013.01); *A61K 38/00* (2013.01); *C07K 2319/31* (2013.01); *C07K 2319/33* (2013.01)

(58) Field of Classification Search
  None
  See application file for complete search history.

(56) References Cited

U.S. PATENT DOCUMENTS

| | | | |
|---|---|---|---|
| 3,331,835 A | 7/1967 | Bassiri et al. |
| 3,920,632 A | 11/1975 | Hohmann et al. |
| 4,339,600 A | 7/1982 | Ondetti et al. |
| 4,415,496 A | 11/1983 | Harris et al. |
| 4,644,069 A | 2/1987 | Baumann et al. |
| 5,015,650 A | 5/1991 | Stoltefuss et al. |
| 5,272,143 A | 12/1993 | Benson et al. |
| 5,272,158 A | 12/1993 | Hartman et al. |
| 5,376,522 A | 12/1994 | Takiguchi et al. |
| 5,463,063 A | 10/1995 | Muller |
| 5,504,080 A | 4/1996 | Karanewsky |
| 5,629,327 A | 5/1997 | D'Amato |
| 5,631,280 A | 5/1997 | Ciccarone et al. |
| 5,635,502 A | 6/1997 | Flynn |
| 5,845,025 A | 12/1998 | Garito et al. |
| 5,856,384 A | 1/1999 | Garito et al. |
| 5,932,582 A | 8/1999 | Young et al. |
| 5,977,134 A | 11/1999 | Ciccarone et al. |
| 6,207,697 B1 | 3/2001 | Han et al. |
| 6,248,740 B1 | 6/2001 | Kawano et al. |
| 6,284,755 B1 | 9/2001 | deSolms et al. |
| 6,388,090 B2 | 5/2002 | Huhtala et al. |
| 6,429,212 B1 | 8/2002 | Hashimoto |
| 6,476,052 B1 | 11/2002 | Muller et al. |
| 6,492,380 B1 | 12/2002 | Ross et al. |
| 6,569,858 B2 | 5/2003 | Prudhomme et al. |
| 6,686,477 B2 | 2/2004 | Boaz et al. |
| 6,719,925 B1 | 4/2004 | Breyne et al. |
| 7,071,181 B2 | 7/2006 | Davis et al. |
| 7,164,014 B2 | 1/2007 | Huang et al. |
| 7,189,738 B2 | 3/2007 | Straub et al. |
| 7,320,992 B2 | 1/2008 | Tegley et al. |
| 7,342,007 B2 | 3/2008 | Herzog et al. |
| 7,405,215 B2 | 7/2008 | Bennani et al. |
| 7,435,745 B2 | 10/2008 | D'Amato |
| 7,569,215 B2 | 8/2009 | Wittrup et al. |
| 7,569,580 B2 | 8/2009 | Thota et al. |
| 7,592,467 B2 | 9/2009 | Niestroj et al. |
| 7,700,641 B2 | 4/2010 | Chafeev et al. |
| 7,893,096 B2 | 2/2011 | Valiante, Jr. |
| 7,893,265 B2 | 2/2011 | Facchetti et al. |
| 7,951,360 B2 | 5/2011 | Wittrup et al. |
| 8,063,225 B2 | 11/2011 | Gregor et al. |
| 8,143,284 B2 | 3/2012 | Gandhi et al. |
| 8,222,248 B2 | 7/2012 | Sung et al. |
| 8,349,311 B2 | 1/2013 | Wittrup et al. |
| 8,362,234 B2 | 1/2013 | Hatala et al. |

(Continued)

FOREIGN PATENT DOCUMENTS

| | | |
|---|---|---|
| CA | 793864 A | 9/1968 |
| CA | 3098765 A1 | 3/2020 |

(Continued)

OTHER PUBLICATIONS

Arena-Ramirez et al. "Interleukin-2: biology, design and application" Trends in Immunology 36:763-777. (Year: 2015).*
Amit et al., "Axin-mediated CKI phosphorylation of β-catenin at Ser 45: a molecular switch for the Wnt pathway," Genes Dev. 2002, 16:1066-76.
Audit, "Thalidomide-induced polyamine acylation: a new insight into the acylation mechanism," Biogenic Amines 1994, 10, 543-54.
Belyaev et al., "A novel synthetic route to L-α-aminoadipic acid," Izsvestiya Akademi Nauk, Seriya Khimicheskaya 1992, 7, 1692-3.
Belyaev et al., "A novel synthetic route to N6-methyl-L-lysine and N5-methyl-L-ornithine via N3-protected (S)-3-aminolactams," Synthesis 1991, 417-20.

(Continued)

*Primary Examiner* — Sudhakar Katakam
*Assistant Examiner* — Zachary J Miknis
(74) *Attorney, Agent, or Firm* — Lin Yu, Esq.; Juniv LLP

(57) ABSTRACT

Provided herein are an interleukin-2 polypeptide and a fusion protein thereof. Also provided herein are their pharmaceutical compositions and methods of use for treating, preventing, or ameliorating one or more symptoms of a proliferative disease.

28 Claims, 1 Drawing Sheet
Specification includes a Sequence Listing.

(56) References Cited

U.S. PATENT DOCUMENTS

| | | |
|---|---|---|
| 8,383,139 B2 | 2/2013 | Kunz et al. |
| 8,697,690 B2 | 4/2014 | Beshore et al. |
| 8,742,097 B2 | 6/2014 | Hernandez et al. |
| 8,815,906 B2 | 8/2014 | Gregor et al. |
| 8,822,500 B2 | 9/2014 | Gregor |
| 8,906,356 B2* | 12/2014 | Wittrup .................. A61P 31/18 424/85.2 |
| 8,945,897 B2 | 2/2015 | Siekmann et al. |
| 9,732,134 B2 | 8/2017 | Gavin et al. |
| 10,035,836 B1 | 7/2018 | Greve |
| 10,604,576 B2 | 3/2020 | Campbell et al. |
| 10,851,144 B2 | 12/2020 | Butz et al. |
| 2003/0114448 A1 | 6/2003 | Zhang et al. |
| 2004/0110757 A1 | 6/2004 | Arrhenius et al. |
| 2004/0127482 A1 | 7/2004 | Robichaud et al. |
| 2004/0175357 A1 | 9/2004 | Shanafelt et al. |
| 2006/0211724 A1 | 9/2006 | Verschueren et al. |
| 2008/0318998 A1 | 12/2008 | Prince et al. |
| 2009/0082368 A1 | 3/2009 | Vohra et al. |
| 2009/0286775 A1 | 11/2009 | Rosales et al. |
| 2010/0074869 A1 | 3/2010 | Paul |
| 2010/0152240 A1 | 6/2010 | Zhang |
| 2010/0222363 A1 | 9/2010 | Rosales et al. |
| 2011/0196150 A1 | 8/2011 | Man et al. |
| 2011/0319411 A1 | 12/2011 | Vu et al. |
| 2012/0192297 A1 | 7/2012 | Handa et al. |
| 2012/0301398 A1 | 11/2012 | Heiser et al. |
| 2013/0310555 A1 | 11/2013 | Chong |
| 2013/0324518 A1 | 12/2013 | Man et al. |
| 2016/0009768 A1* | 1/2016 | Davis .................. A61K 38/164 514/19.2 |
| 2018/0037567 A1 | 2/2018 | Man et al. |
| 2018/0326010 A1 | 11/2018 | Deak et al. |
| 2019/0016793 A1 | 1/2019 | Cini et al. |
| 2019/0031749 A1 | 1/2019 | Dubridge et al. |
| 2019/0062320 A1 | 2/2019 | Chan et al. |
| 2019/0338032 A1 | 11/2019 | Campbell et al. |
| 2019/0352363 A1 | 11/2019 | Seidel, III et al. |
| 2020/0199181 A1 | 6/2020 | Seidel, III et al. |
| 2020/0207824 A1 | 7/2020 | Seidel, III et al. |
| 2021/0213102 A1 | 7/2021 | Kang et al. |
| 2021/0221863 A1 | 7/2021 | Kang et al. |

FOREIGN PATENT DOCUMENTS

| | | |
|---|---|---|
| CA | 3098930 A1 | 3/2020 |
| CN | 104004122 A | 8/2014 |
| CN | 110325205 A | 10/2019 |
| CN | 111647068 A | 9/2020 |
| DE | 292451 | 8/1991 |
| EP | 0595610 B1 | 5/1997 |
| GB | 2450771 A | 1/2009 |
| JP | 2000159761 A | 6/2000 |
| JP | 2009023986 A | 2/2009 |
| JP | 2011153279 A | 8/2011 |
| JP | 2012123292 A | 6/2012 |
| KR | 20130131663 A | 12/2013 |
| KR | 20140039383 A | 4/2014 |
| KR | 20140103447 A | 8/2014 |
| SU | 1708812 A1 | 1/1992 |
| WO | 1999004390 A1 | 1/1999 |
| WO | 2000064917 A2 | 11/2000 |
| WO | 2002079147 A2 | 10/2002 |
| WO | 2004092174 A1 | 10/2004 |
| WO | 2005005638 A2 | 1/2005 |
| WO | 2005007121 A2 | 1/2005 |
| WO | 2005016326 A2 | 2/2005 |
| WO | 2007000337 A1 | 1/2007 |
| WO | 2007028789 A1 | 3/2007 |
| WO | 2007117394 A2 | 10/2007 |
| WO | 2008037266 A1 | 4/2008 |
| WO | 2008073865 A2 | 6/2008 |
| WO | 2009051417 A2 | 4/2009 |
| WO | 2009070533 A1 | 6/2009 |
| WO | 2009072581 A1 | 6/2009 |
| WO | 2009083105 A1 | 7/2009 |
| WO | 2009094668 A1 | 7/2009 |
| WO | 2009112445 A1 | 9/2009 |
| WO | 2010011924 A2 | 1/2010 |
| WO | 2010085495 A1 | 7/2010 |
| WO | 2011136483 A1 | 11/2011 |
| WO | 2012072019 A1 | 6/2012 |
| WO | 2012129562 A2 | 9/2012 |
| WO | 2012158475 A1 | 11/2012 |
| WO | 2013010218 A1 | 1/2013 |
| WO | 2013106409 A1 | 7/2013 |
| WO | 2014055548 A1 | 4/2014 |
| WO | 2014055634 A1 | 4/2014 |
| WO | 2014106019 A2 | 7/2014 |
| WO | 2014113485 A1 | 7/2014 |
| WO | 2016065980 A1 | 5/2016 |
| WO | 2016164937 A2 | 10/2016 |
| WO | WO-2016164937 A2 * | 10/2016 ......... A61K 38/2013 |
| WO | 2016191178 A1 | 12/2016 |
| WO | 2017024318 A1 | 2/2017 |
| WO | 2017158436 A1 | 9/2017 |
| WO | 2017185023 A1 | 10/2017 |
| WO | 2018036661 A1 | 3/2018 |
| WO | 2018104444 A1 | 6/2018 |
| WO | 2018119114 A1 | 6/2018 |
| WO | 2018151868 A2 | 8/2018 |
| WO | 2018170168 A1 | 9/2018 |
| WO | 2018184964 A1 | 10/2018 |
| WO | 2017220989 | 12/2018 |
| WO | 2019051091 A1 | 3/2019 |
| WO | 2019051094 A1 | 3/2019 |
| WO | 2019125732 A1 | 6/2019 |
| WO | 2019139896 A1 | 7/2019 |
| WO | 2019246003 A1 | 12/2019 |
| WO | 2019246004 A1 | 12/2019 |
| WO | 2020057645 A1 | 3/2020 |
| WO | 2020057646 A1 | 3/2020 |
| WO | 2020125743 A1 | 6/2020 |
| WO | 2020172528 A1 | 8/2020 |
| WO | 2021102063 A1 | 5/2021 |

OTHER PUBLICATIONS

Belyaev, "A novel synthetic route to enantiomers of epsilon-hydroxynorleucine and epsilon-chloronorleucine from L- and D,L-lysine," Tetrahedron Lett. 1995, 36, 439-40.
Brito et al., "Polyglycine expansions in eRF3/GSPT1 are associated with gastric cancer susceptibility," Carcinogenesis 2005, 26, 2046-9.
CAS Registry 1212527-87-1, entered: Mar. 21, 2010.
Chauvin et al., "Human eukaryotic release factor 3a depletion causes cell cycle arrest at G1 phase through inhibition of the mTOR pathway," Mol. Cell. Biol. 2007, 27, 5619-29.
Cheong and Virshup, "Casein kinase 1: Complexity in the family," J. Biochem. Cell Biol. 2011, 43, 465-9.
David et al., "Electrooxidation based strategy towards the core 3-amino-6-hydroxy-azepan-2-one," Synlett. 2004, 6, 1029-33.
Eger et al., "Alpha-phthalimidoadipinimide-synthesis, teratogenic properties and effect on the central nervous-system of a homo-thalidomide," Archiv Der Pharmazie 1988, 321, 577.
Eger et al., "Synthesis, central nervous system activity and teratogenicity of a homothalidomide," Arzneimittel-Forschung 1990, 40, 1073-5.
Elyada et al., "CK1α ablation highlights a critical role for p53 in invasiveness control," Nature 2011, 470, 409-13.
Gutschow et al., "Aza analogues of thalidomide: synthesis and evaluation as inhibitors of tumor necrosis factor—alpha production in vitro," Bioorg. Med. Chem. 2001, 9, 1059-65.
Hashimoto et al., "Translation termination factor eRF3 is targeted for caspase-mediated proteolytic cleavage and degradation during DNA damage-induced apoptosis," Apoptosis 2012, 17, 1287-99.
Huart et al., "CK1α plays a central role in mediating MDM2 control of p53 and E2F-1 protein stability," J. Biol. Chem. 2009, 284, 32384-94.

(56) References Cited

OTHER PUBLICATIONS

Ishii et al., "A Novel Rac1-GSPT1 signaling pathway controls astrogliosis following central nervous system injury," J. Biol. Chem. 2017, 292, 1240-50.
Ito et al., "Discovery of 3-benzyl-1-( trans-4-((5-cyanopyridin-2-yl)amino)cyclohexyl)-1-arylurea derivatives as novel and selective cyclin-dependent kinase 12 (CDK12) inhibitors," J. Med. Chem. 2018, 61, 7710-28.
Kralj et al., "Mass spectrometric identification of some nonvolatile organic compounds," Biomedical Mass Spectrometry 1975, 2, 215-8.
Lee et al., "Assessing chiral self-recognition using chiral stationary phases," Tetrahedron 2011, 67, 7143-7.
Levine and Oren, "The first 30 years of p53: growing ever more complex," Nat. Rev. Cancer 2009, 9, 749-58.
Li et al., "eRF3b, a biomarker for hepatocellular carcinoma, influences cell cycle and phosphoralation status of 4E-BP1," PLoS One 2014, 9, e86371.
Malta-Vacas et al., "Differential expression of GSPT1 GGCn alleles in cancer," Cancer Genet. Cytogenet. 2009, 195, 132-42.
Minzel et al., "Small molecules co-targeting CKIα and the transcriptional kinases CDK7/9 control AML in preclinical models," Cell 2018, 175, 171-85.
Miri et al., "GGCn polymorphism of eRF3a/GSPT1 gene and breast cancer susceptibility," Med. Oncol. 2012, 29, 1581-5.
Olson et al., "Pharmacological perturbation of CDK9 using selective CDK9 inhibition or degradation," Nat. Chem. Biol. 2018, 14, 163-70.
Schittek and Sinnberg, "Biological functions of casein kinase 1 isoforms and putative roles in tumorigenesis," Mol. Cancer 2014, 13, Article 231.
Schneider et al., "Role of casein kinase 1A1 in the biology and targeted therapy of del(5q) MDS," Cancer Cell 2014, 26, 509-20.
Stern, "Prevalence of a history of skin cancer in 2007: results of an incidence-based model," Arch. Dermatol. 2010, 146, 279-82.
Wright and Lange, "Newer potential biomarkers in prostate cancer," Rev. Urol. 2007, 9, 207-13.
Abbas et al., "Revisiting IL-2: Biology and therapeutic prospects," Sci. Immunol. 2018, 3, eaat1482.
Agrawalla et al., "Chemoselective dual labeling of native and recombinant proteins," Bioconjugate Chem. 2018, 29, 29-34.
Atkins et al., "High-dose recombinant interleukin 2 therapy for patients with metastatic melanoma: analysis of 270 patients treated between 1985 and 1993," J. Clin. Oncol. 1999, 17, 2105-16.
Bluestone, "The yin and yang of interleukin-2-mediated immunotherapy," N. Engl. J. Med. 2011, 365, 2129-31.
Boyman et al., "The role of interleukin-2 during homeostasis and activation of the immune system," Nat. Rev. Immunol. 2012, 12, 180-90.
Conlon et al., "Cytokines in the treatment of cancer," J. Interferon Cytokine Res. 2019, 39, 6-21.
Conlon et al., "Redistribution, hyperproliferation, activation of natural killer cells and CD8 T cells, and cytokine production during first-in-human clinical trial of recombinant human interleukin-15 in patients with cancer," J. Clin. Oncol. 2015, 33, 74-82.
Dennis et al., "Albumin binding as a general strategy for improving the pharmacokinetics of proteins," J. Biol. Chem. 2002, 277, 35035-43.
Hassanzadeh-Ghassabeh et al., "Nanobodies and their potential applications," Nanomedicine (Lond) 2013, 8, 1013-26.
Heaton et al., "Human interleukin 2 analogues that preferentially bind the intermediate-affinity interleukin 2 receptor lead to reduced secondary cytokine secretion: implications for the use of these interleukin 2 analogues in cancer immunotherapy," Cancer Res. 1993, 53, 2597-602.
Hondowicz et al., "Interleukin-2-dependent allergen-specific tissue-resident memory cells drive asthma," Immunity 2016, 44, 155-66.
Hu et al., "Generation of low-toxicity interleukin-2 fusion proteins devoid of vasopermeability activity," Blood 2002, 101, 4853-61.
Klapper et al., "High-dose interleukin-2 for the treatment of metastatic renal cell carcinoma : a retrospective analysis of response and survival in patients treated in the surgery branch at the National Cancer Institute between 1986 and 2006," Cancer 2008, 113, 293-301.
Liao et al., "IL-2 family cytokines: new insights into the complex roles of IL-2 as a broad regulator of T helper cell differentiation," Curr. Opin. Immunol. 2011, 23, 598-604.
Malek et al., "Interleukin-2 receptor signaling: at the interface between tolerance and immunity," Immunity 2010, 33, 153-65.
PROLEUKIN® Label (2012).
Rham et al., "The proinflammatory cytokines IL-2, IL-15 and IL-21 modulate the repertoire of mature human natural killer cell receptors," Arthritis Res. Ther. 2007, 9, R125.
Richert et al., "Compensatory energetic mechanisms mediating the assembly of signaling complexes between interleukin-2 and its alpha, beta, and gamma(c) receptors," J. Mol. Biol. 2004, 339, 1115-9.
Robb et al., "Low and high affinity cellular receptors for interleukin 2. Implications for the level of Tac antigen," J. Exp. Med. 1984, 160, 1126-46.
Rosenberg, "IL-2: the first effective immunotherapy for human cancer," J. Immunol. 2014, 192, 5451-8.
Rosenberg, "Raising the bar: the curative potential of human cancer immunotherapy," Sci. Transl. Med. 2012, 4, 127ps8.
Skrombolas et al., "Challenges and developing solutions for increasing the benefits of IL-2 treatment in tumor therapy," Expert Rev. Clin. Immunol. 2014, 10, 207-17.
Sola and Griebenow, "Effects of glycosylation on the stability of protein pharmaceuticals," J. Pharm. Sci. 2009, 98, 1223-45.
Sola et al., "Modulation of protein biophysical properties by chemical glycosylation: biochemical insights and biomedical implications," Cell. Mol. Life Sci. 2007, 64, 2133-52.
Spangler et al., "Insights into cytokine-receptor interactions from cytokine engineering," Annu. Rev. Immunol. 2015, 33, 139-67.
Stauber et al., "Crystal structure of the IL-2 signaling complex: Paradigm for a heterotrimeric cytokine receptor," Proc. Natl. Acad. Sci. U.S.A. 2006, 103, 2788-93.
Szabo et al., "High Performance Anion Exchange and Hydrophilic Interaction Liquid Chromatography Approaches for Comprehensive Mass Spectrometry-Based Characterization of the N-Glycome of a Recombinant Human Erythropoietin," J. Proteome. Res. 2018, 17, 1559-74.
Tang and Harding, "The challenges and molecular approaches surrounding interleukin-2-based therapeutics in cancer," Cytokine: X 2019, 1, 100001.
Waldmann et al., "The biology of interleukin-2 and interleukin-15: implications for cancer therapy and vaccine design," Nat. Rev. Immunol. 2006, 6, 595-601.
Waldmann, "The shared and contrasting roles of IL2 and IL15 in the life and death of normal and neoplastic lymphocytes: implications for cancer therapy," Cancer Immunol. Res. 2015, 3, 219-27.
Wang et al., "Structure of the quaternary complex of interleukin-2 with its α, β, and γc receptors," Science 2005, 310, 1159-63.

\* cited by examiner

SEQUENCE LISTING

<160> NUMBER OF SEQ ID NOS: 234

<210> SEQ ID NO 1
<211> LENGTH: 133
<212> TYPE: PRT
<213> ORGANISM: Homo sapiens

<400> SEQUENCE: 1

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

```
Lys Ala Thr Glu Leu Lys His Leu Gln Cys Leu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                    85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 2
<211> LENGTH: 133
<212> TYPE: PRT
<213> ORGANISM: Homo sapiens

<400> SEQUENCE: 2

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                    85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 3
<211> LENGTH: 133
<212> TYPE: PRT
<213> ORGANISM: Homo sapiens

<400> SEQUENCE: 3

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                    85                  90                  95
```

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 4
<211> LENGTH: 133
<212> TYPE: PRT
<213> ORGANISM: Homo sapiens

<400> SEQUENCE: 4

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 5
<211> LENGTH: 133
<212> TYPE: PRT
<213> ORGANISM: Homo sapiens

<400> SEQUENCE: 5

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

```
<210> SEQ ID NO 6
<211> LENGTH: 133
<212> TYPE: PRT
<213> ORGANISM: Homo sapiens

<400> SEQUENCE: 6

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 7
<211> LENGTH: 4
<212> TYPE: PRT
<213> ORGANISM: Artificial Sequence
<220> FEATURE:
<223> OTHER INFORMATION: Linker

<400> SEQUENCE: 7

Gly Gly Ser Gly
1

<210> SEQ ID NO 8
<211> LENGTH: 5
<212> TYPE: PRT
<213> ORGANISM: Artificial Sequence
<220> FEATURE:
<223> OTHER INFORMATION: Linker

<400> SEQUENCE: 8

Gly Gly Ser Gly Gly
1               5

<210> SEQ ID NO 9
<211> LENGTH: 6
<212> TYPE: PRT
<213> ORGANISM: Artificial Sequence
<220> FEATURE:
<223> OTHER INFORMATION: Linker

<400> SEQUENCE: 9

Gly Gly Gly Ser Gly Gly
1               5

<210> SEQ ID NO 10
<211> LENGTH: 6
<212> TYPE: PRT
```

```
<213> ORGANISM: Homo sapiens

<400> SEQUENCE: 10

Asn Tyr Lys Asn Pro Lys
1               5

<210> SEQ ID NO 11
<211> LENGTH: 133
<212> TYPE: PRT
<213> ORGANISM: Homo sapiens

<400> SEQUENCE: 11

Ala Pro Thr Ser Ser Ser Thr Lys Lys Thr Gln Leu Gln Leu Glu Glu
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 12
<211> LENGTH: 133
<212> TYPE: PRT
<213> ORGANISM: Homo sapiens

<400> SEQUENCE: 12

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 13
```

```
<211> LENGTH: 133
<212> TYPE: PRT
<213> ORGANISM: Homo sapiens

<400> SEQUENCE: 13

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Glu Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 14
<211> LENGTH: 133
<212> TYPE: PRT
<213> ORGANISM: Homo sapiens

<400> SEQUENCE: 14

Ala Pro Thr Ser Ser Ser Thr Glu Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 15
<211> LENGTH: 133
<212> TYPE: PRT
<213> ORGANISM: Homo sapiens

<400> SEQUENCE: 15

Ala Pro Thr Ser Ser Ser Thr Lys Glu Thr Gln Leu Gln Leu Glu His
1               5                   10                  15
```

Leu Leu Leu Asp Leu Gln Met Ile Leu Asn Gly Ile Asn Asn Tyr Lys
              20                  25                  30

Asn Pro Lys Leu Thr Asn Met Thr Thr Phe Lys Phe Tyr Met Pro Lys
          35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
            130

<210> SEQ ID NO 16
<211> LENGTH: 133
<212> TYPE: PRT
<213> ORGANISM: Homo sapiens

<400> SEQUENCE: 16

Ala Pro Thr Ser Ser Ser Thr Lys Lys Thr Gln Leu Gln Leu Glu Glu
 1               5                  10                  15

Leu Leu Leu Asp Leu Gln Met Ile Leu Asn Gly Ile Asn Asn Tyr Lys
              20                  25                  30

Asn Pro Lys Leu Thr Asn Met Thr Thr Phe Lys Phe Tyr Met Pro Lys
          35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
            130

<210> SEQ ID NO 17
<211> LENGTH: 133
<212> TYPE: PRT
<213> ORGANISM: Homo sapiens

<400> SEQUENCE: 17

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Glu
              20                  25                  30

Asn Pro Lys Leu Thr Asn Met Thr Thr Phe Lys Phe Tyr Met Pro Lys
          35                  40                  45

Lys Ala Thr Glu Leu Lys His Leu Gln Cys Leu Glu Glu Glu Leu Lys
 50                  55                  60

```
Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130
```

<210> SEQ ID NO 18
<211> LENGTH: 133
<212> TYPE: PRT
<213> ORGANISM: Homo sapiens

<400> SEQUENCE: 18

```
Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
             20                  25                  30

Asn Pro Lys Leu Thr Asn Met Thr Thr Phe Lys Phe Tyr Met Pro Lys
         35                  40                  45

Lys Ala Thr Glu Leu Lys His Leu Gln Cys Leu Glu Glu Glu Leu Lys
     50                  55                  60

Pro Leu Glu Glu Val Leu Asn Leu Ala Gln Ser Glu Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130
```

<210> SEQ ID NO 19
<211> LENGTH: 133
<212> TYPE: PRT
<213> ORGANISM: Homo sapiens

<400> SEQUENCE: 19

```
Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
             20                  25                  30

Asn Pro Lys Leu Thr Asn Met Thr Thr Phe Lys Phe Tyr Met Pro Lys
         35                  40                  45

Lys Ala Thr Glu Leu Lys His Leu Gln Cys Leu Glu Glu Glu Leu Lys
     50                  55                  60

Pro Leu Glu Glu Val Leu Asn Leu Ala Gln Ser Lys Asn Phe Glu Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110
```

```
Thr Ile Val Glu Phe Leu Asn Arg Trp Ile Thr Phe Ser Gln Ser Ile
        115                 120                 125

Ile Ser Thr Leu Thr
        130

<210> SEQ ID NO 20
<211> LENGTH: 133
<212> TYPE: PRT
<213> ORGANISM: Homo sapiens

<400> SEQUENCE: 20

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Glu Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 21
<211> LENGTH: 133
<212> TYPE: PRT
<213> ORGANISM: Homo sapiens

<400> SEQUENCE: 21

Ala Pro Thr Ser Ser Ser Thr Lys Lys Thr Gln Leu Gln Leu Glu Glu
1               5                   10                  15

Leu Leu Leu Asp Leu Gln Met Ile Leu Asn Gly Ile Asn Asn Tyr Glu
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 22
<211> LENGTH: 133
```

```
<212> TYPE: PRT
<213> ORGANISM: Homo sapiens

<400> SEQUENCE: 22

Ala Pro Thr Ser Ser Ser Thr Lys Lys Thr Gln Leu Gln Leu Glu Glu
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Glu Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 23
<211> LENGTH: 133
<212> TYPE: PRT
<213> ORGANISM: Homo sapiens

<400> SEQUENCE: 23

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Glu Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 24
<211> LENGTH: 133
<212> TYPE: PRT
<213> ORGANISM: Homo sapiens

<400> SEQUENCE: 24

Ala Pro Thr Ser Ser Ser Thr Lys Lys Thr Gln Leu Gln Leu Glu Glu
1               5                   10                  15

Leu Leu Leu Asp Leu Gln Met Ile Leu Asn Gly Ile Asn Asn Tyr Lys
```

```
                20                  25                  30

Asn Pro Lys Leu Thr Asn Met Thr Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Glu Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
            130

<210> SEQ ID NO 25
<211> LENGTH: 133
<212> TYPE: PRT
<213> ORGANISM: Homo sapiens

<400> SEQUENCE: 25

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
            20                  25                  30

Asn Pro Lys Leu Thr Asn Met Thr Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Glu Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
            130

<210> SEQ ID NO 26
<211> LENGTH: 127
<212> TYPE: PRT
<213> ORGANISM: Homo sapiens

<400> SEQUENCE: 26

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Leu Thr Asn
            20                  25                  30

Met Thr Thr Phe Lys Phe Tyr Met Pro Lys Lys Ala Thr Glu Leu Lys
            35                  40                  45

His Leu Gln Cys Leu Glu Glu Glu Leu Lys Pro Leu Glu Glu Val Leu
        50                  55                  60

Asn Leu Ala Gln Ser Lys Asn Phe His Leu Arg Pro Arg Asp Leu Ile
```

```
            65                  70                  75                  80
Ser Asn Ile Asn Val Ile Val Leu Glu Leu Lys Gly Ser Glu Thr Thr
                85                  90                  95

Phe Met Cys Glu Tyr Ala Asp Glu Thr Ala Thr Ile Val Glu Phe Leu
                100                 105                 110

Asn Arg Trp Ile Thr Phe Ser Gln Ser Ile Ile Ser Thr Leu Thr
                115                 120                 125
```

<210> SEQ ID NO 27
<211> LENGTH: 128
<212> TYPE: PRT
<213> ORGANISM: Homo sapiens

<400> SEQUENCE: 27

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Gly Leu Thr
                20                  25                  30

Asn Met Thr Thr Phe Lys Phe Tyr Met Pro Lys Lys Ala Thr Glu Leu
                35                  40                  45

Lys His Leu Gln Cys Leu Glu Glu Glu Leu Lys Pro Leu Glu Glu Val
            50                  55                  60

Leu Asn Leu Ala Gln Ser Lys Asn Phe His Leu Arg Pro Arg Asp Leu
65                  70                  75                  80

Ile Ser Asn Ile Asn Val Ile Val Leu Glu Leu Lys Gly Ser Glu Thr
                85                  90                  95

Thr Phe Met Cys Glu Tyr Ala Asp Glu Thr Ala Thr Ile Val Glu Phe
                100                 105                 110

Leu Asn Arg Trp Ile Thr Phe Ser Gln Ser Ile Ile Ser Thr Leu Thr
                115                 120                 125
```

<210> SEQ ID NO 28
<211> LENGTH: 129
<212> TYPE: PRT
<213> ORGANISM: Homo sapiens

<400> SEQUENCE: 28

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Ser Gly Leu
                20                  25                  30

Thr Asn Met Thr Thr Phe Lys Phe Tyr Met Pro Lys Lys Ala Thr Glu
                35                  40                  45

Leu Lys His Leu Gln Cys Leu Glu Glu Glu Leu Lys Pro Leu Glu Glu
            50                  55                  60

Val Leu Asn Leu Ala Gln Ser Lys Asn Phe His Leu Arg Pro Arg Asp
65                  70                  75                  80

Leu Ile Ser Asn Ile Asn Val Ile Val Leu Glu Leu Lys Gly Ser Glu
                85                  90                  95

Thr Thr Phe Met Cys Glu Tyr Ala Asp Glu Thr Ala Thr Ile Val Glu
                100                 105                 110

Phe Leu Asn Arg Trp Ile Thr Phe Ser Gln Ser Ile Ile Ser Thr Leu
                115                 120                 125

Thr
```

<210> SEQ ID NO 29

<211> LENGTH: 130
<212> TYPE: PRT
<213> ORGANISM: Homo sapiens

<400> SEQUENCE: 29

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Gly Gly Ser
            20                  25                  30

Leu Thr Arg Met Leu Thr Phe Lys Phe Tyr Met Pro Lys Lys Ala Thr
        35                  40                  45

Glu Leu Lys His Leu Gln Cys Leu Glu Glu Glu Leu Lys Pro Leu Glu
    50                  55                  60

Glu Val Leu Asn Leu Ala Gln Ser Lys Asn Phe His Leu Arg Pro Arg
65                  70                  75                  80

Asp Leu Ile Ser Asn Ile Asn Val Ile Val Leu Glu Leu Lys Gly Ser
                85                  90                  95

Glu Thr Thr Phe Met Cys Glu Tyr Ala Asp Glu Thr Ala Thr Ile Val
            100                 105                 110

Glu Phe Leu Asn Arg Trp Ile Thr Phe Ser Gln Ser Ile Ile Ser Thr
        115                 120                 125

Leu Thr
    130

<210> SEQ ID NO 30
<211> LENGTH: 130
<212> TYPE: PRT
<213> ORGANISM: Homo sapiens

<400> SEQUENCE: 30

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Gly Gly Ser
            20                  25                  30

Leu Thr Asn Met Thr Thr Phe Lys Phe Tyr Met Pro Lys Lys Ala Thr
        35                  40                  45

Glu Leu Lys His Leu Gln Cys Leu Glu Glu Glu Leu Lys Pro Leu Glu
    50                  55                  60

Glu Val Leu Asn Leu Ala Gln Ser Lys Asn Phe His Leu Arg Pro Arg
65                  70                  75                  80

Asp Leu Ile Ser Asn Ile Asn Val Ile Val Leu Glu Leu Lys Gly Ser
                85                  90                  95

Glu Thr Thr Phe Met Cys Glu Tyr Ala Asp Glu Thr Ala Thr Ile Val
            100                 105                 110

Glu Phe Leu Asn Arg Trp Ile Thr Phe Ser Gln Ser Ile Ile Ser Thr
        115                 120                 125

Leu Thr
    130

<210> SEQ ID NO 31
<211> LENGTH: 131
<212> TYPE: PRT
<213> ORGANISM: Homo sapiens

<400> SEQUENCE: 31

Ala Pro Thr Ser Ser Ser Thr Lys Lys Thr Gln Leu Gln Leu Glu His
1               5                   10                  15

-continued

Leu Leu Leu Asp Leu Gln Met Ile Leu Asn Gly Ile Asn Gly Gly Ser
            20                  25                  30

Gly Leu Thr Arg Met Leu Thr Phe Lys Phe Tyr Met Pro Lys Lys Ala
        35                  40                  45

Thr Glu Leu Lys His Leu Gln Cys Leu Glu Glu Glu Leu Lys Pro Leu
    50                  55                  60

Glu Glu Val Leu Asn Leu Ala Gln Ser Lys Asn Phe His Leu Arg Pro
65                  70                  75                  80

Arg Asp Leu Ile Ser Asn Ile Asn Val Ile Val Leu Glu Leu Lys Gly
                85                  90                  95

Ser Glu Thr Thr Phe Met Cys Glu Tyr Ala Asp Glu Thr Ala Thr Ile
            100                 105                 110

Val Glu Phe Leu Asn Arg Trp Ile Thr Phe Ser Gln Ser Ile Ile Ser
        115                 120                 125

Thr Leu Thr
    130

<210> SEQ ID NO 32
<211> LENGTH: 131
<212> TYPE: PRT
<213> ORGANISM: Homo sapiens

<400> SEQUENCE: 32

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Gly Gly Ser
            20                  25                  30

Gly Leu Thr Asn Met Thr Thr Phe Lys Phe Tyr Met Pro Lys Lys Ala
        35                  40                  45

Thr Glu Leu Lys His Leu Gln Cys Leu Glu Glu Glu Leu Lys Pro Leu
    50                  55                  60

Glu Glu Val Leu Asn Leu Ala Gln Ser Lys Asn Phe His Leu Arg Pro
65                  70                  75                  80

Arg Asp Leu Ile Ser Asn Ile Asn Val Ile Val Leu Glu Leu Lys Gly
                85                  90                  95

Ser Glu Thr Thr Phe Met Cys Glu Tyr Ala Asp Glu Thr Ala Thr Ile
            100                 105                 110

Val Glu Phe Leu Asn Arg Trp Ile Thr Phe Ser Gln Ser Ile Ile Ser
        115                 120                 125

Thr Leu Thr
    130

<210> SEQ ID NO 33
<211> LENGTH: 132
<212> TYPE: PRT
<213> ORGANISM: Homo sapiens

<400> SEQUENCE: 33

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Gly Gly Ser
            20                  25                  30

Gly Gly Leu Thr Asn Met Thr Thr Phe Lys Phe Tyr Met Pro Lys Lys
            35                  40                  45

Ala Thr Glu Leu Lys His Leu Gln Cys Leu Glu Glu Glu Leu Lys Pro
    50                  55                  60

```
Leu Glu Glu Val Leu Asn Leu Ala Gln Ser Lys Asn Phe His Leu Arg
 65                  70                  75                  80

Pro Arg Asp Leu Ile Ser Asn Ile Asn Val Ile Val Leu Glu Leu Lys
                 85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
        130
```

<210> SEQ ID NO 34
<211> LENGTH: 133
<212> TYPE: PRT
<213> ORGANISM: Homo sapiens

<400> SEQUENCE: 34

```
Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Gly Gly Gly
             20                  25                  30

Ser Gly Gly Leu Thr Asn Met Thr Thr Phe Lys Phe Tyr Met Pro Lys
             35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130
```

<210> SEQ ID NO 35
<211> LENGTH: 219
<212> TYPE: PRT
<213> ORGANISM: Homo sapiens

<400> SEQUENCE: 35

```
Glu Leu Cys Asp Asp Asp Pro Pro Glu Ile Pro His Ala Thr Phe Lys
 1               5                  10                  15

Ala Met Ala Tyr Lys Glu Gly Thr Met Leu Asn Cys Glu Cys Lys Arg
             20                  25                  30

Gly Phe Arg Arg Ile Lys Ser Gly Ser Leu Tyr Met Leu Cys Thr Gly
             35                  40                  45

Asn Ser Ser His Ser Ser Trp Asp Asn Gln Cys Gln Cys Thr Ser Ser
 50                  55                  60

Ala Thr Arg Asn Thr Thr Lys Gln Val Thr Pro Gln Pro Glu Glu Gln
 65                  70                  75                  80

Lys Glu Arg Lys Thr Thr Glu Met Gln Ser Pro Met Gln Pro Val Asp
             85                  90                  95

Gln Ala Ser Leu Pro Gly His Cys Arg Glu Pro Pro Pro Trp Glu Asn
            100                 105                 110
```

```
Glu Ala Thr Glu Arg Ile Tyr His Phe Val Val Gly Gln Met Val Tyr
            115                 120                 125

Tyr Gln Cys Val Gln Gly Tyr Arg Ala Leu His Arg Gly Pro Ala Glu
        130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser Cys
                180                 185                 190

Leu Val Thr Thr Thr Asp Phe Gln Ile Gln Thr Glu Met Ala Ala Thr
        195                 200                 205

Met Glu Thr Ser Ile Phe Thr Thr Glu Tyr Gln
    210                 215

<210> SEQ ID NO 36
<211> LENGTH: 213
<212> TYPE: PRT
<213> ORGANISM: Homo sapiens

<400> SEQUENCE: 36

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Arg Trp Asn Gln Thr Cys
        35                  40                  45

Glu Leu Leu Pro Val Ser Gln Ala Ser Trp Ala Cys Asn Leu Ile Leu
    50                  55                  60

Gly Ala Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
        115                 120                 125

Ser Gln Ala Ser His Tyr Phe Glu Arg His Leu Glu Phe Glu Ala Arg
    130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
        195                 200                 205

Ala Leu Gly Lys Asp
    210

<210> SEQ ID NO 37
<211> LENGTH: 240
<212> TYPE: PRT
<213> ORGANISM: Homo sapiens

<400> SEQUENCE: 37
```

```
Leu Asn Thr Thr Ile Leu Thr Pro Asn Gly Asn Glu Asp Thr Thr Ala
1               5                   10                  15

Asp Phe Phe Leu Thr Thr Met Pro Thr Asp Ser Leu Ser Val Ser Thr
            20                  25                  30

Leu Pro Leu Pro Glu Val Gln Cys Phe Val Phe Asn Val Glu Tyr Met
            35                  40                  45

Asn Cys Thr Trp Asn Ser Ser Glu Pro Gln Pro Thr Asn Leu Thr
50                  55                  60

Leu His Tyr Trp Tyr Lys Asn Ser Asp Asn Asp Lys Val Gln Lys Cys
65                  70                  75                  80

Ser His Tyr Leu Phe Ser Glu Glu Ile Thr Ser Gly Cys Gln Leu Gln
                85                  90                  95

Lys Lys Glu Ile His Leu Tyr Gln Thr Phe Val Val Gln Leu Gln Asp
            100                 105                 110

Pro Arg Glu Pro Arg Arg Gln Ala Thr Gln Met Leu Lys Leu Gln Asn
            115                 120                 125

Leu Val Ile Pro Trp Ala Pro Glu Asn Leu Thr Leu His Lys Leu Ser
        130                 135                 140

Glu Ser Gln Leu Glu Leu Asn Trp Asn Asn Arg Phe Leu Asn His Cys
145                 150                 155                 160

Leu Glu His Leu Val Gln Tyr Arg Thr Asp Trp Asp His Ser Trp Thr
                165                 170                 175

Glu Gln Ser Val Asp Tyr Arg His Lys Phe Ser Leu Pro Ser Val Asp
            180                 185                 190

Gly Gln Lys Arg Tyr Thr Phe Arg Val Arg Ser Arg Phe Asn Pro Leu
        195                 200                 205

Cys Gly Ser Ala Gln His Trp Ser Glu Trp Ser His Pro Ile His Trp
210                 215                 220

Gly Ser Asn Thr Ser Lys Glu Asn Pro Phe Leu Phe Ala Leu Glu Ala
225                 230                 235                 240

<210> SEQ ID NO 38
<211> LENGTH: 8
<212> TYPE: PRT
<213> ORGANISM: Artificial Sequence
<220> FEATURE:
<223> OTHER INFORMATION: Based on llima sequence

<400> SEQUENCE: 38

Gly Ser Thr Trp Ser Ile Asn Thr
1               5

<210> SEQ ID NO 39
<211> LENGTH: 7
<212> TYPE: PRT
<213> ORGANISM: Artificial Sequence
<220> FEATURE:
<223> OTHER INFORMATION: Based on llima sequence

<400> SEQUENCE: 39

Ile Ser Ser Gly Gly Ser Thr
1               5

<210> SEQ ID NO 40
<211> LENGTH: 10
<212> TYPE: PRT
<213> ORGANISM: Artificial Sequence
<220> FEATURE:
<223> OTHER INFORMATION: Based on llima sequence
```

```
<400> SEQUENCE: 40

Tyr Ala Gln Ser Thr Trp Tyr Pro Pro Ser
1               5                   10

<210> SEQ ID NO 41
<211> LENGTH: 25
<212> TYPE: PRT
<213> ORGANISM: Homo sapiens

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 42
<211> LENGTH: 17
<212> TYPE: PRT
<213> ORGANISM: Homo sapiens

<400> SEQUENCE: 42

Leu Ala Trp Tyr Arg Gln Ala Pro Gly Lys Gln Arg Asp Leu Val Ala
1               5                   10                  15

Arg

<210> SEQ ID NO 43
<211> LENGTH: 38
<212> TYPE: PRT
<213> ORGANISM: Homo sapiens

<400> SEQUENCE: 43

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 44
<211> LENGTH: 11
<212> TYPE: PRT
<213> ORGANISM: Homo sapiens

<400> SEQUENCE: 44

Trp Gly Gln Gly Thr Leu Val Thr Val Ser Ser
1               5                   10

<210> SEQ ID NO 45
<211> LENGTH: 116
<212> TYPE: PRT
<213> ORGANISM: Artificial Sequence
<220> FEATURE:
<223> OTHER INFORMATION: Based on llima sequence

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Trp Ser Ile Asn
            20                  25                  30

Thr Leu Ala Trp Tyr Arg Gln Ala Pro Gly Lys Gln Arg Asp Leu Val
        35                  40                  45
```

```
Ala Arg Ile Ser Ser Gly Gly Ser Thr Tyr Tyr Ala Asp Ser Val Lys
         50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Tyr
                 85                  90                  95

Ala Gln Ser Thr Trp Tyr Pro Pro Ser Trp Gly Gln Gly Thr Leu Val
            100                 105                 110

Thr Val Ser Ser
        115

<210> SEQ ID NO 46
<211> LENGTH: 8
<212> TYPE: PRT
<213> ORGANISM: Artificial Sequence
<220> FEATURE:
<223> OTHER INFORMATION: Based on llima sequence

<400> SEQUENCE: 46

Gly Phe Ala Phe Arg Gly Phe Gly
1               5

<210> SEQ ID NO 47
<211> LENGTH: 8
<212> TYPE: PRT
<213> ORGANISM: Artificial Sequence
<220> FEATURE:
<223> OTHER INFORMATION: Based on llima sequence

<400> SEQUENCE: 47

Ile Asn Asn Gly Gly Ser Asp Thr
1               5

<210> SEQ ID NO 48
<211> LENGTH: 9
<212> TYPE: PRT
<213> ORGANISM: Artificial Sequence
<220> FEATURE:
<223> OTHER INFORMATION: Based on llima sequence

<400> SEQUENCE: 48

Ala Ile Gly Gly Pro Gly Ala Ser Pro
1               5

<210> SEQ ID NO 49
<211> LENGTH: 25
<212> TYPE: PRT
<213> ORGANISM: Homo sapiens

<400> SEQUENCE: 49

Gln Val Gln Leu Val Glu Ser Gly Gly Val Val Gln Pro Gly Gly
1               5                   10                  15

Ser Leu Arg Leu Ser Cys Ala Ala Ser
            20                  25

<210> SEQ ID NO 50
<211> LENGTH: 17
<212> TYPE: PRT
<213> ORGANISM: Homo sapiens

<400> SEQUENCE: 50

Met Ser Trp Val Arg Gln Ala Pro Gly Lys Gly Leu Glu Trp Val Ser
1               5                   10                  15
```

Ser

<210> SEQ ID NO 51
<211> LENGTH: 11
<212> TYPE: PRT
<213> ORGANISM: Homo sapiens

<400> SEQUENCE: 51

Ser Gly Gln Gly Thr Gln Val Thr Val Ser Ser
1               5                   10

<210> SEQ ID NO 52
<211> LENGTH: 116
<212> TYPE: PRT
<213> ORGANISM: Artificial Sequence
<220> FEATURE:
<223> OTHER INFORMATION: Based on llima sequence

<400> SEQUENCE: 52

Gln Val Gln Leu Val Glu Ser Gly Gly Val Val Gln Pro Gly Gly
1               5                   10                  15

Ser Leu Arg Leu Ser Cys Ala Ala Ser Gly Phe Ala Phe Arg Gly Phe
            20                  25                  30

Gly Met Ser Trp Val Arg Gln Ala Pro Gly Lys Gly Leu Glu Trp Val
        35                  40                  45

Ser Ser Ile Asn Asn Gly Gly Ser Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gly Gly Pro Gly Ala Ser Pro Ser Gly Gln Gly Thr Gln Val
            100                 105                 110

Thr Val Ser Ser
        115

<210> SEQ ID NO 53
<211> LENGTH: 227
<212> TYPE: PRT
<213> ORGANISM: Homo sapiens

<400> SEQUENCE: 53

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

-continued

```
Tyr Thr Leu Pro Pro Ser Arg Glu Glu Met Thr Lys Asn Gln Val Ser
            130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                    165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Lys
225

<210> SEQ ID NO 54
<211> LENGTH: 227
<212> TYPE: PRT
<213> ORGANISM: Homo sapiens

<400> SEQUENCE: 54

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
            130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                    165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Lys
225

<210> SEQ ID NO 55
<211> LENGTH: 227
<212> TYPE: PRT
<213> ORGANISM: Homo sapiens
```

<400> SEQUENCE: 55

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 56
<211> LENGTH: 227
<212> TYPE: PRT
<213> ORGANISM: Homo sapiens

<400> SEQUENCE: 56

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125
```

```
Cys Thr Leu Pro Pro Ser Arg Glu Glu Met Thr Lys Asn Gln Val Ser
        130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                    165                 170                 175

Val Leu Asp Ser Asp Gly Ser Phe Phe Leu Val Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly Lys
225

<210> SEQ ID NO 57
<211> LENGTH: 227
<212> TYPE: PRT
<213> ORGANISM: Homo sapiens

<400> SEQUENCE: 57

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
        130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                    165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly Lys
225

<210> SEQ ID NO 58
<211> LENGTH: 227
<212> TYPE: PRT
```

<213> ORGANISM: Homo sapiens

<400> SEQUENCE: 58

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Glu Glu Met Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 59
<211> LENGTH: 228
<212> TYPE: PRT
<213> ORGANISM: Homo sapiens

<400> SEQUENCE: 59

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln

```
            115                 120                 125
Val Tyr Thr Leu Pro Pro Ser Arg Glu Glu Met Thr Lys Asn Gln Val
        130                 135                 140
Ser Leu Thr Cys Leu Val Lys Gly Phe Tyr Pro Ser Asp Ile Ala Val
145                 150                 155                 160
Glu Trp Glu Ser Asn Gly Gln Pro Glu Asn Asn Tyr Lys Thr Thr Pro
                165                 170                 175
Pro Met Leu Asp Ser Asp Gly Ser Phe Phe Leu Tyr Ser Lys Leu Thr
            180                 185                 190
Val Asp Lys Ser Arg Trp Gln Gln Gly Asn Val Phe Ser Cys Ser Val
                195                 200                 205
Met His Glu Ala Leu His Asn His Tyr Thr Gln Lys Ser Leu Ser Leu
210                 215                 220
Ser Pro Gly Lys
225

<210> SEQ ID NO 60
<211> LENGTH: 229
<212> TYPE: PRT
<213> ORGANISM: Homo sapiens

<400> SEQUENCE: 60

Glu Ser Lys Tyr Gly Pro Pro Cys Pro Pro Cys Pro Ala Pro Glu Phe
1               5                   10                  15
Leu Gly Gly Pro Ser Val Phe Leu Phe Pro Pro Lys Pro Lys Asp Thr
            20                  25                  30
Leu Met Ile Ser Arg Thr Pro Glu Val Thr Cys Val Val Val Asp Val
        35                  40                  45
Ser Gln Glu Asp Pro Glu Val Gln Phe Asn Trp Tyr Val Asp Gly Val
    50                  55                  60
Glu Val His Asn Ala Lys Thr Lys Pro Arg Glu Glu Gln Phe Asn Ser
65                  70                  75                  80
Thr Tyr Arg Val Val Ser Val Leu Thr Val Leu His Gln Asp Trp Leu
                85                  90                  95
Asn Gly Lys Glu Tyr Lys Cys Lys Val Ser Asn Lys Gly Leu Pro Ser
            100                 105                 110
Ser Ile Glu Lys Thr Ile Ser Lys Ala Lys Gly Gln Pro Arg Glu Pro
        115                 120                 125
Gln Val Tyr Thr Leu Pro Pro Ser Gln Glu Glu Met Thr Lys Asn Gln
    130                 135                 140
Val Ser Leu Thr Cys Leu Val Lys Gly Phe Tyr Pro Ser Asp Ile Ala
145                 150                 155                 160
Val Glu Trp Glu Ser Asn Gly Gln Pro Glu Asn Asn Tyr Lys Thr Thr
                165                 170                 175
Pro Pro Val Leu Asp Ser Asp Gly Ser Phe Phe Leu Tyr Ser Arg Leu
            180                 185                 190
Thr Val Asp Lys Ser Arg Trp Gln Glu Gly Asn Val Phe Ser Cys Ser
        195                 200                 205
Val Met His Glu Ala Leu His Asn His Tyr Thr Gln Lys Ser Leu Ser
    210                 215                 220
Leu Ser Leu Gly Lys
225

<210> SEQ ID NO 61
<211> LENGTH: 6
```

```
<212> TYPE: PRT
<213> ORGANISM: Artificial Sequence
<220> FEATURE:
<223> OTHER INFORMATION: Linker

<400> SEQUENCE: 61

Gly Ser Gly Gly Ser Gly
1               5

<210> SEQ ID NO 62
<211> LENGTH: 9
<212> TYPE: PRT
<213> ORGANISM: Artificial Sequence
<220> FEATURE:
<223> OTHER INFORMATION: Linker

<400> SEQUENCE: 62

Gly Ser Gly Gly Ser Gly Gly Ser Gly
1               5

<210> SEQ ID NO 63
<211> LENGTH: 12
<212> TYPE: PRT
<213> ORGANISM: Artificial Sequence
<220> FEATURE:
<223> OTHER INFORMATION: Linker

<400> SEQUENCE: 63

Gly Ser Gly Gly Ser Gly Gly Ser Gly Gly Ser Gly
1               5                   10

<210> SEQ ID NO 64
<211> LENGTH: 4
<212> TYPE: PRT
<213> ORGANISM: Artificial Sequence
<220> FEATURE:
<223> OTHER INFORMATION: Linker

<400> SEQUENCE: 64

Gly Gly Gly Ser
1

<210> SEQ ID NO 65
<211> LENGTH: 8
<212> TYPE: PRT
<213> ORGANISM: Artificial Sequence
<220> FEATURE:
<223> OTHER INFORMATION: Linker

<400> SEQUENCE: 65

Gly Gly Gly Ser Gly Gly Gly Ser
1               5

<210> SEQ ID NO 66
<211> LENGTH: 12
<212> TYPE: PRT
<213> ORGANISM: Artificial Sequence
<220> FEATURE:
<223> OTHER INFORMATION: Linker

<400> SEQUENCE: 66

Gly Gly Gly Ser Gly Gly Gly Ser Gly Gly Gly Ser
1               5                   10

<210> SEQ ID NO 67
<211> LENGTH: 16
<212> TYPE: PRT
```

```
<213> ORGANISM: Artificial Sequence
<220> FEATURE:
<223> OTHER INFORMATION: Linker

<400> SEQUENCE: 67

Gly Gly Gly Ser Gly Gly Gly Ser Gly Gly Gly Ser Gly Gly Gly Ser
1               5                   10                  15

<210> SEQ ID NO 68
<211> LENGTH: 5
<212> TYPE: PRT
<213> ORGANISM: Artificial Sequence
<220> FEATURE:
<223> OTHER INFORMATION: Linker

<400> SEQUENCE: 68

Gly Gly Gly Gly Ser
1               5

<210> SEQ ID NO 69
<211> LENGTH: 10
<212> TYPE: PRT
<213> ORGANISM: Artificial Sequence
<220> FEATURE:
<223> OTHER INFORMATION: Linker

<400> SEQUENCE: 69

Gly Gly Gly Gly Ser Gly Gly Gly Gly Ser
1               5                   10

<210> SEQ ID NO 70
<211> LENGTH: 15
<212> TYPE: PRT
<213> ORGANISM: Artificial Sequence
<220> FEATURE:
<223> OTHER INFORMATION: Linker

<400> SEQUENCE: 70

Gly Gly Gly Gly Ser Gly Gly Gly Gly Ser Gly Gly Gly Gly Ser
1               5                   10                  15

<210> SEQ ID NO 71
<211> LENGTH: 20
<212> TYPE: PRT
<213> ORGANISM: Artificial Sequence
<220> FEATURE:
<223> OTHER INFORMATION: Linker

<400> SEQUENCE: 71

Gly Gly Gly Gly Ser Gly Gly Gly Gly Ser Gly Gly Gly Gly Ser Gly
1               5                   10                  15

Gly Gly Gly Ser
            20

<210> SEQ ID NO 72
<211> LENGTH: 4
<212> TYPE: PRT
<213> ORGANISM: Artificial Sequence
<220> FEATURE:
<223> OTHER INFORMATION: Linker

<400> SEQUENCE: 72

Ser Gly Ser Gly
1

<210> SEQ ID NO 73
```

```
<211> LENGTH: 7
<212> TYPE: PRT
<213> ORGANISM: Artificial Sequence
<220> FEATURE:
<223> OTHER INFORMATION: Linker

<400> SEQUENCE: 73

Ser Gly Ser Gly Gly Ser Gly
1               5

<210> SEQ ID NO 74
<211> LENGTH: 10
<212> TYPE: PRT
<213> ORGANISM: Artificial Sequence
<220> FEATURE:
<223> OTHER INFORMATION: Linker

<400> SEQUENCE: 74

Ser Gly Ser Gly Gly Ser Gly Gly Ser Gly
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Linker

<400> SEQUENCE: 75

Ser Gly Ser Gly Gly Ser Gly Gly Ser Gly Gly Ser Gly
1               5                   10

<210> SEQ ID NO 76
<211> LENGTH: 5
<212> TYPE: PRT
<213> ORGANISM: Artificial Sequence
<220> FEATURE:
<223> OTHER INFORMATION: Linker

<400> SEQUENCE: 76

Ser Gly Gly Gly Ser
1               5

<210> SEQ ID NO 77
<211> LENGTH: 9
<212> TYPE: PRT
<213> ORGANISM: Artificial Sequence
<220> FEATURE:
<223> OTHER INFORMATION: Linker

<400> SEQUENCE: 77

Ser Gly Gly Gly Ser Gly Gly Gly Ser
1               5

<210> SEQ ID NO 78
<211> LENGTH: 13
<212> TYPE: PRT
<213> ORGANISM: Artificial Sequence
<220> FEATURE:
<223> OTHER INFORMATION: Linker

<400> SEQUENCE: 78

Ser Gly Gly Gly Ser Gly Gly Gly Ser Gly Gly Gly Ser
1               5                   10

<210> SEQ ID NO 79
<211> LENGTH: 17
```

```
<212> TYPE: PRT
<213> ORGANISM: Artificial Sequence
<220> FEATURE:
<223> OTHER INFORMATION: Linker

<400> SEQUENCE: 79

Ser Gly Gly Gly Ser Gly Gly Gly Ser Gly Gly Gly Ser Gly Gly
1               5                   10                  15

Ser

<210> SEQ ID NO 80
<211> LENGTH: 6
<212> TYPE: PRT
<213> ORGANISM: Artificial Sequence
<220> FEATURE:
<223> OTHER INFORMATION: Linker

<400> SEQUENCE: 80

Ser Gly Gly Gly Gly Ser
1               5

<210> SEQ ID NO 81
<211> LENGTH: 11
<212> TYPE: PRT
<213> ORGANISM: Artificial Sequence
<220> FEATURE:
<223> OTHER INFORMATION: Linker

<400> SEQUENCE: 81

Ser Gly Gly Gly Gly Ser Gly Gly Gly Gly Ser
1               5                   10

<210> SEQ ID NO 82
<211> LENGTH: 16
<212> TYPE: PRT
<213> ORGANISM: Artificial Sequence
<220> FEATURE:
<223> OTHER INFORMATION: Linker

<400> SEQUENCE: 82

Ser Gly Gly Gly Gly Ser Gly Gly Gly Gly Ser Gly Gly Gly Gly Ser
1               5                   10                  15

<210> SEQ ID NO 83
<211> LENGTH: 21
<212> TYPE: PRT
<213> ORGANISM: Artificial Sequence
<220> FEATURE:
<223> OTHER INFORMATION: Linker

<400> SEQUENCE: 83

Ser Gly Gly Gly Gly Ser Gly Gly Gly Gly Ser Gly Gly Gly Gly Ser
1               5                   10                  15

Gly Gly Gly Gly Ser
            20

<210> SEQ ID NO 84
<211> LENGTH: 5
<212> TYPE: PRT
<213> ORGANISM: Artificial Sequence
<220> FEATURE:
<223> OTHER INFORMATION: Linker

<400> SEQUENCE: 84

Glu Ala Ala Ala Lys
1               5
```

<210> SEQ ID NO 85
<211> LENGTH: 10
<212> TYPE: PRT
<213> ORGANISM: Artificial Sequence
<220> FEATURE:
<223> OTHER INFORMATION: Linker

<400> SEQUENCE: 85

Glu Ala Ala Ala Lys Glu Ala Ala Ala Lys
1               5                   10

<210> SEQ ID NO 86
<211> LENGTH: 15
<212> TYPE: PRT
<213> ORGANISM: Artificial Sequence
<220> FEATURE:
<223> OTHER INFORMATION: Linker

<400> SEQUENCE: 86

Glu Ala Ala Ala Lys Glu Ala Ala Ala Lys Glu Ala Ala Ala Lys
1               5                   10                  15

<210> SEQ ID NO 87
<211> LENGTH: 20
<212> TYPE: PRT
<213> ORGANISM: Artificial Sequence
<220> FEATURE:
<223> OTHER INFORMATION: Linker

<400> SEQUENCE: 87

Glu Ala Ala Ala Lys Glu Ala Ala Ala Lys Glu Ala Ala Ala Lys Glu
1               5                   10                  15

Ala Ala Ala Lys
            20

<210> SEQ ID NO 88
<211> LENGTH: 5
<212> TYPE: PRT
<213> ORGANISM: Artificial Sequence
<220> FEATURE:
<223> OTHER INFORMATION: Linker

<400> SEQUENCE: 88

Pro Ala Pro Ala Pro
1               5

<210> SEQ ID NO 89
<211> LENGTH: 10
<212> TYPE: PRT
<213> ORGANISM: Artificial Sequence
<220> FEATURE:
<223> OTHER INFORMATION: Linker

<400> SEQUENCE: 89

Pro Ala Pro Ala Pro Pro Ala Pro Ala Pro
1               5                   10

<210> SEQ ID NO 90
<211> LENGTH: 15
<212> TYPE: PRT
<213> ORGANISM: Artificial Sequence
<220> FEATURE:
<223> OTHER INFORMATION: Linker

<400> SEQUENCE: 90

```
Pro Ala Pro Ala Pro Ala Pro Ala Pro Ala Pro Ala Pro Ala Pro
1               5                  10                 15
```

<210> SEQ ID NO 91
<211> LENGTH: 20
<212> TYPE: PRT
<213> ORGANISM: Artificial Sequence
<220> FEATURE:
<223> OTHER INFORMATION: Linker

<400> SEQUENCE: 91

```
Pro Ala Pro Ala Pro Ala Pro Ala Pro Ala Pro Ala Pro Ala Pro Pro
1               5                  10                 15

Ala Pro Ala Pro
        20
```

<210> SEQ ID NO 92
<211> LENGTH: 8
<212> TYPE: PRT
<213> ORGANISM: Artificial Sequence
<220> FEATURE:
<223> OTHER INFORMATION: Linker

<400> SEQUENCE: 92

```
Ile Lys Arg Thr Val Ala Ala Pro
1               5
```

<210> SEQ ID NO 93
<211> LENGTH: 261
<212> TYPE: PRT
<213> ORGANISM: Homo sapiens

<400> SEQUENCE: 93

```
Ala Pro Thr Ser Ser Ser Thr Lys Lys Thr Gln Leu Gln Leu Glu His
1               5                  10                 15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Ser Gly Ser Gly Gly Ser Gly Ser
130                 135                 140

Gly Glu Val Gln Leu Val Glu Ser Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
        195                 200                 205
```

```
Lys Gly Arg Phe Thr Ile Ser Arg Asp Asn Ser Lys Asn Thr Leu Tyr
    210                 215                 220
Leu Gln Met Asn Ser Leu Arg Ala Glu Asp Thr Ala Val Tyr Tyr Cys
225                 230                 235                 240
Tyr Ala Gln Ser Thr Trp Tyr Pro Pro Ser Trp Gly Gln Gly Thr Leu
                245                 250                 255
Val Thr Val Ser Ser
            260

<210> SEQ ID NO 94
<211> LENGTH: 261
<212> TYPE: PRT
<213> ORGANISM: Homo sapiens

<400> SEQUENCE: 94

Ala Pro Thr Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
                20                  25                  30
Asn Pro Lys Leu Thr Asn Met Thr Thr Phe Lys Phe Tyr Met Pro Lys
            35                  40                  45
Lys Ala Thr Glu Leu Lys His Leu Gln Cys Leu Glu Glu Leu Lys
50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Ser Gln Ser Ile
        115                 120                 125
Ile Ser Thr Leu Thr Gly Ser Gly Gly Ser Gly Gly Ser
130                 135                 140
Gly Glu Val Gln Leu Val Glu Ser Gly Gly Leu Val Gln Pro Gly
145                 150                 155                 160
Gly Ser Leu Arg Leu Ser Cys Ala Ala Ser Gly Ser Thr Trp Ser Ile
                165                 170                 175
Asn Thr Leu Ala Trp Tyr Arg Gln Ala Pro Gly Lys Gln Arg Asp Leu
            180                 185                 190
Val Ala Arg Ile Ser Ser Gly Gly Ser Thr Tyr Tyr Ala Asp Ser Val
        195                 200                 205
Lys Gly Arg Phe Thr Ile Ser Arg Asp Asn Ser Lys Asn Thr Leu Tyr
    210                 215                 220
Leu Gln Met Asn Ser Leu Arg Ala Glu Asp Thr Ala Val Tyr Tyr Cys
225                 230                 235                 240
Tyr Ala Gln Ser Thr Trp Tyr Pro Pro Ser Trp Gly Gln Gly Thr Leu
                245                 250                 255
Val Thr Val Ser Ser
            260

<210> SEQ ID NO 95
<211> LENGTH: 261
<212> TYPE: PRT
<213> ORGANISM: Homo sapiens

<400> SEQUENCE: 95
```

```
Ala Pro Thr Ser Ser Ser Thr Lys Lys Thr Gln Leu Gln Leu Glu Glu
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Gly Ser Gly Gly Ser Gly Gly Ser
    130                 135                 140

Gly Glu Val Gln Leu Val Glu Ser Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
        195                 200                 205

Lys Gly Arg Phe Thr Ile Ser Arg Asp Asn Ser Lys Asn Thr Leu Tyr
    210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 96
<211> LENGTH: 261
<212> TYPE: PRT
<213> ORGANISM: Homo sapiens

<400> SEQUENCE: 96

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110
```

```
Thr Ile Val Glu Phe Leu Asn Arg Trp Ile Thr Phe Ser Gln Ser Ile
            115                 120                 125

Ile Ser Thr Leu Thr Gly Ser Gly Gly Ser Gly Gly Ser
            130                 135                 140

Gly Glu Val Gln Leu Val Glu Ser Gly Gly Leu Val Gln Pro Gly
145                 150                 155                 160

Gly Ser Leu Arg Leu Ser Cys Ala Ala Ser Gly Ser Thr Trp Ser Ile
            165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
            195                 200                 205

Lys Gly Arg Phe Thr Ile Ser Arg Asp Asn Ser Lys Asn Thr Leu Tyr
            210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
            245                 250                 255

Val Thr Val Ser Ser
            260

<210> SEQ ID NO 97
<211> LENGTH: 261
<212> TYPE: PRT
<213> ORGANISM: Homo sapiens

<400> SEQUENCE: 97

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Glu Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr Gly Ser Gly Gly Ser Gly Gly Ser
            130                 135                 140

Gly Glu Val Gln Leu Val Glu Ser Gly Gly Leu Val Gln Pro Gly
145                 150                 155                 160

Gly Ser Leu Arg Leu Ser Cys Ala Ala Ser Gly Ser Thr Trp Ser Ile
            165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
            195                 200                 205

Lys Gly Arg Phe Thr Ile Ser Arg Asp Asn Ser Lys Asn Thr Leu Tyr
```

<210> SEQ ID NO 98
<211> LENGTH: 261
<212> TYPE: PRT
<213> ORGANISM: Homo sapiens

<400> SEQUENCE: 98

Ala Pro Thr Ser Ser Ser Thr Glu Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr Gly Ser Gly Gly Ser Gly Gly Ser Gly Gly Ser
130                 135                 140

Gly Glu Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
        195                 200                 205

Lys Gly Arg Phe Thr Ile Ser Arg Asp Asn Ser Lys Asn Thr Leu Tyr
    210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 99
<211> LENGTH: 261
<212> TYPE: PRT
<213> ORGANISM: Homo sapiens

<400> SEQUENCE: 99

Ala Pro Thr Ser Ser Ser Thr Lys Glu Thr Gln Leu Gln Leu Glu His

```
1               5                   10                  15
Leu Leu Leu Asp Leu Gln Met Ile Leu Asn Gly Ile Asn Asn Tyr Lys
            20                  25                  30

Asn Pro Lys Leu Thr Asn Met Thr Thr Phe Lys Phe Tyr Met Pro Lys
            35                  40                  45

Lys Ala Thr Glu Leu Lys His Leu Gln Cys Leu Glu Glu Leu Lys
            50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
                115                 120                 125

Ile Ser Thr Leu Thr Gly Ser Gly Ser Gly Gly Ser Gly Gly Ser
                130                 135                 140

Gly Glu Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
                180                 185                 190

Val Ala Arg Ile Ser Ser Gly Gly Ser Thr Tyr Tyr Ala Asp Ser Val
                195                 200                 205

Lys Gly Arg Phe Thr Ile Ser Arg Asp Asn Ser Lys Asn Thr Leu Tyr
                210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
                260

<210> SEQ ID NO 100
<211> LENGTH: 261
<212> TYPE: PRT
<213> ORGANISM: Homo sapiens

<400> SEQUENCE: 100

Ala Pro Thr Ser Ser Ser Thr Lys Lys Thr Gln Leu Gln Leu Glu Glu
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Phe Lys Phe Tyr Met Pro Lys
            35                  40                  45

Lys Ala Thr Glu Leu Lys His Leu Gln Cys Leu Glu Glu Leu Lys
            50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110
```

Thr Ile Val Glu Phe Leu Asn Arg Trp Ile Thr Phe Ser Gln Ser Ile
            115                 120                 125

Ile Ser Thr Leu Thr Gly Ser Gly Gly Ser Gly Gly Ser
130                 135                 140

Gly Glu Val Gln Leu Val Glu Ser Gly Gly Leu Val Gln Pro Gly
145                 150                 155                 160

Gly Ser Leu Arg Leu Ser Cys Ala Ala Ser Gly Ser Thr Trp Ser Ile
            165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
            195                 200                 205

Lys Gly Arg Phe Thr Ile Ser Arg Asp Asn Ser Lys Asn Thr Leu Tyr
            210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
            245                 250                 255

Val Thr Val Ser Ser
            260

<210> SEQ ID NO 101
<211> LENGTH: 261
<212> TYPE: PRT
<213> ORGANISM: Homo sapiens

<400> SEQUENCE: 101

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
            20                  25                  30

Asn Pro Lys Leu Thr Asn Met Thr Thr Phe Lys Phe Tyr Met Pro Lys
            35                  40                  45

Lys Ala Thr Glu Leu Lys His Leu Gln Cys Leu Glu Glu Glu Leu Lys
            50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr Gly Ser Gly Gly Ser Gly Gly Ser
            130                 135                 140

Gly Glu Val Gln Leu Val Glu Ser Gly Gly Leu Val Gln Pro Gly
145                 150                 155                 160

Gly Ser Leu Arg Leu Ser Cys Ala Ala Ser Gly Ser Thr Trp Ser Ile
            165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
            195                 200                 205

Lys Gly Arg Phe Thr Ile Ser Arg Asp Asn Ser Lys Asn Thr Leu Tyr
            210                 215                 220

```
Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 102
<211> LENGTH: 261
<212> TYPE: PRT
<213> ORGANISM: Homo sapiens

<400> SEQUENCE: 102

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Asn Met Thr Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Glu Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Ser Gly Gly Ser Gly Gly Ser
130                 135                 140

Gly Glu Val Gln Leu Val Glu Ser Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
        195                 200                 205

Lys Gly Arg Phe Thr Ile Ser Arg Asp Asn Ser Lys Asn Thr Leu Tyr
    210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 103
<211> LENGTH: 261
<212> TYPE: PRT
<213> ORGANISM: Homo sapiens

<400> SEQUENCE: 103

Ala Pro Thr Ser Ser Thr Lys Lys Thr Gln Leu Gln Leu Glu His
1               5                   10                  15
```

Leu Leu Leu Asp Leu Gln Met Ile Leu Asn Gly Ile Asn Asn Tyr Lys
            20                  25                  30

Asn Pro Lys Leu Thr Asn Met Thr Thr Phe Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe Glu Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
                115                 120                 125

Ile Ser Thr Leu Thr Gly Ser Gly Ser Gly Gly Ser Gly Gly Ser
130                 135                 140

Gly Glu Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
                180                 185                 190

Val Ala Arg Ile Ser Ser Gly Gly Ser Thr Tyr Tyr Ala Asp Ser Val
                195                 200                 205

Lys Gly Arg Phe Thr Ile Ser Arg Asp Asn Ser Lys Asn Thr Leu Tyr
                210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 104
<211> LENGTH: 261
<212> TYPE: PRT
<213> ORGANISM: Homo sapiens

<400> SEQUENCE: 104

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Phe Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Glu Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile

```
            115                 120                 125
Ile Ser Thr Leu Thr Gly Ser Gly Gly Ser Gly Gly Ser
        130                 135                 140

Gly Glu Val Gln Leu Val Glu Ser Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
        195                 200                 205

Lys Gly Arg Phe Thr Ile Ser Arg Asp Asn Ser Lys Asn Thr Leu Tyr
210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 105
<211> LENGTH: 261
<212> TYPE: PRT
<213> ORGANISM: Homo sapiens

<400> SEQUENCE: 105

Ala Pro Thr Ser Ser Thr Lys Lys Thr Gln Leu Gln Leu Glu Glu
1               5                   10                  15

Leu Leu Leu Asp Leu Gln Met Ile Leu Asn Gly Ile Asn Asn Tyr Glu
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Gly Ser Gly Gly Ser Gly Gly Ser
        130                 135                 140

Gly Glu Val Gln Leu Val Glu Ser Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
        195                 200                 205

Lys Gly Arg Phe Thr Ile Ser Arg Asp Asn Ser Lys Asn Thr Leu Tyr
210                 215                 220
```

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
            245                 250                 255

Val Thr Val Ser Ser
            260

<210> SEQ ID NO 106
<211> LENGTH: 261
<212> TYPE: PRT
<213> ORGANISM: Homo sapiens

<400> SEQUENCE: 106

Ala Pro Thr Ser Ser Thr Lys Lys Thr Gln Leu Gln Leu Glu Glu Glu
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Gly Ser Gly Gly Ser Gly Gly Ser
130                 135                 140

Gly Glu Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
        195                 200                 205

Lys Gly Arg Phe Thr Ile Ser Arg Asp Asn Ser Lys Asn Thr Leu Tyr
210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
            245                 250                 255

Val Thr Val Ser Ser
            260

<210> SEQ ID NO 107
<211> LENGTH: 261
<212> TYPE: PRT
<213> ORGANISM: Homo sapiens

<400> SEQUENCE: 107

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
            20                  25                  30

Asn Pro Lys Leu Thr Arg Met Leu Thr Phe Lys Phe Tyr Met Pro Lys
         35                  40                  45

Lys Ala Thr Glu Leu Lys His Leu Gln Cys Leu Glu Glu Glu Leu Lys
     50                  55                  60

Pro Leu Glu Glu Val Leu Asn Leu Ala Gln Ser Glu Asn Phe His Leu
65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr Gly Ser Gly Gly Ser Gly Gly Ser
130                 135                 140

Gly Glu Val Gln Leu Val Glu Ser Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
                195                 200                 205

Lys Gly Arg Phe Thr Ile Ser Arg Asp Asn Ser Lys Asn Thr Leu Tyr
            210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 108
<211> LENGTH: 261
<212> TYPE: PRT
<213> ORGANISM: Homo sapiens

<400> SEQUENCE: 108

Ala Pro Thr Ser Ser Ser Thr Lys Lys Thr Gln Leu Gln Leu Glu Glu
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Phe Lys Phe Tyr Met Pro Lys
         35                  40                  45

Lys Ala Thr Glu Leu Lys His Leu Gln Cys Leu Glu Glu Glu Leu Lys
     50                  55                  60

Pro Leu Glu Glu Val Leu Asn Leu Ala Gln Ser Glu Asn Phe His Leu
65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

```
Ile Ser Thr Leu Thr Gly Ser Gly Gly Ser Gly Gly Ser
        130                 135                 140

Gly Glu Val Gln Leu Val Glu Ser Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
                180                 185                 190

Val Ala Arg Ile Ser Ser Gly Gly Ser Thr Tyr Tyr Ala Asp Ser Val
            195                 200                 205

Lys Gly Arg Phe Thr Ile Ser Arg Asp Asn Ser Lys Asn Thr Leu Tyr
210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 109
<211> LENGTH: 261
<212> TYPE: PRT
<213> ORGANISM: Homo sapiens

<400> SEQUENCE: 109

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
                20                  25                  30

Asn Pro Lys Leu Thr Asn Met Thr Thr Phe Lys Phe Tyr Met Pro Lys
                35                  40                  45

Lys Ala Thr Glu Leu Lys His Leu Gln Cys Leu Glu Glu Glu Leu Lys
            50                  55                  60

Pro Leu Glu Glu Val Leu Asn Leu Ala Gln Ser Glu Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr Gly Ser Gly Gly Ser Gly Gly Ser Gly Gly Ser
        130                 135                 140

Gly Glu Val Gln Leu Val Glu Ser Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
                180                 185                 190

Val Ala Arg Ile Ser Ser Gly Gly Ser Thr Tyr Tyr Ala Asp Ser Val
            195                 200                 205

Lys Gly Arg Phe Thr Ile Ser Arg Asp Asn Ser Lys Asn Thr Leu Tyr
210                 215                 220

Leu Gln Met Asn Ser Leu Arg Ala Glu Asp Thr Ala Val Tyr Tyr Cys
```

```
225                 230                 235                 240
Tyr Ala Gln Ser Thr Trp Tyr Pro Pro Ser Trp Gly Gln Gly Thr Leu
                245                 250                 255
Val Thr Val Ser Ser
            260
```

<210> SEQ ID NO 110
<211> LENGTH: 255
<212> TYPE: PRT
<213> ORGANISM: Homo sapiens

<400> SEQUENCE: 110

```
Ala Pro Thr Ser Ser Thr Lys Lys Thr Gln Leu Gln Leu Glu His
1               5                   10                  15
Leu Leu Leu Asp Leu Gln Met Ile Leu Asn Gly Ile Asn Leu Thr Asn
                20                  25                  30
Met Thr Thr Phe Lys Phe Tyr Met Pro Lys Lys Ala Thr Glu Leu Lys
                35                  40                  45
His Leu Gln Cys Leu Glu Glu Glu Leu Lys Pro Leu Glu Glu Val Leu
            50                  55                  60
Asn Leu Ala Gln Ser Lys Asn Phe His Leu Arg Pro Arg Asp Leu Ile
65                  70                  75                  80
Ser Asn Ile Asn Val Ile Val Leu Glu Leu Lys Gly Ser Glu Thr Thr
                85                  90                  95
Phe Met Cys Glu Tyr Ala Asp Glu Thr Ala Thr Ile Val Glu Phe Leu
                100                 105                 110
Asn Arg Trp Ile Thr Phe Ser Gln Ser Ile Ile Ser Thr Leu Thr Gly
                115                 120                 125
Ser Gly Gly Ser Gly Gly Ser Gly Gly Ser Glu Val Gln Leu Val
                130                 135                 140
Glu Ser Gly Gly Gly Leu Val Gln Pro Gly Gly Ser Leu Arg Leu Ser
145                 150                 155                 160
Cys Ala Ala Ser Gly Ser Thr Trp Ser Ile Asn Thr Leu Ala Trp Tyr
                165                 170                 175
Arg Gln Ala Pro Gly Lys Gln Arg Asp Leu Val Ala Arg Ile Ser Ser
                180                 185                 190
Gly Gly Ser Thr Tyr Tyr Ala Asp Ser Val Lys Gly Arg Phe Thr Ile
                195                 200                 205
Ser Arg Asp Asn Ser Lys Asn Thr Leu Tyr Leu Gln Met Asn Ser Leu
                210                 215                 220
Arg Ala Glu Asp Thr Ala Val Tyr Tyr Cys Tyr Ala Gln Ser Thr Trp
225                 230                 235                 240
Tyr Pro Pro Ser Trp Gly Gln Gly Thr Leu Val Thr Val Ser Ser
                245                 250                 255
```

<210> SEQ ID NO 111
<211> LENGTH: 256
<212> TYPE: PRT
<213> ORGANISM: Homo sapiens

<400> SEQUENCE: 111

```
Ala Pro Thr Ser Ser Thr Lys Lys Thr Gln Leu Gln Leu Glu His
1               5                   10                  15
Leu Leu Leu Asp Leu Gln Met Ile Leu Asn Gly Ile Asn Gly Leu Thr
                20                  25                  30
Asn Met Thr Thr Phe Lys Phe Tyr Met Pro Lys Lys Ala Thr Glu Leu
```

```
            35                  40                  45
Lys His Leu Gln Cys Leu Glu Glu Leu Lys Pro Leu Glu Glu Val
 50                  55                  60
Leu Asn Leu Ala Gln Ser Lys Asn Phe His Leu Arg Pro Arg Asp Leu
 65                  70                  75                  80
Ile Ser Asn Ile Asn Val Ile Val Leu Glu Leu Lys Gly Ser Glu Thr
                 85                  90                  95
Thr Phe Met Cys Glu Tyr Ala Asp Glu Thr Ala Thr Ile Val Glu Phe
                100                 105                 110
Leu Asn Arg Trp Ile Thr Phe Ser Gln Ser Ile Ile Ser Thr Leu Thr
            115                 120                 125
Gly Ser Gly Gly Ser Gly Gly Ser Gly Gly Ser Gly Glu Val Gln Leu
130                 135                 140
Val Glu Ser Gly Gly Gly Leu Val Gln Pro Gly Gly Ser Leu Arg Leu
145                 150                 155                 160
Ser Cys Ala Ala Ser Gly Ser Thr Trp Ser Ile Asn Thr Leu Ala Trp
                165                 170                 175
Tyr Arg Gln Ala Pro Gly Lys Gln Arg Asp Leu Val Ala Arg Ile Ser
            180                 185                 190
Ser Gly Gly Ser Thr Tyr Tyr Ala Asp Ser Val Lys Gly Arg Phe Thr
        195                 200                 205
Ile Ser Arg Asp Asn Ser Lys Asn Thr Leu Tyr Leu Gln Met Asn Ser
210                 215                 220
Leu Arg Ala Glu Asp Thr Ala Val Tyr Tyr Cys Tyr Ala Gln Ser Thr
225                 230                 235                 240
Trp Tyr Pro Pro Ser Trp Gly Gln Gly Thr Leu Val Thr Val Ser Ser
                245                 250                 255

<210> SEQ ID NO 112
<211> LENGTH: 257
<212> TYPE: PRT
<213> ORGANISM: Homo sapiens

<400> SEQUENCE: 112

Ala Pro Thr Ser Ser Ser Thr Lys Lys Thr Gln Leu Gln Leu Glu His
 1               5                  10                  15
Leu Leu Leu Asp Leu Gln Met Ile Leu Asn Gly Ile Asn Ser Gly Leu
                20                  25                  30
Thr Asn Met Thr Thr Phe Lys Phe Tyr Met Pro Lys Lys Ala Thr Glu
            35                  40                  45
Leu Lys His Leu Gln Cys Leu Glu Glu Glu Leu Lys Pro Leu Glu Glu
 50                  55                  60
Val Leu Asn Leu Ala Gln Ser Lys Asn Phe His Leu Arg Pro Arg Asp
 65                  70                  75                  80
Leu Ile Ser Asn Ile Asn Val Ile Val Leu Glu Leu Lys Gly Ser Glu
                 85                  90                  95
Thr Thr Phe Met Cys Glu Tyr Ala Asp Glu Thr Ala Thr Ile Val Glu
                100                 105                 110
Phe Leu Asn Arg Trp Ile Thr Phe Ser Gln Ser Ile Ile Ser Thr Leu
            115                 120                 125
Thr Gly Ser Gly Gly Ser Gly Gly Ser Gly Gly Ser Gly Glu Val Gln
130                 135                 140
Leu Val Glu Ser Gly Gly Gly Leu Val Gln Pro Gly Gly Ser Leu Arg
145                 150                 155                 160
```

Leu Ser Cys Ala Ala Ser Gly Ser Thr Trp Ser Ile Asn Thr Leu Ala
            165                 170                 175

Trp Tyr Arg Gln Ala Pro Gly Lys Gln Arg Asp Leu Val Ala Arg Ile
        180                 185                 190

Ser Ser Gly Gly Ser Thr Tyr Tyr Ala Asp Ser Val Lys Gly Arg Phe
        195                 200                 205

Thr Ile Ser Arg Asp Asn Ser Lys Asn Thr Leu Tyr Leu Gln Met Asn
        210                 215                 220

Ser Leu Arg Ala Glu Asp Thr Ala Val Tyr Tyr Cys Tyr Ala Gln Ser
225                 230                 235                 240

Thr Trp Tyr Pro Pro Ser Trp Gly Gln Gly Thr Leu Val Thr Val Ser
            245                 250                 255

Ser

<210> SEQ ID NO 113
<211> LENGTH: 258
<212> TYPE: PRT
<213> ORGANISM: Homo sapiens

<400> SEQUENCE: 113

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Gly Gly Ser
            20                  25                  30

Leu Thr Arg Met Leu Thr Phe Lys Phe Tyr Met Pro Lys Lys Ala Thr
        35                  40                  45

Glu Leu Lys His Leu Gln Cys Leu Glu Glu Glu Leu Lys Pro Leu Glu
    50                  55                  60

Glu Val Leu Asn Leu Ala Gln Ser Lys Asn Phe His Leu Arg Pro Arg
65                  70                  75                  80

Asp Leu Ile Ser Asn Ile Asn Val Ile Val Leu Glu Leu Lys Gly Ser
                85                  90                  95

Glu Thr Thr Phe Met Cys Glu Tyr Ala Asp Glu Thr Ala Thr Ile Val
            100                 105                 110

Glu Phe Leu Asn Arg Trp Ile Thr Phe Ser Gln Ser Ile Ile Ser Thr
        115                 120                 125

Leu Thr Gly Ser Gly Gly Ser Gly Gly Ser Gly Gly Ser Gly Glu Val
    130                 135                 140

Gln Leu Val Glu Ser Gly Gly Gly Leu Val Gln Pro Gly Gly Ser Leu
145                 150                 155                 160

Arg Leu Ser Cys Ala Ala Ser Gly Ser Thr Trp Ser Ile Asn Thr Leu
                165                 170                 175

Ala Trp Tyr Arg Gln Ala Pro Gly Lys Gln Arg Asp Leu Val Ala Arg
            180                 185                 190

Ile Ser Ser Gly Gly Ser Thr Tyr Tyr Ala Asp Ser Val Lys Gly Arg
        195                 200                 205

Phe Thr Ile Ser Arg Asp Asn Ser Lys Asn Thr Leu Tyr Leu Gln Met
    210                 215                 220

Asn Ser Leu Arg Ala Glu Asp Thr Ala Val Tyr Tyr Cys Tyr Ala Gln
225                 230                 235                 240

Ser Thr Trp Tyr Pro Pro Ser Trp Gly Gln Gly Thr Leu Val Thr Val
                245                 250                 255

Ser Ser

```
<210> SEQ ID NO 114
<211> LENGTH: 258
<212> TYPE: PRT
<213> ORGANISM: Homo sapiens

<400> SEQUENCE: 114

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Gly Gly Ser
                20                  25                  30

Leu Thr Asn Met Thr Thr Phe Lys Phe Tyr Met Pro Lys Lys Ala Thr
            35                  40                  45

Glu Leu Lys His Leu Gln Cys Leu Glu Glu Leu Lys Pro Leu Glu
    50                  55                  60

Glu Val Leu Asn Leu Ala Gln Ser Lys Asn Phe His Leu Arg Pro Arg
65                  70                  75                  80

Asp Leu Ile Ser Asn Ile Asn Val Ile Val Leu Glu Leu Lys Gly Ser
                85                  90                  95

Glu Thr Thr Phe Met Cys Glu Tyr Ala Asp Glu Thr Ala Thr Ile Val
                100                 105                 110

Glu Phe Leu Asn Arg Trp Ile Thr Phe Ser Gln Ser Ile Ile Ser Thr
            115                 120                 125

Leu Thr Gly Ser Gly Gly Ser Gly Gly Ser Gly Ser Gly Glu Val
    130                 135                 140

Gln Leu Val Glu Ser Gly Gly Gly Leu Val Gln Pro Gly Gly Ser Leu
145                 150                 155                 160

Arg Leu Ser Cys Ala Ala Ser Gly Ser Thr Trp Ser Ile Asn Thr Leu
                165                 170                 175

Ala Trp Tyr Arg Gln Ala Pro Gly Lys Gln Arg Asp Leu Val Ala Arg
            180                 185                 190

Ile Ser Ser Gly Gly Ser Thr Tyr Tyr Ala Asp Ser Val Lys Gly Arg
        195                 200                 205

Phe Thr Ile Ser Arg Asp Asn Ser Lys Asn Thr Leu Tyr Leu Gln Met
    210                 215                 220

Asn Ser Leu Arg Ala Glu Asp Thr Ala Val Tyr Tyr Cys Tyr Ala Gln
225                 230                 235                 240

Ser Thr Trp Tyr Pro Pro Ser Trp Gly Gln Gly Thr Leu Val Thr Val
                245                 250                 255

Ser Ser

<210> SEQ ID NO 115
<211> LENGTH: 259
<212> TYPE: PRT
<213> ORGANISM: Homo sapiens

<400> SEQUENCE: 115

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Gly Gly Ser
                20                  25                  30

Gly Leu Thr Arg Met Leu Thr Phe Lys Phe Tyr Met Pro Lys Lys Ala
            35                  40                  45

Thr Glu Leu Lys His Leu Gln Cys Leu Glu Glu Leu Lys Pro Leu
    50                  55                  60

Glu Glu Val Leu Asn Leu Ala Gln Ser Lys Asn Phe His Leu Arg Pro
65                  70                  75                  80
```

Arg Asp Leu Ile Ser Asn Ile Asn Val Ile Val Leu Glu Leu Lys Gly
                85                  90                  95

Ser Glu Thr Thr Phe Met Cys Glu Tyr Ala Asp Glu Thr Ala Thr Ile
            100                 105                 110

Val Glu Phe Leu Asn Arg Trp Ile Thr Phe Ser Gln Ser Ile Ile Ser
            115                 120                 125

Thr Leu Thr Gly Ser Gly Gly Ser Gly Gly Ser Gly Gly Ser Gly Glu
        130                 135                 140

Val Gln Leu Val Glu Ser Gly Gly Leu Val Gln Pro Gly Gly Ser
145                 150                 155                 160

Leu Arg Leu Ser Cys Ala Ala Ser Gly Ser Thr Trp Ser Ile Asn Thr
                165                 170                 175

Leu Ala Trp Tyr Arg Gln Ala Pro Gly Lys Gln Arg Asp Leu Val Ala
            180                 185                 190

Arg Ile Ser Ser Gly Gly Ser Thr Tyr Tyr Ala Asp Ser Val Lys Gly
            195                 200                 205

Arg Phe Thr Ile Ser Arg Asp Asn Ser Lys Asn Thr Leu Tyr Leu Gln
            210                 215                 220

Met Asn Ser Leu Arg Ala Glu Asp Thr Ala Val Tyr Tyr Cys Tyr Ala
225                 230                 235                 240

Gln Ser Thr Trp Tyr Pro Pro Ser Trp Gly Gln Gly Thr Leu Val Thr
                245                 250                 255

Val Ser Ser

<210> SEQ ID NO 116
<211> LENGTH: 259
<212> TYPE: PRT
<213> ORGANISM: Homo sapiens

<400> SEQUENCE: 116

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Gly Gly Ser
            20                  25                  30

Gly Leu Thr Asn Met Thr Thr Phe Lys Phe Tyr Met Pro Lys Lys Ala
        35                  40                  45

Thr Glu Leu Lys His Leu Gln Cys Leu Glu Glu Glu Leu Lys Pro Leu
    50                  55                  60

Glu Glu Val Leu Asn Leu Ala Gln Ser Lys Asn Phe His Leu Arg Pro
65                  70                  75                  80

Arg Asp Leu Ile Ser Asn Ile Asn Val Ile Val Leu Glu Leu Lys Gly
                85                  90                  95

Ser Glu Thr Thr Phe Met Cys Glu Tyr Ala Asp Glu Thr Ala Thr Ile
            100                 105                 110

Val Glu Phe Leu Asn Arg Trp Ile Thr Phe Ser Gln Ser Ile Ile Ser
            115                 120                 125

Thr Leu Thr Gly Ser Gly Gly Ser Gly Gly Ser Gly Gly Ser Gly Glu
        130                 135                 140

Val Gln Leu Val Glu Ser Gly Gly Leu Val Gln Pro Gly Gly Ser
145                 150                 155                 160

Leu Arg Leu Ser Cys Ala Ala Ser Gly Ser Thr Trp Ser Ile Asn Thr
                165                 170                 175

Leu Ala Trp Tyr Arg Gln Ala Pro Gly Lys Gln Arg Asp Leu Val Ala
            180                 185                 190

```
Arg Ile Ser Ser Gly Gly Ser Thr Tyr Tyr Ala Asp Ser Val Lys Gly
        195                 200                 205

Arg Phe Thr Ile Ser Arg Asp Asn Ser Lys Asn Thr Leu Tyr Leu Gln
        210                 215                 220

Met Asn Ser Leu Arg Ala Glu Asp Thr Ala Val Tyr Tyr Cys Tyr Ala
225                 230                 235                 240

Gln Ser Thr Trp Tyr Pro Pro Ser Trp Gly Gln Gly Thr Leu Val Thr
                245                 250                 255

Val Ser Ser

<210> SEQ ID NO 117
<211> LENGTH: 260
<212> TYPE: PRT
<213> ORGANISM: Homo sapiens

<400> SEQUENCE: 117

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Gly Gly Ser
                20                  25                  30

Gly Gly Leu Thr Asn Met Thr Thr Phe Lys Phe Tyr Met Pro Lys Lys
            35                  40                  45

Ala Thr Glu Leu Lys His Leu Gln Cys Leu Glu Glu Glu Leu Lys Pro
        50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr Gly Ser Gly Gly Ser Gly Gly Ser Gly Gly Ser Gly
130                 135                 140

Glu Val Gln Leu Val Glu Ser Gly Gly Gly Leu Val Gln Pro Gly Gly
145                 150                 155                 160

Ser Leu Arg Leu Ser Cys Ala Ala Ser Gly Ser Thr Trp Ser Ile Asn
                165                 170                 175

Thr Leu Ala Trp Tyr Arg Gln Ala Pro Gly Lys Gln Arg Asp Leu Val
            180                 185                 190

Ala Arg Ile Ser Ser Gly Gly Ser Thr Tyr Tyr Ala Asp Ser Val Lys
        195                 200                 205

Gly Arg Phe Thr Ile Ser Arg Asp Asn Ser Lys Asn Thr Leu Tyr Leu
        210                 215                 220

Gln Met Asn Ser Leu Arg Ala Glu Asp Thr Ala Val Tyr Tyr Cys Tyr
225                 230                 235                 240

Ala Gln Ser Thr Trp Tyr Pro Pro Ser Trp Gly Gln Gly Thr Leu Val
                245                 250                 255

Thr Val Ser Ser
            260

<210> SEQ ID NO 118
<211> LENGTH: 261
<212> TYPE: PRT
<213> ORGANISM: Homo sapiens
```

<400> SEQUENCE: 118

```
Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Gly Gly Gly
            20                  25                  30
Ser Gly Gly Leu Thr Asn Met Thr Thr Phe Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Ser Gln Ser Ile
        115                 120                 125
Ile Ser Thr Leu Thr Gly Ser Gly Ser Gly Gly Ser Gly Gly Ser
    130                 135                 140
Gly Glu Val Gln Leu Val Glu Ser Gly Gly Gly Leu Val Gln Pro Gly
145                 150                 155                 160
Gly Ser Leu Arg Leu Ser Cys Ala Ala Ser Gly Ser Thr Trp Ser Ile
                165                 170                 175
Asn Thr Leu Ala Trp Tyr Arg Gln Ala Pro Gly Lys Gln Arg Asp Leu
            180                 185                 190
Val Ala Arg Ile Ser Ser Gly Gly Ser Thr Tyr Tyr Ala Asp Ser Val
        195                 200                 205
Lys Gly Arg Phe Thr Ile Ser Arg Asp Asn Ser Lys Asn Thr Leu Tyr
    210                 215                 220
Leu Gln Met Asn Ser Leu Arg Ala Glu Asp Thr Ala Val Tyr Tyr Cys
225                 230                 235                 240
Tyr Ala Gln Ser Thr Trp Tyr Pro Pro Ser Trp Gly Gln Gly Thr Leu
                245                 250                 255
Val Thr Val Ser Ser
            260
```

<210> SEQ ID NO 119
<211> LENGTH: 133
<212> TYPE: PRT
<213> ORGANISM: Homo sapiens

<400> SEQUENCE: 119

```
Ala Pro Thr Ser Ser Ser Thr Lys Lys Thr Gln Leu Gln Leu Lys His
1               5                   10                  15
Leu Leu Leu Asp Leu Gln Met Ile Leu Asn Gly Ile Asn Asn Tyr Lys
            20                  25                  30
Asn Pro Lys Leu Thr Asn Met Thr Thr Phe Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
```

```
Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 120
<211> LENGTH: 133
<212> TYPE: PRT
<213> ORGANISM: Homo sapiens

<400> SEQUENCE: 120

Ala Pro Thr Ser Ser Thr Lys Lys Thr Gln Leu Gln Leu Gln His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 121
<211> LENGTH: 133
<212> TYPE: PRT
<213> ORGANISM: Homo sapiens

<400> SEQUENCE: 121

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Thr Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130
```

<210> SEQ ID NO 122
<211> LENGTH: 133
<212> TYPE: PRT
<213> ORGANISM: Homo sapiens

<400> SEQUENCE: 122

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Asn Met Thr Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Ala Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 123
<211> LENGTH: 133
<212> TYPE: PRT
<213> ORGANISM: Homo sapiens

<400> SEQUENCE: 123

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Asn Met Thr Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ala Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 124
<211> LENGTH: 133
<212> TYPE: PRT
<213> ORGANISM: Homo sapiens

<400> SEQUENCE: 124

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Lys Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 125
<211> LENGTH: 133
<212> TYPE: PRT
<213> ORGANISM: Homo sapiens

<400> SEQUENCE: 125

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Gln Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 126
<211> LENGTH: 133
<212> TYPE: PRT
<213> ORGANISM: Homo sapiens

<400> SEQUENCE: 126

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Phe Lys Phe Tyr Met Pro Lys
        35                  40                  45

```
Lys Ala Thr Glu Leu Lys His Leu Gln Cys Leu Glu Glu Leu Lys
         50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ala Ile
        115                 120                 125

Ile Ser Thr Leu Thr
        130
```

<210> SEQ ID NO 127
<211> LENGTH: 133
<212> TYPE: PRT
<213> ORGANISM: Homo sapiens

<400> SEQUENCE: 127

```
Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                 20                  25                  30

Asn Pro Lys Leu Thr Asn Met Thr Thr Phe Lys Phe Tyr Met Pro Lys
             35                  40                  45

Lys Ala Thr Glu Leu Lys His Leu Gln Cys Leu Glu Glu Glu Leu Lys
         50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ala Thr Leu Thr
        130
```

<210> SEQ ID NO 128
<211> LENGTH: 261
<212> TYPE: PRT
<213> ORGANISM: Homo sapiens

<400> SEQUENCE: 128

```
Ala Pro Thr Ser Ser Ser Thr Lys Lys Thr Gln Leu Gln Leu Lys His
 1               5                  10                  15

Leu Leu Leu Asp Leu Gln Met Ile Leu Asn Gly Ile Asn Asn Tyr Lys
                 20                  25                  30

Asn Pro Lys Leu Thr Asn Met Thr Thr Phe Lys Phe Tyr Met Pro Lys
             35                  40                  45

Lys Ala Thr Glu Leu Lys His Leu Gln Cys Leu Glu Glu Glu Leu Lys
         50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95
```

```
Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Gly Ser Gly Gly Ser Gly Gly Ser
    130                 135                 140

Gly Glu Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
        195                 200                 205

Lys Gly Arg Phe Thr Ile Ser Arg Asp Asn Ser Lys Asn Thr Leu Tyr
    210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 129
<211> LENGTH: 261
<212> TYPE: PRT
<213> ORGANISM: Homo sapiens

<400> SEQUENCE: 129

Ala Pro Thr Ser Ser Ser Thr Lys Lys Thr Gln Leu Gln Leu Gln His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Gly Ser Gly Gly Ser Gly Gly Ser
    130                 135                 140

Gly Glu Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
        195                 200                 205
```

Lys Gly Arg Phe Thr Ile Ser Arg Asp Asn Ser Lys Asn Thr Leu Tyr
            210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 130
<211> LENGTH: 261
<212> TYPE: PRT
<213> ORGANISM: Homo sapiens

<400> SEQUENCE: 130

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Asn Met Thr Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Thr Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Gly Ser Gly Gly Ser Gly Gly Ser
130                 135                 140

Gly Glu Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
        195                 200                 205

Lys Gly Arg Phe Thr Ile Ser Arg Asp Asn Ser Lys Asn Thr Leu Tyr
            210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 131
<211> LENGTH: 261
<212> TYPE: PRT
<213> ORGANISM: Homo sapiens

<400> SEQUENCE: 131

```
Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Ala Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Gly Ser Gly Gly Ser Gly Gly Ser
    130                 135                 140

Gly Glu Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
                195                 200                 205

Lys Gly Arg Phe Thr Ile Ser Arg Asp Asn Ser Lys Asn Thr Leu Tyr
            210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 132
<211> LENGTH: 261
<212> TYPE: PRT
<213> ORGANISM: Homo sapiens

<400> SEQUENCE: 132

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ala Val Leu Glu Leu
                85                  90                  95

Lys Gly Ser Glu Thr Thr Phe Met Cys Glu Tyr Ala Asp Glu Thr Ala
```

```
            100                 105                 110
Thr Ile Val Glu Phe Leu Asn Arg Trp Ile Thr Phe Ser Gln Ser Ile
            115                 120                 125
Ile Ser Thr Leu Thr Gly Ser Gly Gly Ser Gly Gly Ser Gly Gly Ser
            130                 135                 140
Gly Glu Val Gln Leu Val Glu Ser Gly Gly Gly Leu Val Gln Pro Gly
145                 150                 155                 160
Gly Ser Leu Arg Leu Ser Cys Ala Ala Ser Gly Ser Thr Trp Ser Ile
                165                 170                 175
Asn Thr Leu Ala Trp Tyr Arg Gln Ala Pro Gly Lys Gln Arg Asp Leu
                180                 185                 190
Val Ala Arg Ile Ser Ser Gly Gly Ser Thr Tyr Tyr Ala Asp Ser Val
                195                 200                 205
Lys Gly Arg Phe Thr Ile Ser Arg Asp Asn Ser Lys Asn Thr Leu Tyr
                210                 215                 220
Leu Gln Met Asn Ser Leu Arg Ala Glu Asp Thr Ala Val Tyr Tyr Cys
225                 230                 235                 240
Tyr Ala Gln Ser Thr Trp Tyr Pro Pro Ser Trp Gly Gln Gly Thr Leu
                245                 250                 255
Val Thr Val Ser Ser
                260

<210> SEQ ID NO 133
<211> LENGTH: 261
<212> TYPE: PRT
<213> ORGANISM: Homo sapiens

<400> SEQUENCE: 133

Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
                20                  25                  30
Asn Pro Lys Leu Thr Asn Met Thr Thr Phe Lys Phe Tyr Met Pro Lys
                35                  40                  45
Lys Ala Thr Glu Leu Lys His Leu Gln Cys Leu Glu Glu Glu Leu Lys
            50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Lys Leu
                85                  90                  95
Lys Gly Ser Glu Thr Thr Phe Met Cys Glu Tyr Ala Asp Glu Thr Ala
                100                 105                 110
Thr Ile Val Glu Phe Leu Asn Arg Trp Ile Thr Phe Ser Gln Ser Ile
                115                 120                 125
Ile Ser Thr Leu Thr Gly Ser Gly Gly Ser Gly Gly Ser Gly Gly Ser
            130                 135                 140
Gly Glu Val Gln Leu Val Glu Ser Gly Gly Gly Leu Val Gln Pro Gly
145                 150                 155                 160
Gly Ser Leu Arg Leu Ser Cys Ala Ala Ser Gly Ser Thr Trp Ser Ile
                165                 170                 175
Asn Thr Leu Ala Trp Tyr Arg Gln Ala Pro Gly Lys Gln Arg Asp Leu
                180                 185                 190
Val Ala Arg Ile Ser Ser Gly Gly Ser Thr Tyr Tyr Ala Asp Ser Val
                195                 200                 205
```

Lys Gly Arg Phe Thr Ile Ser Arg Asp Asn Ser Lys Asn Thr Leu Tyr
    210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 134
<211> LENGTH: 261
<212> TYPE: PRT
<213> ORGANISM: Homo sapiens

<400> SEQUENCE: 134

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Gln Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Gly Ser Gly Gly Ser Gly Gly Ser
    130                 135                 140

Gly Glu Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
        195                 200                 205

Lys Gly Arg Phe Thr Ile Ser Arg Asp Asn Ser Lys Asn Thr Leu Tyr
    210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 135
<211> LENGTH: 261
<212> TYPE: PRT
<213> ORGANISM: Homo sapiens

<400> SEQUENCE: 135

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ala Ile
            115                 120                 125

Ile Ser Thr Leu Thr Gly Ser Gly Gly Ser Gly Gly Ser
            130                 135                 140

Gly Glu Val Gln Leu Val Glu Ser Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
                195                 200                 205

Lys Gly Arg Phe Thr Ile Ser Arg Asp Asn Ser Lys Asn Thr Leu Tyr
210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
            245                 250                 255

Val Thr Val Ser Ser
            260

<210> SEQ ID NO 136
<211> LENGTH: 261
<212> TYPE: PRT
<213> ORGANISM: Homo sapiens

<400> SEQUENCE: 136

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110
```

```
Thr Ile Val Glu Phe Leu Asn Arg Trp Ile Thr Phe Ser Gln Ser Ile
            115                 120                 125

Ile Ala Thr Leu Thr Gly Ser Gly Gly Ser Gly Gly Ser
            130                 135                 140

Gly Glu Val Gln Leu Val Glu Ser Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
            195                 200                 205

Lys Gly Arg Phe Thr Ile Ser Arg Asp Asn Ser Lys Asn Thr Leu Tyr
            210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 137
<211> LENGTH: 133
<212> TYPE: PRT
<213> ORGANISM: Homo sapiens

<400> SEQUENCE: 137

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
            20                  25                  30

Asn Pro Lys Leu Thr Ala Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
            130

<210> SEQ ID NO 138
<211> LENGTH: 133
<212> TYPE: PRT
<213> ORGANISM: Homo sapiens

<400> SEQUENCE: 138

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
            20                  25                  30
```

-continued

```
Asn Pro Lys Leu Thr Arg Met Leu Thr Ala Lys Phe Tyr Met Pro Lys
         35                  40                  45

Lys Ala Thr Glu Leu Lys His Leu Gln Cys Leu Glu Glu Glu Leu Lys
     50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130
```

<210> SEQ ID NO 139
<211> LENGTH: 133
<212> TYPE: PRT
<213> ORGANISM: Homo sapiens

<400> SEQUENCE: 139

```
Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Glu
             20                  25                  30

Asn Pro Lys Leu Thr Ala Met Leu Thr Ala Lys Phe Tyr Met Pro Lys
         35                  40                  45

Lys Ala Thr Glu Leu Lys His Leu Gln Cys Leu Glu Glu Glu Leu Lys
     50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130
```

<210> SEQ ID NO 140
<211> LENGTH: 133
<212> TYPE: PRT
<213> ORGANISM: Homo sapiens

<400> SEQUENCE: 140

```
Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Glu
             20                  25                  30

Asn Pro Lys Leu Thr Glu Met Leu Thr Ala Lys Phe Tyr Met Pro Lys
         35                  40                  45

Lys Ala Thr Glu Leu Lys His Leu Gln Cys Leu Glu Glu Glu Leu Lys
     50                  55                  60

Pro Leu Glu Glu Val Leu Asn Leu Ala Gln Ser Lys Asn Phe His Leu
 65                  70                  75                  80
```

```
Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 141
<211> LENGTH: 133
<212> TYPE: PRT
<213> ORGANISM: Homo sapiens

<400> SEQUENCE: 141

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
            20                  25                  30

Asn Pro Lys Leu Thr Gly Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 142
<211> LENGTH: 133
<212> TYPE: PRT
<213> ORGANISM: Homo sapiens

<400> SEQUENCE: 142

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
            20                  25                  30

Asn Pro Lys Leu Thr Ala Met Leu Thr Gly Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125
```

Ile Ser Thr Leu Thr
    130

<210> SEQ ID NO 143
<211> LENGTH: 133
<212> TYPE: PRT
<213> ORGANISM: Homo sapiens

<400> SEQUENCE: 143

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
            20                  25                  30

Asn Pro Lys Leu Thr Glu Met Leu Thr Gly Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
    130

<210> SEQ ID NO 144
<211> LENGTH: 133
<212> TYPE: PRT
<213> ORGANISM: Homo sapiens

<400> SEQUENCE: 144

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
            20                  25                  30

Asn Pro Lys Leu Thr Gly Met Leu Thr Gly Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
    130

<210> SEQ ID NO 145
<211> LENGTH: 133
<212> TYPE: PRT
<213> ORGANISM: Homo sapiens

<400> SEQUENCE: 145

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
                20                  25                  30

Asn Pro Lys Leu Thr Ala Met Leu Thr Lys Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 146
<211> LENGTH: 133
<212> TYPE: PRT
<213> ORGANISM: Homo sapiens

<400> SEQUENCE: 146

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
                20                  25                  30

Asn Pro Lys Leu Thr Glu Met Leu Thr Lys Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 147
<211> LENGTH: 133
<212> TYPE: PRT
<213> ORGANISM: Homo sapiens

<400> SEQUENCE: 147

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
                20                  25                  30

```
Asn Pro Lys Leu Thr Gly Met Leu Thr Lys Lys Phe Tyr Met Pro Lys
            35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
            130

<210> SEQ ID NO 148
<211> LENGTH: 261
<212> TYPE: PRT
<213> ORGANISM: Homo sapiens

<400> SEQUENCE: 148

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Glu
                 20                  25                  30

Asn Pro Lys Leu Thr Ala Met Leu Thr Phe Lys Phe Tyr Met Pro Lys
            35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr Gly Ser Gly Gly Ser Gly Gly Ser
            130                 135                 140

Gly Glu Val Gln Leu Val Glu Ser Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
                195                 200                 205

Lys Gly Arg Phe Thr Ile Ser Arg Asp Asn Ser Lys Asn Thr Leu Tyr
            210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260
```

```
<210> SEQ ID NO 149
<211> LENGTH: 261
<212> TYPE: PRT
<213> ORGANISM: Homo sapiens

<400> SEQUENCE: 149

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Gly Ser Gly Gly Ser
    130                 135                 140

Gly Glu Val Gln Leu Val Glu Ser Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
        195                 200                 205

Lys Gly Arg Phe Thr Ile Ser Arg Asp Asn Ser Lys Asn Thr Leu Tyr
    210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 150
<211> LENGTH: 261
<212> TYPE: PRT
<213> ORGANISM: Homo sapiens

<400> SEQUENCE: 150

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
            20                  25                  30

Asn Pro Lys Leu Thr Ala Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60
```

```
Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Ser Gly Gly Ser Gly Gly Ser
    130                 135                 140

Gly Glu Val Gln Leu Val Glu Ser Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
        195                 200                 205

Lys Gly Arg Phe Thr Ile Ser Arg Asp Asn Ser Lys Asn Thr Leu Tyr
210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
                260

<210> SEQ ID NO 151
<211> LENGTH: 261
<212> TYPE: PRT
<213> ORGANISM: Homo sapiens

<400> SEQUENCE: 151

Ala Pro Thr Ser Ser Ser Thr Lys Lys Thr Gln Leu Gln Leu Glu His
  1               5                  10                  15

Leu Leu Leu Asp Leu Gln Met Ile Leu Asn Gly Ile Asn Asn Tyr Glu
                 20                  25                  30

Asn Pro Lys Leu Thr Glu Met Leu Thr Ala Lys Phe Tyr Met Pro Lys
                 35                  40                  45

Lys Ala Thr Glu Leu Lys His Leu Gln Cys Leu Glu Glu Glu Leu Lys
     50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Ser Gly Gly Ser Gly Gly Ser
    130                 135                 140

Gly Glu Val Gln Leu Val Glu Ser Gly Gly Leu Val Gln Pro Gly
145                 150                 155                 160

Gly Ser Leu Arg Leu Ser Cys Ala Ala Ser Gly Ser Thr Trp Ser Ile
```

| | | 165 | | | | 170 | | | | 175 | |
|---|---|---|---|---|---|---|---|---|---|---|---|

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
            195                 200                 205

Lys Gly Arg Phe Thr Ile Ser Arg Asp Asn Ser Lys Asn Thr Leu Tyr
            210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
            245                 250                 255

Val Thr Val Ser Ser
            260

<210> SEQ ID NO 152
<211> LENGTH: 261
<212> TYPE: PRT
<213> ORGANISM: Homo sapiens

<400> SEQUENCE: 152

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
            20                  25                  30

Asn Pro Lys Leu Thr Gly Met Leu Thr Ala Lys Phe Tyr Met Pro Lys
            35                  40                  45

Lys Ala Thr Glu Leu Lys His Leu Gln Cys Leu Glu Glu Leu Lys
            50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr Gly Ser Gly Gly Ser Gly Gly Ser Gly Gly Ser
130                 135                 140

Gly Glu Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
            165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
            195                 200                 205

Lys Gly Arg Phe Thr Ile Ser Arg Asp Asn Ser Lys Asn Thr Leu Tyr
            210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
            245                 250                 255

Val Thr Val Ser Ser
            260

<210> SEQ ID NO 153
<211> LENGTH: 261
<212> TYPE: PRT
<213> ORGANISM: Homo sapiens

<400> SEQUENCE: 153

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
                20                  25                  30

Asn Pro Lys Leu Thr Ala Met Leu Thr Gly Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Gly Ser Gly Gly Ser Gly Gly Ser
    130                 135                 140

Gly Glu Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
        195                 200                 205

Lys Gly Arg Phe Thr Ile Ser Arg Asp Asn Ser Lys Asn Thr Leu Tyr
    210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 154
<211> LENGTH: 261
<212> TYPE: PRT
<213> ORGANISM: Homo sapiens

<400> SEQUENCE: 154

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
                20                  25                  30

Asn Pro Lys Leu Thr Glu Met Leu Thr Gly Lys Phe Tyr Met Pro Lys
            35                  40                  45

Lys Ala Thr Glu Leu Lys His Leu Gln Cys Leu Glu Glu Glu Leu Lys
        50                  55                  60

```
Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Gly Ser Gly Gly Ser Gly Gly Ser
    130                 135                 140

Gly Glu Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
        195                 200                 205

Lys Gly Arg Phe Thr Ile Ser Arg Asp Asn Ser Lys Asn Thr Leu Tyr
    210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 155
<211> LENGTH: 261
<212> TYPE: PRT
<213> ORGANISM: Homo sapiens

<400> SEQUENCE: 155

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Glu
                 20                  25                  30

Asn Pro Lys Leu Thr Gly Met Leu Thr Gly Lys Phe Tyr Met Pro Lys
             35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Gly Ser Gly Gly Ser Gly Gly Ser
    130                 135                 140

Gly Glu Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
                165                 170                 175
```

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
        195                 200                 205

Lys Gly Arg Phe Thr Ile Ser Arg Asp Asn Ser Lys Asn Thr Leu Tyr
    210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 156
<211> LENGTH: 261
<212> TYPE: PRT
<213> ORGANISM: Homo sapiens

<400> SEQUENCE: 156

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
                20                  25                  30

Asn Pro Lys Leu Thr Ala Met Leu Thr Lys Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Gly Ser Gly Gly Ser Gly Gly Ser
    130                 135                 140

Gly Glu Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
        195                 200                 205

Lys Gly Arg Phe Thr Ile Ser Arg Asp Asn Ser Lys Asn Thr Leu Tyr
    210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 157
<211> LENGTH: 261
<212> TYPE: PRT
<213> ORGANISM: Homo sapiens

<400> SEQUENCE: 157

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
            20                  25                  30

Asn Pro Lys Leu Thr Glu Met Leu Thr Lys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Gly Ser Gly Gly Ser Gly Gly Ser
    130                 135                 140

Gly Glu Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
        195                 200                 205

Lys Gly Arg Phe Thr Ile Ser Arg Asp Asn Ser Lys Asn Thr Leu Tyr
    210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 158
<211> LENGTH: 261
<212> TYPE: PRT
<213> ORGANISM: Homo sapiens

<400> SEQUENCE: 158

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
            20                  25                  30

Asn Pro Lys Leu Thr Gly Met Leu Thr Lys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu

```
                65                  70                  75                  80
Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Gly Ser Gly Gly Ser Gly Gly Ser
    130                 135                 140

Gly Glu Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
        195                 200                 205

Lys Gly Arg Phe Thr Ile Ser Arg Asp Asn Ser Lys Asn Thr Leu Tyr
    210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 159
<211> LENGTH: 133
<212> TYPE: PRT
<213> ORGANISM: Homo sapiens

<400> SEQUENCE: 159

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
            20                  25                  30

Asn Pro Cys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Cys Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 160
<211> LENGTH: 133
<212> TYPE: PRT
<213> ORGANISM: Homo sapiens
```

<400> SEQUENCE: 160

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
            20                  25                  30

Asn Pro Lys Leu Thr Cys Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Cys Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 161
<211> LENGTH: 133
<212> TYPE: PRT
<213> ORGANISM: Homo sapiens

<400> SEQUENCE: 161

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
            20                  25                  30

Asn Pro Lys Leu Thr Arg Met Leu Thr Cys Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Cys Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 162
<211> LENGTH: 133
<212> TYPE: PRT
<213> ORGANISM: Homo sapiens

<400> SEQUENCE: 162

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
            20                  25                  30

Asn Pro Lys Leu Thr Arg Met Leu Thr Phe Lys Phe Cys Met Pro Lys

```
            35                  40                  45
Lys Ala Thr Glu Leu Lys His Leu Gln Cys Leu Glu Glu Cys Leu Lys
 50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
                100                 105                 110
Thr Ile Val Glu Phe Leu Asn Arg Trp Ile Thr Phe Ser Gln Ser Ile
                115                 120                 125
Ile Ser Thr Leu Thr
            130

<210> SEQ ID NO 163
<211> LENGTH: 133
<212> TYPE: PRT
<213> ORGANISM: Homo sapiens

<400> SEQUENCE: 163

Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Glu
                20                  25                  30
Asn Pro Lys Leu Thr Arg Met Leu Thr Cys Lys Phe Tyr Met Pro Lys
            35                  40                  45
Lys Ala Thr Glu Leu Lys His Leu Gln Cys Leu Glu Glu Leu Lys
 50                  55                  60
Pro Leu Glu Glu Val Leu Asn Cys Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
                100                 105                 110
Thr Ile Val Glu Phe Leu Asn Arg Trp Ile Thr Phe Ser Gln Ser Ile
                115                 120                 125
Ile Ser Thr Leu Thr
            130

<210> SEQ ID NO 164
<211> LENGTH: 133
<212> TYPE: PRT
<213> ORGANISM: Homo sapiens

<400> SEQUENCE: 164

Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
                20                  25                  30
Asn Pro Lys Leu Thr Arg Met Leu Thr Cys Lys Phe Tyr Met Pro Lys
            35                  40                  45
Lys Ala Thr Glu Leu Lys His Leu Gln Cys Leu Glu Glu Leu Lys
 50                  55                  60
Pro Leu Glu Glu Cys Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
```

```
                    85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 165
<211> LENGTH: 133
<212> TYPE: PRT
<213> ORGANISM: Homo sapiens

<400> SEQUENCE: 165

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Cys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Cys Leu Asn Leu Ala Gln Ser Glu Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 166
<211> LENGTH: 19
<212> TYPE: PRT
<213> ORGANISM: Homo sapiens

<400> SEQUENCE: 166

Asn Asn Tyr Glu Asn Pro Lys Leu Thr Asp Ala Thr Leu Tyr Met Pro
1               5                   10                  15

Lys Lys Ala

<210> SEQ ID NO 167
<211> LENGTH: 18
<212> TYPE: PRT
<213> ORGANISM: Homo sapiens

<400> SEQUENCE: 167

Gln Ser Met Glu Ile Asp Ala Thr Thr Phe Lys Phe Tyr Met Pro Lys
1               5                   10                  15

Lys Ala

<210> SEQ ID NO 168
<211> LENGTH: 16
<212> TYPE: PRT
<213> ORGANISM: Homo sapiens

<400> SEQUENCE: 168
```

Gln Ser Met Glu Ile Asp Ala Thr Lys Phe Tyr Met Pro Lys Lys Ala
1               5                   10                  15

<210> SEQ ID NO 169
<211> LENGTH: 16
<212> TYPE: PRT
<213> ORGANISM: Homo sapiens

<400> SEQUENCE: 169

Gln Ser Met Glu Ile Asp Ala Thr Leu Phe Tyr Met Pro Lys Lys Ala
1               5                   10                  15

<210> SEQ ID NO 170
<211> LENGTH: 15
<212> TYPE: PRT
<213> ORGANISM: Homo sapiens

<400> SEQUENCE: 170

Gln Ser Met Glu Ile Asp Ala Thr Leu Tyr Thr Glu Ser Asp Val
1               5                   10                  15

<210> SEQ ID NO 171
<211> LENGTH: 22
<212> TYPE: PRT
<213> ORGANISM: Homo sapiens

<400> SEQUENCE: 171

Asn Asn Tyr Lys Asn Pro Lys Leu Thr Arg Met Leu Thr Phe Lys Phe
1               5                   10                  15

Tyr Met Pro Lys Lys Ala
            20

<210> SEQ ID NO 172
<211> LENGTH: 130
<212> TYPE: PRT
<213> ORGANISM: Homo sapiens

<400> SEQUENCE: 172

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
                20                  25                  30

Asn Pro Lys Leu Thr Asp Ala Thr Leu Tyr Met Pro Lys Lys Ala Thr
                35                  40                  45

Glu Leu Lys His Leu Gln Cys Leu Glu Glu Leu Lys Pro Leu Glu
    50                  55                  60

Glu Val Leu Asn Leu Ala Gln Ser Lys Asn Phe His Leu Arg Pro Arg
65                  70                  75                  80

Asp Leu Ile Ser Asn Ile Asn Val Ile Val Leu Glu Leu Lys Gly Ser
                85                  90                  95

Glu Thr Thr Phe Met Cys Glu Tyr Ala Asp Glu Thr Ala Thr Ile Val
                100                 105                 110

Glu Phe Leu Asn Arg Trp Ile Thr Phe Ser Gln Ser Ile Ile Ser Thr
                115                 120                 125

Leu Thr
    130

<210> SEQ ID NO 173
<211> LENGTH: 129
<212> TYPE: PRT

<213> ORGANISM: Homo sapiens

<400> SEQUENCE: 173

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Gln Ser Met Glu
            20                  25                  30

Ile Asp Ala Thr Thr Phe Lys Phe Tyr Met Pro Lys Lys Ala Thr Glu
        35                  40                  45

Leu Lys His Leu Gln Cys Leu Glu Glu Glu Leu Lys Pro Leu Glu Glu
    50                  55                  60

Val Leu Asn Leu Ala Gln Ser Lys Asn Phe His Leu Arg Pro Arg Asp
65                  70                  75                  80

Leu Ile Ser Asn Ile Asn Val Ile Val Leu Glu Leu Lys Gly Ser Glu
                85                  90                  95

Thr Thr Phe Met Cys Glu Tyr Ala Asp Glu Thr Ala Thr Ile Val Glu
            100                 105                 110

Phe Leu Asn Arg Trp Ile Thr Phe Ser Gln Ser Ile Ile Ser Thr Leu
        115                 120                 125

Thr

<210> SEQ ID NO 174
<211> LENGTH: 127
<212> TYPE: PRT
<213> ORGANISM: Homo sapiens

<400> SEQUENCE: 174

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Gln Ser Met Glu
            20                  25                  30

Ile Asp Ala Thr Lys Phe Tyr Met Pro Lys Lys Ala Thr Glu Leu Lys
        35                  40                  45

His Leu Gln Cys Leu Glu Glu Glu Leu Lys Pro Leu Glu Glu Val Leu
    50                  55                  60

Asn Leu Ala Gln Ser Lys Asn Phe His Leu Arg Pro Arg Asp Leu Ile
65                  70                  75                  80

Ser Asn Ile Asn Val Ile Val Leu Glu Leu Lys Gly Ser Glu Thr Thr
                85                  90                  95

Phe Met Cys Glu Tyr Ala Asp Glu Thr Ala Thr Ile Val Glu Phe Leu
            100                 105                 110

Asn Arg Trp Ile Thr Phe Ser Gln Ser Ile Ile Ser Thr Leu Thr
        115                 120                 125

<210> SEQ ID NO 175
<211> LENGTH: 127
<212> TYPE: PRT
<213> ORGANISM: Homo sapiens

<400> SEQUENCE: 175

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Gln Ser Met Glu
            20                  25                  30

Ile Asp Ala Thr Leu Phe Tyr Met Pro Lys Lys Ala Thr Glu Leu Lys
        35                  40                  45

His Leu Gln Cys Leu Glu Glu Leu Lys Pro Leu Glu Val Leu
 50                  55                  60

Asn Leu Ala Gln Ser Lys Asn Phe His Leu Arg Pro Arg Asp Leu Ile
 65                  70                  75                  80

Ser Asn Ile Asn Val Ile Val Leu Glu Leu Lys Gly Ser Glu Thr Thr
                 85                  90                  95

Phe Met Cys Glu Tyr Ala Asp Glu Thr Ala Thr Ile Val Glu Phe Leu
            100                 105                 110

Asn Arg Trp Ile Thr Phe Ser Gln Ser Ile Ile Ser Thr Leu Thr
        115                 120                 125

<210> SEQ ID NO 176
<211> LENGTH: 126
<212> TYPE: PRT
<213> ORGANISM: Homo sapiens

<400> SEQUENCE: 176

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Gln Ser Met Glu
            20                  25                  30

Ile Asp Ala Thr Leu Tyr Thr Glu Ser Asp Val Thr Glu Leu Lys His
        35                  40                  45

Leu Gln Cys Leu Glu Glu Leu Lys Pro Leu Glu Glu Val Leu Asn
 50                  55                  60

Leu Ala Gln Ser Lys Asn Phe His Leu Arg Pro Arg Asp Leu Ile Ser
 65                  70                  75                  80

Asn Ile Asn Val Ile Val Leu Glu Leu Lys Gly Ser Glu Thr Thr Phe
                 85                  90                  95

Met Cys Glu Tyr Ala Asp Glu Thr Ala Thr Ile Val Glu Phe Leu Asn
            100                 105                 110

Arg Trp Ile Thr Phe Ser Gln Ser Ile Ile Ser Thr Leu Thr
        115                 120                 125

<210> SEQ ID NO 177
<211> LENGTH: 261
<212> TYPE: PRT
<213> ORGANISM: Homo sapiens

<400> SEQUENCE: 177

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Glu
            20                  25                  30

Asn Pro Cys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
 50                  55                  60

Pro Leu Glu Glu Val Leu Asn Cys Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

```
Ile Ser Thr Leu Thr Gly Ser Gly Gly Ser Gly Gly Ser
130                 135                 140

Gly Glu Val Gln Leu Val Glu Ser Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
                180                 185                 190

Val Ala Arg Ile Ser Ser Gly Gly Ser Thr Tyr Tyr Ala Asp Ser Val
                195                 200                 205

Lys Gly Arg Phe Thr Ile Ser Arg Asp Asn Ser Lys Asn Thr Leu Tyr
                210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
                260

<210> SEQ ID NO 178
<211> LENGTH: 261
<212> TYPE: PRT
<213> ORGANISM: Homo sapiens

<400> SEQUENCE: 178

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
                20                  25                  30

Asn Pro Lys Leu Thr Cys Met Leu Thr Phe Lys Phe Tyr Met Pro Lys
                35                  40                  45

Lys Ala Thr Glu Leu Lys His Leu Gln Cys Leu Glu Glu Glu Leu Lys
                50                  55                  60

Pro Leu Glu Glu Val Leu Asn Cys Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
                115                 120                 125

Ile Ser Thr Leu Thr Gly Ser Gly Gly Ser Gly Gly Ser Gly Gly Ser
                130                 135                 140

Gly Glu Val Gln Leu Val Glu Ser Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
                180                 185                 190

Val Ala Arg Ile Ser Ser Gly Gly Ser Thr Tyr Tyr Ala Asp Ser Val
                195                 200                 205

Lys Gly Arg Phe Thr Ile Ser Arg Asp Asn Ser Lys Asn Thr Leu Tyr
                210                 215                 220

Leu Gln Met Asn Ser Leu Arg Ala Glu Asp Thr Ala Val Tyr Tyr Cys
225                 230                 235                 240
```

```
Tyr Ala Gln Ser Thr Trp Tyr Pro Pro Ser Trp Gly Gln Gly Thr Leu
                245                 250                 255
Val Thr Val Ser Ser
            260

<210> SEQ ID NO 179
<211> LENGTH: 261
<212> TYPE: PRT
<213> ORGANISM: Homo sapiens

<400> SEQUENCE: 179

Ala Pro Thr Ser Ser Thr Lys Thr Gln Leu Gln Leu Glu His
1               5                   10                  15

Leu Leu Leu Asp Leu Gln Met Ile Leu Asn Gly Ile Asn Asn Tyr Glu
            20                  25                  30

Asn Pro Lys Leu Thr Arg Met Leu Thr Cys Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Cys Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr Gly Ser Gly Gly Ser Gly Gly Ser Gly Gly Ser
    130                 135                 140

Gly Glu Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
            195                 200                 205

Lys Gly Arg Phe Thr Ile Ser Arg Asp Asn Ser Lys Asn Thr Leu Tyr
    210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 180
<211> LENGTH: 261
<212> TYPE: PRT
<213> ORGANISM: Homo sapiens

<400> SEQUENCE: 180

Ala Pro Thr Ser Ser Thr Lys Thr Gln Leu Gln Leu Glu His
1               5                   10                  15

Leu Leu Leu Asp Leu Gln Met Ile Leu Asn Gly Ile Asn Asn Tyr Glu
            20                  25                  30
```

```
Asn Pro Lys Leu Thr Arg Met Leu Thr Phe Lys Phe Cys Met Pro Lys
            35                  40                  45

Lys Ala Thr Glu Leu Lys His Leu Gln Cys Leu Glu Glu Cys Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Gly Ser Gly Gly Ser Gly Gly Ser
    130                 135                 140

Gly Glu Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
        195                 200                 205

Lys Gly Arg Phe Thr Ile Ser Arg Asp Asn Ser Lys Asn Thr Leu Tyr
    210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 181
<211> LENGTH: 261
<212> TYPE: PRT
<213> ORGANISM: Homo sapiens

<400> SEQUENCE: 181

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Glu
            20                  25                  30

Asn Pro Lys Leu Thr Arg Met Leu Thr Cys Lys Phe Tyr Met Pro Lys
            35                  40                  45

Lys Ala Thr Glu Leu Lys His Leu Gln Cys Leu Glu Glu Glu Leu Lys
 50                  55                  60

Pro Leu Glu Glu Val Leu Asn Cys Ala Gln Ser Lys Asn Phe His Leu
 65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Gly Ser Gly Gly Ser Gly Gly Ser
```

```
                130                 135                 140
Gly Glu Val Gln Leu Val Glu Ser Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
                180                 185                 190

Val Ala Arg Ile Ser Ser Gly Gly Ser Thr Tyr Tyr Ala Asp Ser Val
                195                 200                 205

Lys Gly Arg Phe Thr Ile Ser Arg Asp Asn Ser Lys Asn Thr Leu Tyr
                210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gly Gly Thr Leu
                245                 250                 255

Val Thr Val Ser Ser
                260

<210> SEQ ID NO 182
<211> LENGTH: 261
<212> TYPE: PRT
<213> ORGANISM: Homo sapiens

<400> SEQUENCE: 182

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Cys Lys Phe Tyr Met Pro Lys
                35                  40                  45

Lys Ala Thr Glu Leu Lys His Leu Gln Cys Leu Glu Glu Glu Leu Lys
                50                  55                  60

Pro Leu Glu Glu Cys Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
                115                 120                 125

Ile Ser Thr Leu Thr Gly Ser Gly Gly Ser Gly Gly Ser Gly Gly Ser
                130                 135                 140

Gly Glu Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
                180                 185                 190

Val Ala Arg Ile Ser Ser Gly Gly Ser Thr Tyr Tyr Ala Asp Ser Val
                195                 200                 205

Lys Gly Arg Phe Thr Ile Ser Arg Asp Asn Ser Lys Asn Thr Leu Tyr
                210                 215                 220

Leu Gln Met Asn Ser Leu Arg Ala Glu Asp Thr Ala Val Tyr Tyr Cys
225                 230                 235                 240
```

```
Tyr Ala Gln Ser Thr Trp Tyr Pro Pro Ser Trp Gly Gln Gly Thr Leu
                245                 250                 255

Val Thr Val Ser Ser
            260

<210> SEQ ID NO 183
<211> LENGTH: 261
<212> TYPE: PRT
<213> ORGANISM: Homo sapiens

<400> SEQUENCE: 183

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Cys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Cys Leu Asn Leu Ala Gln Ser Glu Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Ser Gly Gly Ser Gly Gly Ser
    130                 135                 140

Gly Glu Val Gln Leu Val Glu Ser Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
        195                 200                 205

Lys Gly Arg Phe Thr Ile Ser Arg Asp Asn Ser Lys Asn Thr Leu Tyr
    210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 184
<211> LENGTH: 258
<212> TYPE: PRT
<213> ORGANISM: Homo sapiens

<400> SEQUENCE: 184

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
            20                  25                  30
```

Asn Pro Lys Leu Thr Asp Ala Thr Leu Tyr Met Pro Lys Lys Ala Thr
            35                  40                  45

Glu Leu Lys His Leu Gln Cys Leu Glu Glu Leu Lys Pro Leu Glu
 50                  55                  60

Glu Val Leu Asn Leu Ala Gln Ser Lys Asn Phe His Leu Arg Pro Arg
 65                  70                  75                  80

Asp Leu Ile Ser Asn Ile Asn Val Ile Val Leu Glu Leu Lys Gly Ser
                85                  90                  95

Glu Thr Thr Phe Met Cys Glu Tyr Ala Asp Glu Thr Ala Thr Ile Val
                100                 105                 110

Glu Phe Leu Asn Arg Trp Ile Thr Phe Ser Gln Ser Ile Ile Ser Thr
                115                 120                 125

Leu Thr Gly Ser Gly Gly Ser Gly Gly Ser Gly Gly Ser Gly Glu Val
    130                 135                 140

Gln Leu Val Glu Ser Gly Gly Gly Leu Val Gln Pro Gly Gly Ser Leu
145                 150                 155                 160

Arg Leu Ser Cys Ala Ala Ser Gly Ser Thr Trp Ser Ile Asn Thr Leu
                165                 170                 175

Ala Trp Tyr Arg Gln Ala Pro Gly Lys Gln Arg Asp Leu Val Ala Arg
                180                 185                 190

Ile Ser Ser Gly Gly Ser Thr Tyr Tyr Ala Asp Ser Val Lys Gly Arg
                195                 200                 205

Phe Thr Ile Ser Arg Asp Asn Ser Lys Asn Thr Leu Tyr Leu Gln Met
                210                 215                 220

Asn Ser Leu Arg Ala Glu Asp Thr Ala Val Tyr Tyr Cys Tyr Ala Gln
225                 230                 235                 240

Ser Thr Trp Tyr Pro Pro Ser Trp Gly Gln Gly Thr Leu Val Thr Val
                245                 250                 255

Ser Ser

<210> SEQ ID NO 185
<211> LENGTH: 257
<212> TYPE: PRT
<213> ORGANISM: Homo sapiens

<400> SEQUENCE: 185

Ala Pro Thr Ser Ser Ser Thr Lys Lys Thr Gln Leu Gln Leu Glu His
 1                   5                  10                  15

Leu Leu Leu Asp Leu Gln Met Ile Leu Asn Gly Ile Gln Ser Met Glu
                20                  25                  30

Ile Asp Ala Thr Thr Phe Lys Phe Tyr Met Pro Lys Lys Ala Thr Glu
                35                  40                  45

Leu Lys His Leu Gln Cys Leu Glu Glu Glu Leu Lys Pro Leu Glu Glu
 50                  55                  60

Val Leu Asn Leu Ala Gln Ser Lys Asn Phe His Leu Arg Pro Arg Asp
 65                  70                  75                  80

Leu Ile Ser Asn Ile Asn Val Ile Val Leu Glu Leu Lys Gly Ser Glu
                85                  90                  95

Thr Thr Phe Met Cys Glu Tyr Ala Asp Glu Thr Ala Thr Ile Val Glu
                100                 105                 110

Phe Leu Asn Arg Trp Ile Thr Phe Ser Gln Ser Ile Ile Ser Thr Leu
                115                 120                 125

Thr Gly Ser Gly Gly Ser Gly Gly Ser Gly Gly Ser Gly Glu Val Gln
    130                 135                 140

```
Leu Val Glu Ser Gly Gly Gly Leu Val Gln Pro Gly Gly Ser Leu Arg
145                 150                 155                 160

Leu Ser Cys Ala Ala Ser Gly Ser Thr Trp Ser Ile Asn Thr Leu Ala
                165                 170                 175

Trp Tyr Arg Gln Ala Pro Gly Lys Gln Arg Asp Leu Val Ala Arg Ile
            180                 185                 190

Ser Ser Gly Gly Ser Thr Tyr Tyr Ala Asp Ser Val Lys Gly Arg Phe
        195                 200                 205

Thr Ile Ser Arg Asp Asn Ser Lys Asn Thr Leu Tyr Leu Gln Met Asn
    210                 215                 220

Ser Leu Arg Ala Glu Asp Thr Ala Val Tyr Tyr Cys Tyr Ala Gln Ser
225                 230                 235                 240

Thr Trp Tyr Pro Pro Ser Trp Gly Gln Gly Thr Leu Val Thr Val Ser
                245                 250                 255

Ser

<210> SEQ ID NO 186
<211> LENGTH: 255
<212> TYPE: PRT
<213> ORGANISM: Homo sapiens

<400> SEQUENCE: 186

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Gln Ser Met Glu
                20                  25                  30

Ile Asp Ala Thr Lys Phe Tyr Met Pro Lys Lys Ala Thr Glu Leu Lys
            35                  40                  45

His Leu Gln Cys Leu Glu Glu Glu Leu Lys Pro Leu Glu Glu Val Leu
        50                  55                  60

Asn Leu Ala Gln Ser Lys Asn Phe His Leu Arg Pro Arg Asp Leu Ile
65                  70                  75                  80

Ser Asn Ile Asn Val Ile Val Leu Glu Leu Lys Gly Ser Glu Thr Thr
                85                  90                  95

Phe Met Cys Glu Tyr Ala Asp Glu Thr Ala Thr Ile Val Glu Phe Leu
            100                 105                 110

Asn Arg Trp Ile Thr Phe Ser Gln Ser Ile Ile Ser Thr Leu Thr Gly
        115                 120                 125

Ser Gly Ser Gly Gly Ser Gly Gly Ser Gly Glu Val Gln Leu Val
    130                 135                 140

Glu Ser Gly Gly Gly Leu Val Gln Pro Gly Gly Ser Leu Arg Leu Ser
145                 150                 155                 160

Cys Ala Ala Ser Gly Ser Thr Trp Ser Ile Asn Thr Leu Ala Trp Tyr
                165                 170                 175

Arg Gln Ala Pro Gly Lys Gln Arg Asp Leu Val Ala Arg Ile Ser Ser
            180                 185                 190

Gly Gly Ser Thr Tyr Tyr Ala Asp Ser Val Lys Gly Arg Phe Thr Ile
        195                 200                 205

Ser Arg Asp Asn Ser Lys Asn Thr Leu Tyr Leu Gln Met Asn Ser Leu
    210                 215                 220

Arg Ala Glu Asp Thr Ala Val Tyr Tyr Cys Tyr Ala Gln Ser Thr Trp
225                 230                 235                 240

Tyr Pro Pro Ser Trp Gly Gln Gly Thr Leu Val Thr Val Ser Ser
                245                 250                 255
```

<210> SEQ ID NO 187
<211> LENGTH: 255
<212> TYPE: PRT
<213> ORGANISM: Homo sapiens

<400> SEQUENCE: 187

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Gln Ser Met Glu
                20                  25                  30

Ile Asp Ala Thr Leu Phe Tyr Met Pro Lys Lys Ala Thr Glu Leu Lys
                35                  40                  45

His Leu Gln Cys Leu Glu Glu Glu Leu Lys Pro Leu Glu Glu Val Leu
    50                  55                  60

Asn Leu Ala Gln Ser Lys Asn Phe His Leu Arg Pro Arg Asp Leu Ile
65                  70                  75                  80

Ser Asn Ile Asn Val Ile Val Leu Glu Leu Lys Gly Ser Glu Thr Thr
                85                  90                  95

Phe Met Cys Glu Tyr Ala Asp Glu Thr Ala Thr Ile Val Glu Phe Leu
                100                 105                 110

Asn Arg Trp Ile Thr Phe Ser Gln Ser Ile Ile Ser Thr Leu Thr Gly
            115                 120                 125

Ser Gly Gly Ser Gly Gly Ser Gly Gly Ser Glu Val Gln Leu Val
130                 135                 140

Glu Ser Gly Gly Gly Leu Val Gln Pro Gly Gly Ser Leu Arg Leu Ser
145                 150                 155                 160

Cys Ala Ala Ser Gly Ser Thr Trp Ser Ile Asn Thr Leu Ala Trp Tyr
                165                 170                 175

Arg Gln Ala Pro Gly Lys Gln Arg Asp Leu Val Ala Arg Ile Ser Ser
            180                 185                 190

Gly Gly Ser Thr Tyr Tyr Ala Asp Ser Val Lys Gly Arg Phe Thr Ile
        195                 200                 205

Ser Arg Asp Asn Ser Lys Asn Thr Leu Tyr Leu Gln Met Asn Ser Leu
    210                 215                 220

Arg Ala Glu Asp Thr Ala Val Tyr Tyr Cys Tyr Ala Gln Ser Thr Trp
225                 230                 235                 240

Tyr Pro Pro Ser Trp Gly Gln Gly Thr Leu Val Thr Val Ser Ser
                245                 250                 255

<210> SEQ ID NO 188
<211> LENGTH: 254
<212> TYPE: PRT
<213> ORGANISM: Homo sapiens

<400> SEQUENCE: 188

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Gln Ser Met Glu
                20                  25                  30

Ile Asp Ala Thr Leu Tyr Thr Glu Ser Asp Val Thr Glu Leu Lys His
                35                  40                  45

Leu Gln Cys Leu Glu Glu Glu Leu Lys Pro Leu Glu Glu Val Leu Asn
    50                  55                  60

Leu Ala Gln Ser Lys Asn Phe His Leu Arg Pro Arg Asp Leu Ile Ser
65                  70                  75                  80

-continued

```
Asn Ile Asn Val Ile Val Leu Glu Leu Lys Gly Ser Glu Thr Thr Phe
                85                  90                  95

Met Cys Glu Tyr Ala Asp Glu Thr Ala Thr Ile Val Glu Phe Leu Asn
            100                 105                 110

Arg Trp Ile Thr Phe Ser Gln Ser Ile Ile Ser Thr Leu Thr Gly Ser
            115                 120                 125

Gly Gly Ser Gly Gly Ser Gly Gly Ser Gly Glu Val Gln Leu Val Glu
        130                 135                 140

Ser Gly Gly Gly Leu Val Gln Pro Gly Gly Ser Leu Arg Leu Ser Cys
145                 150                 155                 160

Ala Ala Ser Gly Ser Thr Trp Ser Ile Asn Thr Leu Ala Trp Tyr Arg
                165                 170                 175

Gln Ala Pro Gly Lys Gln Arg Asp Leu Val Ala Arg Ile Ser Ser Gly
            180                 185                 190

Gly Ser Thr Tyr Tyr Ala Asp Ser Val Lys Gly Arg Phe Thr Ile Ser
            195                 200                 205

Arg Asp Asn Ser Lys Asn Thr Leu Tyr Leu Gln Met Asn Ser Leu Arg
        210                 215                 220

Ala Glu Asp Thr Ala Val Tyr Tyr Cys Tyr Ala Gln Ser Thr Trp Tyr
225                 230                 235                 240

Pro Pro Ser Trp Gly Gln Gly Thr Leu Val Thr Val Ser Ser
                245                 250

<210> SEQ ID NO 189
<211> LENGTH: 133
<212> TYPE: PRT
<213> ORGANISM: Homo sapiens

<400> SEQUENCE: 189

Ala Pro Ala Ser Ser Ser Thr Lys Lys Thr Gln Leu Glu Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 190
<211> LENGTH: 133
<212> TYPE: PRT
<213> ORGANISM: Homo sapiens

<400> SEQUENCE: 190

Ala Pro Ala Ser Ser Ser Thr Lys Lys Thr Gln Leu Gln Leu Val His
1               5                   10                  15
```

Leu Leu Leu Asp Leu Gln Met Ile Leu Asn Gly Ile Asn Asn Tyr Lys
            20                  25                  30

Asn Pro Lys Leu Thr Asn Met Thr Thr Ala Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
                115                 120                 125

Ile Ser Thr Leu Thr
            130

<210> SEQ ID NO 191
<211> LENGTH: 133
<212> TYPE: PRT
<213> ORGANISM: Homo sapiens

<400> SEQUENCE: 191

Ala Pro Ala Ser Ser Ser Thr Lys Lys Thr Gln Leu Gln Leu Glu Asn
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Ala Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
                115                 120                 125

Ile Ser Thr Leu Thr
            130

<210> SEQ ID NO 192
<211> LENGTH: 133
<212> TYPE: PRT
<213> ORGANISM: Homo sapiens

<400> SEQUENCE: 192

Ala Pro Ala Ser Ser Ser Thr Lys Lys Thr Gln Leu Gln Leu Glu His
1               5                   10                  15

Leu Leu Leu Asp Leu Gln Lys Ile Leu Asn Gly Ile Asn Asn Tyr Lys
            20                  25                  30

Asn Pro Lys Leu Thr Asn Met Thr Thr Ala Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 193
<211> LENGTH: 133
<212> TYPE: PRT
<213> ORGANISM: Homo sapiens

<400> SEQUENCE: 193

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Asn Met Thr Thr Ala Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Ile Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 194
<211> LENGTH: 133
<212> TYPE: PRT
<213> ORGANISM: Homo sapiens

<400> SEQUENCE: 194

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Asn Met Thr Thr Ala Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Asn Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 195
<211> LENGTH: 133
<212> TYPE: PRT
<213> ORGANISM: Homo sapiens

<400> SEQUENCE: 195

Ala Pro Thr Ser Ser Thr Lys Lys Thr Gln Leu Asn Leu Glu His
1               5                   10                  15

Leu Leu Leu Asp Leu Gln Met Ile Leu Asn Gly Ile Asn Asn Tyr Glu
            20                  25                  30

Asn Pro Lys Leu Thr Arg Met Leu Thr Cys Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Cys Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 196
<211> LENGTH: 133
<212> TYPE: PRT
<213> ORGANISM: Homo sapiens

<400> SEQUENCE: 196

Ala Pro Thr Ser Ser Thr Lys Lys Thr Gln Leu Gln Leu Glu His
1               5                   10                  15

Leu Leu Ser Asp Leu Gln Met Ile Leu Asn Gly Ile Asn Asn Tyr Glu
            20                  25                  30

Asn Pro Lys Leu Thr Arg Met Leu Thr Cys Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Cys Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 197
<211> LENGTH: 133

```
<212> TYPE: PRT
<213> ORGANISM: Homo sapiens

<400> SEQUENCE: 197

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
                20                  25                  30

Asn Pro Lys Leu Thr Arg Met Leu Thr Cys Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Cys Leu Asn Leu Ala Gln Ser Lys Asn Phe His Leu
65                  70                  75                  80

Arg Pro Arg Thr Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 198
<211> LENGTH: 133
<212> TYPE: PRT
<213> ORGANISM: Homo sapiens

<400> SEQUENCE: 198

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
                20                  25                  30

Asn Pro Lys Leu Thr Arg Met Leu Thr Cys Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Cys Leu Asn Leu Ala Gln Ser Lys Asn Phe His Leu
65                  70                  75                  80

Arg Pro Arg Asp Leu Ile Glu Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 199
<211> LENGTH: 133
<212> TYPE: PRT
<213> ORGANISM: Homo sapiens

<400> SEQUENCE: 199

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
```

```
            20                  25                  30
Asn Pro Lys Leu Thr Arg Met Leu Thr Cys Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Cys Leu Asn Leu Ala Gln Ser Lys Asn Phe His Leu
65                  70                  75                  80
Arg Pro Arg Asp Leu Ile Asp Asn Ile Asn Val Ile Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Ser Gln Ser Ile
        115                 120                 125
Ile Ser Thr Leu Thr
        130

<210> SEQ ID NO 200
<211> LENGTH: 133
<212> TYPE: PRT
<213> ORGANISM: Homo sapiens

<400> SEQUENCE: 200

Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Glu
            20                  25                  30
Asn Pro Lys Leu Thr Arg Met Leu Thr Cys Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Cys Leu Asn Leu Ala Gln Ser Lys Asn Phe His Leu
65                  70                  75                  80
Arg Pro Arg Asp Leu Ile Ser Asn Ile Asn Ile Leu Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Ser Gln Ser Ile
        115                 120                 125
Ile Ser Thr Leu Thr
        130

<210> SEQ ID NO 201
<211> LENGTH: 133
<212> TYPE: PRT
<213> ORGANISM: Homo sapiens

<400> SEQUENCE: 201

Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Glu
            20                  25                  30
Asn Pro Lys Leu Thr Arg Met Leu Thr Cys Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Cys Leu Asn Leu Ala Gln Ser Lys Asn Phe His Leu
```

```
                65                  70                  75                  80
Arg Pro Arg Asp Leu Ile Ser Asn Ile Asn Val Leu Val Leu Glu Leu
                    85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
                115                 120                 125

Ile Ser Thr Leu Thr
                130

<210> SEQ ID NO 202
<211> LENGTH: 133
<212> TYPE: PRT
<213> ORGANISM: Homo sapiens

<400> SEQUENCE: 202

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
                20                  25                  30

Asn Pro Lys Leu Thr Arg Met Leu Thr Cys Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Cys Leu Asn Leu Ala Gln Ser Lys Asn Phe His Leu
65                  70                  75                  80

Arg Pro Arg Asp Leu Ile Ser Asn Ile Asn Val Ile Val Leu Asn Leu
                    85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
                115                 120                 125

Ile Ser Thr Leu Thr
                130

<210> SEQ ID NO 203
<211> LENGTH: 133
<212> TYPE: PRT
<213> ORGANISM: Homo sapiens

<400> SEQUENCE: 203

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
                20                  25                  30

Asn Pro Lys Leu Thr Arg Met Leu Thr Cys Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Cys Leu Asn Leu Ala Gln Ser Lys Asn Phe His Leu
65                  70                  75                  80

Arg Pro Arg Asp Leu Ile Ser Asn Ile Asn Val Ile Val Leu Gln Leu
                    85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
```

-continued

```
            115                 120                 125
Ile Ser Thr Leu Thr
            130

<210> SEQ ID NO 204
<211> LENGTH: 261
<212> TYPE: PRT
<213> ORGANISM: Homo sapiens

<400> SEQUENCE: 204

Ala Pro Ala Ser Ser Ser Thr Lys Lys Thr Gln Leu Glu Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Gly Ser Gly Gly Ser Gly Gly Ser
    130                 135                 140

Gly Glu Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
        195                 200                 205

Lys Gly Arg Phe Thr Ile Ser Arg Asp Asn Ser Lys Asn Thr Leu Tyr
    210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 205
<211> LENGTH: 261
<212> TYPE: PRT
<213> ORGANISM: Homo sapiens

<400> SEQUENCE: 205

Ala Pro Ala Ser Ser Ser Thr Lys Lys Thr Gln Leu Gln Leu Val His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Ala Lys Phe Tyr Met Pro Lys
```

```
                35                  40                  45
Lys Ala Thr Glu Leu Lys His Leu Gln Cys Leu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr Gly Ser Gly Gly Ser Gly Gly Ser Gly Gly Ser
        130                 135                 140

Gly Glu Val Gln Leu Val Glu Ser Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
        195                 200                 205

Lys Gly Arg Phe Thr Ile Ser Arg Asp Asn Ser Lys Asn Thr Leu Tyr
    210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 206
<211> LENGTH: 261
<212> TYPE: PRT
<213> ORGANISM: Homo sapiens

<400> SEQUENCE: 206

Ala Pro Ala Ser Ser Ser Thr Lys Lys Thr Gln Leu Gln Leu Glu Asn
 1                   5                  10                  15

Leu Leu Leu Asp Leu Gln Met Ile Leu Asn Gly Ile Asn Asn Tyr Lys
                20                  25                  30

Asn Pro Lys Leu Thr Asn Met Thr Ala Lys Phe Tyr Met Pro Lys
             35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr Gly Ser Gly Gly Ser Gly Gly Ser Gly Gly Ser
        130                 135                 140
```

Gly Glu Val Gln Leu Val Glu Ser Gly Gly Leu Val Gln Pro Gly
145                 150                 155                 160

Gly Ser Leu Arg Leu Ser Cys Ala Ala Ser Gly Ser Thr Trp Ser Ile
            165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
            195                 200                 205

Lys Gly Arg Phe Thr Ile Ser Arg Asp Asn Ser Lys Asn Thr Leu Tyr
            210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
            245                 250                 255

Val Thr Val Ser Ser
            260

<210> SEQ ID NO 207
<211> LENGTH: 261
<212> TYPE: PRT
<213> ORGANISM: Homo sapiens

<400> SEQUENCE: 207

Ala Pro Ala Ser Ser Thr Lys Lys Thr Gln Leu Gln Leu Glu His
1               5                   10                  15

Leu Leu Leu Asp Leu Gln Lys Ile Leu Asn Gly Ile Asn Asn Tyr Lys
            20                  25                  30

Asn Pro Lys Leu Thr Asn Met Thr Thr Ala Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr Gly Ser Gly Gly Ser Gly Gly Ser Gly Gly Ser
130                 135                 140

Gly Glu Val Gln Leu Val Glu Ser Gly Gly Leu Val Gln Pro Gly
145                 150                 155                 160

Gly Ser Leu Arg Leu Ser Cys Ala Ala Ser Gly Ser Thr Trp Ser Ile
            165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
            195                 200                 205

Lys Gly Arg Phe Thr Ile Ser Arg Asp Asn Ser Lys Asn Thr Leu Tyr
            210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
            245                 250                 255

Val Thr Val Ser Ser
            260

<210> SEQ ID NO 208
<211> LENGTH: 261
<212> TYPE: PRT
<213> ORGANISM: Homo sapiens

<400> SEQUENCE: 208

Ala Pro Ala Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Asn Met Thr Thr Ala Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Gly Ser Gly Gly Ser Gly Gly Ser
    130                 135                 140

Gly Glu Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
        195                 200                 205

Lys Gly Arg Phe Thr Ile Ser Arg Asp Asn Ser Lys Asn Thr Leu Tyr
    210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 209
<211> LENGTH: 261
<212> TYPE: PRT
<213> ORGANISM: Homo sapiens

<400> SEQUENCE: 209

Ala Pro Ala Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Asn Met Thr Thr Ala Lys Phe Tyr Met Pro Lys
            35                  40                  45

```
Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Asn Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr Gly Ser Gly Gly Ser Gly Gly Ser Gly Gly Ser
        130                 135                 140

Gly Glu Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
        195                 200                 205

Lys Gly Arg Phe Thr Ile Ser Arg Asp Asn Ser Lys Asn Thr Leu Tyr
210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 210
<211> LENGTH: 261
<212> TYPE: PRT
<213> ORGANISM: Homo sapiens

<400> SEQUENCE: 210

Ala Pro Thr Ser Ser Ser Thr Lys Lys Thr Gln Leu Asn Leu Glu His
1               5                   10                  15

Leu Leu Leu Asp Leu Gln Met Ile Leu Asn Gly Ile Asn Asn Tyr Glu
            20                  25                  30

Asn Pro Lys Leu Thr Arg Met Leu Thr Cys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Cys Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr Gly Ser Gly Gly Ser Gly Gly Ser Gly Gly Ser
        130                 135                 140

Gly Glu Val Gln Leu Val Glu Ser Gly Gly Gly Leu Val Gln Pro Gly
```

```
                145                 150                 155                 160
Gly Ser Leu Arg Leu Ser Cys Ala Ala Ser Gly Ser Thr Trp Ser Ile
            165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
            195                 200                 205

Lys Gly Arg Phe Thr Ile Ser Arg Asp Asn Ser Lys Asn Thr Leu Tyr
            210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
            245                 250                 255

Val Thr Val Ser Ser
            260

<210> SEQ ID NO 211
<211> LENGTH: 261
<212> TYPE: PRT
<213> ORGANISM: Homo sapiens

<400> SEQUENCE: 211

Ala Pro Thr Ser Ser Thr Lys Lys Thr Gln Leu Gln Leu Glu His
1               5                   10                  15

Leu Leu Ser Asp Leu Gln Met Ile Leu Asn Gly Ile Asn Asn Tyr Glu
            20                  25                  30

Asn Pro Lys Leu Thr Arg Met Leu Thr Cys Lys Phe Tyr Met Pro Lys
            35                  40                  45

Lys Ala Thr Glu Leu Lys His Leu Gln Cys Leu Glu Glu Glu Leu Lys
            50                  55                  60

Pro Leu Glu Glu Cys Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr Gly Ser Gly Ser Gly Ser Gly Gly Ser
            130                 135                 140

Gly Glu Val Gln Leu Val Glu Ser Gly Gly Leu Val Gln Pro Gly
145                 150                 155                 160

Gly Ser Leu Arg Leu Ser Cys Ala Ala Ser Gly Ser Thr Trp Ser Ile
            165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
            195                 200                 205

Lys Gly Arg Phe Thr Ile Ser Arg Asp Asn Ser Lys Asn Thr Leu Tyr
            210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
            245                 250                 255
```

Val Thr Val Ser Ser
            260

<210> SEQ ID NO 212
<211> LENGTH: 261
<212> TYPE: PRT
<213> ORGANISM: Homo sapiens

<400> SEQUENCE: 212

Ala Pro Thr Ser Ser Thr Lys Lys Thr Gln Leu Gln Leu Glu His
1               5                   10                  15

Leu Leu Asp Leu Gln Met Ile Leu Asn Gly Ile Asn Asn Tyr Glu
            20                  25                  30

Asn Pro Lys Leu Thr Arg Met Leu Thr Cys Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Cys Leu Asn Leu Ala Gln Ser Lys Asn Phe His Leu
65                  70                  75                  80

Arg Pro Arg Thr Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr Gly Ser Gly Gly Ser Gly Gly Ser Gly Gly Ser
            130                 135                 140

Gly Glu Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
            195                 200                 205

Lys Gly Arg Phe Thr Ile Ser Arg Asp Asn Ser Lys Asn Thr Leu Tyr
            210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 213
<211> LENGTH: 261
<212> TYPE: PRT
<213> ORGANISM: Homo sapiens

<400> SEQUENCE: 213

Ala Pro Thr Ser Ser Thr Lys Lys Thr Gln Leu Gln Leu Glu His
1               5                   10                  15

Leu Leu Asp Leu Gln Met Ile Leu Asn Gly Ile Asn Asn Tyr Glu
            20                  25                  30

Asn Pro Lys Leu Thr Arg Met Leu Thr Cys Lys Phe Tyr Met Pro Lys
            35                  40                  45

```
Lys Ala Thr Glu Leu Lys His Leu Gln Cys Leu Glu Glu Leu Lys
        50                  55                  60

Pro Leu Glu Glu Cys Leu Asn Leu Ala Gln Ser Lys Asn Phe His Leu
 65                  70                  75                  80

Arg Pro Arg Asp Leu Ile Glu Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr Gly Ser Gly Gly Ser Gly Gly Ser Gly Gly Ser
        130                 135                 140

Gly Glu Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
            195                 200                 205

Lys Gly Arg Phe Thr Ile Ser Arg Asp Asn Ser Lys Asn Thr Leu Tyr
            210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 214
<211> LENGTH: 261
<212> TYPE: PRT
<213> ORGANISM: Homo sapiens

<400> SEQUENCE: 214

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Glu
                20                  25                  30

Asn Pro Lys Leu Thr Arg Met Leu Thr Cys Lys Phe Tyr Met Pro Lys
            35                  40                  45

Lys Ala Thr Glu Leu Lys His Leu Gln Cys Leu Glu Glu Leu Lys
        50                  55                  60

Pro Leu Glu Glu Cys Leu Asn Leu Ala Gln Ser Lys Asn Phe His Leu
 65                  70                  75                  80

Arg Pro Arg Asp Leu Ile Asp Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr Gly Ser Gly Gly Ser Gly Gly Ser Gly Gly Ser
        130                 135                 140

Gly Glu Val Gln Leu Val Glu Ser Gly Gly Gly Leu Val Gln Pro Gly
145                 150                 155                 160
```

```
Gly Ser Leu Arg Leu Ser Cys Ala Ala Ser Gly Ser Thr Trp Ser Ile
            165                 170                 175

Asn Thr Leu Ala Trp Tyr Arg Gln Ala Pro Gly Lys Gln Arg Asp Leu
        180                 185                 190

Val Ala Arg Ile Ser Ser Gly Gly Ser Thr Tyr Tyr Ala Asp Ser Val
            195                 200                 205

Lys Gly Arg Phe Thr Ile Ser Arg Asp Asn Ser Lys Asn Thr Leu Tyr
        210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
            245                 250                 255

Val Thr Val Ser Ser
            260

<210> SEQ ID NO 215
<211> LENGTH: 261
<212> TYPE: PRT
<213> ORGANISM: Homo sapiens

<400> SEQUENCE: 215

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
            20                  25                  30

Asn Pro Lys Leu Thr Arg Met Leu Thr Cys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Cys Leu Asn Leu Ala Gln Ser Lys Asn Phe His Leu
65                  70                  75                  80

Arg Pro Arg Asp Leu Ile Ser Asn Ile Asn Leu Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Gly Ser Gly Gly Ser Gly Gly Ser
        130                 135                 140

Gly Glu Val Gln Leu Val Glu Ser Gly Gly Leu Val Gln Pro Gly
145                 150                 155                 160

Gly Ser Leu Arg Leu Ser Cys Ala Ala Ser Gly Ser Thr Trp Ser Ile
            165                 170                 175

Asn Thr Leu Ala Trp Tyr Arg Gln Ala Pro Gly Lys Gln Arg Asp Leu
        180                 185                 190

Val Ala Arg Ile Ser Ser Gly Gly Ser Thr Tyr Tyr Ala Asp Ser Val
            195                 200                 205

Lys Gly Arg Phe Thr Ile Ser Arg Asp Asn Ser Lys Asn Thr Leu Tyr
        210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
            245                 250                 255

Val Thr Val Ser Ser
```

<210> SEQ ID NO 216
<211> LENGTH: 261
<212> TYPE: PRT
<213> ORGANISM: Homo sapiens

<400> SEQUENCE: 216

```
Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
            20                  25                  30

Asn Pro Lys Leu Thr Arg Met Leu Thr Cys Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Cys Leu Asn Leu Ala Gln Ser Lys Asn Phe His Leu
65                  70                  75                  80

Arg Pro Arg Asp Leu Ile Ser Asn Ile Asn Val Leu Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Gly Ser Gly Gly Ser Gly Gly Ser
    130                 135                 140

Gly Glu Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
        195                 200                 205

Lys Gly Arg Phe Thr Ile Ser Arg Asp Asn Ser Lys Asn Thr Leu Tyr
    210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260
```

<210> SEQ ID NO 217
<211> LENGTH: 261
<212> TYPE: PRT
<213> ORGANISM: Homo sapiens

<400> SEQUENCE: 217

```
Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Glu
            20                  25                  30

Asn Pro Lys Leu Thr Arg Met Leu Thr Cys Lys Phe Tyr Met Pro Lys
            35                  40                  45

Lys Ala Thr Glu Leu Lys His Leu Gln Cys Leu Glu Glu Glu Leu Lys
```

```
            50                  55                  60
Pro Leu Glu Glu Cys Leu Asn Leu Ala Gln Ser Lys Asn Phe His Leu
 65                  70                  75                  80

Arg Pro Arg Asp Leu Ile Ser Asn Ile Asn Val Ile Val Leu Asn Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Gly Ser Gly Gly Ser Gly Gly Ser
    130                 135                 140

Gly Glu Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
        195                 200                 205

Lys Gly Arg Phe Thr Ile Ser Arg Asp Asn Ser Lys Asn Thr Leu Tyr
    210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 218
<211> LENGTH: 261
<212> TYPE: PRT
<213> ORGANISM: Homo sapiens

<400> SEQUENCE: 218

Ala Pro Thr Ser Ser Ser Thr Lys Lys Thr Gln Leu Gln Leu Glu His
  1               5                  10                  15

Leu Leu Leu Asp Leu Gln Met Ile Leu Asn Gly Ile Asn Asn Tyr Glu
                 20                  25                  30

Asn Pro Lys Leu Thr Arg Met Leu Thr Cys Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Cys Leu Asn Leu Ala Gln Ser Lys Asn Phe His Leu
 65                  70                  75                  80

Arg Pro Arg Asp Leu Ile Ser Asn Ile Asn Val Ile Val Leu Gln Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Gly Ser Gly Gly Ser Gly Gly Ser
    130                 135                 140

Gly Glu Val Gln Leu Val Glu Ser Gly Gly Gly Leu Val Gln Pro Gly
145                 150                 155                 160
```

```
Gly Ser Leu Arg Leu Ser Cys Ala Ala Ser Gly Ser Thr Trp Ser Ile
            165                 170                 175

Asn Thr Leu Ala Trp Tyr Arg Gln Ala Pro Gly Lys Gln Arg Asp Leu
        180                 185                 190

Val Ala Arg Ile Ser Ser Gly Gly Ser Thr Tyr Tyr Ala Asp Ser Val
            195                 200                 205

Lys Gly Arg Phe Thr Ile Ser Arg Asp Asn Ser Lys Asn Thr Leu Tyr
        210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser
            260

<210> SEQ ID NO 219
<211> LENGTH: 19
<212> TYPE: PRT
<213> ORGANISM: Homo sapiens

<400> SEQUENCE: 219

Asn Asn Tyr His Asn Pro Lys Leu Thr Asp Ala Thr Leu Tyr Met Pro
1               5                   10                  15

Lys Lys Ala

<210> SEQ ID NO 220
<211> LENGTH: 18
<212> TYPE: PRT
<213> ORGANISM: Homo sapiens

<400> SEQUENCE: 220

Gln Ser Met His Ile Asp Ala Thr Thr Phe Lys Phe Tyr Met Pro Lys
1               5                   10                  15

Lys Ala

<210> SEQ ID NO 221
<211> LENGTH: 16
<212> TYPE: PRT
<213> ORGANISM: Homo sapiens

<400> SEQUENCE: 221

Gln Ser Met His Ile Asp Ala Thr Lys Phe Tyr Met Pro Lys Lys Ala
1               5                   10                  15

<210> SEQ ID NO 222
<211> LENGTH: 16
<212> TYPE: PRT
<213> ORGANISM: Homo sapiens

<400> SEQUENCE: 222

Gln Ser Met His Ile Asp Ala Thr Leu Phe Tyr Met Pro Lys Lys Ala
1               5                   10                  15

<210> SEQ ID NO 223
<211> LENGTH: 15
<212> TYPE: PRT
<213> ORGANISM: Homo sapiens

<400> SEQUENCE: 223

Gln Ser Met His Ile Asp Ala Thr Leu Tyr Thr Glu Ser Asp Val
1               5                   10                  15
```

<210> SEQ ID NO 224
<211> LENGTH: 129
<212> TYPE: PRT
<213> ORGANISM: Homo sapiens

<400> SEQUENCE: 224

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Gln Ser Met His
            20                  25                  30

Ile Asp Ala Thr Thr Phe Lys Phe Tyr Met Pro Lys Lys Ala Thr Glu
        35                  40                  45

Leu Lys His Leu Gln Cys Leu Glu Glu Glu Leu Lys Pro Leu Glu Glu
    50                  55                  60

Val Leu Asn Leu Ala Gln Ser Lys Asn Phe His Leu Arg Pro Arg Asp
65                  70                  75                  80

Leu Ile Ser Asn Ile Asn Val Ile Val Leu Glu Leu Lys Gly Ser Glu
                85                  90                  95

Thr Thr Phe Met Cys Glu Tyr Ala Asp Glu Thr Ala Thr Ile Val Glu
            100                 105                 110

Phe Leu Asn Arg Trp Ile Thr Phe Ser Gln Ser Ile Ile Ser Thr Leu
        115                 120                 125

Thr

<210> SEQ ID NO 225
<211> LENGTH: 129
<212> TYPE: PRT
<213> ORGANISM: Homo sapiens

<400> SEQUENCE: 225

Ala Pro Thr Ser Ser Ser Thr Lys Lys Thr Gln Leu Gln Leu Lys His
1               5                   10                  15

Leu Leu Leu Asp Leu Gln Met Ile Leu Asn Gly Ile Gln Ser Met Glu
            20                  25                  30

Ile Asp Ala Thr Thr Phe Lys Phe Tyr Met Pro Lys Lys Ala Thr Glu
        35                  40                  45

Leu Lys His Leu Gln Cys Leu Glu Glu Glu Leu Lys Pro Leu Glu Glu
    50                  55                  60

Val Leu Asn Leu Ala Gln Ser Lys Asn Phe His Leu Arg Pro Arg Asp
65                  70                  75                  80

Leu Ile Ser Asn Ile Asn Val Ile Val Leu Glu Leu Lys Gly Ser Glu
                85                  90                  95

Thr Thr Phe Met Cys Glu Tyr Ala Asp Glu Thr Ala Thr Ile Val Glu
            100                 105                 110

Phe Leu Asn Arg Trp Ile Thr Phe Ser Gln Ser Ile Ile Ser Thr Leu
        115                 120                 125

Thr

<210> SEQ ID NO 226
<211> LENGTH: 129
<212> TYPE: PRT
<213> ORGANISM: Homo sapiens

<400> SEQUENCE: 226

Ala Pro Thr Ser Ser Ser Thr Lys Lys Thr Gln Leu Gln Leu Glu His
1               5                   10                  15

```
Leu Leu Leu Asp Leu Gln Met Ile Leu Asn Gly Ile Gln Ser Met Glu
            20                  25                  30

Ile Asp Ala Thr Thr Phe Lys Phe Tyr Met Pro Lys Lys Ala Thr Glu
            35                  40                  45

Leu Lys His Leu Gln Cys Leu Glu Glu Glu Leu Lys Pro Leu Glu Glu
 50                  55                  60

Val Leu Asn Leu Ala Gln Ser Lys Asn Phe His Leu Arg Pro Arg Asp
 65                  70                  75                  80

Leu Ile Glu Asn Ile Asn Val Ile Val Leu Glu Leu Lys Gly Ser Glu
                85                  90                  95

Thr Thr Phe Met Cys Glu Tyr Ala Asp Glu Thr Ala Thr Ile Val Glu
            100                 105                 110

Phe Leu Asn Arg Trp Ile Thr Phe Ser Gln Ser Ile Ile Ser Thr Leu
            115                 120                 125

Thr
```

<210> SEQ ID NO 227
<211> LENGTH: 129
<212> TYPE: PRT
<213> ORGANISM: Homo sapiens

<400> SEQUENCE: 227

```
Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Gln Ser Met Glu
            20                  25                  30

Ile Asp Ala Thr Thr Phe Lys Phe Tyr Met Pro Lys Lys Ala Thr Glu
            35                  40                  45

Leu Lys His Leu Gln Cys Leu Glu Glu Glu Leu Lys Pro Leu Glu Glu
 50                  55                  60

Val Leu Asn Leu Ala Gln Ser Lys Asn Phe His Leu Arg Pro Arg Asp
 65                  70                  75                  80

Leu Ile Asp Asn Ile Asn Val Ile Val Leu Glu Leu Lys Gly Ser Glu
                85                  90                  95

Thr Thr Phe Met Cys Glu Tyr Ala Asp Glu Thr Ala Thr Ile Val Glu
            100                 105                 110

Phe Leu Asn Arg Trp Ile Thr Phe Ser Gln Ser Ile Ile Ser Thr Leu
            115                 120                 125

Thr
```

<210> SEQ ID NO 228
<211> LENGTH: 129
<212> TYPE: PRT
<213> ORGANISM: Homo sapiens

<400> SEQUENCE: 228

```
Ala Pro Thr Ser Ser Ser Thr Lys Lys Thr Gln Leu Gln Leu Lys His
 1               5                  10                  15

Leu Leu Leu Asp Leu Gln Met Ile Leu Asn Gly Ile Gln Ser Met Glu
            20                  25                  30

Ile Asp Ala Thr Thr Phe Lys Phe Tyr Met Pro Lys Lys Ala Thr Glu
            35                  40                  45

Leu Lys His Leu Gln Cys Leu Glu Glu Glu Leu Lys Pro Leu Glu Glu
 50                  55                  60

Val Leu Asn Leu Ala Gln Ser Lys Asn Phe His Leu Arg Pro Arg Asp
```

```
                65                  70                  75                  80
Leu Ile Glu Asn Ile Asn Val Ile Val Leu Glu Leu Lys Gly Ser Glu
                85                  90                  95
Thr Thr Phe Met Cys Glu Tyr Ala Asp Glu Thr Ala Thr Ile Val Glu
            100                 105                 110
Phe Leu Asn Arg Trp Ile Thr Phe Ser Gln Ser Ile Ile Ser Thr Leu
            115                 120                 125
Thr

<210> SEQ ID NO 229
<211> LENGTH: 129
<212> TYPE: PRT
<213> ORGANISM: Homo sapiens

<400> SEQUENCE: 229

Ala Pro Thr Ser Ser Ser Thr Lys Lys Thr Gln Leu Gln Leu Lys His
1               5                   10                  15
Leu Leu Leu Asp Leu Gln Met Ile Leu Asn Gly Ile Gln Ser Met Glu
                20                  25                  30
Ile Asp Ala Thr Thr Phe Lys Phe Tyr Met Pro Lys Lys Ala Thr Glu
            35                  40                  45
Leu Lys His Leu Gln Cys Leu Glu Glu Glu Leu Lys Pro Leu Glu Glu
        50                  55                  60
Val Leu Asn Leu Ala Gln Ser Lys Asn Phe His Leu Arg Pro Arg Asp
65                  70                  75                  80
Leu Ile Asp Asn Ile Asn Val Ile Val Leu Glu Leu Lys Gly Ser Glu
                85                  90                  95
Thr Thr Phe Met Cys Glu Tyr Ala Asp Glu Thr Ala Thr Ile Val Glu
            100                 105                 110
Phe Leu Asn Arg Trp Ile Thr Phe Ser Gln Ser Ile Ile Ser Thr Leu
            115                 120                 125
Thr

<210> SEQ ID NO 230
<211> LENGTH: 129
<212> TYPE: PRT
<213> ORGANISM: Homo sapiens

<400> SEQUENCE: 230

Ala Pro Thr Ser Ser Ser Thr Lys Lys Thr Gln Leu Gln Leu Lys His
1               5                   10                  15
Leu Leu Leu Asp Leu Gln Met Ile Leu Asn Gly Ile Gln Ser Met His
                20                  25                  30
Ile Asp Ala Thr Thr Phe Lys Phe Tyr Met Pro Lys Lys Ala Thr Glu
            35                  40                  45
Leu Lys His Leu Gln Cys Leu Glu Glu Glu Leu Lys Pro Leu Glu Glu
        50                  55                  60
Val Leu Asn Leu Ala Gln Ser Lys Asn Phe His Leu Arg Pro Arg Asp
65                  70                  75                  80
Leu Ile Ser Asn Ile Asn Val Ile Val Leu Glu Leu Lys Gly Ser Glu
                85                  90                  95
Thr Thr Phe Met Cys Glu Tyr Ala Asp Glu Thr Ala Thr Ile Val Glu
            100                 105                 110
Phe Leu Asn Arg Trp Ile Thr Phe Ser Gln Ser Ile Ile Ser Thr Leu
            115                 120                 125
```

Thr

<210> SEQ ID NO 231
<211> LENGTH: 129
<212> TYPE: PRT
<213> ORGANISM: Homo sapiens

<400> SEQUENCE: 231

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Gln Ser Met His
            20                  25                  30

Ile Asp Ala Thr Thr Phe Lys Phe Tyr Met Pro Lys Lys Ala Thr Glu
        35                  40                  45

Leu Lys His Leu Gln Cys Leu Glu Glu Glu Leu Lys Pro Leu Glu Glu
    50                  55                  60

Val Leu Asn Leu Ala Gln Ser Lys Asn Phe His Leu Arg Pro Arg Asp
65                  70                  75                  80

Leu Ile Glu Asn Ile Asn Val Ile Val Leu Glu Leu Lys Gly Ser Glu
                85                  90                  95

Thr Thr Phe Met Cys Glu Tyr Ala Asp Glu Thr Ala Thr Ile Val Glu
            100                 105                 110

Phe Leu Asn Arg Trp Ile Thr Phe Ser Gln Ser Ile Ile Ser Thr Leu
        115                 120                 125

Thr

<210> SEQ ID NO 232
<211> LENGTH: 129
<212> TYPE: PRT
<213> ORGANISM: Homo sapiens

<400> SEQUENCE: 232

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Gln Ser Met His
            20                  25                  30

Ile Asp Ala Thr Thr Phe Lys Phe Tyr Met Pro Lys Lys Ala Thr Glu
        35                  40                  45

Leu Lys His Leu Gln Cys Leu Glu Glu Glu Leu Lys Pro Leu Glu Glu
    50                  55                  60

Val Leu Asn Leu Ala Gln Ser Lys Asn Phe His Leu Arg Pro Arg Asp
65                  70                  75                  80

Leu Ile Asp Asn Ile Asn Val Ile Val Leu Glu Leu Lys Gly Ser Glu
                85                  90                  95

Thr Thr Phe Met Cys Glu Tyr Ala Asp Glu Thr Ala Thr Ile Val Glu
            100                 105                 110

Phe Leu Asn Arg Trp Ile Thr Phe Ser Gln Ser Ile Ile Ser Thr Leu
        115                 120                 125

Thr

<210> SEQ ID NO 233
<211> LENGTH: 129
<212> TYPE: PRT
<213> ORGANISM: Homo sapiens

<400> SEQUENCE: 233

Ala Pro Thr Ser Ser Ser Thr Lys Lys Thr Gln Leu Gln Leu Lys His

```
              1               5                  10                 15
Leu Leu Leu Asp Leu Gln Met Ile Leu Asn Gly Ile Gln Ser Met His
                 20                  25                 30

Ile Asp Ala Thr Thr Phe Lys Phe Tyr Met Pro Lys Lys Ala Thr Glu
                 35                  40                 45

Leu Lys His Leu Gln Cys Leu Glu Glu Leu Lys Pro Leu Glu Glu
                 50              55                 60

Val Leu Asn Leu Ala Gln Ser Lys Asn Phe His Leu Arg Pro Arg Asp
 65                  70                  75                 80

Leu Ile Glu Asn Ile Asn Val Ile Val Leu Glu Leu Lys Gly Ser Glu
                 85                  90                 95

Thr Thr Phe Met Cys Glu Tyr Ala Asp Glu Thr Ala Thr Ile Val Glu
                100                 105                110

Phe Leu Asn Arg Trp Ile Thr Phe Ser Gln Ser Ile Ile Ser Thr Leu
                115                 120                 125

Thr

<210> SEQ ID NO 234
<211> LENGTH: 129
<212> TYPE: PRT
<213> ORGANISM: Homo sapiens

<400> SEQUENCE: 234

Ala Pro Thr Ser Ser Ser Thr Lys Lys Thr Gln Leu Gln Leu Lys His
 1               5                  10                 15

Leu Leu Leu Asp Leu Gln Met Ile Leu Asn Gly Ile Gln Ser Met His
                 20                  25                 30

Ile Asp Ala Thr Thr Phe Lys Phe Tyr Met Pro Lys Lys Ala Thr Glu
                 35                  40                 45

Leu Lys His Leu Gln Cys Leu Glu Glu Leu Lys Pro Leu Glu Glu
                 50              55                 60

Val Leu Asn Leu Ala Gln Ser Lys Asn Phe His Leu Arg Pro Arg Asp
 65                  70                  75                 80

Leu Ile Asp Asn Ile Asn Val Ile Val Leu Glu Leu Lys Gly Ser Glu
                 85                  90                 95

Thr Thr Phe Met Cys Glu Tyr Ala Asp Glu Thr Ala Thr Ile Val Glu
                100                 105                110

Phe Leu Asn Arg Trp Ile Thr Phe Ser Gln Ser Ile Ile Ser Thr Leu
                115                 120                 125

Thr
```

INTERLEUKIN-2 POLYPEPTIDES AND FUSION PROTEINS THEREOF, AND THEIR PHARMACEUTICAL COMPOSITIONS AND THERAPEUTIC APPLICATIONS

CROSS REFERENCE TO RELATED APPLICATION

This application claims the benefit of U.S. Provisional Application Nos. 63/016,289, filed Apr. 28, 2020; 63/027,929, filed May 20, 2020; and 63/047,867, filed Jul. 2, 2020; the disclosure of each of which is incorporated herein by reference in its entirety.

FIELD

Provided herein are an interleukin-2 polypeptide and a fusion protein thereof. Also provided herein are their pharmaceutical compositions and methods of use for treating, preventing, or ameliorating one or more symptoms of a proliferative disease.

REFERENCE TO A SEQUENCE LISTING

The present specification is being filed with a Sequence Listing in Computer Readable Form (CRF), which is entitled 216A007US01_SEQ_LIST_ST25.txt of 309,651 bytes in size and created Apr. 26, 2021; the content of which is incorporated herein by reference in its entirety.

BACKGROUND

An interleukin-2 (IL-2) is a pleiotropic cytokine that orchestrates the proliferation, survival, and function of both immune effector (Teff) cells and regulatory T (Treg) cells to maintain immune homeostasis. Bluestone, *N. Engl. J. Med.* 2011, 365, 2129-31; Boyman et al., *Nat. Rev. Immunol.* 2012, 12, 180-90. The IL-2 drives T-cell growth, augments natural killer (NK) cytolytic activity, induces the differentiation of regulatory T (Treg) cells, and mediates activation-induced cell death. Liao et al., *Curr. Opin. Immunol.* 2011, 23, 598-604. Native IL-2 possesses a single disulfide bond between Cys 58 and Cys 105. Agrawalla et al., *Bioconjugate Chem.* 2018, 29, 29-34.

An interleukin-2 receptor (IL-2R) has three different interleukin-2 receptor chains: α chain (IL-2Rα or CD25), β chain (IL-2Rβ or CD122), and γ chain (IL-2Rγ, $γ_c$, or CD132). Wang et al., *Science* 2005, 310, 1159-63. The IL-2 binds the IL-2Rα with a low affinity ($K_d \approx 10$ nM). Id. From a crystal structure of a quaternary IL-2 signaling complex, fifteen amino acid residues (K35, T37, R38, T41, F42, K43, F44, Y45, E61, E62, K64, P65, E68, L72, and Y107) on the IL-2 are identified as interface residues between the IL-2 and IL-2Rα. Stauber et al., *Proc. Natl. Acad. Sci. U.S.A.* 2006, 103, 2788-93. The IL-2 binds a heterodimeric complex of the IL-2Rβ and IL-2Rγ ("IL-2Rβ/γ"), expressed on memory T cells and NK cells, with an intermediate affinity ($K_d \approx 1$ nM). Wang et al., *Science* 2005, 310, 1159-63. The IL-2 binds a heterotrimeric complex of the IL-2Rα, IL-2Rβ, and IL-2Rγ, expressed on Treg cells, with a high affinity ($K_d \approx 10$ pM). Id. The IL-2 binds the IL-2Rβ alone with a dissociation constant ($K_d$) of about 100 nM and has no detectable binding affinity to the IL-2Rγ alone. Id. The IL-2Rα by itself has no signal-transducing activity. Id. The IL-2 signals through the intermediate-affinity heterodimeric IL-2Rβ/γ complex or the high-affinity heterotrimeric IL-2Rα/β/γ complex. Liao et al., *Curr. Opin. Immunol.* 2011, 23, 598-604. The binding of the IL-2 to the intermediate-affinity heterodimeric IL-2Rβ/γ complex leads to the activation and proliferation of immunostimulatory Teff cells, while the binding of the IL-2 to the high-affinity heterotrimeric IL-2Rα/β/γ complex results in the activation and proliferation of immunosuppressive Treg cells. Malek et al., *Immunity* 2010, 33, 153-65; Bluestone, *N. Engl. J. Med.* 2011, 365, 2129-31; Boyman et al., *Nat. Rev. Immunol.* 2012, 12, 180-90; Spangler et al., *Annu. Rev. Immunol.* 2015, 33, 139-67. These dual opposing functions of immunostimulation and immunosuppression pose a major challenge in developing the IL-2 as a safe and effective therapeutic agent. Skrombolas et al., *Expert Rev. Clin. Immunol.* 2014, 10, 207-17; Abbas et al., *Sci. Immunol.* 2018, 3, eaat 1482.

Aldesleukin, a recombinant human IL-2, was approved by the FDA in 1992 for metastatic renal cell carcinoma and in 1998 for metastatic melanoma. Rosenberg, *J. Immunol.* 2014, 192, 5451-58. Patients with metastatic melanoma or renal cancer experience a 5 to 10% rate of complete cancer regression, with an additional 10% experiencing a partial regression. Atkins et al., *J. Clin. Oncol.* 1999, 17, 2105-16; Klapper et al., *Cancer* 2008, 113, 293-301. Approximately 70% of complete responders to the IL-2 therapy do not recur. Rosenberg, *Sci. Transl. Med.* 2012, 4, 127ps8. However, the success of the IL-2 as an immunotherapy for cancer has been hampered by its severe toxicities and limited efficacy. One major limiting factor for its efficacy as an anticancer agent is immunosuppression resulting from the IL-2-driven preferential expansion of Treg cells. Abbas et al., *Sci. Immunol.* 2018, 3, eaat 1482. A high dose therapeutic schedule is required for the IL-2 to be effective in cancer treatment. Bluestone, *N. Engl. J. Med.* 2011, 365, 2129-31; Abbas et al., *Sci. Immunol.* 2018, 3, eaat 1482. This dosing regimen, however, causes vascular leak syndrome and limits the application of IL-2 in cancer treatment. Abbas et al., *Sci. Immunol.* 2018, 3, eaat 1482. Therefore, there is a need for an effective IL-2 immunotherapy for treating cancer.

SUMMARY OF THE DISCLOSURE

Provided herein is an interleukin-2 polypeptide comprising an amino acid sequence of SEQ ID NO: 1, 2, 3, 4, or 5, wherein the interleukin-2 polypeptide comprises: (i) an amino acid substitution at position 8, 9, 13, 15, 16, 19, 23, 32, 76, 79, 81, 84, 87, 88, 91, 92, 95, 127, or 130 as set forth in SEQ ID NO: 1, 2, 3, 4, or 5; (ii) a deletion or replacement of the amino acid residues from positions 30 to 35 as set forth in SEQ ID NO: 1, 2, 3, 4, or 5 with a peptide linker; (iii) a disulfide bond formed between two amino acids from positions 30 to 80 as set forth in SEQ ID NO: 1, 2, 3, 4, or 5; or (iv) a replacement of the amino acid residues from positions 29 to 50 as set forth in SEQ ID NO: 1, 2, 3, 4, or 5 with a peptide comprising the amino acid sequence of an IL-15 hinge or a fragment thereof.

Also provided herein is an interleukin-2 polypeptide comprising an amino acid sequence of SEQ ID NO: 1, 2, 3, 4, or 5, wherein the interleukin-2 polypeptide comprises: (i) an amino acid substitution at position 8, 9, 15, 16, 32, 76, 79, 81, 84, 88, 92, 95, 127, or 130 as set forth in SEQ ID NO: 1, 2, 3, 4, or 5; (ii) a deletion or replacement of the amino acid residues from positions 30 to 35 as set forth in SEQ ID NO: 1, 2, 3, 4, or 5 with a peptide linker; (iii) a disulfide bond formed between two amino acids from positions 30 to 80 as set forth in SEQ ID NO: 1, 2, 3, 4, or 5; or (iv) a replacement of the amino acid residues from positions 29 to 50 as set forth in SEQ ID NO: 1, 2, 3, 4, or 5 with a peptide comprising the amino acid sequence of an IL-15 hinge or a fragment thereof.

Additionally provided herein is an interleukin-2 polypeptide comprising an amino acid sequence of SEQ ID NO: 1, 2, 3, 4, or 5, wherein the interleukin-2 polypeptide comprises: (i) an amino acid substitution at position 8, 9, 15, 16, 32, 76, 79, 81, 84, 88, 92, 95, 127, or 130 as set forth in SEQ ID NO: 1, 2, 3, 4, or 5; or (ii) a deletion or replacement of the amino acid residues from positions 30 to 35 as set forth in SEQ ID NO: 1, 2, 3, 4, or 5 with a peptide linker.

Furthermore, provided herein is an interleukin-2 polypeptide comprising an amino acid sequence of SEQ ID NO: 1, 2, 3, 4, or 5, wherein the interleukin-2 polypeptide comprises an amino acid substitution at position 8, 9, 13, 15, 16, 19, 23, 32, 76, 79, 81, 84, 87, 88, 91, 92, 95, 127, or 130 as set forth in SEQ ID NO: 1, 2, 3, 4, or 5.

Provided herein is an interleukin-2 polypeptide comprising an amino acid sequence of SEQ ID NO: 1, 2, 3, 4, or 5, wherein the interleukin-2 polypeptide comprises an amino acid substitution at position 8, 9, 15, 16, 32, 76, 79, 81, 84, 88, 92, 95, 127, or 130 as set forth in SEQ ID NO: 1, 2, 3, 4, or 5.

Provided herein is an interleukin-2 polypeptide comprising an amino acid sequence of SEQ ID NO: 1, 2, 3, 4, or 5, wherein the interleukin-2 polypeptide comprises an amino acid substitution at position 8, 9, 16, 32, 76, 79, or 81 as set forth in SEQ ID NO: 1, 2, 3, 4, or 5.

Provided herein is an interleukin-2 polypeptide comprising an amino acid sequence of SEQ ID NO: 1, 2, 3, 4, or 5, wherein the interleukin-2 polypeptide comprises an amino acid substitution at position 16, 84, 88, 92, or 95 as set forth in SEQ ID NO: 1, 2, 3, 4, or 5.

Provided herein is an interleukin-2 polypeptide comprising an amino acid sequence of SEQ ID NO: 1, 2, 3, 4, or 5, wherein the interleukin-2 polypeptide comprises an amino acid substitution at position 15 as set forth in SEQ ID NO: 1, 2, 3, 4, or 5.

Provided herein is an interleukin-2 polypeptide comprising an amino acid sequence of SEQ ID NO: 1, 2, 3, 4, or 5, wherein the interleukin-2 polypeptide comprises an amino acid substitution at position 127 or 130 as set forth in SEQ ID NO: 1, 2, 3, 4, or 5.

Provided herein is an interleukin-2 polypeptide comprising an amino acid sequence of SEQ ID NO: 1, 2, 3, 4, or 5, wherein the interleukin-2 polypeptide comprises an amino acid substitution at position 13, 15, 16, 19, 23, 84, 87, 91, or 95 as set forth in SEQ ID NO: 1, 2, 3, 4, or 5.

Provided herein is an interleukin-2 polypeptide comprising an amino acid sequence of SEQ ID NO: 1, 2, 3, 4, or 5, wherein the interleukin-2 polypeptide comprises an amino acid substitution at position 13, 15, 16, 23, 91, or 95 as set forth in SEQ ID NO: 1, 2, 3, 4, or 5.

Provided herein is an interleukin-2 polypeptide comprising an amino acid sequence of SEQ ID NO: 1, 2, 3, 4, or 5, wherein the interleukin-2 polypeptide comprises an amino acid substitution at position 13, 19, 84, 87, 91, 92, or 95 as set forth in SEQ ID NO: 1, 2, 3, 4, or 5.

Provided herein is an interleukin-2 polypeptide comprising an amino acid sequence of SEQ ID NO: 1, 2, 3, 4, or 5, wherein the interleukin-2 polypeptide comprises a deletion or replacement of the amino acid residues from positions 30 to 35 as set forth in SEQ ID NO: 1, 2, 3, 4, or 5 with a peptide linker.

Provided herein is an interleukin-2 polypeptide comprising an amino acid sequence of SEQ ID NO: 1, 2, 3, 4, or 5, wherein the interleukin-2 polypeptide comprises a disulfide bond formed between two amino acids from positions 30 to 80 as set forth in SEQ ID NO: 1, 2, 3, 4, or 5.

Provided herein is an interleukin-2 polypeptide comprising an amino acid sequence of SEQ ID NO: 1, 2, 3, 4, or 5, wherein the interleukin-2 polypeptide comprises two or more disulfide bonds.

Provided herein is an interleukin-2 polypeptide comprising an amino acid sequence of SEQ ID NO: 1, 2, 3, 4, or 5, wherein the interleukin-2 polypeptide comprises a replacement of the amino acid residues from positions 29 to 50 as set forth in SEQ ID NO: 1, 2, 3, 4, or 5 with a peptide comprising the amino acid sequence of an IL-15 hinge or a fragment thereof.

Provided herein is a fusion protein comprising an interleukin-2 polypeptide domain and a half-life-extension domain; wherein the interleukin-2 polypeptide domain comprises an amino acid sequence of an interleukin-2 polypeptide provided herein.

Provided herein is a fusion protein comprising an interleukin-2 polypeptide domain, an albumin binding domain, and optionally a peptide linker; wherein the C-terminus of the interleukin-2 polypeptide domain is connected to the N-terminus of the albumin binding domain directly or via the peptide linker, or the C-terminus of the albumin binding domain is connected to the N-terminus of the interleukin-2 polypeptide domain directly or via the peptide linker; and wherein the interleukin-2 polypeptide domain comprises an amino acid sequence of an interleukin-2 polypeptide provided herein.

Provided herein is a fusion protein comprising an interleukin-2 polypeptide domain and a fragment crystallizable domain having a first and second peptide chains, and optionally a peptide linker; wherein the C-terminus of the interleukin-2 polypeptide domain is connected to the N-terminus of the first peptide chain of the fragment crystallizable domain directly or via the peptide linker, or the N-terminus of the interleukin-2 polypeptide domain is connected to the C-terminus of the first peptide chain of the fragment crystallizable domain directly or via the peptide linker; and wherein the interleukin-2 polypeptide domain comprises an amino acid sequence of an interleukin-2 polypeptide provided herein.

Provided herein is a pharmaceutical composition comprising an interleukin-2 polypeptide or fusion protein provided herein; and a pharmaceutically acceptable excipient.

Provided herein is a method of treating, preventing, or ameliorating one or more symptoms of a proliferative disease in a subject, comprising administering to the subject a therapeutically effective amount of an interleukin-2 polypeptide or fusion protein provided herein.

Provided herein is a method of activating an immune effector cell, comprising contacting the cell with an effective amount of an interleukin-2 polypeptide or fusion protein provided herein.

DETAILED DESCRIPTION

Figure 1:
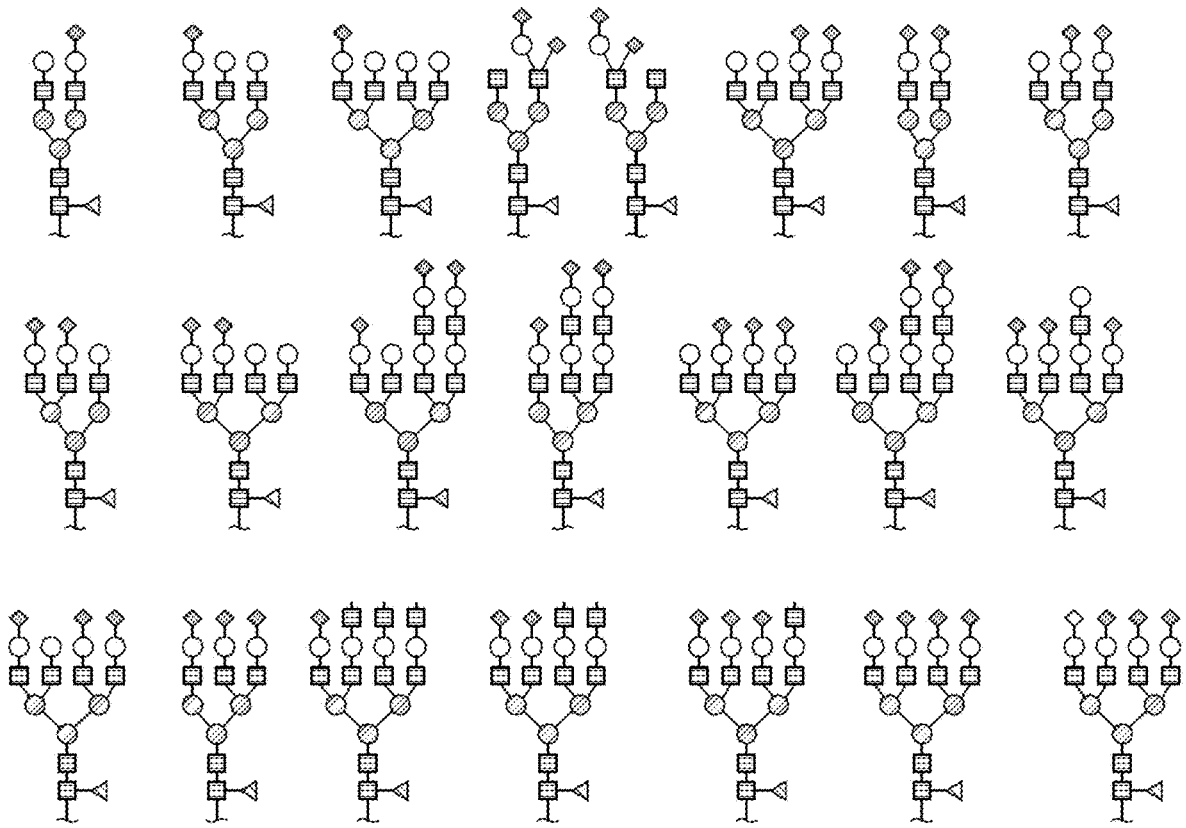
FIG. 1 illustrates the structures of certain N-glycans.
Figure 2:
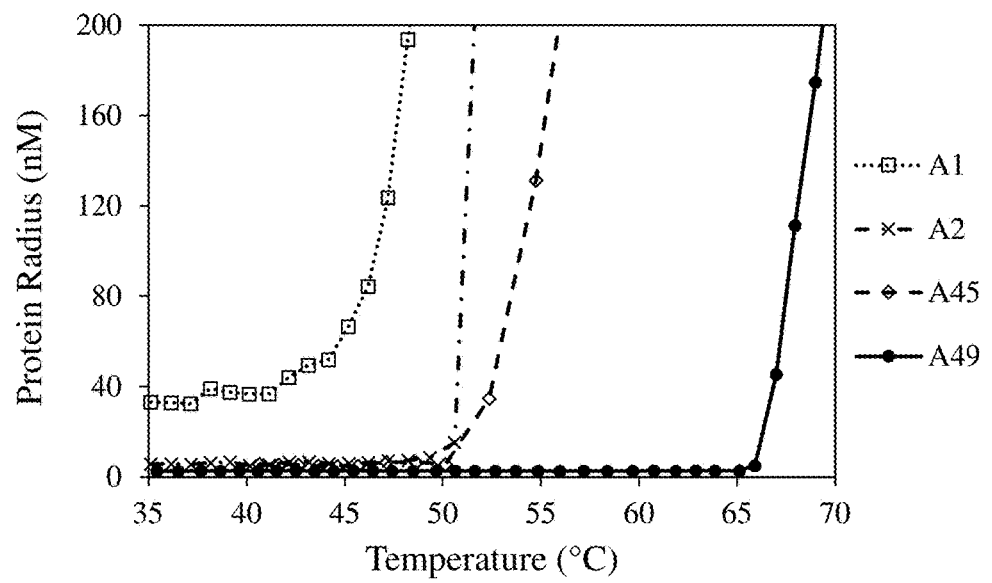
FIG. 2 shows a comparison of the aggregation onset temperatures $T_{Agg}$ of a wild type IL-2 (A1), a glycosylated IL-2 (A2), an IL-2 mutein with R38E/F42K (A45), and an IL-2 with an additional disulfide bond (A49).

To facilitate understanding of the disclosure set forth herein, a number of terms are defined below.

Generally, the nomenclature used herein and the laboratory procedures in biochemistry, biology, cell biology, molecular biology, and pharmacology described herein are those well-known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject. In one embodiment, the subject is a human.

The terms "treat," "treating," and "treatment" are meant to include alleviating or abrogating a disorder, disease, or condition, or one or more of its attendant symptoms; or alleviating or eradicating the cause(s) of the disorder, disease, or condition itself.

The terms "prevent," "preventing," and "prevention" are meant to include delaying and/or precluding the onset of a disorder, disease, or condition, and/or one or more of its attendant symptoms; barring a subject from acquiring a disorder, disease, or condition; or reducing a subject's risk of acquiring a disorder, disease, or condition.

The terms "alleviate" and "alleviating" refer to easing or reducing one or more symptoms (e.g., pain) of a disorder, disease, or condition. The terms can also refer to reducing adverse effects associated with an active ingredient. Sometimes, the beneficial effects that a subject derives from a prophylactic or therapeutic agent do not result in a cure of the disorder, disease, or condition.

The term "contacting" or "contact" is meant to refer to bringing together of a therapeutic agent and cell or tissue such that a physiological and/or chemical effect takes place as a result of such contact. Contacting can take place in vitro, ex vivo, or in vivo. In one embodiment, a therapeutic agent is contacted with a cell in cell culture (in vitro) to determine the effect of the therapeutic agent on the cell. In another embodiment, the contacting of a therapeutic agent with a cell or tissue includes the administration of a therapeutic agent to a subject having the cell or tissue to be contacted.

The term "therapeutically effective amount" or "effective amount" is meant to include the amount of a compound that, when administered, is sufficient to prevent development of, or alleviate to some extent, one or more of the symptoms of the disorder, disease, or condition being treated. The term "therapeutically effective amount" or "effective amount" also refers to the amount of a compound that is sufficient to elicit a biological or medical response of a biological molecule (e.g., a protein, enzyme, RNA, or DNA), cell, tissue, system, animal, or human, which is being sought by a researcher, veterinarian, medical doctor, or clinician.

The term "IC$_{50}$" or "EC$_{50}$" refers to an amount, concentration, or dosage of a compound that is required for 50% inhibition of a maximal response in an assay that measures such a response.

The term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of a subject (e.g., a human) without excessive toxicity, irritation, allergic response, immunogenicity, or other problems or complications, commensurate with a reasonable benefit/risk ratio. See, e.g., *Remington: The Science and Practice of Pharmacy,* 22nd ed.; Allen Ed.: Philadelphia, PA, 2012; *Handbook of Pharmaceutical Excipients,* 8th ed.; Sheskey et al., Eds.; The Pharmaceutical Press: 2017; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, FL, 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "substantially pure" and "substantially homogeneous" mean sufficiently homogeneous to appear free of readily detectable impurities as determined by a standard analytical method used by one of ordinary skill in the art, including, but not limited to, gel electrophoresis, high performance liquid chromatography (HPLC), and mass spectrometry (MS); or sufficiently pure such that further purification would not detectably alter the physical, chemical, biological, and/or pharmacological properties, such as enzymatic and biological activities, of the substance. In certain embodiments, "substantially pure" or "substantially homogeneous" refers to a collection of molecules, wherein at least about 80%, at least about 90%, at least about 92%, at least about 95%, at least about 96%, at least about 97%, at least about 98%, at least about 99%, or at least about 99.5% by weight of the molecules are a single compound as determined by a standard analytical method.

Interleukin-2 Polypeptides

In one embodiment, provided herein is an interleukin-2 polypeptide comprising an amino acid sequence of SEQ ID NO: 1, 2, 3, 4, or 5, wherein the interleukin-2 polypeptide comprises: (i) an amino acid substitution at position 8, 9, 13, 15, 16, 19, 23, 32, 76, 79, 81, 84, 87, 88, 91, 92, 95, 127, or 130 as set forth in SEQ ID NO: 1, 2, 3, 4, or 5, with the proviso that the amino acid substitution at position 88 is not N88R; (ii) a deletion or replacement of the amino acid residues from positions 30 to 35 as set forth in SEQ ID NO: 1, 2, 3, 4, or 5 with a peptide linker; (iii) a disulfide bond formed between two amino acids from positions 30 to 80 as set forth in SEQ ID NO: 1, 2, 3, 4, or 5; or (iv) a replacement of the amino acid residues from positions 29 to 50 as set forth in SEQ ID NO: 1, 2, 3, 4, or 5 with a peptide comprising the amino acid sequence of an IL-15 hinge or a fragment thereof ("an IL-15 hinge fragment-containing peptide").

In another embodiment, provided herein is an interleukin-2 polypeptide comprising an amino acid sequence of SEQ ID NO: 1, 2, 3, 4, or 5, wherein the interleukin-2 polypeptide comprises: (i) an amino acid substitution at position 8, 9, 15, 16, 32, 76, 79, 81, 84, 88, 92, 95, 127, or 130 as set forth in SEQ ID NO: 1, 2, 3, 4, or 5, with the proviso that the amino acid substitution at position 88 is not N88R; (ii) a deletion or replacement of the amino acid residues from positions 30 to 35 as set forth in SEQ ID NO: 1, 2, 3, 4, or 5 with a peptide linker; (iii) a disulfide bond formed between two amino acids from positions 30 to 80 as set forth in SEQ ID NO: 1, 2, 3, 4, or 5; or (iv) a replacement of the amino acid residues from positions 29 to 50 as set forth in SEQ ID NO: 1, 2, 3, 4, or 5 with an IL-15 hinge fragment-containing peptide.

In yet another embodiment, provided herein is an interleukin-2 polypeptide comprising an amino acid sequence of SEQ ID NO: 1, 2, 3, 4, or 5, wherein the interleukin-2 polypeptide comprises: (i) an amino acid substitution at position 8, 9, 15, 16, 32, 76, 79, 81, 84, 88, 92, 95, 127, or 130 as set forth in SEQ ID NO: 1, 2, 3, 4, or 5, with the proviso that the amino acid substitution at position 88 is not N88R; or (ii) a deletion or replacement of the amino acid residues from positions 30 to 35 as set forth in SEQ ID NO: 1, 2, 3, 4, or 5. In certain embodiments, the peptide linker is a flexible peptide linker.

In yet another embodiment, provided herein is an interleukin-2 polypeptide comprising an amino acid sequence of SEQ ID NO: 1, 2, 3, 4, or 5, wherein the interleukin-2 polypeptide comprises: (i) an amino acid substitution at position K8, K9, Q13, E15, H16, L19, M23, K32, K76, H79, R81, D84, S87, N88, V91, I92, E95, S127, or S130 as set forth in SEQ ID NO: 1, 2, 3, 4, or 5, with the proviso that the amino acid substitution at position 88 is not N88R; (ii) a deletion or replacement of the amino acid residues from positions N30 to K35 as set forth in SEQ ID NO: 1, 2, 3, 4, or 5 with a flexible peptide linker; (iii) a disulfide bond formed between two amino acids from positions N30 to L80 as set forth in SEQ ID NO: 1, 2, 3, 4, or 5; or (iv) a replacement of the amino acid residues from positions N29 to A50 as set forth in SEQ ID NO: 1, 2, 3, 4, or 5 with an IL-15 hinge fragment-containing peptide.

In yet another embodiment, provided herein is an interleukin-2 polypeptide comprising an amino acid sequence of SEQ ID NO: 1, 2, 3, 4, or 5, wherein the interleukin-2 polypeptide comprises: (i) an amino acid substitution at position K8, K9, E15, H16, K32, K76, H79, R81, D84, N88, I92, E95, S127, or S130 as set forth in SEQ ID NO: 1, 2, 3, 4, or 5, with the proviso that the amino acid substitution at position 88 is not N88R; (ii) a deletion or replacement of the amino acid residues from positions N30 to K35 as set forth in SEQ ID NO: 1, 2, 3, 4, or 5 with a flexible peptide linker; (iii) a disulfide bond formed between two amino acids from positions N30 to L80 as set forth in SEQ ID NO: 1, 2, 3, 4, or 5; or (iv) a replacement of the amino acid residues from positions N29 to A50 as set forth in SEQ ID NO: 1, 2, 3, 4, or 5 with an IL-15 hinge fragment-containing peptide.

In yet another embodiment, provided herein is an interleukin-2 polypeptide comprising an amino acid sequence of SEQ ID NO: 1, 2, 3, 4, or 5, wherein the interleukin-2 polypeptide comprises: (i) an amino acid substitution at position K8, K9, E15, H16, K32, K76, H79, R81, D84, N88, I92, E95, S127, or S130 as set forth in SEQ ID NO: 1, 2, 3, 4, or 5, with the proviso that the amino acid substitution at position 88 is not N88R; or (ii) a deletion or replacement of the amino acid residues from positions N30 to K35 as set forth in SEQ ID NO: 1, 2, 3, 4, or 5 with a flexible peptide linker.

In still another embodiment, provided herein is an interleukin-2 polypeptide comprising an amino acid sequence of SEQ ID NO: 1, 2, 3, 4, or 5, wherein the interleukin-2 polypeptide comprises: (i) an amino acid substitution at position K8, K9, Q13, E15, H16, L19, M23, K32, K76, H79, R81, D84, S87, N88, V91, I92, E95, S127, or S130 as set forth in SEQ ID NO: 1, 2, 3, 4, or 5, with the proviso that the amino acid substitution at position 88 is not N88R.

In certain embodiments, the amino acid at position 8 as set forth in SEQ ID NO: 1, 2, 3, 4, or 5 is one of the twenty natural amino acids (i.e., Ala (A), Cys (C), Asp (D), Glu (E), Phe (F), Gly (G), His (H), Ile (I), Lys (K), Leu (L), Met (M), Asn (N), Pro (P), Gln (Q), Arg (R), Ser (S), Thr (T), Val (V), Trp (W), and Tyr (Y)) other than K. In certain embodiments, the amino acid at position 8 as set forth in SEQ ID NO: 1, 2, 3, 4, or 5 is D, E, or Q. In certain embodiments, the amino acid at position 8 as set forth in SEQ ID NO: 1, 2, 3, 4, or 5 is D. In certain embodiments, the amino acid at position 8 as set forth in SEQ ID NO: 1, 2, 3, 4, or 5 is E. In certain embodiments, the amino acid at position 8 as set forth in SEQ ID NO: 1, 2, 3, 4, or 5 is Q.

In certain embodiments, the amino acid at position 9 as set forth in SEQ ID NO: 1, 2, 3, 4, or 5 is one of the twenty natural amino acids other than K. In certain embodiments, the amino acid at position 9 as set forth in SEQ ID NO: 1, 2, 3, 4, or 5 is D, E, or Q. In certain embodiments, the amino acid at position 9 as set forth in SEQ ID NO: 1, 2, 3, 4, or 5 is D. In certain embodiments, the amino acid at position 9 as set forth in SEQ ID NO: 1, 2, 3, 4, or 5 is E. In certain embodiments, the amino acid at position 9 as set forth in SEQ ID NO: 1, 2, 3, 4, or 5 is Q.

In certain embodiments, the amino acid at position 13 as set forth in SEQ ID NO: 1, 2, 3, 4, or 5 is one of the twenty natural amino acids other than Q. In certain embodiments, the amino acid at position 13 as set forth in SEQ ID NO: 1, 2, 3, 4, or 5 is E or N. In certain embodiments, the amino acid at position 13 as set forth in SEQ ID NO: 1, 2, 3, 4, or 5 is E. In certain embodiments, the amino acid at position 13 as set forth in SEQ ID NO: 1, 2, 3, 4, or 5 is N.

In certain embodiments, the amino acid at position 15 as set forth in SEQ ID NO: 1, 2, 3, 4, or 5 is one of the twenty natural amino acids other than E. In certain embodiments, the amino acid at position 15 as set forth in SEQ ID NO: 1, 2, 3, 4, or 5 is K, Q, or V. In certain embodiments, the amino acid at position 15 as set forth in SEQ ID NO: 1, 2, 3, 4, or 5 is K or Q. In certain embodiments, the amino acid at position 15 as set forth in SEQ ID NO: 1, 2, 3, 4, or 5 is K. In certain embodiments, the amino acid at position 15 as set forth in SEQ ID NO: 1, 2, 3, 4, or 5 is Q. In certain embodiments, the amino acid at position 15 as set forth in SEQ ID NO: 1, 2, 3, 4, or 5 is V.

In certain embodiments, the amino acid at position 16 as set forth in SEQ ID NO: 1, 2, 3, 4, or 5 is one of the twenty natural amino acids other than H. In certain embodiments, the amino acid at position 16 as set forth in SEQ ID NO: 1, 2, 3, 4, or 5 is D, E, N, or Q. In certain embodiments, the amino acid at position 16 as set forth in SEQ ID NO: 1, 2, 3, 4, or 5 is D, E, or Q. In certain embodiments, the amino acid at position 16 as set forth in SEQ ID NO: 1, 2, 3, 4, or 5 is D. In certain embodiments, the amino acid at position 16 as set forth in SEQ ID NO: 1, 2, 3, 4, or 5 is E. In certain embodiments, the amino acid at position 16 as set forth in SEQ ID NO: 1, 2, 3, 4, or 5 is N. In certain embodiments, the amino acid at position 16 as set forth in SEQ ID NO: 1, 2, 3, 4, or 5 is Q.

In certain embodiments, the amino acid at position 19 as set forth in SEQ ID NO: 1, 2, 3, 4, or 5 is one of the twenty natural amino acids other than L. In certain embodiments, the amino acid at position 19 as set forth in SEQ ID NO: 1, 2, 3, 4, or 5 is S.

In certain embodiments, the amino acid at position 23 as set forth in SEQ ID NO: 1, 2, 3, 4, or 5 is one of the twenty natural amino acids other than M. In certain embodiments, the amino acid at position 23 as set forth in SEQ ID NO: 1, 2, 3, 4, or 5 is K.

In certain embodiments, the amino acid at position 32 as set forth in SEQ ID NO: 1, 2, 3, 4, or 5 is one of the twenty natural amino acids other than K. In certain embodiments, the amino acid at position 32 as set forth in SEQ ID NO: 1, 2, 3, 4, or 5 is D, E, or Q. In certain embodiments, the amino acid at position 32 as set forth in SEQ ID NO: 1, 2, 3, 4, or 5 is D. In certain embodiments, the amino acid at position 32 as set forth in SEQ ID NO: 1, 2, 3, 4, or 5 is E. In certain embodiments, the amino acid at position 32 as set forth in SEQ ID NO: 1, 2, 3, 4, or 5 is Q.

In certain embodiments, the amino acid at position 76 as set forth in SEQ ID NO: 1, 2, 3, 4, or 5 is one of the twenty natural amino acids other than K. In certain embodiments, the amino acid at position 76 as set forth in SEQ ID NO: 1, 2, 3, 4, or 5 is D, E, or Q. In certain embodiments, the amino acid at position 76 as set forth in SEQ ID NO: 1, 2, 3, 4, or 5 is D. In certain embodiments, the amino acid at position 76 as set forth in SEQ ID NO: 1, 2, 3, 4, or 5 is E. In certain embodiments, the amino acid at position 76 as set forth in SEQ ID NO: 1, 2, 3, 4, or 5 is Q.

In certain embodiments, the amino acid at position 79 as set forth in SEQ ID NO: 1, 2, 3, 4, or 5 is one of the twenty natural amino acids other than H. In certain embodiments, the amino acid at position 79 as set forth in SEQ ID NO: 1, 2, 3, 4, or 5 is D, E, or Q. In certain embodiments, the amino acid at position 79 as set forth in SEQ ID NO: 1, 2, 3, 4, or 5 is D. In certain embodiments, the amino acid at position 79 as set forth in SEQ ID NO: 1, 2, 3, 4, or 5 is E. In certain embodiments, the amino acid at position 79 as set forth in SEQ ID NO: 1, 2, 3, 4, or 5 is Q.

In certain embodiments, the amino acid at position 81 as set forth in SEQ ID NO: 1, 2, 3, 4, or 5 is one of the twenty natural amino acids other than R. In certain embodiments, the amino acid at position 81 as set forth in SEQ ID NO: 1, 2, 3, 4, or 5 is D, E, or Q. In certain embodiments, the amino acid at position 81 as set forth in SEQ ID NO: 1, 2, 3, 4, or 5 is D. In certain embodiments, the amino acid at position 81 as set forth in SEQ ID NO: 1, 2, 3, 4, or 5 is E. In certain embodiments, the amino acid at position 81 as set forth in SEQ ID NO: 1, 2, 3, 4, or 5 is Q.

In certain embodiments, the amino acid at position 84 as set forth in SEQ ID NO: 1, 2, 3, 4, or 5 is one of the twenty natural amino acids other than D. In certain embodiments, the amino acid at position 84 as set forth in SEQ ID NO: 1, 2, 3, 4, or 5 is T.

In certain embodiments, the amino acid at position 87 as set forth in SEQ ID NO: 1, 2, 3, 4, or 5 is one of the twenty natural amino acids other than S. In certain embodiments, the amino acid at position 87 as set forth in SEQ ID NO: 1, 2, 3, 4, or 5 is D or E. In certain embodiments, the amino acid at position 87 as set forth in SEQ ID NO: 1, 2, 3, 4, or 5 is D. In certain embodiments, the amino acid at position 87 as set forth in SEQ ID NO: 1, 2, 3, 4, or 5 is E.

In certain embodiments, the amino acid at position 88 as set forth in SEQ ID NO: 1, 2, 3, 4, or 5 is one of the twenty natural amino acids other than N and R. In certain embodiments, the amino acid at position 88 as set forth in SEQ ID NO: 1, 2, 3, 4, or 5 is one of the twenty natural amino acids other than N. In certain embodiments, the amino acid at position 88 as set forth in SEQ ID NO: 1, 2, 3, 4, or 5 is one of the twenty natural amino acids other than R. In certain embodiments, the amino acid at position 88 as set forth in SEQ ID NO: 1, 2, 3, 4, or 5 is A.

In certain embodiments, the amino acid at position 91 as set forth in SEQ ID NO: 1, 2, 3, 4, or 5 is one of the twenty natural amino acids other than V. In certain embodiments, the amino acid at position 91 as set forth in SEQ ID NO: 1, 2, 3, 4, or 5 is I.

In certain embodiments, the amino acid at position 92 as set forth in SEQ ID NO: 1, 2, 3, 4, or 5 is one of the twenty natural amino acids other than I. In certain embodiments, the amino acid at position 92 as set forth in SEQ ID NO: 1, 2, 3, 4, or 5 is A or L. In certain embodiments, the amino acid at position 92 as set forth in SEQ ID NO: 1, 2, 3, 4, or 5 is A. In certain embodiments, the amino acid at position 92 as set forth in SEQ ID NO: 1, 2, 3, 4, or 5 is L.

In certain embodiments, the amino acid at position 95 as set forth in SEQ ID NO: 1, 2, 3, 4, or 5 is one of the twenty natural amino acids other than E. In certain embodiments, the amino acid at position 95 as set forth in SEQ ID NO: 1, 2, 3, 4, or 5 is K, N, or Q. In certain embodiments, the amino acid at position 95 as set forth in SEQ ID NO: 1, 2, 3, 4, or 5 is K or Q. In certain embodiments, the amino acid at position 95 as set forth in SEQ ID NO: 1, 2, 3, 4, or 5 is K. In certain embodiments, the amino acid at position 95 as set forth in SEQ ID NO: 1, 2, 3, 4, or 5 is N. In certain embodiments, the amino acid at position 95 as set forth in SEQ ID NO: 1, 2, 3, 4, or 5 is Q.

In certain embodiments, the amino acid at position 127 as set forth in SEQ ID NO: 1, 2, 3, 4, or 5 is one of the twenty natural amino acids other than S. In certain embodiments, the amino acid at position 127 as set forth in SEQ ID NO: 1, 2, 3, 4, or 5 is A, E, F, or W. In certain embodiments, the amino acid at position 127 as set forth in SEQ ID NO: 1, 2, 3, 4, or 5 is A. In certain embodiments, the amino acid at position 127 as set forth in SEQ ID NO: 1, 2, 3, 4, or 5 is E. In certain embodiments, the amino acid at position 127 as set forth in SEQ ID NO: 1, 2, 3, 4, or 5 is F. In certain embodiments, the amino acid at position 127 as set forth in SEQ ID NO: 1, 2, 3, 4, or 5 is W.

In certain embodiments, the amino acid at position 130 as set forth in SEQ ID NO: 1, 2, 3, 4, or 5 is one of the twenty natural amino acids other than S. In certain embodiments, the amino acid at position 130 as set forth in SEQ ID NO: 1, 2, 3, 4, or 5 is A, E, F, or W. In certain embodiments, the amino acid at position 130 as set forth in SEQ ID NO: 1, 2, 3, 4, or 5 is A. In certain embodiments, the amino acid at position 130 as set forth in SEQ ID NO: 1, 2, 3, 4, or 5 is E. In certain embodiments, the amino acid at position 130 as set forth in SEQ ID NO: 1, 2, 3, 4, or 5 is F. In certain embodiments, the amino acid at position 130 as set forth in SEQ ID NO: 1, 2, 3, 4, or 5 is W.

In certain embodiments, the flexible peptide linker comprises an amino acid sequence selected from G, SG, GGS, and SEQ ID NOs: 7 to 9. In certain embodiments, the flexible peptide linker comprises an amino acid sequence of G. In certain embodiments, the flexible peptide linker comprises an amino acid sequence of SG. In certain embodiments, the flexible peptide linker comprises an amino acid sequence of GGS. In certain embodiments, the flexible peptide linker comprises an amino acid sequence of SEQ ID NO: 7. In certain embodiments, the flexible peptide linker comprises an amino acid sequence of SEQ ID NO: 8. In certain embodiments, the flexible peptide linker comprises an amino acid sequence of SEQ ID NO: 9.

In certain embodiments, the two amino acids that form the disulfide bond are at two different positions, each independently selected from positions 30 to 80 as set forth in SEQ ID NO: 1, 2, 3, 4, or 5. In certain embodiments, the two amino acids that form the disulfide bond are at two different positions, each independently selected from positions 35 to 72 as set forth in SEQ ID NO: 1, 2, 3, 4, or 5. In certain embodiments, the two amino acids that form the disulfide bond are at two different positions, each independently selected from positions 35 to 69 as set forth in SEQ ID NO: 1, 2, 3, 4, or 5.

In certain embodiments, the two amino acids that form the disulfide bond are at two different positions, each independently selected from positions N30 to L80 as set forth in SEQ ID NO: 1, 2, 3, 4, or 5. In certain embodiments, the two amino acids that form the disulfide bond are at two different positions, each independently selected from positions K35 to L72 as set forth in SEQ ID NO: 1, 2, 3, 4, or 5. In certain embodiments, the two amino acids that form the disulfide bond are at two different positions, each independently selected from positions K35 to V69 as set forth in SEQ ID NO: 1, 2, 3, 4, or 5.

In certain embodiments, the two amino acids that form the disulfide bond are at two different positions, each independently selected from positions 35, 38, 42, 45, 62, 69, and 72 as set forth in SEQ ID NO: 1, 2, 3, 4, or 5. In certain embodiments, one of the two amino acids that form the disulfide bond is at position 35, 38, 42, or 45; and the other is at position 62, 69, or 72 as set forth in SEQ ID NO: 1, 2, 3, 4, or 5. In certain embodiments, one of the two amino acids that form the disulfide bond is at position 35; and the other is at position 62, 69, or 72 as set forth in SEQ ID NO: 1, 2, 3, 4, or 5. In certain embodiments, one of the two amino acids that form the disulfide bond is at position 38; and the other is at position 62, 69, or 72 as set forth in SEQ ID NO: 1, 2, 3, 4, or 5. In certain embodiments, one of the two amino acids that form the disulfide bond is at position 42; and the other is at position 62, 69, or 72 as set forth in SEQ ID NO: 1, 2, 3, 4, or 5. In certain embodiments, one of the two amino acids that form the disulfide bond is at position 45; and the other is at position 62, 69, or 72 as set forth in SEQ ID NO: 1, 2, 3, 4, or 5. In certain embodiments, one of the two amino acids that form the disulfide bond is at position 35, 38, 42, or 45; and the other is at position 62 as set forth in SEQ ID NO: 1, 2, 3, 4, or 5. In certain embodiments, the two amino acids that form the disulfide bond are at positions 35, 38, 42, or 45; and the other is at position 69 as set forth in SEQ ID NO: 1, 2, 3, 4, or 5. In certain embodiments, the two amino acids that form the disulfide bond are at positions 35, 38, 42, or 45; and the other is at position 72 as set forth in SEQ ID NO: 1, 2, 3, 4, or 5.

In certain embodiments, the two amino acids that form the disulfide bond are at two different positions, each independently selected from positions K35, R38, F42, Y45, E62, V69, and L72 as set forth in SEQ ID NO: 1, 2, 3, 4, or 5. In certain embodiments, one of the two amino acids that form the disulfide bond is at position K35, R38, F42, or Y45; and the other is at position E62, V69, or L72 as set forth in SEQ ID NO: 1, 2, 3, 4, or 5. In certain embodiments, one of the two amino acids that form the disulfide bond is at position K35; and the other is at position E62, V69, or L72 as set forth in SEQ ID NO: 1, 2, 3, 4, or 5. In certain embodiments, one of the two amino acids that form the disulfide bond is at position R38; and the other is at position E62, V69, or L72 as set forth in SEQ ID NO: 1, 2, 3, 4, or 5. In certain embodiments, one of the two amino acids that form the disulfide bond is at position F42; and the other is at position E62, V69, or L72 as set forth in SEQ ID NO: 1, 2, 3, 4, or 5. In certain embodiments, one of the two amino acids that form the disulfide bond is at position Y45; and the other is at position E62, V69, or L72 as set forth in SEQ ID NO: 1, 2, 3, 4, or 5. In certain embodiments, one of the two amino acids that form the disulfide bond is at position K35, R38, F42, or Y45; and the other is at position F62 as set forth in SEQ ID NO: 1, 2, 3, 4, or 5. In certain embodiments, the two amino acids that form the disulfide bond are at positions K35, R38, F42, or Y45; and the other is at position V69 as set forth in SEQ ID NO: 1, 2, 3, 4, or 5. In certain embodiments, the two amino acids that form the disulfide bond are at positions K35, R38, F42, or Y45; and the other is at position L72 as set forth in SEQ ID NO: 1, 2, 3, 4, or 5.

In certain embodiments, the two amino acids that form the disulfide bond are at positions 35 and 72, 38 and 72, 42 and 69, 42 and 72, or 45 and 62 as set forth in SEQ ID NO: 1, 2, 3, 4, or 5. In certain embodiments, the two amino acids that form the disulfide bond are at positions 35 and 72 as set forth in SEQ ID NO: 1, 2, 3, 4, or 5. In certain embodiments, the two amino acids that form the disulfide bond are at positions 38 and 72 as set forth in SEQ ID NO: 1, 2, 3, 4, or 5. In certain embodiments, the two amino acids that form the disulfide bond are at positions 42 and 69 as set forth in SEQ ID NO: 1, 2, 3, 4, or 5. In certain embodiments, the two amino acids that form the disulfide bond are at positions 42 and 72 as set forth in SEQ ID NO: 1, 2, 3, 4, or 5. In certain embodiments, the two amino acids that form the disulfide bond are at positions 45 and 62 as set forth in SEQ ID NO: 1, 2, 3, 4, or 5.

In certain embodiments, the two amino acids that form the disulfide bond are at positions K35 and L72, R38 and L72, F42 and V69, F42 and L72, or Y45 and E62 as set forth in SEQ ID NO: 1, 2, 3, 4, or 5. In certain embodiments, the two amino acids that form the disulfide bond are at positions K35 and L72 as set forth in SEQ ID NO: 1, 2, 3, 4, or 5. In certain embodiments, the two amino acids that form the disulfide bond are at positions R38 and L72 as set forth in SEQ ID NO: 1, 2, 3, 4, or 5. In certain embodiments, the two amino acids that form the disulfide bond are at positions F42 and V69 as set forth in SEQ ID NO: 1, 2, 3, 4, or 5. In certain embodiments, the two amino acids that form the disulfide bond are at positions F42 and L72 as set forth in SEQ ID NO: 1, 2, 3, 4, or 5. In certain embodiments, the two amino acids that form the disulfide bond are at positions Y45 and E62 as set forth in SEQ ID NO: 1, 2, 3, 4, or 5.

In certain embodiments, the IL-15 hinge fragment-containing peptide comprises an amino acid sequence of one of SEQ ID NOs: 166 to 170 and 219 to 223.

In certain embodiments, the IL-15 hinge fragment-containing peptide comprises an amino acid sequence of SEQ ID NO: 166, 167, 168, 169, or 170. In certain embodiments, the IL-15 hinge fragment-containing peptide comprises an amino acid sequence of SEQ ID NO: 166. In certain embodiments, the IL-15 hinge fragment-containing peptide comprises an amino acid sequence of SEQ ID NO: 167. In certain embodiments, the IL-15 hinge fragment-containing peptide comprises an amino acid sequence of SEQ ID NO: 168. In certain embodiments, the IL-15 hinge fragment-containing peptide comprises an amino acid sequence of SEQ ID NO: 169. In certain embodiments, the IL-15 hinge fragment-containing peptide comprises an amino acid sequence of SEQ ID NO: 170.

In certain embodiments, the IL-15 hinge fragment-containing peptide comprises an amino acid sequence of SEQ ID NO: 219, 220, 221, 222, or 223. In certain embodiments, the IL-15 hinge fragment-containing peptide comprises an amino acid sequence of SEQ ID NO: 219. In certain embodiments, the IL-15 hinge fragment-containing peptide comprises an amino acid sequence of SEQ ID NO: 220. In certain embodiments, the IL-15 hinge fragment-containing peptide comprises an amino acid sequence of SEQ ID NO: 221. In certain embodiments, the IL-15 hinge fragment-containing peptide comprises an amino acid sequence of SEQ ID NO: 222. In certain embodiments, the IL-15 hinge fragment-containing peptide comprises an amino acid sequence of SEQ ID NO: 223.

In one embodiment, provided herein is an interleukin-2 polypeptide comprising an amino acid sequence of SEQ ID NO: 1, 2, 3, 4, or 5, wherein the interleukin-2 polypeptide comprises: (i) an amino acid substitution selected from K8D, K8E, K8Q, K9D, K9E, K9Q, Q13E, Q13N, E15K, E15Q, E15V, H16D, H16E, H16N, H16Q, L19S, M23K, K32D, K32E, K32Q, K76D, K76E, K76Q, H79D, H79E, H79Q, R81D, R81E, R81Q, D84T, S87D, S87E, N88A, V91I, I92A, I92L, E95K, E95N, E95Q, S127A, S127E, S127F, S127W, S130A, S130E, S130F, and S130W; (ii) a deletion or replacement of the amino acid residues from positions 30 to 35 having an amino acid sequence of SEQ ID NO: 10 with a flexible peptide linker having an amino acid sequence selected from G, SG, GGS, and SEQ ID NOs: 7 to 9; (iii) a disulfide bond formed between two amino acids at two different positions, each independently selected from positions K35, R38, F42, Y45, E62, V69, and L72; or (iv) a replacement of the amino acid residues from positions 29 to 50 having an amino acid sequence of SEQ ID NO: 171 with an IL-15 hinge fragment-containing peptide having an amino acid sequence of SEQ ID NO: 166, 167, 168, 169, or 170.

In another embodiment, provided herein is an interleukin-2 polypeptide comprising an amino acid sequence of SEQ ID NO: 1, 2, 3, 4, or 5, wherein the interleukin-2 polypeptide comprises: (i) an amino acid substitution selected from K8D, K8E, K8Q, K9D, K9E, K9Q, E15K, E15Q, H16D, H16E, H16Q, K32D, K32E, K32Q, K76D, K76E, K76Q, H79D, H79E, H79Q, R81D, R81E, R81Q, D84T, N88A, I92A, E95K, E95Q, S127A, S127E, S127F, S127W, S130A, S130E, S130F, and S130W; (ii) a deletion or replacement of the amino acid residues from positions 30 to 35 having an amino acid sequence of SEQ ID NO: 10 with a flexible peptide linker having an amino acid sequence selected from G, SG, GGS, and SEQ ID NOs: 7 to 9; (iii) a disulfide bond formed between two amino acids at two different positions, each independently selected from positions K35, R38, F42, Y45, E62, V69, and L72; or (iv) a replacement of the amino acid residues from positions 29 to 50 having an amino acid sequence of SEQ ID NO: 171 with an IL-15 hinge fragment-containing peptide having an amino acid sequence of SEQ ID NO: 166, 167, 168, 169, or 170.

In yet another embodiment, provided herein is an interleukin-2 polypeptide comprising an amino acid sequence of SEQ ID NO: 1, 2, 3, 4, or 5, wherein the interleukin-2 polypeptide comprises: (i) an amino acid substitution selected from K8E, K9E, E15K, E15Q, H16E, K32E, K76E, H79E, R81E, D84T, N88A, I92A, E95K, E95Q, S127A, and S130A; (ii) a deletion or replacement of the amino acid residues from positions 30 to 35 having an amino acid sequence of SEQ ID NO: 10 with a flexible peptide linker having an amino acid sequence selected from G, SG, GGS, and SEQ ID NOs: 7 to 9; (iii) a disulfide bond formed between two amino acids: one at position K35, R38, F42, or Y45, and the other at position E62, V69, or L72; or (iv) a replacement of the amino acid residues from positions 29 to 50 having an amino acid sequence of SEQ ID NO: 171 with an IL-15 hinge fragment-containing peptide having an amino acid sequence of SEQ ID NO: 166, 167, 168, 169, or 170.

In yet another embodiment, provided herein is an interleukin-2 polypeptide comprising an amino acid sequence of SEQ ID NO: 1, 2, 3, 4, or 5, wherein the interleukin-2 polypeptide comprises: (i) an amino acid substitution selected from K8D, K8E, K8Q, K9D, K9E, K9Q, E15K, E15Q, H16D, H16E, H16Q, K32D, K32E, K32Q, K76D, K76E, K76Q, H79D, H79E, H79Q, R81D, R81E, R81Q, D84T, N88A, I92A, E95K, E95Q, S127A, S127E, S127F, S127W, S130A, S130E, S130F, and S130W; or (ii) a deletion or replacement of the amino acid residues from positions 30 to 35 having an amino acid sequence of SEQ ID NO: 10 with a flexible peptide linker having an amino acid sequence selected from G, SG, GGS, and SEQ ID NOs: 7 to 9.

In still another embodiment, provided herein is an interleukin-2 polypeptide comprising an amino acid sequence of SEQ ID NO: 1, 2, 3, 4, or 5, wherein the interleukin-2 polypeptide comprises: (i) an amino acid substitution selected from K8E, K9E, E15K, E15Q, H16E, K32E, K76E, H79E, R81E, D84T, N88A, I92A, E95K, E95Q, S127A, and S130A; or (ii) a deletion or replacement of the amino acid residues from positions 30 to 35 having an amino acid sequence of SEQ ID NO: 10 with a flexible peptide linker having an amino acid sequence selected from G, SG, GGS, and SEQ ID NOs: 7 to 9.

In one embodiment, provided herein is an interleukin-2 polypeptide comprising an amino acid sequence of SEQ ID NO: 1, 2, 3, 4, or 5, wherein the interleukin-2 polypeptide comprises an amino acid substitution at position 8, 9, 13, 15, 16, 19, 23, 32, 76, 79, 81, 84, 87, 88, 91, 92, 95, 127, or 130 as set forth in SEQ ID NO: 1, 2, 3, 4, or 5; with the proviso that the amino acid substitution at position 88 is not N88R.

In another embodiment, provided herein is an interleukin-2 polypeptide comprising an amino acid sequence of SEQ ID NO: 1, 2, 3, 4, or 5, wherein the interleukin-2 polypeptide comprises an amino acid substitution at position K8, K9, Q13, E15, H16, L19, M23, K32, K76, H79, R81, D84, S87, N88, V91, I92, E95, S127, or S130 as set forth in SEQ ID NO: 1, 2, 3, 4, or 5; with the proviso that the amino acid substitution at position 88 is not N88R.

In yet another embodiment, provided herein is an interleukin-2 polypeptide comprising an amino acid sequence of SEQ ID NO: 1, 2, 3, 4, or 5, wherein the interleukin-2 polypeptide comprises an amino acid substitution of K8D, K8E, K8Q, K9D, K9E, K9Q, Q13E, Q13N, E15K, E15Q, E15V, H16D, H16E, H16N, H16Q, L19S, M23K, K32D, K32E, K32Q, K76D, K76E, K76Q, H79D, H79E, H79Q, R81D, R81E, R81Q, D84T, S87D, S87E, N88A, V91I, I92A, I92L, E95K, E95N, E95Q, S127A, S127E, S127F, S127W, S130A, S130E, S130F, or S130W.

In one embodiment, provided herein is an interleukin-2 polypeptide comprising an amino acid sequence of SEQ ID NO: 1, 2, 3, 4, or 5, wherein the interleukin-2 polypeptide comprises an amino acid substitution at position 8, 9, 15, 16, 32, 76, 79, 81, 84, 88, 92, 95, 127, or 130 as set forth in SEQ ID NO: 1, 2, 3, 4, or 5; with the proviso that the amino acid substitution at position 88 is not N88R.

In another embodiment, provided herein is an interleukin-2 polypeptide comprising an amino acid sequence of SEQ ID NO: 1, 2, 3, 4, or 5, wherein the interleukin-2 polypeptide comprises an amino acid substitution at position K8, K9, E15, H16, K32, K76, H79, R81, D84, N88, I92, E95, S127, or S130 as set forth in SEQ ID NO: 1, 2, 3, 4, or 5; with the proviso that the amino acid substitution at position 88 is not N88R.

In yet another embodiment, provided herein is an interleukin-2 polypeptide comprising an amino acid sequence of SEQ ID NO: 1, 2, 3, 4, or 5, wherein the interleukin-2 polypeptide comprises an amino acid substitution selected from K8D, K8E, K8Q, K9D, K9E, K9Q, E15K, E15Q, H16D, H16E, H16Q, K32D, K32E, K32Q, K76D, K76E, K76Q, H79D, H79E, H79Q, R81D, R81E, R81Q, D84T, N88A, I92A, E95K, E95Q, S127A, S127E, S127F, S127W, S130A, S130E, S130F, and S130W.

In still another embodiment, provided herein is an interleukin-2 polypeptide comprising an amino acid sequence of SEQ ID NO: 1, 2, 3, 4, or 5, wherein the interleukin-2 polypeptide comprises an amino acid substitution selected from K8E, K9E, E15K, E15Q, H16E, K32E, K76E, H79E, R81E, D84T, N88A, I92A, E95K, E95Q, S127A, and S130A.

In one embodiment, provided herein is an interleukin-2 polypeptide comprising an amino acid sequence of SEQ ID NO: 1, 2, 3, 4, or 5, wherein the interleukin-2 polypeptide comprises an amino acid substitution at position 13, 15, 16, 19, 23, 84, 87, 91, 92, or 95 as set forth in SEQ ID NO: 1, 2, 3, 4, or 5.

In another embodiment, provided herein is an interleukin-2 polypeptide comprising an amino acid sequence of SEQ ID NO: 1, 2, 3, 4, or 5, wherein the interleukin-2 polypeptide comprises an amino acid substitution at position Q13, E15, H16, L19, M23, D84, S87, V91, I92, or E95 as set forth in SEQ ID NO: 1, 2, 3, 4, or 5.

In yet another embodiment, provided herein is an interleukin-2 polypeptide comprising an amino acid sequence of SEQ ID NO: 1, 2, 3, 4, or 5, wherein the interleukin-2 polypeptide comprises an amino acid substitution of Q13E, Q13N, E15V, H16N, L19S, M23K, D84T, S87D, S87E, V91I, I92L, E95N, or E95Q.

In one embodiment, provided herein is an interleukin-2 polypeptide comprising an amino acid sequence of SEQ ID NO: 1, 2, 3, 4, or 5, wherein the interleukin-2 polypeptide comprises an amino acid substitution at position 13, 15, 16, 23, 91, or 95 as set forth in SEQ ID NO: 1, 2, 3, 4, or 5.

In another embodiment, provided herein is an interleukin-2 polypeptide comprising an amino acid sequence of SEQ ID NO: 1, 2, 3, 4, or 5, wherein the interleukin-2 polypeptide comprises an amino acid substitution at position Q13, E15, H16, M23, V91, or E95 as set forth in SEQ ID NO: 1, 2, 3, 4, or 5.

In yet another embodiment, provided herein is an interleukin-2 polypeptide comprising an amino acid sequence of SEQ ID NO: 1, 2, 3, 4, or 5, wherein the interleukin-2 polypeptide comprises an amino acid substitution of Q13E, E15V, H16N, M23K, V91I, or E95N.

In one embodiment, provided herein is an interleukin-2 polypeptide comprising an amino acid sequence of SEQ ID NO: 1, 2, 3, 4, or 5, wherein the interleukin-2 polypeptide comprises an amino acid substitution at position 13, 19, 84, 87, 91, 92, or 95 as set forth in SEQ ID NO: 1, 2, 3, 4, or 5.

In another embodiment, provided herein is an interleukin-2 polypeptide comprising an amino acid sequence of SEQ ID NO: 1, 2, 3, 4, or 5, wherein the interleukin-2 polypeptide comprises an amino acid substitution at position Q13, L19, D84, S87, V91, I92, or E95 as set forth in SEQ ID NO: 1, 2, 3, 4, or 5.

In yet another embodiment, provided herein is an interleukin-2 polypeptide comprising an amino acid sequence of SEQ ID NO: 1, 2, 3, 4, or 5, wherein the interleukin-2 polypeptide comprises an amino acid substitution of Q13N, L19S, D84T, S87D, S87E, V91I, I92L, E95N, or E95Q.

In one embodiment, the interleukin-2 polypeptide provided herein comprises an amino acid sequence selected from SEQ ID NOs: 11 to 25, 95 to 109, 119 to 165, 177 to 182, and 189 to 218. In another embodiment, the interleukin-2 polypeptide provided herein comprises an amino acid sequence selected from SEQ ID NOs: 11 to 25, 119 to 127, 137 to 147, 159 to 165, and 189 to 203. In yet another embodiment, the interleukin-2 polypeptide provided herein comprises an amino acid sequence selected from SEQ ID NOs: 95 to 109, 128 to 136, 148 to 158, 177 to 182, and 204 to 218.

In one embodiment, the amino acid sequence of the interleukin-2 polypeptide provided herein is one selected from SEQ ID NOs: 11 to 25, 95 to 109, 119 to 165, 177 to 182, and 189 to 218. In another embodiment, the amino acid sequence of the interleukin-2 polypeptide provided herein is one selected from SEQ ID NOs: 11 to 25, 119 to 127, 137 to 147, 159 to 165, and 189 to 203. In yet another embodiment, the amino acid sequence of the interleukin-2 polypeptide provided herein is one selected from SEQ ID NOs: 95 to 109, 128 to 136, 148 to 158, 177 to 182, and 204 to 218.

In one embodiment, provided herein is an interleukin-2 polypeptide that has an enhanced stability and/or an enhanced production yield as compared to a wild-type IL-2.

In one embodiment, the wild-type interleukin-2 is a human wild-type interleukin-2. In another embodiment, the human wild-type interleukin-2 has an amino acid sequence of SEQ ID NO: 1, 2, 3, 4, or 5. In yet another embodiment, the human wild-type interleukin-2 has an amino acid sequence of SEQ ID NO: 1. In yet another embodiment, the human wild-type interleukin-2 has an amino acid sequence of SEQ ID NO: 2. In yet another embodiment, the human wild-type interleukin-2 has an amino acid sequence of SEQ ID NO: 3. In yet another embodiment, the human wild-type interleukin-2 has an amino acid sequence of SEQ ID NO: 4. In still another embodiment, the human wild-type interleukin-2 has an amino acid sequence of SEQ ID NO: 5.

In one embodiment, provided herein is an interleukin-2 polypeptide comprising an amino acid sequence of SEQ ID NO: 1, 2, 3, 4, or 5, wherein the interleukin-2 polypeptide comprises an amino acid substitution at position 8, 9, 16, 32, 76, 79, or 81 as set forth in SEQ ID NO: 1, 2, 3, 4, or 5.

In certain embodiments, the interleukin-2 polypeptide provided herein comprises an amino acid substitution at position 8 as set forth in SEQ ID NO: 1, 2, 3, 4, or 5 with one of the twenty natural amino acids other than K. In certain embodiments, the interleukin-2 polypeptide provided herein comprises an amino acid substitution at position 9 as set forth in SEQ ID NO: 1, 2, 3, 4, or 5 with one of the twenty natural amino acids other than K. In certain embodiments, the interleukin-2 polypeptide provided herein comprises an amino acid substitution at position 16 as set forth in SEQ ID NO: 1, 2, 3, 4, or 5 with one of the twenty natural amino acids other than H. In certain embodiments, the interleukin-2 polypeptide provided herein comprises an amino acid substitution at position 32 as set forth in SEQ ID NO: 1, 2, 3, 4, or 5 with one of the twenty natural amino acids other than K. In certain embodiments, the interleukin-2 polypeptide provided herein comprises an amino acid substitution at position 76 as set forth in SEQ ID NO: 1, 2, 3, 4, or 5 with one of the twenty natural amino acids other than K. In certain embodiments, the interleukin-2 polypeptide provided herein comprises an amino acid substitution at position 79 as set forth in SEQ ID NO: 1, 2, 3, 4, or 5 with one of the twenty natural amino acids other than H. In certain embodiments, the interleukin-2 polypeptide provided herein comprises an amino acid substitution at position 81 as set forth in SEQ ID NO: 1, 2, 3, 4, or 5 with one of the twenty natural amino acids other than R.

In another embodiment, provided herein is an interleukin-2 polypeptide comprising an amino acid sequence of SEQ ID NO: 1, 2, 3, 4, or 5, wherein the interleukin-2 polypeptide comprises an amino acid substitution at position K8, K9, H16, K32, K76, H79, or R81 as set forth in SEQ ID NO: 1, 2, 3, 4, or 5.

In certain embodiments, the interleukin-2 polypeptide provided herein comprises an amino acid substitution at position K8 as set forth in SEQ ID NO: 1, 2, 3, 4, or 5 with one of the twenty natural amino acids other than K. In certain embodiments, the interleukin-2 polypeptide provided herein comprises an amino acid substitution at position K9 as set forth in SEQ ID NO: 1, 2, 3, 4, or 5 with one of the twenty natural amino acids other than K. In certain embodiments, the interleukin-2 polypeptide provided herein comprises an amino acid substitution at position H16 as set forth in SEQ ID NO: 1, 2, 3, 4, or 5 with one of the twenty natural amino acids other than H. In certain embodiments, the interleukin-2 polypeptide provided herein comprises an amino acid substitution at position K32 as set forth in SEQ ID NO: 1, 2, 3, 4, or 5 with one of the twenty natural amino acids other than K. In certain embodiments, the interleukin-2 polypeptide provided herein comprises an amino acid substitution at position K76 as set forth in SEQ ID NO: 1, 2, 3, 4, or 5 with one of the twenty natural amino acids other than K. In certain embodiments, the interleukin-2 polypeptide provided herein comprises an amino acid substitution at position H79 as set forth in SEQ ID NO: 1, 2, 3, 4, or 5 with one of the twenty natural amino acids other than H. In certain embodiments, the interleukin-2 polypeptide provided herein comprises an amino acid substitution at position R81 as set forth in SEQ ID NO: 1, 2, 3, 4, or 5 with one of the twenty natural amino acids other than R.

In yet another embodiment, provided herein is an interleukin-2 polypeptide comprising an amino acid sequence of SEQ ID NO: 1, 2, 3, 4, or 5, wherein the interleukin-2 polypeptide comprises an amino acid substitution selected from K8D, K8E, K8Q, K9D, K9E, K9Q, H16D, H16E, H16Q, K32D, K32E, K32Q, K76D, K76E, K76Q, H79D, H79E, H79Q, R81D, R81E, and R81Q.

In certain embodiments, the interleukin-2 polypeptide provided herein comprises an amino acid substitution selected from K8D, K8E, and K8Q. In certain embodiments, the interleukin-2 polypeptide provided herein comprises an amino acid substitution selected from K9D, K9E, and K9Q. In certain embodiments, the interleukin-2 polypeptide provided herein comprises an amino acid substitution selected from H16D, H16E, and H16Q. In certain embodiments, the interleukin-2 polypeptide provided herein comprises an amino acid substitution selected from K32D, K32E, and K32Q. In certain embodiments, the interleukin-2 polypeptide provided herein comprises an amino acid substitution selected from K76D, K76E, and K76Q. In certain embodiments, the interleukin-2 polypeptide provided herein comprises an amino acid substitution selected from H79D, H79E, and H79Q. In certain embodiments, the interleukin-2 polypeptide provided herein comprises an amino acid substitution selected from R81D, R81E, and R81Q.

In still another embodiment, provided herein is an interleukin-2 polypeptide comprising an amino acid sequence of SEQ ID NO: 1, 2, 3, 4, or 5, wherein the interleukin-2 polypeptide comprises an amino acid substitution selected from K8E, K9E, H16E, K32E, K76E, H79E, and R81E.

In certain embodiments, the interleukin-2 polypeptide provided herein comprises an amino acid substitution of K8E. In certain embodiments, the interleukin-2 polypeptide provided herein comprises an amino acid substitution of K9E. In certain embodiments, the interleukin-2 polypeptide provided herein comprises an amino acid substitution of H16E. In certain embodiments, the interleukin-2 polypeptide provided herein comprises an amino acid substitution of K32E. In certain embodiments, the interleukin-2 polypeptide provided herein comprises an amino acid substitution of K76E. In certain embodiments, the interleukin-2 polypeptide provided herein comprises an amino acid substitution of H79E. In certain embodiments, the interleukin-2 polypeptide provided herein comprises an amino acid substitution of R81E.

In one embodiment, the interleukin-2 polypeptide provided herein comprises an amino acid sequence selected from SEQ ID NOs: 11 to 25, 95 to 109, and 137 to 158. In another embodiment, the interleukin-2 polypeptide provided herein comprises an amino acid sequence selected from SEQ ID NOs: 11 to 25 and 119 to 127. In yet another embodiment, the interleukin-2 polypeptide provided herein comprises an amino acid sequence selected from SEQ ID NOs: 95 to 109 and 128 to 158.

In one embodiment, the amino acid sequence of the interleukin-2 polypeptide provided herein is one selected from SEQ ID NOs: 11 to 25, 95 to 109, and 137 to 158. In another embodiment, the amino acid sequence of the interleukin-2 polypeptide provided herein is one selected from SEQ ID NOs: 11 to 25 and 137 to 147. In yet another embodiment, the amino acid sequence of the interleukin-2 polypeptide provided herein is one selected from SEQ ID NOs: 95 to 109 and 148 to 158.

In one embodiment, provided herein is an interleukin-2 polypeptide comprising an amino acid sequence of SEQ ID NO: 1, 2, 3, 4, or 5, wherein the interleukin-2 polypeptide comprises two, three, four, five, or six amino acid substitutions, each independently at position 9, 16, 32, 76, 79, or 81 as set forth in SEQ ID NO: 1, 2, 3, 4, or 5.

In one embodiment, provided herein is an interleukin-2 polypeptide comprising an amino acid sequence of SEQ ID NO: 1, 2, 3, 4, or 5, wherein the interleukin-2 polypeptide comprises two amino acid substitutions at two of positions 9, 16, 32, 76, 79, and 81 as set forth in SEQ ID NO: 1, 2, 3, 4, or 5.

In another embodiment, provided herein is an interleukin-2 polypeptide comprising an amino acid sequence of SEQ ID NO: 1, 2, 3, 4, or 5, wherein the interleukin-2 polypeptide comprises three amino acid substitutions at three of positions 9, 16, 32, 76, 79, and 81 as set forth in SEQ ID NO: 1, 2, 3, 4, or 5.

In yet another embodiment, provided herein is an interleukin-2 polypeptide comprising an amino acid sequence of SEQ ID NO: 1, 2, 3, 4, or 5, wherein the interleukin-2 polypeptide comprises four amino acid substitutions at four of positions 9, 16, 32, 76, 79, and 81 as set forth in SEQ ID NO: 1, 2, 3, 4, or 5.

In yet another embodiment, provided herein is an interleukin-2 polypeptide comprising an amino acid sequence of SEQ ID NO: 1, 2, 3, 4, or 5, wherein the interleukin-2 polypeptide comprises five amino acid substitutions at five of positions 9, 16, 32, 76, 79, and 81 as set forth in SEQ ID NO: 1, 2, 3, 4, or 5.

In still another embodiment, provided herein is an interleukin-2 polypeptide comprising an amino acid sequence of SEQ ID NO: 1, 2, 3, 4, or 5, wherein the interleukin-2 polypeptide comprises six amino acid substitutions at positions 9, 16, 32, 76, 79, and 81 as set forth in SEQ ID NO: 1, 2, 3, 4, or 5.

In one embodiment, provided herein is an interleukin-2 polypeptide comprising an amino acid sequence of SEQ ID NO: 1, 2, 3, 4, or 5, wherein the interleukin-2 polypeptide comprises two amino acid substitutions: one at position 8 and the other at position 9, 16, 32, 76, 79, or 81 as set forth in SEQ ID NO: 1, 2, 3, 4, or 5.

In certain embodiments, the interleukin-2 polypeptide provided herein comprises amino acid substitutions at positions 8 and 9 as set forth in SEQ ID NO: 1, 2, 3, 4, or 5. In certain embodiments, the interleukin-2 polypeptide provided herein comprises amino acid substitutions at positions 8 and 16 as set forth in SEQ ID NO: 1, 2, 3, 4, or 5. In certain embodiments, the interleukin-2 polypeptide provided herein comprises amino acid substitutions at positions 8 and 32 as set forth in SEQ ID NO: 1, 2, 3, 4, or 5. In certain embodiments, the interleukin-2 polypeptide provided herein comprises amino acid substitutions at positions 8 and 76 as set forth in SEQ ID NO: 1, 2, 3, 4, or 5. In certain embodiments, the interleukin-2 polypeptide provided herein comprises amino acid substitutions at positions 8 and 79 as set forth in SEQ ID NO: 1, 2, 3, 4, or 5. In certain embodiments, the interleukin-2 polypeptide provided herein comprises amino acid substitutions at positions 8 and 81 as set forth in SEQ ID NO: 1, 2, 3, 4, or 5.

In another embodiment, provided herein is an interleukin-2 polypeptide comprising an amino acid sequence of SEQ ID NO: 1, 2, 3, 4, or 5, wherein the interleukin-2 polypeptide comprises two amino acid substitutions: one at position 9 and the other at position 8, 16, 32, 76, 79, or 81 as set forth in SEQ ID NO: 1, 2, 3, 4, or 5.

In certain embodiments, the interleukin-2 polypeptide provided herein comprises amino acid substitutions at positions 9 and 16 as set forth in SEQ ID NO: 1, 2, 3, 4, or 5. In certain embodiments, the interleukin-2 polypeptide provided herein comprises amino acid substitutions at positions 9 and 32 as set forth in SEQ ID NO: 1, 2, 3, 4, or 5. In certain embodiments, the interleukin-2 polypeptide provided herein comprises amino acid substitutions at positions 9 and 76 as set forth in SEQ ID NO: 1, 2, 3, 4, or 5. In certain embodiments, the interleukin-2 polypeptide provided herein comprises amino acid substitutions at positions 9 and 79 as set forth in SEQ ID NO: 1, 2, 3, 4, or 5. In certain embodiments, the interleukin-2 polypeptide provided herein comprises amino acid substitutions at positions 9 and 81 as set forth in SEQ ID NO: 1, 2, 3, 4, or 5.

In yet another embodiment, provided herein is an interleukin-2 polypeptide comprising an amino acid sequence of SEQ ID NO: 1, 2, 3, 4, or 5, wherein the interleukin-2 polypeptide comprises two amino acid substitutions: one at position 16 and the other at position 8, 9, 32, 76, 79, or 81 as set forth in SEQ ID NO: 1, 2, 3, 4, or 5.

In certain embodiments, the interleukin-2 polypeptide provided herein comprises amino acid substitutions at positions 16 and 32 as set forth in SEQ ID NO: 1, 2, 3, 4, or 5. In certain embodiments, the interleukin-2 polypeptide provided herein comprises amino acid substitutions at positions 16 and 76 as set forth in SEQ ID NO: 1, 2, 3, 4, or 5. In certain embodiments, the interleukin-2 polypeptide provided herein comprises amino acid substitutions at positions 16 and 79 as set forth in SEQ ID NO: 1, 2, 3, 4, or 5. In certain embodiments, the interleukin-2 polypeptide provided herein comprises amino acid substitutions at positions 16 and 81 as set forth in SEQ ID NO: 1, 2, 3, 4, or 5.

In yet another embodiment, provided herein is an interleukin-2 polypeptide comprising an amino acid sequence of SEQ ID NO: 1, 2, 3, 4, or 5, wherein the interleukin-2 polypeptide comprises two amino acid substitutions: one at position 32 and the other at position 8, 9, 16, 76, 79, or 81 as set forth in SEQ ID NO: 1, 2, 3, 4, or 5.

In certain embodiments, the interleukin-2 polypeptide provided herein comprises amino acid substitutions at positions 32 and 76 as set forth in SEQ ID NO: 1, 2, 3, 4, or 5. In certain embodiments, the interleukin-2 polypeptide provided herein comprises amino acid substitutions at positions 32 and 79 as set forth in SEQ ID NO: 1, 2, 3, 4, or 5. In certain embodiments, the interleukin-2 polypeptide provided herein comprises amino acid substitutions at positions 32 and 81 as set forth in SEQ ID NO: 1, 2, 3, 4, or 5.

In yet another embodiment, provided herein is an interleukin-2 polypeptide comprising an amino acid sequence of SEQ ID NO: 1, 2, 3, 4, or 5, wherein the interleukin-2 polypeptide comprises two amino acid substitutions: one at position 76 and the other at position 8, 9, 16, 32, 79, or 81 as set forth in SEQ ID NO: 1, 2, 3, 4, or 5.

In certain embodiments, the interleukin-2 polypeptide provided herein comprises amino acid substitutions at positions 76 and 79 as set forth in SEQ ID NO: 1, 2, 3, 4, or 5. In certain embodiments, the interleukin-2 polypeptide provided herein comprises amino acid substitutions at positions 76 and 81 as set forth in SEQ ID NO: 1, 2, 3, 4, or 5.

In still another embodiment, provided herein is an interleukin-2 polypeptide comprising an amino acid sequence of SEQ ID NO: 1, 2, 3, 4, or 5, wherein the interleukin-2 polypeptide comprises two amino acid substitutions: one at position 79 and the other at position 8, 9, 16, 32, 76, or 81 as set forth in SEQ ID NO: 1, 2, 3, 4, or 5.

In certain embodiments, the interleukin-2 polypeptide provided herein comprises amino acid substitutions at positions 79 and 81 as set forth in SEQ ID NO: 1, 2, 3, 4, or 5.

In one embodiment, provided herein is an interleukin-2 polypeptide comprising an amino acid sequence of SEQ ID NO: 1, 2, 3, 4, or 5, wherein the interleukin-2 polypeptide comprises two amino acid substitutions: one at position K8 and the other at position K9, H16, K32, K76, H79, or R81 as set forth in SEQ ID NO: 1, 2, 3, 4, or 5.

In certain embodiments, the interleukin-2 polypeptide provided herein comprises amino acid substitutions at positions K8 and K9 as set forth in SEQ ID NO: 1, 2, 3, 4, or 5. In certain embodiments, the interleukin-2 polypeptide provided herein comprises amino acid substitutions at positions K8 and H16 as set forth in SEQ ID NO: 1, 2, 3, 4, or 5. In certain embodiments, the interleukin-2 polypeptide provided herein comprises amino acid substitutions at positions K8 and K32 as set forth in SEQ ID NO: 1, 2, 3, 4, or 5. In certain embodiments, the interleukin-2 polypeptide provided herein comprises amino acid substitutions at positions K8 and K76 as set forth in SEQ ID NO: 1, 2, 3, 4, or 5. In certain embodiments, the interleukin-2 polypeptide provided herein comprises amino acid substitutions at positions K8 and H79 as set forth in SEQ ID NO: 1, 2, 3, 4, or 5. In certain embodiments, the interleukin-2 polypeptide provided herein comprises amino acid substitutions at positions K8 and R81 as set forth in SEQ ID NO: 1, 2, 3, 4, or 5.

In another embodiment, provided herein is an interleukin-2 polypeptide comprising an amino acid sequence of SEQ ID NO: 1, 2, 3, 4, or 5, wherein the interleukin-2 polypeptide comprises two amino acid substitutions: one at position K9 and the other at position K8, H16, K32, K76, H79, or R81 as set forth in SEQ ID NO: 1, 2, 3, 4, or 5.

In certain embodiments, the interleukin-2 polypeptide provided herein comprises amino acid substitutions at positions K9 and H16 as set forth in SEQ ID NO: 1, 2, 3, 4, or 5. In certain embodiments, the interleukin-2 polypeptide provided herein comprises amino acid substitutions at positions K9 and K32 as set forth in SEQ ID NO: 1, 2, 3, 4, or 5. In certain embodiments, the interleukin-2 polypeptide provided herein comprises amino acid substitutions at positions K9 and K76 as set forth in SEQ ID NO: 1, 2, 3, 4, or 5. In certain embodiments, the interleukin-2 polypeptide provided herein comprises amino acid substitutions at positions K9 and H79 as set forth in SEQ ID NO: 1, 2, 3, 4, or 5. In certain embodiments, the interleukin-2 polypeptide provided herein comprises amino acid substitutions at positions K9 and R81 as set forth in SEQ ID NO: 1, 2, 3, 4, or 5.

In yet another embodiment, provided herein is an interleukin-2 polypeptide comprising an amino acid sequence of SEQ ID NO: 1, 2, 3, 4, or 5, wherein the interleukin-2 polypeptide comprises two amino acid substitutions: one at position H16 and the other at position K8, K9, K32, K76, H79, or R81 as set forth in SEQ ID NO: 1, 2, 3, 4, or 5.

In certain embodiments, the interleukin-2 polypeptide provided herein comprises amino acid substitutions at positions H16 and K32 as set forth in SEQ ID NO: 1, 2, 3, 4, or 5. In certain embodiments, the interleukin-2 polypeptide provided herein comprises amino acid substitutions at positions H16 and K76 as set forth in SEQ ID NO: 1, 2, 3, 4, or 5. In certain embodiments, the interleukin-2 polypeptide provided herein comprises amino acid substitutions at positions H16 and H79 as set forth in SEQ ID NO: 1, 2, 3, 4, or 5. In certain embodiments, the interleukin-2 polypeptide provided herein comprises amino acid substitutions at positions H16 and R81 as set forth in SEQ ID NO: 1, 2, 3, 4, or 5.

In yet another embodiment, provided herein is an interleukin-2 polypeptide comprising an amino acid sequence of SEQ ID NO: 1, 2, 3, 4, or 5, wherein the interleukin-2 polypeptide comprises two amino acid substitutions: one at position K32 and the other at position K8, K9, H16, K76, H79, or R81 as set forth in SEQ ID NO: 1, 2, 3, 4, or 5.

In certain embodiments, the interleukin-2 polypeptide provided herein comprises amino acid substitutions at positions K32 and K76 as set forth in SEQ ID NO: 1, 2, 3, 4, or 5. In certain embodiments, the interleukin-2 polypeptide provided herein comprises amino acid substitutions at positions K32 and H79 as set forth in SEQ ID NO: 1, 2, 3, 4, or 5. In certain embodiments, the interleukin-2 polypeptide provided herein comprises amino acid substitutions at positions K32 and R81 as set forth in SEQ ID NO: 1, 2, 3, 4, or 5.

In still another embodiment, provided herein is an interleukin-2 polypeptide comprising an amino acid sequence of SEQ ID NO: 1, 2, 3, 4, or 5, wherein the interleukin-2 polypeptide comprises two amino acid substitutions: one at position K76 and the other at position K8, K9, H16, K32, H79, or R81 as set forth in SEQ ID NO: 1, 2, 3, 4, or 5.

In certain embodiments, the interleukin-2 polypeptide provided herein comprises amino acid substitutions at positions K76 and H79 as set forth in SEQ ID NO: 1, 2, 3, 4, or 5. In certain embodiments, the interleukin-2 polypeptide provided herein comprises amino acid substitutions at positions K76 and R81 as set forth in SEQ ID NO: 1, 2, 3, 4, or 5.

In still another embodiment, provided herein is an interleukin-2 polypeptide comprising an amino acid sequence of SEQ ID NO: 1, 2, 3, 4, or 5, wherein the interleukin-2 polypeptide comprises two amino acid substitutions: one at position H79 and the other at position K8, K9, H16, K32, K76, or R81 as set forth in SEQ ID NO: 1, 2, 3, 4, or 5.

In certain embodiments, the interleukin-2 polypeptide provided herein comprises amino acid substitutions at positions H79 and R81 as set forth in SEQ ID NO: 1, 2, 3, 4, or 5.

In one embodiment, provided herein is an interleukin-2 polypeptide comprising an amino acid sequence of SEQ ID NO: 1, 2, 3, 4, or 5, wherein the interleukin-2 polypeptide comprises two amino acid substitutions: one selected from K8D, K8E, and K8Q; and the other selected from K9D, K9E, K9Q, H16D, H16E, H16Q, K32D, K32E, K32Q, K76D, K76E, K76Q, H79D, H79E, H79Q, R81D, R81E, and R81Q.

In certain embodiments, the interleukin-2 polypeptide provided herein comprises two amino acid substitutions: one selected from K8D, K8E, and K8Q; and the other selected from K9D, K9E, and K9Q. In certain embodiments, the interleukin-2 polypeptide provided herein comprises two amino acid substitutions: one selected from K8D, K8E, and K8Q; and the other selected from H16D, H16E, and H16Q. In certain embodiments, the interleukin-2 polypeptide provided herein comprises two amino acid substitutions: one selected from K8D, K8E, and K8Q; and the other selected from K32D, K32E, and K32Q. In certain embodiments, the interleukin-2 polypeptide provided herein comprises two amino acid substitutions: one selected from K8D, K8E, and K8Q; and the other selected from K76D, K76E, and K76Q. In certain embodiments, the interleukin-2 polypeptide provided herein comprises two amino acid substitutions: one selected from K8D, K8E, and K8Q; and the other selected from H79D, H79E, and H79Q. In certain embodiments, the interleukin-2 polypeptide provided herein comprises two amino acid substitutions: one selected from K8D, K8E, and K8Q; and the other selected from R81D, R81E, and R81Q.

In another embodiment, provided herein is an interleukin-2 polypeptide comprising an amino acid sequence of SEQ ID NO: 1, 2, 3, 4, or 5, wherein the interleukin-2 polypeptide comprises two amino acid substitutions: one selected from K9D, K9E, and K9Q; and the other selected from K8D, K8E, K8Q, H16D, H16E, H16Q, K32D, K32E, K32Q, K76D, K76E, K76Q, H79D, H79E, H79Q, R81D, R81E, and R81Q.

In certain embodiments, the interleukin-2 polypeptide provided herein comprises two amino acid substitutions: one selected from K9D, K9E, and K9Q; and the other selected from H16D, H16E, and H16Q. In certain embodiments, the interleukin-2 polypeptide provided herein comprises two amino acid substitutions: one selected from K9D, K9E, and K9Q; and the other selected from K32D, K32E, and K32Q. In certain embodiments, the interleukin-2 polypeptide provided herein comprises two amino acid substitutions: one selected from K9D, K9E, and K9Q; and the other selected from K76D, K76E, and K76Q. In certain embodiments, the interleukin-2 polypeptide provided herein comprises two amino acid substitutions: one selected from K9D, K9E, and K9Q; and the other selected from H79D, H79E, and H79Q. In certain embodiments, the interleukin-2 polypeptide provided herein comprises two amino acid substitutions: one selected from K9D, K9E, and K9Q; and the other selected from R81D, R81E, and R81Q.

In yet another embodiment, provided herein is an interleukin-2 polypeptide comprising an amino acid sequence of SEQ ID NO: 1, 2, 3, 4, or 5, wherein the interleukin-2 polypeptide comprises two amino acid substitutions: one selected from H16D, H16E, and H16Q; and the other selected from K8D, K8E, K8Q, K9D, K9E, K9Q, K32D, K32E, K32Q, K76D, K76E, K76Q, H79D, H79E, H79Q, R81D, R81E, and R81Q.

In certain embodiments, the interleukin-2 polypeptide provided herein comprises two amino acid substitutions: one selected from H16D, H16E, and H16Q; and the other selected from K32D, K32E, and K32Q. In certain embodiments, the interleukin-2 polypeptide provided herein comprises two amino acid substitutions: one selected from H16D, H16E, and H16Q; and the other selected from K76D, K76E, and K76Q. In certain embodiments, the interleukin-2 polypeptide provided herein comprises two amino acid substitutions: one selected from H16D, H16E, and H16Q; and the other selected from H79D, H79E, and H79Q. In certain embodiments, the interleukin-2 polypeptide provided herein comprises two amino acid substitutions: one selected from H16D, H16E, and H16Q; and the other selected from R81D, R81E, and R81Q.

In yet another embodiment, provided herein is an interleukin-2 polypeptide comprising an amino acid sequence of SEQ ID NO: 1, 2, 3, 4, or 5, wherein the interleukin-2 polypeptide comprises two amino acid substitutions: one selected from K32D, K32E, and K32Q; and the other selected from K8D, K8E, K8Q, K9D, K9E, K9Q, H16D, H16E, H16Q, K76D, K76E, K76Q, H79D, H79E, H79Q, R81D, R81E, and R81Q.

In certain embodiments, the interleukin-2 polypeptide provided herein comprises two amino acid substitutions: one selected from K32D, K32E, and K32Q; and the other selected from K76D, K76E, and K76Q. In certain embodiments, the interleukin-2 polypeptide provided herein comprises two amino acid substitutions: one selected from K32D, K32E, and K32Q; and the other selected from H79D, H79E, and H79Q. In certain embodiments, the interleukin-2 polypeptide provided herein comprises two amino acid substitutions: one selected from K32D, K32E, and K32Q; and the other selected from R81D, R81E, and R81Q.

In yet another embodiment, provided herein is an interleukin-2 polypeptide comprising an amino acid sequence of SEQ ID NO: 1, 2, 3, 4, or 5, wherein the interleukin-2 polypeptide comprises two amino acid substitutions: one selected from K76D, K76E, and K76Q; and the other selected from K8D, K8E, K8Q, K9D, K9E, K9Q, H16D, H16E, H16Q, K32D, K32E, K32Q, H79D, H79E, H79Q, R81D, R81E, and R81Q.

In certain embodiments, the interleukin-2 polypeptide provided herein comprises two amino acid substitutions: one selected from K76D, K76E, and K76Q; and the other selected from H79D, H79E, and H79Q. In certain embodiments, the interleukin-2 polypeptide provided herein comprises two amino acid substitutions: one selected from K76D, K76E, and K76Q; and the other selected from R81D, R81E, and R81Q.

In still another embodiment, provided herein is an interleukin-2 polypeptide comprising an amino acid sequence of SEQ ID NO: 1, 2, 3, 4, or 5, wherein the interleukin-2 polypeptide comprises two amino acid substitutions: one selected from H79D, H79E, and H79Q; and the other selected from K8D, K8E, K8Q, K9D, K9E, K9Q, H16D, H16E, H16Q, K32D, K32E, K32Q, K76D, K76E, K76Q, R81D, R81E, and R81Q.

In certain embodiments, the interleukin-2 polypeptide provided herein comprises two amino acid substitutions: one selected from H79D, H79E, and H79Q; and the other selected from R81D, R81E, and R81Q.

In one embodiment, provided herein is an interleukin-2 polypeptide comprising an amino acid sequence of SEQ ID NO: 1, 2, 3, 4, or 5, wherein the interleukin-2 polypeptide comprises two amino acid substitutions: K8E and one selected from K9E, H16E, K32E, K76E, H79E, and R81E.

In certain embodiments, the interleukin-2 polypeptide provided herein comprises amino acid substitutions of K8E and K9E. In certain embodiments, the interleukin-2 polypeptide provided herein comprises amino acid substitutions of K8E and H16E. In certain embodiments, the interleukin-2 polypeptide provided herein comprises amino acid substitutions of K8E and K32E. In certain embodiments, the interleukin-2 polypeptide provided herein comprises amino acid substitutions of K8E and K76E. In certain embodiments, the interleukin-2 polypeptide provided herein comprises amino acid substitutions of K8E and H79E. In certain embodiments, the interleukin-2 polypeptide provided herein comprises amino acid substitutions of K8E and R81E.

In another embodiment, provided herein is an interleukin-2 polypeptide comprising an amino acid sequence of SEQ ID NO: 1, 2, 3, 4, or 5, wherein the interleukin-2 polypeptide comprises two amino acid substitutions: K9E and one selected from K8E, H16E, K32E, K76E, H79E, and R81E.

In certain embodiments, the interleukin-2 polypeptide provided herein comprises amino acid substitutions of K9E and H16E. In certain embodiments, the interleukin-2 polypeptide provided herein comprises amino acid substitutions of K9E and K32E. In certain embodiments, the interleukin-2 polypeptide provided herein comprises amino acid substitutions of K9E and K76E. In certain embodiments, the interleukin-2 polypeptide provided herein comprises amino acid substitutions of K9E and H79E. In certain embodiments, the interleukin-2 polypeptide provided herein comprises amino acid substitutions of K9E and R81E.

In yet another embodiment, provided herein is an interleukin-2 polypeptide comprising an amino acid sequence of SEQ ID NO: 1, 2, 3, 4, or 5, wherein the interleukin-2 polypeptide comprises two amino acid substitutions: H16E and one selected from K8E, K9E, K32E, K76E, H79E, and R81E.

In certain embodiments, the interleukin-2 polypeptide provided herein comprises amino acid substitutions of H16E and K32E. In certain embodiments, the interleukin-2 polypeptide provided herein comprises amino acid substitutions of H16E and K76E. In certain embodiments, the interleukin-2 polypeptide provided herein comprises amino acid substitutions of H16E and H79E. In certain embodiments, the interleukin-2 polypeptide provided herein comprises amino acid substitutions of H16E and R81E.

In yet another embodiment, provided herein is an interleukin-2 polypeptide comprising an amino acid sequence of SEQ ID NO: 1, 2, 3, 4, or 5, wherein the interleukin-2 polypeptide comprises two amino acid substitutions: K32E and one selected from K8E, K9E, H16E, K76E, H79E, and R81E.

In certain embodiments, the interleukin-2 polypeptide provided herein comprises amino acid substitutions of K32E and K76E. In certain embodiments, the interleukin-2 polypeptide provided herein comprises amino acid substitutions of K32E and H79E. In certain embodiments, the interleukin-2 polypeptide provided herein comprises amino acid substitutions of K32E and R81E.

In yet another embodiment, provided herein is an interleukin-2 polypeptide comprising an amino acid sequence of SEQ ID NO: 1, 2, 3, 4, or 5, wherein the interleukin-2 polypeptide comprises two amino acid substitutions: K76E and one selected from K8E, K9E, H16E, K32E, H79E, and R81E.

In certain embodiments, the interleukin-2 polypeptide provided herein comprises amino acid substitutions of K76E and H79E. In certain embodiments, the interleukin-2 polypeptide provided herein comprises amino acid substitutions of K76E and H79E.

In still another embodiment, provided herein is an interleukin-2 polypeptide comprising an amino acid sequence of SEQ ID NO: 1, 2, 3, 4, or 5, wherein the interleukin-2 polypeptide comprises two amino acid substitutions: H79E and one selected from K8E, K9E, H16E, K32E, K76E, and R81E.

In certain embodiments, the interleukin-2 polypeptide provided herein comprises amino acid substitutions of H79E and R81E.

In one embodiment, the interleukin-2 polypeptide provided herein comprises an amino acid sequence selected from SEQ ID NOs: 21 to 25 and 105 to 109. In another embodiment, the interleukin-2 polypeptide provided herein comprises an amino acid sequence selected from SEQ ID NOs: 21 to 25. In yet another embodiment, the interleukin-2 polypeptide provided herein comprises an amino acid sequence selected from SEQ ID NOs: 105 to 109.

In one embodiment, the amino acid sequence of the interleukin-2 polypeptide provided herein is one selected from SEQ ID NOs: 21 to 25 and 105 to 109. In another embodiment, the amino acid sequence of the interleukin-2 polypeptide provided herein is one selected from SEQ ID NOs: 21 to 25. In yet another embodiment, the amino acid sequence of the interleukin-2 polypeptide provided herein is one selected from 105 to 109.

In one embodiment, the interleukin-2 polypeptide provided herein that comprises an amino acid substitution at position 8, 9, 16, 32, 76, 79, or 81 as set forth in SEQ ID NO: 1, 2, 3, 4, or 5 has an enhanced stability and/or an enhanced production yield as compared to a wild-type interleukin-2 described herein.

In one embodiment, the interleukin-2 polypeptide provided herein that comprises an amino acid substitution at position 8, 9, 16, 32, 76, 79, or 81 as set forth in SEQ ID NO: 1, 2, 3, 4, or 5 has a production yield that is no less than about 2, no less than about 5, or no less than about 10 time higher than that of a wild-type interleukin-2 described herein. In another embodiment, the interleukin-2 polypeptide provided herein that comprises an amino acid substitution at position 8, 9, 16, 32, 76, 79, or 81 as set forth in SEQ ID NO: 1, 2, 3, 4, or 5 has a production yield that is from about 2 to about 1,000 times, from about 2 to about 100 times, from about 2 to about 50 times, from about 2 to about 20 times, or from about 2 to about 10 times higher than that of a wild-type interleukin-2 described herein.

In one embodiment, provided herein is an interleukin-2 polypeptide comprising an amino acid sequence of SEQ ID NO: 1, 2, 3, 4, or 5, wherein the interleukin-2 polypeptide comprises a deletion or replacement of the amino acid residues from positions 30 to 35 as set forth in SEQ ID NO: 1, 2, 3, 4, or 5 with a peptide linker as defined herein.

In certain embodiments, the interleukin-2 polypeptide provided herein comprises a deletion of the amino acid residues from positions 30 to 35 as set forth in SEQ ID NO: 1, 2, 3, 4, or 5. In certain embodiments, the interleukin-2 polypeptide provided herein comprises a replacement of the amino acid residues from positions 30 to 35 as set forth in SEQ ID NO: 1, 2, 3, 4, or 5 with a peptide linker as defined herein.

In another embodiment, provided herein is an interleukin-2 polypeptide comprising an amino acid sequence of SEQ ID NO: 1, 2, 3, 4, or 5, wherein the interleukin-2 polypeptide comprises a deletion or replacement of the amino acid residues from positions N30 to K35 as set forth in SEQ ID NO: 1, 2, 3, 4, or 5 with a flexible peptide linker as defined herein.

In certain embodiments, the interleukin-2 polypeptide provided herein comprises a deletion of the amino acid residues from positions N30 to K35 as set forth in SEQ ID NO: 1, 2, 3, 4, or 5. In certain embodiments, the interleukin-2 polypeptide provided herein comprises a replacement of the amino acid residues from positions N30 to K35 as set forth in SEQ ID NO: 1, 2, 3, 4, or 5 with a flexible peptide linker as defined herein.

In yet another embodiment, provided herein is an interleukin-2 polypeptide comprising an amino acid sequence of SEQ ID NO: 1, 2, 3, 4, or 5, wherein the interleukin-2 polypeptide comprises a deletion or replacement of an amino acid sequence of SEQ ID NO: 10 with an amino acid sequence selected from G, SG, GGS, and SEQ ID NOs: 7 to 9.

In certain embodiments, the interleukin-2 polypeptide provided herein comprises a deletion of an amino acid sequence of SEQ ID NO: 10. In certain embodiments, the interleukin-2 polypeptide provided herein comprises a replacement of an amino acid sequence of SEQ ID NO: 10 with an amino acid sequence selected from G, SG, GGS, and SEQ ID NOs: 7 to 9. In certain embodiments, the interleukin-2 polypeptide provided herein comprises a replacement of an amino acid sequence of SEQ ID NO: 10 with an amino acid sequence of G. In certain embodiments, the interleukin-2 polypeptide provided herein comprises a replacement of an amino acid sequence of SEQ ID NO: 10 with an amino acid sequence of SG. In certain embodiments, the interleukin-2 polypeptide provided herein comprises a replacement of an amino acid sequence of SEQ ID NO: 10 with an amino acid sequence of GGS. In certain embodiments, the interleukin-2 polypeptide provided herein comprises a replacement of an amino acid sequence of SEQ ID NO: 10 with an amino acid sequence of SEQ ID NO: 7. In certain embodiments, the interleukin-2 polypeptide provided herein comprises a replacement of an amino acid sequence of SEQ ID NO: 10 with an amino acid sequence of SEQ ID NO: 8. In certain embodiments, the interleukin-2 polypeptide provided herein comprises a replacement of an amino acid sequence of SEQ ID NO: 10 with an amino acid sequence of SEQ ID NO: 9.

In one embodiment, the interleukin-2 polypeptide provided herein comprises an amino acid sequence selected from SEQ ID NOs: 26 to 34 and 110 to 118. In another embodiment, the interleukin-2 polypeptide provided herein comprises an amino acid sequence selected from SEQ ID NOs: 26 to 34. In yet another embodiment, the interleukin-2 polypeptide provided herein comprises an amino acid sequence selected from SEQ ID NOs: 110 to 118.

In one embodiment, the amino acid sequence of the interleukin-2 polypeptide provided herein is one selected from SEQ ID NOs: 26 to 34 and 110 to 118. In another embodiment, the amino acid sequence of the interleukin-2 polypeptide provided herein is one selected from SEQ ID NOs: 26 to 34. In yet another embodiment, the amino acid sequence of the interleukin-2 polypeptide provided herein is one selected from SEQ ID NOs: 110 to 118.

In one embodiment, the interleukin-2 polypeptide provided herein that comprises a deletion or replacement of the amino acid residues from positions 30 to 35 as set forth in SEQ ID NO: 1, 2, 3, 4, or 5 with a peptide linker has an enhanced stability and/or an enhanced production yield as compared to a wild-type interleukin-2 described herein.

In one embodiment, the interleukin-2 polypeptide provided herein that comprises a deletion or replacement of the amino acid residues from positions 30 to 35 as set forth in SEQ ID NO: 1, 2, 3, 4, or 5 with a peptide linker has a production yield that is no less than about 2, no less than about 5, or no less than about 10 time higher than that of a wild-type interleukin-2 described herein. In another embodiment, the interleukin-2 polypeptide provided that comprises a deletion or replacement of the amino acid residues from positions 30 to 35 as set forth in SEQ ID NO: 1, 2, 3, 4, or 5 with an peptide linker has a production yield that is from about 2 to about 1,000 times, from about 2 to 100 times, from about 2 to about 50 times, from about 2 to about 20 times, or from about 2 to about 10 times higher than that of a wild-type interleukin-2 described herein.

In certain embodiments, the interleukin-2 polypeptide provided herein has a reduced binding affinity to an interleukin-2 receptor-β (IL-2Rβ) chain as compared to a wild-type interleukin-2 described herein. In certain embodiments, the binding affinity of the interleukin-2 polypeptide provided herein to an IL-2Rβ is measured by its association constant ($K_a$), which is the inverse of its dissociation constant ($K_d$).

In one embodiment, provided herein is an interleukin-2 polypeptide comprising an amino acid sequence of SEQ ID NO: 1, 2, 3, 4, or 5, wherein the interleukin-2 polypeptide comprises a disulfide bond formed between two amino acids from positions 30 to 80 as set forth in SEQ ID NO: 1, 2, 3, 4, or 5.

In one embodiment, interleukin-2 polypeptide provided herein comprises a disulfide bond formed between two amino acids from positions 35 to 72 as set forth in SEQ ID NO: 1, 2, 3, 4, or 5. In another embodiment, the interleukin-2 polypeptide provided herein comprises a disulfide bond formed between two amino acids from positions 35 to 69 as set forth in SEQ ID NO: 1, 2, 3, 4, or 5.

In one embodiment, the interleukin-2 polypeptide provided herein comprises a disulfide bond formed between two amino acids from positions N30 to L80 as set forth in SEQ ID NO: 1, 2, 3, 4, or 5. In another embodiment, the interleukin-2 polypeptide provided herein comprises a disulfide bond formed between two amino acids from positions K35 to L72 as set forth in SEQ ID NO: 1, 2, 3, 4, or 5. In yet another embodiment, the interleukin-2 polypeptide provided herein comprises a disulfide bond formed between two amino acids from positions K35 to V69 as set forth in SEQ ID NO: 1, 2, 3, 4, or 5.

In one embodiment, the interleukin-2 polypeptide provided herein comprises a disulfide bond formed between two amino acids at two different positions, each independently selected from positions 35, 38, 42, 45, 62, 69, and 72 as set forth in SEQ ID NO: 1, 2, 3, 4, or 5. In another embodiment, the interleukin-2 polypeptide provided herein comprises a disulfide bond formed between an amino acid at position 35, 38, 42, or 45; and an amino acid at position 62, 69, or 72 as set forth in SEQ ID NO: 1, 2, 3, 4, or 5. In yet another embodiment, the interleukin-2 polypeptide provided herein comprises a disulfide bond formed between an amino acid at position 35 and an amino acid at position 62, 69, or 72 as set forth in SEQ ID NO: 1, 2, 3, 4, or 5. In yet another embodiment, the interleukin-2 polypeptide provided herein comprises a disulfide bond formed between an amino acid at position 38 and an amino acid at position 62, 69, or 72 as set forth in SEQ ID NO: 1, 2, 3, 4, or 5. In yet another embodiment, the interleukin-2 polypeptide provided herein comprises a disulfide bond formed between an amino acid at position 42 and an amino acid at position 62, 69, or 72 as set forth in SEQ ID NO: 1, 2, 3, 4, or 5. In yet another embodiment, the interleukin-2 polypeptide provided herein comprises a disulfide bond formed between an amino acid at position 45 and an amino acid at position 62, 69, or 72 as set forth in SEQ ID NO: 1, 2, 3, 4, or 5. In yet another embodiment, the interleukin-2 polypeptide provided herein comprises a disulfide bond formed between an amino acid at position 35, 38, 42, or 45, and an amino acid at position 62 as set forth in SEQ ID NO: 1, 2, 3, 4, or 5. In yet another embodiment, the interleukin-2 polypeptide provided herein comprises a disulfide bond formed between an amino acid at position 35, 38, 42, or 45, and an amino acid at position 69 as set forth in SEQ ID NO: 1, 2, 3, 4, or 5. In still another embodiment, the interleukin-2 polypeptide provided herein comprises a disulfide bond formed between an amino acid at position 35, 38, 42, or 45, and an amino acid at position 72 as set forth in SEQ ID NO: 1, 2, 3, 4, or 5.

In one embodiment, the interleukin-2 polypeptide provided herein comprises a disulfide bond formed between two amino acids at two different positions, each independently selected from positions K35, R38, F42, Y45, E62, V69, and L72 as set forth in SEQ ID NO: 1, 2, 3, 4, or 5. In another embodiment, the interleukin-2 polypeptide provided herein comprises a disulfide bond formed between an amino acid at position K35, R38, F42, or Y45; and an amino acid at position E62, V69, or L72 as set forth in SEQ ID NO: 1, 2, 3, 4, or 5. In yet another embodiment, the interleukin-2 polypeptide provided herein comprises a disulfide bond formed between an amino acid at position K35 and an amino acid at position E62, V69, or L72 as set forth in SEQ ID NO: 1, 2, 3, 4, or 5. In yet another embodiment, the interleukin-2 polypeptide provided herein comprises a disulfide bond formed between an amino acid at position E38 and an amino acid at position E62, V69, or L72 as set forth in SEQ ID NO: 1, 2, 3, 4, or 5. In yet another embodiment, the interleukin-2 polypeptide provided herein comprises a disulfide bond formed between an amino acid at position F42 and an amino acid at position E62, V69, or L72 as set forth in SEQ ID NO: 1, 2, 3, 4, or 5. In yet another embodiment, the interleukin-2 polypeptide provided herein comprises a disulfide bond formed between an amino acid at position Y45 and an amino acid at position E62, V69, or L72 as set forth in SEQ ID NO: 1, 2, 3, 4, or 5. In yet another embodiment, the interleukin-2 polypeptide provided herein comprises a disulfide bond formed between an amino acid at position K35, R38, F42, or Y45, and an amino acid at position E62 as set forth in SEQ ID NO: 1, 2, 3, 4, or 5. In yet another embodiment, the interleukin-2 polypeptide provided herein comprises a disulfide bond formed between an amino acid at position K35, R38, F42, or Y45, and an amino acid at position V69 as set forth in SEQ ID NO: 1, 2, 3, 4, or 5. In still another embodiment, the interleukin-2 polypeptide provided herein comprises a disulfide bond formed between an amino acid at position K35, R38, F42, or Y45, and an amino acid at position L72 as set forth in SEQ ID NO: 1, 2, 3, 4, or 5.

In one embodiment, the interleukin-2 polypeptide provided herein comprises a disulfide bond formed between two amino acids at positions 35 and 72, 38 and 72, 42 and 69, 42 and 72, or 45 and 62 as set forth in SEQ ID NO: 1, 2, 3, 4, or 5. In another embodiment, the interleukin-2 polypeptide comprises a disulfide bond formed between two amino acids at positions 35 and 72 as set forth in SEQ ID NO: 1, 2, 3, 4, or 5. In yet another embodiment, the interleukin-2 polypeptide comprises a disulfide bond formed between two amino acids at positions 38 and 72 as set forth in SEQ ID NO: 1, 2, 3, 4, or 5. In yet another embodiment, the interleukin-2 polypeptide comprises a disulfide bond formed between two amino acids at positions 42 and 69 as set forth in SEQ ID NO: 1, 2, 3, 4, or 5. In yet another embodiment, the interleukin-2 polypeptide comprises a disulfide bond formed between two amino acids at positions 42 and 72 as set forth in SEQ ID NO: 1, 2, 3, 4, or 5. In still another embodiment, the interleukin-2 polypeptide comprises a disulfide bond formed between two amino acids at positions 45 and 62 as set forth in SEQ ID NO: 1, 2, 3, 4, or 5.

In one embodiment, the interleukin-2 polypeptide provided herein comprises a disulfide bond formed between K35C and L72C, R38C and L72C, F42C and V69C, Y42C and L72C, or Y45C and E62C as set forth in SEQ ID NO: 1, 2, 3, 4, or 5. In another embodiment, the interleukin-2 polypeptide comprises a disulfide bond formed between K35C and L72C as set forth in SEQ ID NO: 1, 2, 3, 4, or 5. In yet another embodiment, the interleukin-2 polypeptide comprises a disulfide bond formed between R38C and L72C as set forth in SEQ ID NO: 1, 2, 3, 4, or 5. In yet another embodiment, the interleukin-2 polypeptide comprises a disulfide bond formed between F42C and V69C as set forth in SEQ ID NO: 1, 2, 3, 4, or 5. In yet another embodiment, the interleukin-2 polypeptide comprises a disulfide bond formed between Y42C and L72C as set forth in SEQ ID NO: 1, 2, 3, 4, or 5. In still another embodiment, the interleukin-2 polypeptide comprises a disulfide bond formed between Y45C and E62C as set forth in SEQ ID NO: 1, 2, 3, 4, or 5.

In one embodiment, provided herein is an interleukin-2 polypeptide comprising an amino acid sequence of SEQ ID NO: 1, 2, 3, 4, or 5, wherein the interleukin-2 polypeptide comprises (i) a disulfide bond formed between two amino acids from positions 30 to 80; and (ii) an amino acid substitution at position 32 or 76 as set forth in SEQ ID NO: 1, 2, 3, 4, or 5.

In one embodiment, interleukin-2 polypeptide provided herein comprises (i) a disulfide bond formed between two amino acids from positions 35 to 72; and (ii) an amino acid substitution at position 32 or 76 as set forth in SEQ ID NO: 1, 2, 3, 4, or 5. In another embodiment, the interleukin-2 polypeptide provided herein comprises (i) a disulfide bond formed between two amino acids from positions 35 to 69; and (ii) an amino acid substitution at position 32 or 76 as set forth in SEQ ID NO: 1, 2, 3, 4, or 5.

In one embodiment, the interleukin-2 polypeptide provided herein comprises (i) a disulfide bond formed between two amino acids from positions N30 to L80; and (ii) an amino acid substitution at position K32 or K76 as set forth in SEQ ID NO: 1, 2, 3, 4, or 5. In another embodiment, the interleukin-2 polypeptide provided herein comprises (i) a disulfide bond formed between two amino acids from positions K35 to L72; and (ii) an amino acid substitution at position K32 or K76 as set forth in SEQ ID NO: 1, 2, 3, 4, or 5. In yet another embodiment, the interleukin-2 polypeptide provided herein comprises (i) a disulfide bond formed between two amino acids from positions K35 to V69; and (ii) an amino acid substitution at position K32 or K76 as set forth in SEQ ID NO: 1, 2, 3, 4, or 5.

In one embodiment, the interleukin-2 polypeptide provided herein comprises (i) a disulfide bond formed between two amino acids at two different positions, each independently selected from positions 35, 38, 42, 45, 62, 69, and 72; and (ii) an amino acid substitution at position 32 or 76 as set forth in SEQ ID NO: 1, 2, 3, 4, or 5. In another embodiment, the interleukin-2 polypeptide provided herein comprises (i) a disulfide bond formed between an amino acid at position 35, 38, 42, or 45; and an amino acid at position 62, 69, or 72; and (ii) an amino acid substitution at position 32 or 76 as set forth in SEQ ID NO: 1, 2, 3, 4, or 5. In yet another embodiment, the interleukin-2 polypeptide provided herein comprises (i) a disulfide bond formed between an amino acid at position 35 and an amino acid at position 62, 69, or 72; and (ii) an amino acid substitution at position 32 or 76 as set forth in SEQ ID NO: 1, 2, 3, 4, or 5. In yet another embodiment, the interleukin-2 polypeptide provided herein comprises (i) a disulfide bond formed between an amino acid at position 38 and an amino acid at position 62, 69, or 72; and (ii) an amino acid substitution at position 32 or 76 as set forth in SEQ ID NO: 1, 2, 3, 4, or 5. In yet another embodiment, the interleukin-2 polypeptide provided herein comprises (i) a disulfide bond formed between an amino acid at position 42 and an amino acid at position 62, 69, or 72; and (ii) an amino acid substitution at position 32 or 76 as set forth in SEQ ID NO: 1, 2, 3, 4, or 5. In yet another embodiment, the interleukin-2 polypeptide provided herein comprises (i) a disulfide bond formed between an amino acid at position 45 and an amino acid at position 62, 69, or 72; and (ii) an amino acid substitution at position 32 or 76 as set forth in SEQ ID NO: 1, 2, 3, 4, or 5. In yet another embodiment, the interleukin-2 polypeptide provided herein comprises (i) a disulfide bond formed between an amino acid at position 35, 38, 42, or 45, and an amino acid at position 62; and (ii) an amino acid substitution at position 32 or 76 as set forth in SEQ ID NO: 1, 2, 3, 4, or 5. In yet another embodiment, the interleukin-2 polypeptide provided herein comprises (i) a disulfide bond formed between an amino acid at position 35, 38, 42, or 45, and an amino acid at position 69; and (ii) an amino acid substitution at position 32 or 76 as set forth in SEQ ID NO: 1, 2, 3, 4, or 5. In still another embodiment, the interleukin-2 polypeptide provided herein comprises (i) a disulfide bond formed between an amino acid at position 35, 38, 42, or 45, and an amino acid at position 72; and (ii) an amino acid substitution at position 32 or 76 as set forth in SEQ ID NO: 1, 2, 3, 4, or 5.

In one embodiment, the interleukin-2 polypeptide provided herein comprises (i) a disulfide bond formed between two amino acids at two different positions, each independently selected from positions K35, R38, F42, Y45, E62, V69, and L72; and (ii) an amino acid substitution at position K32 or K76 as set forth in SEQ ID NO: 1, 2, 3, 4, or 5. In another embodiment, the interleukin-2 polypeptide provided herein comprises (i) a disulfide bond formed between an amino acid at position K35, R38, F42, or Y45; and an amino acid at position E62, V69, or L72; and (ii) an amino acid substitution at position K32 or K76 as set forth in SEQ ID NO: 1, 2, 3, 4, or 5. In yet another embodiment, the interleukin-2 polypeptide provided herein comprises (i) a disulfide bond formed between an amino acid at position K35 and an amino acid at position E62, V69, or L72; and (ii) an amino acid substitution at position K32 or K76 as set forth in SEQ ID NO: 1, 2, 3, 4, or 5. In yet another embodiment, the interleukin-2 polypeptide provided herein comprises (i) a disulfide bond formed between an amino acid at position E38 and an amino acid at position E62, V69, or L72; and (ii) an amino acid substitution at position K32 or K76 as set forth in SEQ ID NO: 1, 2, 3, 4, or 5. In yet another embodiment, the interleukin-2 polypeptide provided herein comprises (i) a disulfide bond formed between an amino acid at position F42 and an amino acid at position E62, V69, or L72; and (ii) an amino acid substitution at position K32 or K76 as set forth in SEQ ID NO: 1, 2, 3, 4, or 5. In yet another embodiment, the interleukin-2 polypeptide provided herein comprises (i) a disulfide bond formed between an amino acid at position Y45 and an amino acid at position E62, V69, or L72; and (ii) an amino acid substitution at position K32 or K76 as set forth in SEQ ID NO: 1, 2, 3, 4, or 5. In yet another embodiment, the interleukin-2 polypeptide provided herein comprises (i) a disulfide bond formed between an amino acid at position K35, R38, F42, or Y45, and an amino acid at position E62; and (ii) an amino acid substitution at position K32 or K76 as set forth in SEQ ID NO: 1, 2, 3, 4, or 5. In yet another embodiment, the interleukin-2 polypeptide provided herein comprises (i) a disulfide bond formed between an amino acid at position K35, R38, F42, or Y45, and an amino acid at position V69; and (ii) an amino acid substitution at position K32 or K76 as set forth in SEQ ID NO: 1, 2, 3, 4, or 5. In still another embodiment, the interleukin-2 polypeptide provided herein comprises (i) a disulfide bond formed between an amino acid at position K35, R38, F42, or Y45, and an amino acid at position L72; and (ii) an amino acid substitution at position K32 or K76 as set forth in SEQ ID NO: 1, 2, 3, 4, or 5.

In one embodiment, the interleukin-2 polypeptide provided herein comprises (i) a disulfide bond formed between two amino acids at positions 35 and 72, 38 and 72, 42 and 69, 42 and 72, or 45 and 62; and (ii) an amino acid substitution at position 32 or 76 as set forth in SEQ ID NO: 1, 2, 3, 4, or 5. In another embodiment, the interleukin-2 polypeptide comprises (i) a disulfide bond formed between two amino acids at positions 35 and 72; and (ii) an amino acid substitution at position 32 or 76 as set forth in SEQ ID NO: 1, 2, 3, 4, or 5. In yet another embodiment, the interleukin-2 polypeptide comprises (i) a disulfide bond formed between two amino acids at positions 38 and 72; and (ii) an amino acid substitution at position 32 or 76 as set forth in SEQ ID NO: 1, 2, 3, 4, or 5. In yet another embodiment, the interleukin-2 polypeptide comprises (i) a disulfide bond formed between two amino acids at positions 42 and 69; and (ii) an amino acid substitution at position 32 or 76 as set forth in SEQ ID NO: 1, 2, 3, 4, or 5. In yet another embodiment, the interleukin-2 polypeptide comprises (i) a disulfide bond formed between two amino acids at positions 42 and 72; and (ii) an amino acid substitution at position 32 or 76 as set forth in SEQ ID NO: 1, 2, 3, 4, or 5. In still another embodiment, the interleukin-2 polypeptide comprises (i) a disulfide bond formed between two amino acids at positions 45 and 62; and (ii) an amino acid substitution at position 32 or 76 as set forth in SEQ ID NO: 1, 2, 3, 4, or 5.

In one embodiment, the interleukin-2 polypeptide provided herein comprises (i) a disulfide bond formed between K35C and L72C, R38C and L72C, F42C and V69C, Y42C and L72C, or Y45C and E62C; and (ii) an amino acid substitution of K32E or K76E. In another embodiment, the interleukin-2 polypeptide comprises (i) a disulfide bond formed between K35C and L72C; and (ii) an amino acid substitution of K32E or K76E. In yet another embodiment, the interleukin-2 polypeptide comprises (i) a disulfide bond formed between R38C and L72C; and (ii) an amino acid substitution of K32E or K76E. In yet another embodiment, the interleukin-2 polypeptide comprises (i) a disulfide bond formed between F42C and V69C; and (ii) an amino acid substitution of K32E or K76E. In yet another embodiment, the interleukin-2 polypeptide comprises (i) a disulfide bond formed between Y42C and L72C; and (ii) an amino acid substitution of K32 or K76 as set forth in SEQ ID NO: 1, 2, 3, 4, or 5. In still another embodiment, the interleukin-2 polypeptide comprises (i) a disulfide bond formed between Y45C and E62C; and (ii) an amino acid substitution of K32E or K76E.

In one embodiment, provided herein is an interleukin-2 polypeptide comprising an amino acid sequence of SEQ ID NO: 1, 2, 3, 4, or 5, wherein the interleukin-2 polypeptide comprises (i) a disulfide bond formed between two amino acids from positions 30 to 80; (ii) an amino acid substitution at position 32 or 76 as set forth in SEQ ID NO: 1, 2, 3, 4, or 5; and (iii) an amino acid substitution at position 13, 19, 84, 87, 91, 92, or 95 as set forth in SEQ ID NO: 1, 2, 3, 4, or 5.

In another embodiment, interleukin-2 polypeptide provided herein comprises (i) a disulfide bond formed between two amino acids from positions 35 to 72; (ii) an amino acid substitution at position 32 or 76 as set forth in SEQ ID NO: 1, 2, 3, 4, or 5; and (iii) an amino acid substitution at position 13, 19, 84, 87, 91, 92, or 95 as set forth in SEQ ID NO: 1, 2, 3, 4, or 5.

In yet another embodiment, the interleukin-2 polypeptide provided herein comprises (i) a disulfide bond formed between two amino acids from positions 35 to 69; (ii) an amino acid substitution at position 32 or 76 as set forth in SEQ ID NO: 1, 2, 3, 4, or 5; and (iii) an amino acid substitution at position 13, 19, 84, 87, 91, 92, or 95 as set forth in SEQ ID NO: 1, 2, 3, 4, or 5.

In one embodiment, the interleukin-2 polypeptide provided herein comprises (i) a disulfide bond formed between two amino acids from positions N30 to L80; (ii) an amino acid substitution at position K32 or K76 as set forth in SEQ ID NO: 1, 2, 3, 4, or 5; and (iii) an amino acid substitution at position Q13, L19, D84, S87, V91, I92, or E95 as set forth in SEQ ID NO: 1, 2, 3, 4, or 5.

In another embodiment, the interleukin-2 polypeptide provided herein comprises (i) a disulfide bond formed between two amino acids from positions K35 to L72; (ii) an amino acid substitution at position K32 or K76 as set forth in SEQ ID NO: 1, 2, 3, 4, or 5; and (iii) an amino acid substitution at position Q13, L19, D84, S87, V91, I92, or E95 as set forth in SEQ ID NO: 1, 2, 3, 4, or 5.

In yet another embodiment, the interleukin-2 polypeptide provided herein comprises (i) a disulfide bond formed between two amino acids from positions K35 to V69; (ii) an amino acid substitution at position K32 or K76 as set forth in SEQ ID NO: 1, 2, 3, 4, or 5; and (iii) an amino acid substitution at position Q13, L19, D84, S87, V91, I92, or E95 as set forth in SEQ ID NO: 1, 2, 3, 4, or 5.

In one embodiment, the interleukin-2 polypeptide provided herein comprises (i) a disulfide bond formed between two amino acids at two different positions, each independently selected from positions 35, 38, 42, 45, 62, 69, and 72; (ii) an amino acid substitution at position 32 or 76 as set forth in SEQ ID NO: 1, 2, 3, 4, or 5; and (iii) an amino acid substitution at position 13, 19, 84, 87, 91, 92, or 95 as set forth in SEQ ID NO: 1, 2, 3, 4, or 5. In another embodiment, the interleukin-2 polypeptide provided herein comprises (i) a disulfide bond formed between an amino acid at position 35, 38, 42, or 45; and an amino acid at position 62, 69, or 72; (ii) an amino acid substitution at position 32 or 76 as set forth in SEQ ID NO: 1, 2, 3, 4, or 5; and (iii) an amino acid substitution at position 13, 19, 84, 87, 91, 92, or 95 as set forth in SEQ ID NO: 1, 2, 3, 4, or 5. In yet another embodiment, the interleukin-2 polypeptide provided herein comprises (i) a disulfide bond formed between an amino acid at position 35 and an amino acid at position 62, 69, or 72; (ii) an amino acid substitution at position 32 or 76 as set forth in SEQ ID NO: 1, 2, 3, 4, or 5; and (iii) an amino acid substitution at position 13, 19, 84, 87, 91, 92, or 95 as set forth in SEQ ID NO: 1, 2, 3, 4, or 5. In yet another embodiment, the interleukin-2 polypeptide provided herein comprises (i) a disulfide bond formed between an amino acid at position 38 and an amino acid at position 62, 69, or 72; (ii) an amino acid substitution at position 32 or 76 as set forth in SEQ ID NO: 1, 2, 3, 4, or 5; and (iii) an amino acid substitution at position 13, 19, 84, 87, 91, 92, or 95 as set forth in SEQ ID NO: 1, 2, 3, 4, or 5. In yet another embodiment, the interleukin-2 polypeptide provided herein comprises (i) a disulfide bond formed between an amino acid at position 42 and an amino acid at position 62, 69, or 72; (ii) an amino acid substitution at position 32 or 76 as set forth in SEQ ID NO: 1, 2, 3, 4, or 5; and (iii) an amino acid substitution at position 13, 19, 84, 87, 91, 92, or 95 as set forth in SEQ ID NO: 1, 2, 3, 4, or 5. In yet another embodiment, the interleukin-2 polypeptide provided herein comprises (i) a disulfide bond formed between an amino acid at position 45 and an amino acid at position 62, 69, or 72; (ii) an amino acid substitution at position 32 or 76 as set forth in SEQ ID NO: 1, 2, 3, 4, or 5; and (iii) an amino acid substitution at position 13, 19, 84, 87, 91, 92, or 95 as set forth in SEQ ID NO: 1, 2, 3, 4, or 5. In yet another embodiment, the interleukin-2 polypeptide provided herein comprises (i) a disulfide bond formed between an amino acid at position 35, 38, 42, or 45, and an amino acid at position 62; (ii) an amino acid substitution at position 32 or 76 as set forth in SEQ ID NO: 1, 2, 3, 4, or 5; and (iii) an amino acid substitution at position 13, 19, 84, 87, 91, 92, or 95 as set forth in SEQ ID NO: 1, 2, 3, 4, or 5. In yet another embodiment, the interleukin-2 polypeptide provided herein comprises (i) a disulfide bond formed between an amino acid at position 35, 38, 42, or 45, and an amino acid at position 69; (ii) an amino acid substitution at position 32 or 76 as set forth in SEQ ID NO: 1, 2, 3, 4, or 5; and (iii) an amino acid substitution at position 13, 19, 84, 87, 91, 92, or 95 as set forth in SEQ ID NO: 1, 2, 3, 4, or 5. In still another embodiment, the interleukin-2 polypeptide provided herein comprises (i) a disulfide bond formed between an amino acid at position 35, 38, 42, or 45, and an amino acid at position 72; (ii) an amino acid substitution at position 32 or 76 as set forth in SEQ ID NO: 1, 2, 3, 4, or 5; and (iii) an amino acid substitution at position 13, 19, 84, 87, 91, 92, or 95 as set forth in SEQ ID NO: 1, 2, 3, 4, or 5.

In one embodiment, the interleukin-2 polypeptide provided herein comprises (i) a disulfide bond formed between two amino acids at two different positions, each independently selected from positions K35, R38, F42, Y45, E62, V69, and L72; (ii) an amino acid substitution at position K32 or K76 as set forth in SEQ ID NO: 1, 2, 3, 4, or 5; and (iii) an amino acid substitution at position Q13, L19, D84, S87, V91, I92, or E95 as set forth in SEQ ID NO: 1, 2, 3, 4, or 5. In another embodiment, the interleukin-2 polypeptide provided herein comprises (i) a disulfide bond formed between an amino acid at position K35, R38, F42, or Y45; and an amino acid at position E62, V69, or L72; (ii) an amino acid substitution at position K32 or K76 as set forth in SEQ ID NO: 1, 2, 3, 4, or 5; and (iii) an amino acid substitution at position Q13, L19, D84, S87, V91, I92, or E95 as set forth in SEQ ID NO: 1, 2, 3, 4, or 5. In yet another embodiment, the interleukin-2 polypeptide provided herein comprises (i) a disulfide bond formed between an amino acid at position K35 and an amino acid at position E62, V69, or L72; (ii) an amino acid substitution at position K32 or K76 as set forth in SEQ ID NO: 1, 2, 3, 4, or 5; and (iii) an amino acid substitution at position Q13, L19, D84, S87, V91, I92, or E95 as set forth in SEQ ID NO: 1, 2, 3, 4, or 5. In yet another embodiment, the interleukin-2 polypeptide provided herein comprises (i) a disulfide bond formed between an amino acid at position E38 and an amino acid at position E62, V69, or L72; (ii) an amino acid substitution at position K32 or K76 as set forth in SEQ ID NO: 1, 2, 3, 4, or 5; and (iii) an amino acid substitution at position Q13, L19, D84, S87, V91, I92, or E95 as set forth in SEQ ID NO: 1, 2, 3, 4, or 5. In yet another embodiment, the interleukin-2 polypeptide provided herein comprises (i) a disulfide bond formed between an amino acid at position F42 and an amino acid at position E62, V69, or L72; (ii) an amino acid substitution at position K32 or K76 as set forth in SEQ ID NO: 1, 2, 3, 4, or 5; and (iii) an amino acid substitution at position Q13, L19, D84, S87, V91, I92, or E95 as set forth in SEQ ID NO: 1, 2, 3, 4, or 5. In yet another embodiment, the interleukin-2 polypeptide provided herein comprises (i) a disulfide bond formed between an amino acid at position Y45 and an amino acid at position E62, V69, or L72; (ii) an amino acid substitution at position K32 or K76 as set forth in SEQ ID NO: 1, 2, 3, 4, or 5; and (iii) an amino acid substitution at position Q13, L19, D84, 587, V91, I92, or E95 as set forth in SEQ ID NO: 1, 2, 3, 4, or 5. In yet another embodiment, the interleukin-2 polypeptide provided herein comprises (i) a disulfide bond formed between an amino acid at position K35, R38, F42, or Y45, and an amino acid at position E62; (ii) an amino acid substitution at position K32 or K76 as set forth in SEQ ID NO: 1, 2, 3, 4, or 5; and (iii) an amino acid substitution at position Q13, L19, D84, S87, V91, I92, or E95 as set forth in SEQ ID NO: 1, 2, 3, 4, or 5. In yet another embodiment, the interleukin-2 polypeptide provided herein comprises (i) a disulfide bond formed between an amino acid at position K35, R38, F42, or Y45, and an amino acid at position V69; (ii) an amino acid substitution at position K32 or K76 as set forth in SEQ ID NO: 1, 2, 3, 4, or 5; and (iii) an amino acid substitution at position Q13, L19, D84, S87, V91, I92, or E95 as set forth in SEQ ID NO: 1, 2, 3, 4, or 5. In still another embodiment, the interleukin-2 polypeptide provided herein comprises (i) a disulfide bond formed between an amino acid at position K35, R38, F42, or Y45, and an amino acid at position L72; (ii) an amino acid substitution at position K32 or K76 as set forth in SEQ ID NO: 1, 2, 3, 4, or 5; and (iii) an amino acid substitution at position Q13, L19, D84, S87, V91, I92, or E95 as set forth in SEQ ID NO: 1, 2, 3, 4, or 5.

In one embodiment, the interleukin-2 polypeptide provided herein comprises (i) a disulfide bond formed between two amino acids at positions 35 and 72, 38 and 72, 42 and 69, 42 and 72, or 45 and 62; (ii) an amino acid substitution at position 32 or 76 as set forth in SEQ ID NO: 1, 2, 3, 4, or 5; and (iii) an amino acid substitution at position 13, 19, 84, 87, 91, 92, or 95 as set forth in SEQ ID NO: 1, 2, 3, 4, or 5. In another embodiment, the interleukin-2 polypeptide comprises (i) a disulfide bond formed between two amino acids at positions 35 and 72; (ii) an amino acid substitution at position 32 or 76 as set forth in SEQ ID NO: 1, 2, 3, 4, or 5; and (iii) an amino acid substitution at position 13, 19, 84, 87, 91, 92, or 95 as set forth in SEQ ID NO: 1, 2, 3, 4, or 5. In yet another embodiment, the interleukin-2 polypeptide comprises (i) a disulfide bond formed between two amino acids at positions 38 and 72; (ii) an amino acid substitution at position 32 or 76 as set forth in SEQ ID NO: 1, 2, 3, 4, or 5; and (iii) an amino acid substitution at position 13, 19, 84, 87, 91, 92, or 95 as set forth in SEQ ID NO: 1, 2, 3, 4, or 5. In yet another embodiment, the interleukin-2 polypeptide comprises (i) a disulfide bond formed between two amino acids at positions 42 and 69; (ii) an amino acid substitution at position 32 or 76 as set forth in SEQ ID NO: 1, 2, 3, 4, or 5; and (iii) an amino acid substitution at position 13, 19, 84, 87, 91, 92, or 95 as set forth in SEQ ID NO: 1, 2, 3, 4, or 5. In yet another embodiment, the interleukin-2 polypeptide comprises (i) a disulfide bond formed between two amino acids at positions 42 and 72; (ii) an amino acid substitution at position 32 or 76 as set forth in SEQ ID NO: 1, 2, 3, 4, or 5; and (iii) an amino acid substitution at position 13, 19, 84, 87, 91, 92, or 95 as set forth in SEQ ID NO: 1, 2, 3, 4, or 5. In still another embodiment, the interleukin-2 polypeptide comprises (i) a disulfide bond formed between two amino acids at positions 45 and 62; (ii) an amino acid substitution at position 32 or 76 as set forth in SEQ ID NO:

1, 2, 3, 4, or 5; and (iii) an amino acid substitution at position 13, 19, 84, 87, 91, 92, or 95 as set forth in SEQ ID NO: 1, 2, 3, 4, or 5.

In one embodiment, the interleukin-2 polypeptide provided herein comprises (i) a disulfide bond formed between K35C and L72C, R38C and L72C, F42C and V69C, Y42C and L72C, or Y45C and E62C; (ii) an amino acid substitution of K32E or K76E; and (iii) an amino acid substitution of Q13N, L19S, D84T, S87D, S87E, V91I, I92L, E95N, or E95Q. In another embodiment, the interleukin-2 polypeptide comprises (i) a disulfide bond formed between K35C and L72C; (ii) an amino acid substitution of K32E or K76E; and (iii) an amino acid substitution of Q13N, L19S, D84T, S87D, S87E, V91I, I92L, E95N, or E95Q. In yet another embodiment, the interleukin-2 polypeptide comprises (i) a disulfide bond formed between R38C and L72C; (ii) an amino acid substitution of K32E or K76E; and (iii) an amino acid substitution of Q13N, L19S, D84T, S87D, S87E, V91I, I92L, E95N, or E95Q. In yet another embodiment, the interleukin-2 polypeptide comprises (i) a disulfide bond formed between F42C and V69C; (ii) an amino acid substitution of K32E or K76E; and (iii) an amino acid substitution of Q13N, L19S, D84T, S87D, S87E, V91I, I92L, E95N, or E95Q. In yet another embodiment, the interleukin-2 polypeptide comprises (i) a disulfide bond formed between Y42C and L72C; (ii) an amino acid substitution of K32E or K76E; and (iii) an amino acid substitution of Q13N, L19S, D84T, S87D, S87E, V91I, I92L, E95N, or E95Q. In still another embodiment, the interleukin-2 polypeptide comprises (i) a disulfide bond formed between Y45C and E62C; (ii) an amino acid substitution of K32E or K76E; and (iii) an amino acid substitution of Q13N, L19S, D84T, S87D, S87E, V91I, I92L, E95N, or E95Q.

In one embodiment, the interleukin-2 polypeptide provided herein comprises (i) a disulfide bond formed between F42C and V69C; (ii) an amino acid substitution of K32E; and (iii) an amino acid substitution of Q13N, L19S, D84T, S87D, S87E, V91I, I92L, E95N, or E95Q. In another embodiment, the interleukin-2 polypeptide provided herein comprises (i) a disulfide bond formed between F42C and V69C; (ii) an amino acid substitution of K32E; and (iii) an amino acid substitution of Q13N. In yet another embodiment, the interleukin-2 polypeptide provided herein comprises (i) a disulfide bond formed between F42C and V69C; (ii) an amino acid substitution of K32E; and (iii) an amino acid substitution of L19S. In yet another embodiment, the interleukin-2 polypeptide provided herein comprises (i) a disulfide bond formed between F42C and V69C; (ii) an amino acid substitution of K32E; and (iii) an amino acid substitution of D84T. In yet another embodiment, the interleukin-2 polypeptide provided herein comprises (i) a disulfide bond formed between F42C and V69C; (ii) an amino acid substitution of K32E; and (iii) an amino acid substitution of S87D. In yet another embodiment, the interleukin-2 polypeptide provided herein comprises (i) a disulfide bond formed between F42C and V69C; (ii) an amino acid substitution of K32E; and (iii) an amino acid substitution of S87E. In yet another embodiment, the interleukin-2 polypeptide provided herein comprises (i) a disulfide bond formed between F42C and V69C; (ii) an amino acid substitution of K32E; and (iii) an amino acid substitution of V91I. In yet another embodiment, the interleukin-2 polypeptide provided herein comprises (i) a disulfide bond formed between F42C and V69C; (ii) an amino acid substitution of K32E; and (iii) an amino acid substitution of I92L. In yet another embodiment, the interleukin-2 polypeptide provided herein comprises (i) a disulfide bond formed between F42C and V69C; (ii) an amino acid substitution of K32E; and (iii) amino acid substitutions of V91I and I92L. In yet another embodiment, the interleukin-2 polypeptide provided herein comprises (i) a disulfide bond formed between F42C and V69C; (ii) an amino acid substitution of K32E; and (iii) an amino acid substitution of E95N. In still another embodiment, the interleukin-2 polypeptide provided herein comprises (i) a disulfide bond formed between F42C and V69C; (ii) an amino acid substitution of K32E; and (iii) an amino acid substitution of E95Q.

In one embodiment, the interleukin-2 polypeptide provided herein comprises (i) a disulfide bond formed between F42C and V69C; (ii) an amino acid substitution of K32E; (iii) an amino acid substitution of Q13N, L19S, D84T, S87D, S87E, V91I, I92L, E95N, or E95Q; and (iv) C125S. In another embodiment, the interleukin-2 polypeptide provided herein comprises (i) a disulfide bond formed between F42C and V69C; (ii) an amino acid substitution of K32E; (iii) an amino acid substitution of Q13N; and (iv) C125S. In yet another embodiment, the interleukin-2 polypeptide provided herein comprises (i) a disulfide bond formed between F42C and V69C; (ii) an amino acid substitution of K32E; (iii) an amino acid substitution of L19S; and (iv) C125S. In yet another embodiment, the interleukin-2 polypeptide provided herein comprises (i) a disulfide bond formed between F42C and V69C; (ii) an amino acid substitution of K32E; (iii) an amino acid substitution of D84T; and (iv) C125S. In yet another embodiment, the interleukin-2 polypeptide provided herein comprises (i) a disulfide bond formed between F42C and V69C; (ii) an amino acid substitution of K32E; (iii) an amino acid substitution of S87D; and (iv) C125S. In yet another embodiment, the interleukin-2 polypeptide provided herein comprises (i) a disulfide bond formed between F42C and V69C; (ii) an amino acid substitution of K32E; (iii) an amino acid substitution of S87E; and (iv) C125S. In yet another embodiment, the interleukin-2 polypeptide provided herein comprises (i) a disulfide bond formed between F42C and V69C; (ii) an amino acid substitution of K32E; (iii) an amino acid substitution of V91I; and (iv) C125S. In yet another embodiment, the interleukin-2 polypeptide provided herein comprises (i) a disulfide bond formed between F42C and V69C; (ii) an amino acid substitution of K32E; (iii) an amino acid substitution of I92L; and (iv) C125S. In yet another embodiment, the interleukin-2 polypeptide provided herein comprises (i) a disulfide bond formed between F42C and V69C; (ii) an amino acid substitution of K32E; (iii) amino acid substitutions of V91I and I92L; and (iv) C125S. In yet another embodiment, the interleukin-2 polypeptide provided herein comprises (i) a disulfide bond formed between F42C and V69C; (ii) an amino acid substitution of K32E; (iii) an amino acid substitution of E95N; and (iv) C125S. In still another embodiment, the interleukin-2 polypeptide provided herein comprises (i) a disulfide bond formed between F42C and V69C; (ii) an amino acid substitution of K32E; (iii) an amino acid substitution of E95Q; and (iv) C125S.

In one embodiment, the interleukin-2 polypeptide provided herein comprises an amino acid sequence selected from SEQ ID NOs: 159 to 165 and 177 to 183. In another embodiment, the interleukin-2 polypeptide provided herein comprises an amino acid sequence selected from SEQ ID NOs: 159 to 165. In yet another embodiment, the interleukin-2 polypeptide provided herein comprises an amino acid sequence selected from SEQ ID NOs: 177 to 183.

In one embodiment, the interleukin-2 polypeptide provided herein comprises an amino acid sequence selected from SEQ ID NOs: 159 to 165, 177 to 183, 195 to 203, and 210 to 218. In another embodiment, the interleukin-2 polypeptide provided herein comprises an amino acid sequence selected from SEQ ID NOs: 159 to 165 and 195 to 203. In yet another embodiment, the interleukin-2 polypeptide provided herein comprises an amino acid sequence selected from SEQ ID NOs: 177 to 183 and 210 to 218.

In one embodiment, provided herein is an interleukin-2 polypeptide comprising an amino acid sequence of SEQ ID NO: 1, 2, 3, 4, or 5, wherein the interleukin-2 polypeptide comprises two or more disulfide bonds. In certain embodiments, the interleukin-2 polypeptide comprising two or more disulfide bonds have a thermostability of no less than about 50° C., no less than about 55° C., no less than about 60° C., or no less than about 65° C. In certain embodiments, the interleukin-2 polypeptide comprising two or more disulfide bonds have a thermostability of no less than about 50° C. In certain embodiments, the interleukin-2 polypeptide comprising two or more disulfide bonds have a thermostability of no less than about 55° C. In certain embodiments, the interleukin-2 polypeptide comprising two or more disulfide bonds have a thermostability of no less than about 60° C. In certain embodiments, the interleukin-2 polypeptide comprising two or more disulfide bonds have a thermostability of no less than about 65° C.

In another embodiment, provided herein is an interleukin-2 polypeptide comprising an amino acid sequence of SEQ ID NO: 1, 2, 3, 4, or 5, wherein the interleukin-2 polypeptide comprises two disulfide bonds. In certain embodiments, the interleukin-2 polypeptide comprising two disulfide bonds have a thermostability of no less than about 50° C., no less than about 55° C., no less than about 60° C., or no less than about 65° C. In certain embodiments, the interleukin-2 polypeptide comprising two disulfide bonds have a thermostability of no less than about 50° C. In certain embodiments, the interleukin-2 polypeptide comprising two disulfide bonds have a thermostability of no less than about 55° C. In certain embodiments, the interleukin-2 polypeptide comprising two disulfide bonds have a thermostability of no less than about 60° C. In certain embodiments, the interleukin-2 polypeptide comprising two disulfide bonds have a thermostability of no less than about 65° C.

In one embodiment, the amino acid sequence of the interleukin-2 polypeptide provided herein is one of SEQ ID NOs: 159 to 165 and 177 to 183. In another embodiment, the amino acid sequence of the interleukin-2 polypeptide provided herein is one of SEQ ID NOs: 159 to 165. In yet another embodiment, the amino acid sequence of the interleukin-2 polypeptide provided herein is one of SEQ ID NOs: 177 to 183.

In one embodiment, the amino acid sequence of the interleukin-2 polypeptide provided herein is one of SEQ ID NOs: 159 to 165, 177 to 183, 195 to 203, and 210 to 218. In another embodiment, the amino acid sequence of the interleukin-2 polypeptide provided herein is one of SEQ ID NOs: 159 to 165 and 195 to 203. In yet another embodiment, the amino acid sequence of the interleukin-2 polypeptide provided herein is one of SEQ ID NOs: 177 to 183 and 210 to 218.

In one embodiment, the interleukin-2 polypeptide provided herein that comprises a disulfide bond formed between two amino acids from positions 30 to 80 as set forth in SEQ ID NO: 1, 2, 3, 4, or 5 has an enhanced stability and/or an enhanced production yield as compared to a wild-type interleukin-2 described herein.

In one embodiment, the interleukin-2 polypeptide provided herein that comprises a disulfide bond formed between two amino acids from positions 30 to 80 as set forth in SEQ ID NO: 1, 2, 3, 4, or 5 has a production yield that is no less than about 2, no less than about 5, or no less than about 10 time higher than that of a wild-type interleukin-2 described herein. In another embodiment, the interleukin-2 polypeptide provided herein that comprises a disulfide bond formed between two amino acids from positions 30 to 80 as set forth in SEQ ID NO: 1, 2, 3, 4, or 5 has a production yield that is from about 2 to about 1,000 times, from about 2 to 100 times, from about 2 to about 50 times, from about 2 to about 20 times, or from about 2 to about 10 times higher than that of a wild-type interleukin-2 described herein.

In one embodiment, provided herein is an interleukin-2 polypeptide comprising an amino acid sequence of SEQ ID NO: 1, 2, 3, 4, or 5, wherein the interleukin-2 polypeptide comprises a replacement of the amino acid residues from positions 29 to 50 as set forth in SEQ ID NO: 1, 2, 3, 4, or 5 with an IL-15 hinge fragment-containing peptide.

In one embodiment, the interleukin-2 polypeptide provided herein comprises a replacement of the amino acid residues from positions N29 to A50 as set forth in SEQ ID NO: 1, 2, 3, 4, or 5 with an IL-15 hinge fragment-containing peptide as defined herein.

In another embodiment, the interleukin-2 polypeptide provided herein comprises a replacement of an amino acid sequence of SEQ ID NO: 171 with an amino acid sequence of one of SEQ ID NOs: 166 to 170 and 219 to 223.

In yet another embodiment, the interleukin-2 polypeptide provided herein comprises a replacement of an amino acid sequence of SEQ ID NO: 171 with an amino acid sequence of SEQ ID NO: 166, 167, 168, 169, or 170. In certain embodiments, the interleukin-2 polypeptide provided herein comprises a replacement of an amino acid sequence of SEQ ID NO: 171 with an amino acid sequence of SEQ ID NO: 166. In certain embodiments, the interleukin-2 polypeptide provided herein comprises a replacement of an amino acid sequence of SEQ ID NO: 171 with an amino acid sequence of SEQ ID NO: 167. In certain embodiments, the interleukin-2 polypeptide provided herein comprises a replacement of an amino acid sequence of SEQ ID NO: 171 with an amino acid sequence of SEQ ID NO: 168. In certain embodiments, the interleukin-2 polypeptide provided herein comprises a replacement of an amino acid sequence of SEQ ID NO: 171 with an amino acid sequence of SEQ ID NO: 169. In certain embodiments, the interleukin-2 polypeptide provided herein comprises a replacement of an amino acid sequence of SEQ ID NO: 171 with an amino acid sequence of SEQ ID NO: 170.

In still another embodiment, the interleukin-2 polypeptide provided herein comprises a replacement of an amino acid sequence of SEQ ID NO: 171 with an amino acid sequence of SEQ ID NO: 219, 220, 221, 222, or 223. In certain embodiments, the interleukin-2 polypeptide provided herein comprises a replacement of an amino acid sequence of SEQ ID NO: 171 with an amino acid sequence of SEQ ID NO: 219. In certain embodiments, the interleukin-2 polypeptide provided herein comprises a replacement of an amino acid sequence of SEQ ID NO: 171 with an amino acid sequence of SEQ ID NO: 220. In certain embodiments, the interleukin-2 polypeptide provided herein comprises a replacement of an amino acid sequence of SEQ ID NO: 171 with an amino acid sequence of SEQ ID NO: 221. In certain embodiments, the interleukin-2 polypeptide provided herein comprises a replacement of an amino acid sequence of SEQ ID NO: 171 with an amino acid sequence of SEQ ID NO: 222. In certain embodiments, the interleukin-2 polypeptide provided herein comprises a replacement of an amino acid sequence of SEQ ID NO: 171 with an amino acid sequence of SEQ ID NO: 223.

In one embodiment, provided herein is an interleukin-2 polypeptide comprising an amino acid sequence of SEQ ID NO: 1, 2, 3, 4, or 5, wherein the interleukin-2 polypeptide comprises (i) a replacement of the amino acid residues from positions 29 to 50 as set forth in SEQ ID NO: 1, 2, 3, 4, or 5 with an IL-15 hinge fragment-containing peptide; and (ii) an amino acid substitution at position 76 as set forth in SEQ ID NO: 1, 2, 3, 4, or 5.

In another embodiment, the interleukin-2 polypeptide provided herein comprises (i) a replacement of the amino acid residues from positions N29 to A50 as set forth in SEQ ID NO: 1, 2, 3, 4, or 5 with an IL-15 hinge fragment-containing peptide as defined herein; and (ii) an amino acid substitution at position K76 as set forth in SEQ ID NO: 1, 2, 3, 4, or 5.

In yet another embodiment, the interleukin-2 polypeptide provided herein comprises (i) a replacement of an amino acid sequence of SEQ ID NO: 171 with an amino acid sequence of one of SEQ ID NOs: 166 to 170 and 219 to 223; and (ii) an amino acid substitution at position K76 as set forth in SEQ ID NO: 1, 2, 3, 4, or 5.

In yet another embodiment, the interleukin-2 polypeptide provided herein comprises (i) a replacement of an amino acid sequence of SEQ ID NO: 171 with an amino acid sequence of SEQ ID NO: 166, 167, 168, 169, or 170; and (ii) an amino acid substitution at position K76 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 166; and (ii) an amino acid substitution at position K76 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 167; and (ii) an amino acid substitution at position K76 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 168; and (ii) an amino acid substitution at position K76 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 169; and (ii) an amino acid substitution at position K76 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 170; and (ii) an amino acid substitution at position K76 as set forth in SEQ ID NO: 1, 2, 3, 4, or 5.

In still another embodiment, the interleukin-2 polypeptide provided herein comprises (i) a replacement of an amino acid sequence of SEQ ID NO: 171 with an amino acid sequence of SEQ ID NO: 219, 220, 221, 222, or 223; and (ii) an amino acid substitution at position K76 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 219; and (ii) an amino acid substitution at position K76 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 220; and (ii) an amino acid substitution at position K76 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 221; and (ii) an amino acid substitution at position K76 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 222; and (ii) an amino acid substitution at position K76 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 223; and (ii) an amino acid substitution at position K76 as set forth in SEQ ID NO: 1, 2, 3, 4, or 5.

In one embodiment, provided herein is an interleukin-2 polypeptide comprising an amino acid sequence of SEQ ID NO: 1, 2, 3, 4, or 5, wherein the interleukin-2 polypeptide comprises (i) a replacement of the amino acid residues from positions 29 to 50 as set forth in SEQ ID NO: 1, 2, 3, 4, or 5 with an IL-15 hinge fragment-containing peptide; and (ii) an amino acid substitution at position 15 as set forth in SEQ ID NO: 1, 2, 3, 4, or 5.

In another embodiment, the interleukin-2 polypeptide provided herein comprises (i) a replacement of the amino acid residues from positions 29 to 50 as set forth in SEQ ID NO: 1, 2, 3, 4, or 5 with an IL-15 hinge fragment-containing peptide; and (ii) an amino acid substitution at position E15 as set forth in SEQ ID NO: 1, 2, 3, 4, or 5.

In yet another embodiment, the interleukin-2 polypeptide provided herein comprises (i) a replacement of an amino acid sequence of SEQ ID NO: 171 with an amino acid sequence of one of SEQ ID NOs: 166 to 170 and 219 to 223; and (ii) an amino acid substitution at position E15 as set forth in SEQ ID NO: 1, 2, 3, 4, or 5.

In yet another embodiment, the interleukin-2 polypeptide provided herein comprises (i) a replacement of an amino acid sequence of SEQ ID NO: 171 with an amino acid sequence of SEQ ID NO: 166, 167, 168, 169, or 170; and (ii) an amino acid substitution at position E15 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 166; and (ii) an amino acid substitution at position E15 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 167; and (ii) an amino acid substitution at position E15 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 168; and (ii) an amino acid substitution at position E15 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 169; and (ii) an amino acid substitution at position E15 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 170; and (ii) an amino acid substitution at position E15 as set forth in SEQ ID NO: 1, 2, 3, 4, or 5.

In still another embodiment, the interleukin-2 polypeptide provided herein comprises (i) a replacement of an amino acid sequence of SEQ ID NO: 171 with an amino acid sequence of SEQ ID NO: 219, 220, 221, 222, or 223; and (ii) an amino acid substitution at position E15 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 219; and (ii) an amino acid substitution at position E15 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 220; and (ii) an amino acid substitution at position E15 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 221; and (ii) an amino acid substitution at position E15 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 222; and (ii) an amino acid substitution at position E15 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 223; and (ii) an amino acid substitution at position E15 as set forth in SEQ ID NO: 1, 2, 3, 4, or 5.

In one embodiment, provided herein is an interleukin-2 polypeptide comprising an amino acid sequence of SEQ ID NO: 1, 2, 3, 4, or 5, wherein the interleukin-2 polypeptide comprises (i) a replacement of the amino acid residues from positions 29 to 50 as set forth in SEQ ID NO: 1, 2, 3, 4, or 5 with an IL-15 hinge fragment-containing peptide; and (ii) an amino acid substitution at position 87 as set forth in SEQ ID NO: 1, 2, 3, 4, or 5.

In another embodiment, the interleukin-2 polypeptide provided herein comprises (i) a replacement of the amino acid residues from positions 29 to 50 as set forth in SEQ ID NO: 1, 2, 3, 4, or 5 with an IL-15 hinge fragment-containing peptide; and (ii) an amino acid substitution at position S87 as set forth in SEQ ID NO: 1, 2, 3, 4, or 5.

In yet another embodiment, the interleukin-2 polypeptide provided herein comprises (i) a replacement of an amino acid sequence of SEQ ID NO: 171 with an amino acid sequence of one of SEQ ID NOs: 166 to 170 and 219 to 223; and (ii) an amino acid substitution at position S87 as set forth in SEQ ID NO: 1, 2, 3, 4, or 5.

In yet another embodiment, the interleukin-2 polypeptide provided herein comprises (i) a replacement of an amino acid sequence of SEQ ID NO: 171 with an amino acid sequence of SEQ ID NO: 166, 167, 168, 169, or 170; and (ii) an amino acid substitution at position S87 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 166; and (ii) an amino acid substitution at position S87 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 167; and (ii) an amino acid substitution at position S87 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 168; and (ii) an amino acid substitution at position S87 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 169; and (ii) an amino acid substitution at position S87 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 170; and (ii) an amino acid substitution at position S87 as set forth in SEQ ID NO: 1, 2, 3, 4, or 5.

In still another embodiment, the interleukin-2 polypeptide provided herein comprises (i) a replacement of an amino acid sequence of SEQ ID NO: 171 with an amino acid sequence of SEQ ID NO: 219, 220, 221, 222, or 223; and (ii) an amino acid substitution at position S87 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 219; and (ii) an amino acid substitution at position S87 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 220; and (ii) an amino acid substitution at position S87 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 221; and (ii) an amino acid substitution at position S87 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 222; and (ii) an amino acid substitution at position S87 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 223; and (ii) an amino acid substitution at position S87 as set forth in SEQ ID NO: 1, 2, 3, 4, or 5.

In one embodiment, provided herein is an interleukin-2 polypeptide comprising an amino acid sequence of SEQ ID NO: 1, 2, 3, 4, or 5, wherein the interleukin-2 polypeptide comprises (i) a replacement of the amino acid residues from positions 29 to 50 as set forth in SEQ ID NO: 1, 2, 3, 4, or 5 with an IL-15 hinge fragment-containing peptide; and (ii) amino acid substitutions at positions 15 and 87 as set forth in SEQ ID NO: 1, 2, 3, 4, or 5.

In another embodiment, the interleukin-2 polypeptide provided herein comprises (i) a replacement of the amino acid residues from positions 29 to 50 as set forth in SEQ ID NO: 1, 2, 3, 4, or 5 with an IL-15 hinge fragment-containing peptide; and (ii) amino acid substitutions at positions E15 and S87 as set forth in SEQ ID NO: 1, 2, 3, 4, or 5.

In yet another embodiment, the interleukin-2 polypeptide provided herein comprises (i) a replacement of an amino acid sequence of SEQ ID NO: 171 with an amino acid sequence of one of SEQ ID NOs: 166 to 170 and 219 to 223;

and (ii) amino acid substitutions at positions E15 and S87 as set forth in SEQ ID NO: 1, 2, 3, 4, or 5.

In yet another embodiment, the interleukin-2 polypeptide provided herein comprises (i) a replacement of an amino acid sequence of SEQ ID NO: 171 with an amino acid sequence of SEQ ID NO: 166, 167, 168, 169, or 170; and (ii) amino acid substitutions at positions E15 and S87 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 166; and (ii) amino acid substitutions at positions E15 and S87 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 167; and (ii) amino acid substitutions at positions E15 and S87 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 168; and (ii) amino acid substitutions at positions E15 and S87 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 169; and (ii) amino acid substitutions at positions E15 and S87 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 170; and (ii) amino acid substitutions at positions E15 and S87 as set forth in SEQ ID NO: 1, 2, 3, 4, or 5.

In still another embodiment, the interleukin-2 polypeptide provided herein comprises (i) a replacement of an amino acid sequence of SEQ ID NO: 171 with an amino acid sequence of SEQ ID NO: 219, 220, 221, 222, or 223; and (ii) amino acid substitutions at positions E15 and S87 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 219; and (ii) amino acid substitutions at positions E15 and S87 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 220; and (ii) amino acid substitutions at positions E15 and S87 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 221; and (ii) amino acid substitutions at positions E15 and S87 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 222; and (ii) amino acid substitutions at positions E15 and S87 as set forth in SEQ ID NO: 1, 2, 3, 4, or 5. In certain embodiments, the interleukin-2 polypeptide provided herein comprises (i) a replacement of an amino acid sequence of SEQ ID NO: 171 with an amino acid sequence of SEQ ID NO: 223; and (ii) amino acid substitutions at positions E15 and S87 as set forth in SEQ ID NO: 1, 2, 3, 4, or 5.

In one embodiment, the interleukin-2 polypeptide provided herein comprises (i) a replacement of an amino acid sequence of SEQ ID NO: 171 with an amino acid sequence of SEQ ID NO: 167 or 220; and (ii) an amino acid substitution of E15K, S87D, or S87E. In another embodiment, the interleukin-2 polypeptide provided herein comprises (i) a replacement of an amino acid sequence of SEQ ID NO: 171 with an amino acid sequence of SEQ ID NO: 167 or 220; and (ii) amino acid substitutions of E15K, and S87D or S87E.

In one embodiment, the interleukin-2 polypeptide provided herein comprises an amino acid sequence selected from SEQ ID NOs: 172 to 176, 184 to 188, and 224 to 234. In another embodiment, the interleukin-2 polypeptide provided herein comprises an amino acid sequence selected from SEQ ID NOs: 172 to 176 and 224 to 234. In yet another embodiment, the interleukin-2 polypeptide provided herein comprises an amino acid sequence selected from SEQ ID NOs: 184 to 188.

In one embodiment, the amino acid sequence of the interleukin-2 polypeptide provided herein is one of SEQ ID NOs: 172 to 176, 184 to 188, and 224 to 234. In another embodiment, the amino acid sequence of the interleukin-2 polypeptide provided herein is one of SEQ ID NOs: 172 to 176 and 224 to 234. In yet another embodiment, the amino acid sequence of the interleukin-2 polypeptide provided herein is one of SEQ ID NOs: 184 to 188.

In one embodiment, the interleukin-2 polypeptide provided herein that comprises a replacement of the amino acid residues from positions 29 to 50 as set forth in SEQ ID NO: 1, 2, 3, 4, or 5 with an IL-15 hinge fragment-containing peptide has an enhanced stability and/or an enhanced production yield as compared to a wild-type interleukin-2 described herein.

In one embodiment, the interleukin-2 polypeptide provided herein that comprises a replacement of the amino acid residues from positions 29 to 50 as set forth in SEQ ID NO: 1, 2, 3, 4, or 5 with an IL-15 hinge fragment-containing peptide has a production yield that is no less than about 2, no less than about 5, or no less than about 10 time higher than that of a wild-type interleukin-2 described herein. In another embodiment, the interleukin-2 polypeptide provided that comprises a replacement of the amino acid residues from positions 29 to 50 as set forth in SEQ ID NO: 1, 2, 3, 4, or 5 with an IL-15 hinge fragment-containing peptide has a production yield that is from about 2 to about 1,000 times, from about 2 to 100 times, from about 2 to about 50 times, from about 2 to about 20 times, or from about 2 to about 10 times higher than that of a wild-type interleukin-2 described herein.

In one embodiment, provided herein is an interleukin-2 polypeptide comprising an amino acid sequence of SEQ ID NO: 1, 2, 3, 4, or 5, wherein the interleukin-2 polypeptide comprises an amino acid substitution at position 16, 84, 88, 92, or 95 as set forth in SEQ ID NO: 1, 2, 3, 4, or 5; with the proviso that the amino acid substitution at position 88 is not N88R.

In certain embodiments, the interleukin-2 polypeptide provided herein comprises an amino acid substitution at position 16 as set forth in SEQ ID NO: 1, 2, 3, 4, or 5 with one of the twenty natural amino acids other than H. In certain embodiments, the interleukin-2 polypeptide provided herein comprises an amino acid substitution at position 84 as set forth in SEQ ID NO: 1, 2, 3, 4, or 5 with one of the twenty natural amino acids other than D. In certain embodiments, the interleukin-2 polypeptide provided herein comprises an amino acid substitution at position 88 as set forth in SEQ ID NO: 1, 2, 3, 4, or 5 with one of the twenty natural amino acids other than N. In certain embodiments, the interleukin-2 polypeptide provided herein comprises an amino acid substitution at position 92 as set forth in SEQ ID NO: 1, 2, 3, 4, or 5 with one of the twenty natural amino acids other than I. In certain embodiments, the interleukin-2 polypeptide provided herein comprises an amino acid substitution at position 95 as set forth in SEQ ID NO: 1, 2, 3, 4, or 5 with one of the twenty natural amino acids other than E.

In another embodiment, provided herein is an interleukin-2 polypeptide comprising an amino acid sequence of SEQ ID NO: 1, 2, 3, 4, or 5, wherein the interleukin-2 polypeptide comprises an amino acid substitution at position H16, D84, N88, I92, or E95 as set forth in SEQ ID NO: 1, 2, 3, 4, or 5; with the proviso that the amino acid substitution at position N88 is not N88R.

In certain embodiments, the interleukin-2 polypeptide provided herein comprises an amino acid substitution at position H16 as set forth in SEQ ID NO: 1, 2, 3, 4, or 5 with one of the twenty natural amino acids other than H. In certain embodiments, the interleukin-2 polypeptide provided herein comprises an amino acid substitution at position D84 as set forth in SEQ ID NO: 1, 2, 3, 4, or 5 with one of the twenty natural amino acids other than D. In certain embodiments, the interleukin-2 polypeptide provided herein comprises an amino acid substitution at position N88 as set forth in SEQ ID NO: 1, 2, 3, 4, or 5 with one of the twenty natural amino acids other than N. In certain embodiments, the interleukin-2 polypeptide provided herein comprises an amino acid substitution at position 192 as set forth in SEQ ID NO: 1, 2, 3, 4, or 5 with one of the twenty natural amino acids other than I. In certain embodiments, the interleukin-2 polypeptide provided herein comprises an amino acid substitution at position E95 as set forth in SEQ ID NO: 1, 2, 3, 4, or 5 with one of the twenty natural amino acids other than E.

In yet another embodiment, provided herein is an interleukin-2 polypeptide comprising an amino acid sequence of SEQ ID NO: 1, 2, 3, 4, or 5, wherein the interleukin-2 polypeptide comprises an amino acid substitution selected from H16D, H16E, H16Q, D84T, N88A, I92A, E95K, and E95Q.

In certain embodiments, the interleukin-2 polypeptide provided herein comprises an amino acid substitution selected from H16D, H16E, and H16Q. In certain embodiments, the interleukin-2 polypeptide provided herein comprises an amino acid substitution selected from E95K and E95Q.

In still another embodiment, provided herein is an interleukin-2 polypeptide comprising an amino acid sequence of SEQ ID NO: 1, 2, 3, 4, or 5, wherein the interleukin-2 polypeptide comprises an amino acid substitution selected from H16E, D84T, N88A, I92A, E95K, and E95Q.

In certain embodiments, the interleukin-2 polypeptide provided herein comprises an amino acid substitution of H16E. In certain embodiments, the interleukin-2 polypeptide provided herein comprises an amino acid substitution of D84T. In certain embodiments, the interleukin-2 polypeptide provided herein comprises an amino acid substitution of N88A. In certain embodiments, the interleukin-2 polypeptide provided herein comprises an amino acid substitution of I92A. In certain embodiments, the interleukin-2 polypeptide provided herein comprises an amino acid substitution of E95K. In certain embodiments, the interleukin-2 polypeptide provided herein comprises an amino acid substitution of E95Q.

In one embodiment, the interleukin-2 polypeptide provided herein comprises an amino acid sequence selected from SEQ ID NOs: 11, 16, 21, 22, 24, 95, 100, 105, 106, 108, 121 to 125, and 130 to 134. In another embodiment, the interleukin-2 polypeptide provided herein comprises an amino acid sequence selected from SEQ ID NOs: 11, 16, 21, 22, 24, and 121 to 125. In yet another embodiment, the interleukin-2 polypeptide provided herein comprises an amino acid sequence selected from SEQ ID NOs: 95, 100, 105, 106, 108, and 130 to 134.

In one embodiment, the amino acid sequence of the interleukin-2 polypeptide provided herein is one of selected from SEQ ID NOs: 11, 16, 21, 22, 24, 95, 100, 105, 106, 108, 121 to 125, and 130 to 134. In another embodiment, the amino acid sequence of the interleukin-2 polypeptide provided herein is one of selected from SEQ ID NOs: 11, 16, 21, 22, 24, and 121 to 125. In yet another embodiment, the amino acid sequence of the interleukin-2 polypeptide provided herein is one of selected from SEQ ID NOs: 95, 100, 105, 106, 108, and 130 to 134.

In certain embodiments, the interleukin-2 polypeptide provided herein that comprises an amino acid substitution at position 16, 84, 88, 92, or 95 has a reduced binding affinity to an IL-2Rβ chain as compared to a wild-type interleukin-2 described herein.

In certain embodiments, the interleukin-2 polypeptide provided herein that comprises an amino acid substitution at position 16, 84, 88, 92, or 95 has a $K_d$ to the IL-2Rβ of no less than about 2 times, no less than about 5 times, no less than about 10 times, no less than about 100 times, no less than about 1,000 times, or no less than about 10,000 times higher than that of the wild-type interleukin-2 to the IL-2Rβ. In one embodiment, the interleukin-2 polypeptide provided herein that comprises an amino acid substitution at position 16, 84, 88, 92, or 95 has a $K_d$ to the IL-2Rβ of no less than about 2 times higher than that of the wild-type interleukin-2 to the IL-2Rβ. In another embodiment, the interleukin-2 polypeptide provided herein that comprises an amino acid substitution at position 16, 84, 88, 92, or 95 has a $K_d$ to the IL-2Rβ of no less than about 5 times higher than that of the wild-type interleukin-2 to the IL-2Rβ. In yet another embodiment, the interleukin-2 polypeptide provided herein that comprises an amino acid substitution at position 16, 84, 88, 92, or 95 has a $K_d$ to the IL-2Rβ of no less than about 10 times higher than that of the wild-type interleukin-2 to the IL-2Rβ. In yet another embodiment, the interleukin-2 polypeptide provided herein that comprises an amino acid substitution at position 16, 84, 88, 92, or 95 has a $K_d$ to the IL-2Rβ of no less than about 100 times higher than that of the wild-type interleukin-2 to the IL-2Rβ. In yet another embodiment, the interleukin-2 polypeptide provided herein that comprises an amino acid substitution at position 16, 84, 88, 92, or 95 has a $K_d$ to the IL-2Rβ of no less than about 1,000 times higher than that of the wild-type interleukin-2 to the IL-2Rβ. In still another embodiment, the interleukin-2 polypeptide provided herein that comprises an amino acid substitution at position 16, 84, 88, 92, or 95 has a $K_d$ to the IL-2Rβ of no less than about 10,000 times higher than that of the wild-type interleukin-2 to the IL-2Rβ.

In certain embodiments, the interleukin-2 polypeptide provided herein that comprises an amino acid substitution at position 16, 84, 88, 92, or 95 has a $K_d$ to the IL-2Rβ that is from about 2 to about 50,000 times, from about 5 to about 10,000 times, from about 10 to about 2,000 times, from about 10 to about 1,000 times, from about 10 to about 500 times, from about 10 to about 200 times, or from about 10 to about 100 times higher than that of the wild-type interleukin-2 to the IL-2Rβ. In one embodiment, the interleukin-2 polypeptide provided herein that comprises an amino acid substitution at position 16, 84, 88, 92, or 95 has a $K_d$ to the IL-2Rβ that is from about 2 to about 50,000 times higher than that of the wild-type interleukin-2 to the IL-2Rβ. In another embodiment, the interleukin-2 polypeptide provided herein that comprises an amino acid substitution at position 16, 84, 88, 92, or 95 has a $K_d$ to the IL-2Rβ that is from about 5 to about 10,000 times higher than that of the wild-type interleukin-2 to the IL-2Rβ. In yet another embodiment, the interleukin-2 polypeptide provided herein that comprises an amino acid substitution at position 16, 84, 88, 92, or 95 has a $K_d$ to the IL-2Rβ that is from about 10 to about 2,000 times higher than that of the wild-type interleukin-2 to the IL-2Rβ. In yet another embodiment, the interleukin-2 polypeptide provided herein that comprises an amino acid substitution at position 16, 84, 88, 92, or 95 has a $K_d$ to the IL-2Rβ that is from about 10 to about 1,000 times higher than that of the wild-type interleukin-2 to the IL-2Rβ. In yet another embodiment, the interleukin-2 polypeptide provided herein that comprises an amino acid substitution at position 16, 84, 88, 92, or 95 has a $K_d$ to the IL-2Rβ that is from about 10 to about 500 times higher than that of the wild-type interleukin-2 to the IL-2Rβ. In yet another embodiment, the interleukin-2 polypeptide provided herein that comprises an amino acid substitution at position 16, 84, 88, 92, or 95 has a $K_d$ to the IL-2Rβ that is from about 10 to about 200 times higher than that of the wild-type interleukin-2 to the IL-2Rβ. In still another embodiment, the interleukin-2 polypeptide provided herein that comprises an amino acid substitution at position 16, 84, 88, 92, or 95 has a $K_d$ to the IL-2Rβ that is from about 10 to about 100 times higher than that of the wild-type interleukin-2 to the IL-2Rβ.

In certain embodiments, the interleukin-2 polypeptide provided herein that comprises an amino acid substitution at position 16, 84, 88, 92, or 95 binds to the IL-2Rβ with a $K_d$ ranging from about 100 nM to about 100 μM, from about 200 nM to about 20 μM, from about 500 nM to about 10 μM, from about 500 nM to about 5 μM, or from about 500 nM to about 2 μM.

In one embodiment, the interleukin-2 polypeptide provided herein that comprises an amino acid substitution at position 16, 84, 88, 92, or 95 binds to the IL-2Rβ with a $K_d$ ranging from about 100 nM to about 100 μM. In another embodiment, the interleukin-2 polypeptide provided herein that comprises an amino acid substitution at position 16, 84, 88, 92, or 95 binds to the IL-2Rβ with a $K_d$ ranging from about 200 nM to about 20 μM. In yet another embodiment, the interleukin-2 polypeptide provided herein that comprises an amino acid substitution at position 16, 84, 88, 92, or 95 binds to the IL-2Rβ with a $K_d$ ranging from about 500 nM to about 10 μM. In yet another embodiment, the interleukin-2 polypeptide provided herein that comprises an amino acid substitution at position 16, 84, 88, 92, or 95 binds to the IL-2Rβ with a $K_d$ ranging from about 500 nM to about 5 μM. In still another embodiment, the interleukin-2 polypeptide provided herein that comprises an amino acid substitution at position 16, 84, 88, 92, or 95 binds to the IL-2Rβ with a $K_d$ ranging from about 500 nM to about 2 μM.

In certain embodiments, the interleukin-2 polypeptide provided herein has an enhanced binding affinity to an IL-2Rβ chain as compared to a wild-type interleukin-2 described herein.

In one embodiment, provided herein is an interleukin-2 polypeptide comprising an amino acid sequence of SEQ ID NO: 1, 2, 3, 4, or 5, wherein the interleukin-2 polypeptide comprises an amino acid substitution at position 15 as set forth in SEQ ID NO: 1, 2, 3, 4, or 5 with one of the twenty natural amino acids other than E.

In another embodiment, provided herein is an interleukin-2 polypeptide comprising an amino acid sequence of SEQ ID NO: 1, 2, 3, 4, or 5, wherein the interleukin-2 polypeptide comprises an amino acid substitution at position E15 as set forth in SEQ ID NO: 1, 2, 3, 4, or 5 with one of the twenty natural amino acids other than E.

In yet another embodiment, provided herein is an interleukin-2 polypeptide comprising an amino acid sequence of SEQ ID NO: 1, 2, 3, 4, or 5, wherein the interleukin-2 polypeptide comprises an amino acid substitution of E15K or E15Q.

In yet another embodiment, provided herein is an interleukin-2 polypeptide comprising an amino acid sequence of SEQ ID NO: 1, 2, 3, 4, or 5, wherein the interleukin-2 polypeptide comprises an amino acid substitution of E15K.

In still another embodiment, provided herein is an interleukin-2 polypeptide comprising an amino acid sequence of SEQ ID NO: 1, 2, 3, 4, or 5, wherein the interleukin-2 polypeptide comprises an amino acid substitution of E15Q.

In one embodiment, the interleukin-2 polypeptide provided herein comprises an amino acid sequence of SEQ ID NO: 119, 120, 128, or 129. In another embodiment, the interleukin-2 polypeptide provided herein comprises an amino acid sequence of SEQ ID NO: 119 or 120. In yet another embodiment, the interleukin-2 polypeptide provided herein comprises an amino acid sequence of SEQ ID NO: 128 or 129.

In one embodiment, the amino acid sequence of the interleukin-2 polypeptide provided herein is one of SEQ ID NO: 119, 120, 128, or 129. In another embodiment, the amino acid sequence of the interleukin-2 polypeptide provided herein is one of SEQ ID NO: 119 or 120. In yet another embodiment, the amino acid sequence of the interleukin-2 polypeptide provided herein is one of SEQ ID NO: 128 or 129.

In certain embodiments, the interleukin-2 polypeptide provided herein that comprises an amino acid substitution at position 15 as set forth in SEQ ID NO: 1, 2, 3, 4, or 5 has an enhanced binding affinity to an IL-2Rβ chain as compared to a wild-type interleukin-2 described herein.

In certain embodiments, the interleukin-2 polypeptide provided herein has a reduced binding affinity to an interleukin-2 receptor-γ (IL-2Rγ) chain as compared to a wild-type interleukin-2 described herein.

In one embodiment, provided herein is an interleukin-2 polypeptide comprising an amino acid sequence of SEQ ID NO: 1, 2, 3, 4, or 5, wherein the interleukin-2 polypeptide comprises an amino acid substitution at position 127 or 130 as set forth in SEQ ID NO: 1, 2, 3, 4, or 5.

In certain embodiments, the interleukin-2 polypeptide provided herein comprises an amino acid substitution at position 127 as set forth in SEQ ID NO: 1, 2, 3, 4, or 5 with one of the twenty natural amino acids other than S. In certain embodiments, the interleukin-2 polypeptide provided herein comprises an amino acid substitution at position 130 as set forth in SEQ ID NO: 1, 2, 3, 4, or 5 with one of the twenty natural amino acids other than S.

In another embodiment, provided herein is an interleukin-2 polypeptide comprising an amino acid sequence of SEQ ID NO: 1, 2, 3, 4, or 5, wherein the interleukin-2 polypeptide comprises an amino acid substitution at position S127 or S130 as set forth in SEQ ID NO: 1, 2, 3, 4, or 5.

In certain embodiments, the interleukin-2 polypeptide provided herein comprises an amino acid substitution at position S127 as set forth in SEQ ID NO: 1, 2, 3, 4, or 5 with one of the twenty natural amino acids other than S. In certain embodiments, the interleukin-2 polypeptide provided herein comprises an amino acid substitution at position S130 as set forth in SEQ ID NO: 1, 2, 3, 4, or 5 with one of the twenty natural amino acids other than S.

In yet another embodiment, provided herein is an interleukin-2 polypeptide comprising an amino acid sequence of SEQ ID NO: 1, 2, 3, 4, or 5, wherein the interleukin-2 polypeptide comprises an amino acid substitution selected from S127A, S127E, S127F, S127W, S130A, S130E, S130F, and S130W.

In certain embodiments, the interleukin-2 polypeptide provided herein comprises an amino acid substitution selected from S127A, S127E, S127F, and S127W. In certain embodiments, the interleukin-2 polypeptide provided herein comprises an amino acid substitution selected from S130A, S130E, S130F, and S130W.

In still another embodiment, provided herein is an interleukin-2 polypeptide comprising an amino acid sequence of SEQ ID NO: 1, 2, 3, 4, or 5, wherein the interleukin-2 polypeptide comprises an amino acid substitution selected from S127A and S130A.

In certain embodiments, the interleukin-2 polypeptide provided herein comprises an amino acid substitution of S127A. In certain embodiments, the interleukin-2 polypeptide provided herein comprises an amino acid substitution of S130A.

In one embodiment, the interleukin-2 polypeptide provided herein comprises an amino acid sequence of SEQ ID NO: 126, 127, 135, or 136. In another embodiment, the interleukin-2 polypeptide provided herein comprises an amino acid sequence of SEQ ID NO: 126 or 127. In yet another embodiment, the interleukin-2 polypeptide provided herein comprises an amino acid sequence of SEQ ID NO: 135 or 136.

In one embodiment, the amino acid sequence of the interleukin-2 polypeptide provided herein is one of SEQ ID NO: 126, 127, 135, or 136. In another embodiment, the amino acid sequence of the interleukin-2 polypeptide provided herein is one of SEQ ID NO: 126 or 127. In another embodiment, the amino acid sequence of the interleukin-2 polypeptide provided herein is one of 135 or 136.

In certain embodiments, the interleukin-2 polypeptide provided herein that comprises an amino acid substitution at position 127 or 130 has a reduced binding affinity to an IL-2Rγ chain as compared to a wild-type interleukin-2 described herein.

In one embodiment, the interleukin-2 polypeptide provided herein further comprises an amino acid substitution at position 38 or 42 as set forth in SEQ ID NO: 1, 2, 3, 4, or 5. In another embodiment, the interleukin-2 polypeptide provided herein further comprises amino acid substitutions at positions 38 and 42 as set forth in SEQ ID NO: 1, 2, 3, 4, or 5.

In certain embodiments, the amino acid at position 38 as set forth in SEQ ID NO: 1, 2, 3, 4, or 5 is one of the twenty natural amino acids other than R. In certain embodiments, the amino acid at position 38 as set forth in SEQ ID NO: 1, 2, 3, 4, or 5 is A, E, G, or N. In certain embodiments, the amino acid at position 38 as set forth in SEQ ID NO: 1, 2, 3, 4, or 5 is A, E, or G. In certain embodiments, the amino acid at position 38 as set forth in SEQ ID NO: 1, 2, 3, 4, or 5 is A. In certain embodiments, the amino acid at position 38 as set forth in SEQ ID NO: 1, 2, 3, 4, or 5 is E. In certain embodiments, the amino acid at position 38 as set forth in SEQ ID NO: 1, 2, 3, 4, or 5 is G. In certain embodiments, the amino acid at position 38 as set forth in SEQ ID NO: 1, 2, 3, 4, or 5 is N.

In certain embodiments, the amino acid at position 42 as set forth in SEQ ID NO: 1, 2, 3, 4, or 5 is one of the twenty natural amino acids other than F. In certain embodiments, the amino acid at position 42 as set forth in SEQ ID NO: 1, 2, 3, 4, or 5 is A, G, K, or N. In certain embodiments, the amino acid at position 42 as set forth in SEQ ID NO: 1, 2, 3, 4, or 5 is A, G, or K. In certain embodiments, the amino acid at position 42 as set forth in SEQ ID NO: 1, 2, 3, 4, or 5 is A. In certain embodiments, the amino acid at position 42 as set forth in SEQ ID NO: 1, 2, 3, 4, or 5 is E. In certain embodiments, the amino acid at position 42 as set forth in SEQ ID NO: 1, 2, 3, 4, or 5 is K. In certain embodiments, the amino acid at position 42 as set forth in SEQ ID NO: 1, 2, 3, 4, or 5 is N.

In one embodiment, the interleukin-2 polypeptide provided herein further comprises an amino acid substitution at position R38 or F42 as set forth in SEQ ID NO: 1, 2, 3, 4, or 5. In another embodiment, the interleukin-2 polypeptide provided herein further comprises amino acid substitutions at positions R38 and F42 as set forth in SEQ ID NO: 1, 2, 3, 4, or 5.

In one embodiment, the interleukin-2 polypeptide provided herein further comprises an amino acid substitution of (i) R38A, R38E, R38G, or R38N; or (ii) F42A, F42G, F42K, or F42N. In another embodiment, the interleukin-2 polypeptide provided herein further comprises amino acid substitutions of (i) R38A, R38E, R38G, or R38N; and (ii) F42A, F42G, F42K, or F42N.

In one embodiment, the interleukin-2 polypeptide provided herein further comprises an amino acid substitution of (i) R38A, R38E, or R38G; or (ii) F42A, F42G, or F42K. In another embodiment, the interleukin-2 polypeptide provided herein further comprises amino acid substitutions of (i) R38A, R38E, or R38G; and (ii) F42A, F42G, or F42K.

In one embodiment, the interleukin-2 polypeptide provided herein further comprises an amino acid substitution of (i) R38A, R38E, or R38G; or (ii) F42A or F42K. In another embodiment, the interleukin-2 polypeptide provided herein further comprises amino acid substitutions of (i) R38A, R38E, or R38G; and (ii) F42A or F42K.

In one embodiment, the interleukin-2 polypeptide provided herein further comprises an amino acid substitution of F42A, F42K, or F42N. In another embodiment, the interleukin-2 polypeptide provided herein further comprises an amino acid substitution of F42A or F42K. In yet another embodiment, the interleukin-2 polypeptide provided herein further comprises an amino acid substitution of F42A. In still another embodiment, the interleukin-2 polypeptide provided herein further comprises an amino acid substitution of F42K.

In one embodiment, the interleukin-2 polypeptide provided herein further comprises amino acid substitutions of (i) R38A, R38E, or R38G; and (ii) F42A or F42K. In another embodiment, the interleukin-2 polypeptide provided herein further comprises amino acid substitutions of (i) R38A, R38E, or R38G; and (ii) F42A. In yet another embodiment, the interleukin-2 polypeptide provided herein further comprises amino acid substitutions of R38A and F42A. In yet another embodiment, the interleukin-2 polypeptide provided herein further comprises amino acid substitutions of R38E and F42A. In yet another embodiment, the interleukin-2 polypeptide provided herein further comprises amino acid substitutions of R38G and F42A. In yet another embodiment, the interleukin-2 polypeptide provided herein further comprises amino acid substitutions of (i) R38A, R38E, or R38G; and (ii) F42K. In yet another embodiment, the interleukin-2 polypeptide provided herein further comprises amino acid substitutions of R38A and F42K. In yet another embodiment, the interleukin-2 polypeptide provided herein further comprises amino acid substitutions of R38E and F42K. In still another embodiment, the interleukin-2 polypeptide provided herein further comprises amino acid substitutions of R38G and F42K.

In one embodiment, the interleukin-2 polypeptide provided herein comprises:
  (a) (i) an amino acid substitution at position 8, 9, 15, 16, 32, 76, 79, 81, 84, 88, 92, 95, 127, or 130 as set forth in SEQ ID NO: 1, 2, 3, 4, or 5; or (ii) a deletion or replacement of the amino acid residues from positions 30 to 35 as set forth in SEQ ID NO: 1, 2, 3, 4, or 5 with a peptide linker; and
  (b) an amino acid substitution at position 38 or 42 as set forth in SEQ ID NO: 1, 2, 3, 4, or 5.

In another embodiment, the interleukin-2 polypeptide provided herein comprises:
  (a) (i) an amino acid substitution at position K8, K9, E15, H16, K32, K76, H79, R81, D84, N88, I92, E95, S127, or S130 as set forth in SEQ ID NO: 1, 2, 3, 4, or 5; or (ii) a deletion or replacement of the amino acid residues from positions N30 to K35 as set forth in SEQ ID NO: 1, 2, 3, 4, or 5 with a peptide linker; and
  (b) an amino acid substitution at position R38 or F42 as set forth in SEQ ID NO: 1, 2, 3, 4, or 5.

In yet another embodiment, the interleukin-2 polypeptide provided herein comprises:
  (a) (i) an amino acid substitution selected from K8D, K8E, K8Q, K9D, K9E, K9Q, E15K, E15Q, H16D, H16E, H16Q, K32D, K32E, K32Q, K76D, K76E, K76Q, H79D, H79E, H79Q, R81D, R81E, R81Q, D84T, N88A, I92A, E95K, E95Q, S127A, S127E, S127F, S127W, S130A, S130E, S130F, and S130W; or (ii) a deletion or replacement of the amino acid residues from positions 30 to 35 having an amino acid sequence of SEQ ID NO: 10 with a flexible peptide linker having an amino acid sequence selected from G, SG, GGS, and SEQ ID NOs: 7 to 9; and
  (b) an amino acid substitution of (i) R38A, R38E, R38G, or R38N; or (ii) F42A, F42G, F42K, or F42N.

In yet another embodiment, the interleukin-2 polypeptide provided herein comprises:
  (a) (i) an amino acid substitution selected from K8D, K8E, K8Q, K9D, K9E, K9Q, E15K, E15Q, H16D, H16E, H16Q, K32D, K32E, K32Q, K76D, K76E, K76Q, H79D, H79E, H79Q, R81D, R81E, R81Q, D84T, N88A, I92A, E95K, E95Q, S127A, S127E, S127F, S127W, S130A, S130E, S130F, and S130W; or (ii) a deletion or replacement of the amino acid residues from positions 30 to 35 having an amino acid sequence of SEQ ID NO: 10 with a flexible peptide linker having an amino acid sequence selected from G, SG, GGS, and SEQ ID NOs: 7 to 9; and
  (b) an amino acid substitution of (i) R38A, R38E, or R38G; or (ii) F42A, F42G, or F42K.

In still another embodiment, the interleukin-2 polypeptide provided herein comprises:
  (a) (i) an amino acid substitution selected from K8E, K9E, E15K, E15Q, H16E, K32E, K76E, H79E, R81E, D84T, N88A, I92A, E95K, E95Q, S127A, and S130A; or (ii) a deletion or replacement of the amino acid residues from positions 30 to 35 having an amino acid sequence of SEQ ID NO: 10 with a flexible peptide linker having an amino acid sequence selected from G, SG, GGS, and SEQ ID NOs: 7 to 9; and
  (b) an amino acid substitution of (i) R38A, R38E, or R38G; or (ii) F42A or F42K.

In one embodiment, the interleukin-2 polypeptide provided herein comprises: (a) an amino acid substitution at position 8, 9, 13, 15, 16, 19, 23, 32, 76, 79, 81, 84, 87, 88, 91, 92, 95, 127, or 130 as set forth in SEQ ID NO: 1, 2, 3, 4, or 5; and (b) an amino acid substitution at position 38 or 42 as set forth in SEQ ID NO: 1, 2, 3, 4, or 5.

In another embodiment, the interleukin-2 polypeptide provided herein comprises: (a) an amino acid substitution at position K8, K9, Q13, E15, H16, L19, M23, K32, K76, H79, R81, D84, S87, N88, V91, I92, E95, S127, or S130 as set forth in SEQ ID NO: 1, 2, 3, 4, or 5; and (b) an amino acid substitution at position R38 or F42 as set forth in SEQ ID NO: 1, 2, 3, 4, or 5.

In yet another embodiment, the interleukin-2 polypeptide provided herein comprises: (a) an amino acid substitution of K8D, K8E, K8Q, K9D, K9E, K9Q, Q13E, Q13N, E15K, E15Q, E15V, H16D, H16E, H16N, H16Q, L19S, M23K, K32D, K32E, K32Q, K76D, K76E, K76Q, H79D, H79E, H79Q, R81D, R81E, R81Q, D84T, S87D, S87E, N88A, V91I, I92A, I92L, E95K, E95N, E95Q, S127A, S127E, S127F, S127W, S130A, S130E, S130F, or S130W; and (b) an amino acid substitution of (i) R38A, R38E, R38G, or R38N; or (ii) F42A, F42G, F42K, or F42N.

In yet another embodiment, the interleukin-2 polypeptide provided herein comprises: (a) an amino acid substitution of K8D, K8E, K8Q, K9D, K9E, K9Q, Q13E, Q13N, E15K, E15Q, E15V, H16D, H16E, H16N, H16Q, L19S, M23K, K32D, K32E, K32Q, K76D, K76E, K76Q, H79D, H79E, H79Q, R81D, R81E, R81Q, D84T, S87D, S87E, N88A, V91I, I92A, I92L, E95K, E95N, E95Q, S127A, S127E, S127F, S127W, S130A, S130E, S130F, or S130W; and (b) an amino acid substitution of (i) R38A, R38E, or R38G; or (ii) F42A, F42G, or F42K.

In yet another embodiment, the interleukin-2 polypeptide provided herein comprises: (a) an amino acid substitution of K8D, K8E, K8Q, K9D, K9E, K9Q, Q13E, Q13N, E15K, E15Q, E15V, H16D, H16E, H16N, H16Q, L19S, M23K, K32D, K32E, K32Q, K76D, K76E, K76Q, H79D, H79E, H79Q, R81D, R81E, R81Q, D84T, S87D, S87E, N88A, V91I, I92A, I92L, E95K, E95N, E95Q, S127A, S127E, S127F, S127W, S130A, S130E, S130F, or S130W; and (b) an amino acid substitution of (i) R38A, R38E, or R38G; or (ii) F42A or F42K.

In still another embodiment, the interleukin-2 polypeptide provided herein comprises: (a) an amino acid substitution of K8D, K8E, K8Q, K9D, K9E, K9Q, Q13E, Q13N, E15K, E15Q, E15V, H16D, H16E, H16N, H16Q, L19S, M23K, K32D, K32E, K32Q, K76D, K76E, K76Q, H79D, H79E, H79Q, R81D, R81E, R81Q, D84T, S87D, S87E, N88A, V91I, I92A, I92L, E95K, E95N, E95Q, S127A, S127E, S127F, S127W, S130A, S130E, S130F, or S130W; and (b) an amino acid substitution of R38N or F42A.

In one embodiment, the interleukin-2 polypeptide provided herein comprises: (a) an amino acid substitution at position 13, 15, 16, 19, 23, 84, 87, 91, 92, or 95 as set forth in SEQ ID NO: 1, 2, 3, 4, or 5; and (b) an amino acid substitution at position 38 or 42 as set forth in SEQ ID NO: 1, 2, 3, 4, or 5.

In another embodiment, the interleukin-2 polypeptide provided herein comprises: (a) an amino acid substitution at position Q13, E15, H16, L19, M23, D84, S87, V91, I92, or E95 as set forth in SEQ ID NO: 1, 2, 3, 4, or 5; and (b) an amino acid substitution at position R38 or F42 as set forth in SEQ ID NO: 1, 2, 3, 4, or 5.

In yet another embodiment, the interleukin-2 polypeptide provided herein comprises: (a) an amino acid substitution of Q13E, Q13N, E15V, H16N, L19S, M23K, D84T, S87D, S87E, V91I, I92L, E95N, or E95Q; and (b) an amino acid substitution of (i) R38A, R38E, R38G, or R38N; or (ii) F42A, F42G, F42K, or F42N.

In yet another embodiment, the interleukin-2 polypeptide provided herein comprises: (a) an amino acid substitution of Q13E, Q13N, E15V, H16N, L19S, M23K, D84T, S87D, S87E, V91I, I92L, E95N, or E95Q; and (b) an amino acid substitution of (i) R38A, R38E, or R38G; or (ii) F42A, F42G, or F42K.

In yet another embodiment, the interleukin-2 polypeptide provided herein comprises: (a) an amino acid substitution of Q13E, Q13N, E15V, H16N, L19S, M23K, D84T, S87D, S87E, V91I, I92L, E95N, or E95Q; and (b) an amino acid substitution of (i) R38A, R38E, or R38G; or (ii) F42A or F42K.

In still another embodiment, the interleukin-2 polypeptide provided herein comprises: (a) an amino acid substitution of Q13E, Q13N, E15V, H16N, L19S, M23K, D84T, S87D, S87E, V91I, I92L, E95N, or E95Q; and (b) an amino acid substitution of R38N or F42A.

In one embodiment, the interleukin-2 polypeptide provided herein comprises: (a) an amino acid substitution at position 13, 15, 16, 23, 91, or 95 as set forth in SEQ ID NO: 1, 2, 3, 4, or 5; and (b) an amino acid substitution at position 38 or 42 as set forth in SEQ ID NO: 1, 2, 3, 4, or 5.

In another embodiment, the interleukin-2 polypeptide provided herein comprises: (a) an amino acid substitution at position Q13, E15, H16, M23, V91, or E95 as set forth in SEQ ID NO: 1, 2, 3, 4, or 5; and (b) an amino acid substitution at position R38 or F42 as set forth in SEQ ID NO: 1, 2, 3, 4, or 5.

In yet another embodiment, the interleukin-2 polypeptide provided herein comprises: (a) an amino acid substitution of Q13E, E15V, H16N, M23K, V91I, or E95N; and (b) an amino acid substitution of (i) R38A, R38E, R38G, or R38N; or (ii) F42A, F42G, F42K, or F42N.

In yet another embodiment, the interleukin-2 polypeptide provided herein comprises: (a) an amino acid substitution of Q13E, E15V, H16N, M23K, V91I, or E95N; and (b) an amino acid substitution of (i) R38A, R38E, or R38G; or (ii) F42A, F42G, or F42K.

In yet another embodiment, the interleukin-2 polypeptide provided herein comprises: (a) an amino acid substitution of Q13E, E15V, H16N, M23K, V91I, or E95N; and (b) an amino acid substitution of (i) R38A, R38E, or R38G; or (ii) F42A or F42K.

In still another embodiment, the interleukin-2 polypeptide provided herein comprises: (a) an amino acid substitution of Q13E, E15V, H16N, M23K, V91I, or E95N; and (b) an amino acid substitution of R38N or F42A.

In one embodiment, the interleukin-2 polypeptide provided herein comprises: (a) an amino acid substitution at position 8, 9, 15, 16, 32, 76, 79, 81, 84, 88, 92, 95, 127, or 130 as set forth in SEQ ID NO: 1, 2, 3, 4, or 5; and (b) an amino acid substitution at position 38 or 42 as set forth in SEQ ID NO: 1, 2, 3, 4, or 5.

In another embodiment, the interleukin-2 polypeptide provided herein comprises: (a) an amino acid substitution at position K8, K9, E15, H16, K32, K76, H79, R81, D84, N88, I92, E95, S127, or S130 as set forth in SEQ ID NO: 1, 2, 3, 4, or 5; and (b) an amino acid substitution at position R38 or F42 as set forth in SEQ ID NO: 1, 2, 3, 4, or 5.

In yet another embodiment, the interleukin-2 polypeptide provided herein comprises: (a) an amino acid substitution of K8D, K8E, K8Q, K9D, K9E, K9Q, E15K, E15Q, H16D, H16E, H16Q, K32D, K32E, K32Q, K76D, K76E, K76Q, H79D, H79E, H79Q, R81D, R81E, R81Q, D84T, N88A, I92A, E95K, E95Q, S127A, S127E, S127F, S127W, S130A, S130E, S130F, or S130W; and (b) an amino acid substitution of (i) R38A, R38E, R38G, or R38N; or (ii) F42A, F42G, F42K, or F42N.

In yet another embodiment, the interleukin-2 polypeptide provided herein comprises: (a) an amino acid substitution of K8D, K8E, K8Q, K9D, K9E, K9Q, E15K, E15Q, H16D, H16E, H16Q, K32D, K32E, K32Q, K76D, K76E, K76Q, H79D, H79E, H79Q, R81D, R81E, R81Q, D84T, N88A, I92A, E95K, E95Q, S127A, S127E, S127F, S127W, S130A, S130E, S130F, or S130W; and (b) an amino acid substitution of (i) R38A, R38E, or R38G; or (ii) F42A, F42G, or F42K.

In still another embodiment, the interleukin-2 polypeptide provided herein comprises: (a) an amino acid substitution of K8E, K9E, E15K, E15Q, H16E, K32E, K76E, H79E, R81E, D84T, N88A, I92A, E95K, E95Q, S127A, or S130A; and (b) an amino acid substitution of (i) R38A, R38E, or R38G; or (ii) F42A or F42K.

In one embodiment, the interleukin-2 polypeptide provided herein comprises: (a) an amino acid substitution at position 8, 9, 16, 32, 76, 79, or 81 as set forth in SEQ ID NO: 1, 2, 3, 4, or 5; and (b) an amino acid substitution at position 38 or 42 as set forth in SEQ ID NO: 1, 2, 3, 4, or 5.

In another embodiment, the interleukin-2 polypeptide provided herein comprises: (a) an amino acid substitution at position K8, K9, H16, K32, K76, H79, or R81 as set forth in SEQ ID NO: 1, 2, 3, 4, or 5; and (b) an amino acid substitution at position R38 or F42 as set forth in SEQ ID NO: 1, 2, 3, 4, or 5.

In yet another embodiment, the interleukin-2 polypeptide provided herein comprises: (a) an amino acid substitution of K8D, K8E, K8Q, K9D, K9E, K9Q, H16D, H16E, H16Q, K32D, K32E, K32Q, K76D, K76E, K76Q, H79D, H79E, H79Q, R81D, R81E, or R81Q; and (b) an amino acid substitution of (i) R38A, R38E, R38G, or R38N; or (ii) F42A, F42G, F42K, or F42N.

In yet another embodiment, the interleukin-2 polypeptide provided herein comprises: (a) an amino acid substitution of K8D, K8E, K8Q, K9D, K9E, K9Q, H16D, H16E, H16Q, K32D, K32E, K32Q, K76D, K76E, K76Q, H79D, H79E, H79Q, R81D, R81E, or R81Q; and (b) an amino acid substitution of (i) R38A, R38E, or R38G; or (ii) F42A, F42G, or F42K.

In still another embodiment, the interleukin-2 polypeptide provided herein comprises: (a) an amino acid substitution of K8E, K9E, H16E, K32E, K76E, H79E, or R81E; and (b) an amino acid substitution of (i) R38A, R38E, or R38G; or (ii) F42A or F42K.

In one embodiment, the interleukin-2 polypeptide provided herein comprises: (a) an amino acid substitution at position 16, 84, 88, 92, or 95 as set forth in SEQ ID NO: 1, 2, 3, 4, or 5; and (b) an amino acid substitution at position 38 or 42 as set forth in SEQ ID NO: 1, 2, 3, 4, or 5.

In another embodiment, the interleukin-2 polypeptide provided herein comprises: (a) an amino acid substitution at position H16, D84, N88, I92, or E95 as set forth in SEQ ID NO: 1, 2, 3, 4, or 5; and (b) an amino acid substitution at position R38 or F42 as set forth in SEQ ID NO: 1, 2, 3, 4, or 5.

In yet another embodiment, the interleukin-2 polypeptide provided herein comprises: (a) an amino acid substitution of H16D, H16E, H16Q, D84T, N88A, I92A, E95K, or E95Q; and (b) an amino acid substitution of (i) R38A, R38E, R38G, or R38N; or (ii) F42A, F42G, F42K, or F42N.

In yet another embodiment, the interleukin-2 polypeptide provided herein comprises: (a) an amino acid substitution of H16D, H16E, H16Q, D84T, N88A, I92A, E95K, or E95Q;

and (b) an amino acid substitution of (i) R38A, R38E, or R38G; or (ii) F42A, F42G, or F42K.

In still another embodiment, the interleukin-2 polypeptide provided herein comprises: (a) an amino acid substitution of H16E, D84T, N88A, I92A, E95K, or E95Q; and (b) an amino acid substitution of (i) R38A, R38E, or R38G; or (ii) F42A or F42K.

In one embodiment, the interleukin-2 polypeptide provided herein comprises: (a) an amino acid substitution at position 15 as set forth in SEQ ID NO: 1, 2, 3, 4, or 5; and (b) an amino acid substitution at position 38 or 42 as set forth in SEQ ID NO: 1, 2, 3, 4, or 5.

In another embodiment, the interleukin-2 polypeptide provided herein comprises: (a) an amino acid substitution at position E15 as set forth in SEQ ID NO: 1, 2, 3, 4, or 5; and (b) an amino acid substitution at position R38 or F42 as set forth in SEQ ID NO: 1, 2, 3, 4, or 5.

In yet another embodiment, the interleukin-2 polypeptide provided herein comprises: (a) an amino acid substitution of E15K or E15Q; and (b) an amino acid substitution of (i) R38A, R38E, R38G, or R38N; or (ii) F42A, F42G, F42K, or F42N.

In yet another embodiment, the interleukin-2 polypeptide provided herein comprises: (a) an amino acid substitution of E15K or E15Q; and (b) an amino acid substitution of (i) R38A, R38E, or R38G; or (ii) F42A, F42G, or F42K.

In still another embodiment, the interleukin-2 polypeptide provided herein comprises: (a) an amino acid substitution of E15K or E15Q; and (b) an amino acid substitution of (i) R38A, R38E, or R38G; or (ii) F42A or F42K.

In one embodiment, the interleukin-2 polypeptide provided herein comprises: (a) an amino acid substitution at position 127 or 130 as set forth in SEQ ID NO: 1, 2, 3, 4, or 5; and (b) an amino acid substitution at position 38 or 42 as set forth in SEQ ID NO: 1, 2, 3, 4, or 5.

In another embodiment, the interleukin-2 polypeptide provided herein comprises: (a) an amino acid substitution at position S127 or S130 as set forth in SEQ ID NO: 1, 2, 3, 4, or 5; and (b) an amino acid substitution at position R38 or F42 as set forth in SEQ ID NO: 1, 2, 3, 4, or 5.

In yet another embodiment, the interleukin-2 polypeptide provided herein comprises: (a) an amino acid substitution selected from S127A, S127E, S127F, S127W, S130A, S130E, S130F, and S130W; and (b) an amino acid substitution of (i) R38A, R38E, R38G, or (ii) R38N; or F42A, F42G, F42K, or F42N.

In yet another embodiment, the interleukin-2 polypeptide provided herein comprises: (a) an amino acid substitution selected from S127A, S127E, S127F, S127W, S130A, S130E, S130F, and S130W; and (b) an amino acid substitution of (i) R38A, R38E, or R38G; or (ii) F42A, F42G, or F42K.

In still another embodiment, the interleukin-2 polypeptide provided herein comprises: (a) an amino acid substitution of S127A or S130A; and (b) an amino acid substitution of (i) R38A, R38E, or R38G; or (ii) F42A or F42K.

In one embodiment, the interleukin-2 polypeptide provided herein comprises: (a) a deletion or replacement of the amino acid residues from positions 30 to 35 as set forth in SEQ ID NO: 1, 2, 3, 4, or 5 with a peptide linker; and (b) an amino acid substitution at position 38 or 42 as set forth in SEQ ID NO: 1, 2, 3, 4, or 5.

In another embodiment, the interleukin-2 polypeptide provided herein comprises: (a) a deletion or replacement of the amino acid residues from positions N30 to K35 as set forth in SEQ ID NO: 1, 2, 3, 4, or 5 with a peptide linker; and (b) an amino acid substitution at position R38 or F42 as set forth in SEQ ID NO: 1, 2, 3, 4, or 5.

In yet another embodiment, the interleukin-2 polypeptide provided herein comprises: (a) a deletion or replacement of the amino acid residues from positions 30 to 35 having an amino acid sequence of SEQ ID NO: 10 with a flexible peptide linker having an amino acid sequence selected from G, SG, GGS, and SEQ ID NOs: 7 to 9; and (b) an amino acid substitution of (i) R38A, R38E, R38G, or R38N; or (ii) F42A, F42G, F42K, or F42N.

In yet another embodiment, the interleukin-2 polypeptide provided herein comprises: (a) a deletion or replacement of the amino acid residues from positions 30 to 35 having an amino acid sequence of SEQ ID NO: 10 with a flexible peptide linker having an amino acid sequence selected from G, SG, GGS, and SEQ ID NOs: 7 to 9; and (b) an amino acid substitution of (i) R38A, R38E, or R38G; or (ii) F42A, F42G, or F42K.

In still another embodiment, the interleukin-2 polypeptide provided herein comprises: (a) a deletion or replacement of the amino acid residues from positions 30 to 35 having an amino acid sequence of SEQ ID NO: 10 with a flexible peptide linker having an amino acid sequence selected from G, SG, GGS, and SEQ ID NOs: 7 to 9; and (b) an amino acid substitution of (i) R38A, R38E, or R38G; or (ii) F42A or F42K.

In one embodiment, the interleukin-2 polypeptide provided herein comprises:
 (a) (i) an amino acid substitution at position 8, 9, 15, 16, 32, 76, 79, 81, 84, 88, 92, 95, 127, or 130 as set forth in SEQ ID NO: 1, 2, 3, 4, or 5; or (ii) a deletion or replacement of the amino acid residues from positions 30 to 35 as set forth in SEQ ID NO: 1, 2, 3, 4, or 5 with a peptide linker; and
 (b) an amino acid substitution at position 42 as set forth in SEQ ID NO: 1, 2, 3, 4, or 5.

In another embodiment, the interleukin-2 polypeptide provided herein comprises:
 (a) (i) an amino acid substitution at position K8, K9, E15, H16, K32, K76, H79, R81, D84, N88, I92, E95, S127, or S130 as set forth in SEQ ID NO: 1, 2, 3, 4, or 5; or (ii) a deletion or replacement of the amino acid residues from positions N30 to K35 as set forth in SEQ ID NO: 1, 2, 3, 4, or 5 with a peptide linker; and
 (b) an amino acid substitution at position F42 as set forth in SEQ ID NO: 1, 2, 3, 4, or 5.

In yet another embodiment, the interleukin-2 polypeptide provided herein comprises:
 (a) (i) an amino acid substitution selected from K8D, K8E, K8Q, K9D, K9E, K9Q, E15K, E15Q, H16D, H16E, H16Q, K32D, K32E, K32Q, K76D, K76E, K76Q, H79D, H79E, H79Q, R81D, R81E, R81Q, D84T, N88A, I92A, E95K, E95Q, S127A, S127E, S127F, S127W, S130A, S130E, S130F, and S130W; or
 (ii) a deletion or replacement of the amino acid residues from positions 30 to 35 having an amino acid sequence of SEQ ID NO: 10 with a flexible peptide linker having an amino acid sequence selected from G, SG, GGS, and SEQ ID NOs: 7 to 9; and
 (b) an amino acid substitution of F42A, F42G, F42K, or F42N.

In yet another embodiment, the interleukin-2 polypeptide provided herein comprises:
 (a) (i) an amino acid substitution selected from K8D, K8E, K8Q, K9D, K9E, K9Q, E15K, E15Q, H16D, H16E, H16Q, K32D, K32E, K32Q, K76D, K76E, K76Q, H79D, H79E, H79Q, R81D, R81E, R81Q, D84T, N88A, I92A, E95K, E95Q, S127A, S127E, S127F, S127W, S130A, S130E, S130F, and S130W; or
(ii) a deletion or replacement of the amino acid residues from positions 30 to 35 having an amino acid sequence of SEQ ID NO: 10 with a flexible peptide linker having an amino acid sequence selected from G, SG, GGS, and SEQ ID NOs: 7 to 9; and (b) an amino acid substitution of F42A, F42G, or F42K.

In still another embodiment, the interleukin-2 polypeptide provided herein comprises:

(a) (i) an amino acid substitution selected from K8E, K9E, E15K, E15Q, H16E, K32E, K76E, H79E, R81E, D84T, N88A, I92A, E95K, E95Q, S127A, and S130A; or (ii) a deletion or replacement of the amino acid residues from positions 30 to 35 having an amino acid sequence of SEQ ID NO: 10 with a flexible peptide linker having an amino acid sequence selected from G, SG, GGS, and SEQ ID NOs: 7 to 9; and (b) an amino acid substitution of F42A or F42K.

In one embodiment, the interleukin-2 polypeptide provided herein comprises: (a) an amino acid substitution at position 8, 9, 15, 16, 32, 76, 79, 81, 84, 88, 92, 95, 127, or 130 as set forth in SEQ ID NO: 1, 2, 3, 4, or 5; and (b) an amino acid substitution at position 42 as set forth in SEQ ID NO: 1, 2, 3, 4, or 5.

In another embodiment, the interleukin-2 polypeptide provided herein comprises: (a) an amino acid substitution at position K8, K9, E15, H16, K32, K76, H79, R81, D84, N88, I92, E95, S127, or S130 as set forth in SEQ ID NO: 1, 2, 3, 4, or 5; and (b) an amino acid substitution at position F42 as set forth in SEQ ID NO: 1, 2, 3, 4, or 5.

In yet another embodiment, the interleukin-2 polypeptide provided herein comprises: (a) an amino acid substitution of K8D, K8E, K8Q, K9D, K9E, K9Q, E15K, E15Q, H16D, H16E, H16Q, K32D, K32E, K32Q, K76D, K76E, K76Q, H79D, H79E, H79Q, R81D, R81E, R81Q, D84T, N88A, I92A, E95K, E95Q, S127A, S127E, S127F, S127W, S130A, S130E, S130F, or S130W; and (b) an amino acid substitution of F42A, F42G, F42K, or F42N.

In yet another embodiment, the interleukin-2 polypeptide provided herein comprises: (a) an amino acid substitution of K8D, K8E, K8Q, K9D, K9E, K9Q, E15K, E15Q, H16D, H16E, H16Q, K32D, K32E, K32Q, K76D, K76E, K76Q, H79D, H79E, H79Q, R81D, R81E, R81Q, D84T, N88A, I92A, E95K, E95Q, S127A, S127E, S127F, S127W, S130A, S130E, S130F, or S130W; and (b) an amino acid substitution of F42A, F42G, or F42K.

In still another embodiment, the interleukin-2 polypeptide provided herein comprises: (a) an amino acid substitution of K8E, K9E, E15K, E15Q, H16E, K32E, K76E, H79E, R81E, D84T, N88A, I92A, E95K, E95Q, S127A, or S130A; and (b) an amino acid substitution of F42A or F42K.

In one embodiment, the interleukin-2 polypeptide provided herein comprises: (a) an amino acid substitution at position 8, 9, 16, 32, 76, 79, or 81 as set forth in SEQ ID NO: 1, 2, 3, 4, or 5; and (b) an amino acid substitution at position 42 as set forth in SEQ ID NO: 1, 2, 3, 4, or 5.

In another embodiment, the interleukin-2 polypeptide provided herein comprises: (a) an amino acid substitution at position K8, K9, H16, K32, K76, H79, or R81 as set forth in SEQ ID NO: 1, 2, 3, 4, or 5; and (b) an amino acid substitution at position F42 as set forth in SEQ ID NO: 1, 2, 3, 4, or 5.

In yet another embodiment, the interleukin-2 polypeptide provided herein comprises: (a) an amino acid substitution of K8D, K8E, K8Q, K9D, K9E, K9Q, H16D, H16E, H16Q, K32D, K32E, K32Q, K76D, K76E, K76Q, H79D, H79E, H79Q, R81D, R81E, or R81Q; and (b) an amino acid substitution of F42A, F42G, F42K, or F42N.

In yet another embodiment, the interleukin-2 polypeptide provided herein comprises: (a) an amino acid substitution of K8D, K8E, K8Q, K9D, K9E, K9Q, H16D, H16E, H16Q, K32D, K32E, K32Q, K76D, K76E, K76Q, H79D, H79E, H79Q, R81D, R81E, or R81Q; and (b) an amino acid substitution of F42A, F42G, or F42K.

In still another embodiment, the interleukin-2 polypeptide provided herein comprises: (a) an amino acid substitution of K8E, K9E, H16E, K32E, K76E, H79E, or R81E; and (b) an amino acid substitution of F42A or F42K.

In one embodiment, the interleukin-2 polypeptide provided herein comprises: (a) an amino acid substitution at position 16, 32, or 76 as set forth in SEQ ID NO: 1, 2, 3, 4, or 5; and (b) an amino acid substitution at position 42 as set forth in SEQ ID NO: 1, 2, 3, 4, or 5.

In another embodiment, the interleukin-2 polypeptide provided herein comprises: (a) an amino acid substitution at position H16, K32, or K76 as set forth in SEQ ID NO: 1, 2, 3, 4, or 5; and (b) an amino acid substitution at position F42 as set forth in SEQ ID NO: 1, 2, 3, 4, or 5.

In yet another embodiment, the interleukin-2 polypeptide provided herein comprises: (a) an amino acid substitution of H16D, H16E, H16Q, K32D, K32E, K32Q, K76D, K76E, or K76Q; and (b) an amino acid substitution of F42A, F42G, F42K, or F42N.

In yet another embodiment, the interleukin-2 polypeptide provided herein comprises: (a) an amino acid substitution of H16D, H16E, H16Q, K32D, K32E, K32Q, K76D, or K76E; and (b) an amino acid substitution of F42A, F42G, or F42K.

In still another embodiment, the interleukin-2 polypeptide provided herein comprises: (a) an amino acid substitution of H16E, K32E, or K76E; and (b) an amino acid substitution of F42A or F42K.

In one embodiment, the interleukin-2 polypeptide provided herein comprises: (a) an amino acid substitution of H16E; and (b) an amino acid substitution of F42A or F42K. In another embodiment, the interleukin-2 polypeptide provided herein comprises amino acid substitutions of H16E and F42A. In yet another embodiment, the interleukin-2 polypeptide provided herein comprises amino acid substitutions of H16E and F42K.

In one embodiment, the interleukin-2 polypeptide provided herein comprises: (a) an amino acid substitution of K32E; and (b) an amino acid substitution of F42A or F42K. In another embodiment, the interleukin-2 polypeptide provided herein comprises amino acid substitutions of K32E and F42A. In yet another embodiment, the interleukin-2 polypeptide provided herein comprises amino acid substitutions of K32E and F42K.

In one embodiment, the interleukin-2 polypeptide provided herein comprises: (a) an amino acid substitution of K76E; and (b) an amino acid substitution of F42A or F42K. In another embodiment, the interleukin-2 polypeptide provided herein comprises amino acid substitutions of F42A and K76E. In yet another embodiment, the interleukin-2 polypeptide provided herein comprises amino acid substitutions of F42K and K76E.

In one embodiment, the interleukin-2 polypeptide provided herein comprises an amino acid sequence selected from SEQ ID NOs: 137 to 158. In another embodiment, the interleukin-2 polypeptide provided herein comprises an amino acid sequence selected from SEQ ID NOs: 137 to 147. In yet another embodiment, the interleukin-2 polypeptide provided herein comprises an amino acid sequence selected from SEQ ID NOs: 148 to 158.

In one embodiment, the amino acid sequence of the interleukin-2 polypeptide provided herein is one selected from SEQ ID NOs: 137 to 158. In another embodiment, the amino acid sequence of the interleukin-2 polypeptide provided herein is one selected from SEQ ID NOs: 137 to 147. In yet another embodiment, the amino acid sequence of the interleukin-2 polypeptide provided herein is one selected from SEQ ID NOs: 148 to 158.

In one embodiment, the interleukin-2 polypeptide provided herein comprises an amino acid sequence selected from SEQ ID NOs: 138 to 141, 143, 145 to 147, 149 to 152, 154, and 156 to 158. In another embodiment, the interleukin-2 polypeptide provided herein comprises an amino acid sequence selected from SEQ ID NOs: 138 to 141, 143, and 145 to 147. In yet another embodiment, the interleukin-2 polypeptide provided herein comprises an amino acid sequence selected from SEQ ID NOs: 149 to 152, 154, and 156 to 158.

In one embodiment, the amino acid sequence of the interleukin-2 polypeptide provided herein is one selected from SEQ ID NOs: 138 to 141, 143, 145 to 147, 149 to 152, 154, and 156 to 158. In another embodiment, the amino acid sequence of the interleukin-2 polypeptide provided herein is one selected from SEQ ID NOs: 138 to 141, 143, and 145 to 147. In yet another embodiment, the amino acid sequence of the interleukin-2 polypeptide provided herein is one selected from SEQ ID NOs: 149 to 152, 154, and 156 to 158.

In one embodiment, the interleukin-2 polypeptide provided herein comprises: (a) an amino acid substitution at position 16, 84, 88, 92, or 95 as set forth in SEQ ID NO: 1, 2, 3, 4, or 5; and (b) an amino acid substitution at position 42 as set forth in SEQ ID NO: 1, 2, 3, 4, or 5.

In another embodiment, the interleukin-2 polypeptide provided herein comprises: (a) an amino acid substitution at position H16, D84, N88, I92, or E95 as set forth in SEQ ID NO: 1, 2, 3, 4, or 5; and (b) an amino acid substitution at position F42 as set forth in SEQ ID NO: 1, 2, 3, 4, or 5.

In yet another embodiment, the interleukin-2 polypeptide provided herein comprises: (a) an amino acid substitution of H16D, H16E, H16Q, D84T, N88A, I92A, E95K, or E95Q; and (b) an amino acid substitution of F42A, F42G, F42K, or F42N.

In yet another embodiment, the interleukin-2 polypeptide provided herein comprises: (a) an amino acid substitution of H16D, H16E, H16Q, D84T, N88A, I92A, E95K, or E95Q; and (b) an amino acid substitution of F42A, F42G, or F42K.

In still another embodiment, the interleukin-2 polypeptide provided herein comprises: (a) an amino acid substitution of H16E, D84T, N88A, I92A, E95K, and E95Q; or (b) an amino acid substitution of F42A or F42K.

In one embodiment, the interleukin-2 polypeptide provided herein comprises: (a) an amino acid substitution at position 15 as set forth in SEQ ID NO: 1, 2, 3, 4, or 5; and (b) an amino acid substitution at position 42 as set forth in SEQ ID NO: 1, 2, 3, 4, or 5.

In another embodiment, the interleukin-2 polypeptide provided herein comprises: (a) an amino acid substitution at position E15 as set forth in SEQ ID NO: 1, 2, 3, 4, or 5; and (b) an amino acid substitution at position F42 as set forth in SEQ ID NO: 1, 2, 3, 4, or 5.

In yet another embodiment, the interleukin-2 polypeptide provided herein comprises: (a) an amino acid substitution of E15K or E15Q; and (b) an amino acid substitution of F42A, F42G, F42K, or F42N.

In yet another embodiment, the interleukin-2 polypeptide provided herein comprises: (a) an amino acid substitution of E15K or E15Q; and (b) an amino acid substitution of F42A, F42G, or F42K.

In still another embodiment, the interleukin-2 polypeptide provided herein comprises: (a) an amino acid substitution of E15K or E15Q; and (b) an amino acid substitution of F42A or F42K.

In one embodiment, the interleukin-2 polypeptide provided herein comprises: (a) an amino acid substitution at position 127 or 130 as set forth in SEQ ID NO: 1, 2, 3, 4, or 5; and (b) an amino acid substitution at position 42 as set forth in SEQ ID NO: 1, 2, 3, 4, or 5.

In another embodiment, the interleukin-2 polypeptide provided herein comprises: (a) an amino acid substitution at position S127 or S130 as set forth in SEQ ID NO: 1, 2, 3, 4, or 5; and (b) an amino acid substitution at position F42 as set forth in SEQ ID NO: 1, 2, 3, 4, or 5.

In yet another embodiment, the interleukin-2 polypeptide provided herein comprises: (a) an amino acid substitution selected from S127A, S127E, S127F, S127W, S130A, S130E, S130F, and S130W; and (b) an amino acid substitution of R38N; or F42A, F42G, F42K, or F42N.

In yet another embodiment, the interleukin-2 polypeptide provided herein comprises: (a) an amino acid substitution selected from S127A, S127E, S127F, S127W, S130A, S130E, S130F, and S130W; and (b) an amino acid substitution of F42A, F42G, or F42K.

In still another embodiment, the interleukin-2 polypeptide provided herein comprises: (a) an amino acid substitution of S127A or S130A; and (b) an amino acid substitution of F42A or F42K.

In one embodiment, the interleukin-2 polypeptide provided herein comprises: (a) a deletion or replacement of the amino acid residues from positions 30 to 35 as set forth in SEQ ID NO: 1, 2, 3, 4, or 5 with a peptide linker; and (b) an amino acid substitution at position 42 as set forth in SEQ ID NO: 1, 2, 3, 4, or 5.

In another embodiment, the interleukin-2 polypeptide provided herein comprises: (a) a deletion or replacement of the amino acid residues from positions N30 to K35 as set forth in SEQ ID NO: 1, 2, 3, 4, or 5 with a peptide linker; and (b) an amino acid substitution at position F42 as set forth in SEQ ID NO: 1, 2, 3, 4, or 5.

In yet another embodiment, the interleukin-2 polypeptide provided herein comprises: (a) a deletion or replacement of the amino acid residues from positions 30 to 35 having an amino acid sequence of SEQ ID NO: 10 with a flexible peptide linker having an amino acid sequence selected from G, SG, GGS, and SEQ ID NOs: 7 to 9; and (b) an amino acid substitution of F42A, F42G, F42K, or F42N.

In yet another embodiment, the interleukin-2 polypeptide provided herein comprises: (a) a deletion or replacement of the amino acid residues from positions 30 to 35 having an amino acid sequence of SEQ ID NO: 10 with a flexible peptide linker having an amino acid sequence selected from G, SG, GGS, and SEQ ID NOs: 7 to 9; and (b) an amino acid substitution of F42A, F42G, or F42K.

In still another embodiment, the interleukin-2 polypeptide provided herein comprises: (a) a deletion or replacement of the amino acid residues from positions 30 to 35 having an amino acid sequence of SEQ ID NO: 10 with a flexible peptide linker having an amino acid sequence selected from G, SG, GGS, and SEQ ID NOs: 7 to 9; and (b) an amino acid substitution of F42A or F42K.

In one embodiment, the interleukin-2 polypeptide provided herein comprises:
(a) (i) an amino acid substitution at position 8, 9, 15, 16, 32, 76, 79, 81, 84, 88, 92, 95, 127, or 130 as set forth in SEQ ID NO: 1, 2, 3, 4, or 5; or (ii) a deletion or replacement of the amino acid residues from positions 30 to 35 as set forth in SEQ ID NO: 1, 2, 3, 4, or 5 with a peptide linker; and
(b) amino acid substitutions at positions 38 and 42 as set forth in SEQ ID NO: 1, 2, 3, 4, or 5.

In another embodiment, the interleukin-2 polypeptide provided herein comprises:
(a) (i) an amino acid substitution at position K8, K9, E15, H16, K32, K76, H79, R81, D84, N88, I92, E95, S127, or S130 as set forth in SEQ ID NO: 1, 2, 3, 4, or 5; or (ii) a deletion or replacement of the amino acid residues from positions N30 to K35 as set forth in SEQ ID NO: 1, 2, 3, 4, or 5 with a peptide linker; and
(b) amino acid substitutions at positions R38 and F42 as set forth in SEQ ID NO: 1, 2, 3, 4, or 5.

In yet another embodiment, the interleukin-2 polypeptide provided herein comprises:
(a) (i) an amino acid substitution selected from K8D, K8E, K8Q, K9D, K9E, K9Q, E15K, E15Q, H16D, H16E, H16Q, K32D, K32E, K32Q, K76D, K76E, K76Q, H79D, H79E, H79Q, R81D, R81E, R81Q, D84T, N88A, I92A, E95K, E95Q, S127A, S127E, S127F, S127W, S130A, S130E, S130F, and S130W; or (ii) a deletion or replacement of the amino acid residues from positions 30 to 35 having an amino acid sequence of SEQ ID NO: 10 with a flexible peptide linker having an amino acid sequence selected from G, SG, GGS, and SEQ ID NOs: 7 to 9; and
(b) amino acid substitutions of (i) R38A, R38E, R38G, or R38N; and (ii) F42A, F42G, F42K, or F42N.

In yet another embodiment, the interleukin-2 polypeptide provided herein comprises:
(a) (i) an amino acid substitution selected from K8D, K8E, K8Q, K9D, K9E, K9Q, E15K, E15Q, H16D, H16E, H16Q, K32D, K32E, K32Q, K76D, K76E, K76Q, H79D, H79E, H79Q, R81D, R81E, R81Q, D84T, N88A, I92A, E95K, E95Q, S127A, S127E, S127F, S127W, S130A, S130E, S130F, and S130W; or (ii) a deletion or replacement of the amino acid residues from positions 30 to 35 having an amino acid sequence of SEQ ID NO: 10 with a flexible peptide linker having an amino acid sequence selected from G, SG, GGS, and SEQ ID NOs: 7 to 9; and
(b) amino acid substitutions of (i) R38A, R38E, or R38G; and (ii) F42A, F42G, or F42K.

In still another embodiment, the interleukin-2 polypeptide provided herein comprises:
(a) (i) an amino acid substitution selected from K8E, K9E, E15K, E15Q, H16E, K32E, K76E, H79E, R81E, D84T, N88A, I92A, E95K, E95Q, S127A, and S130A; or (ii) a deletion or replacement of the amino acid residues from positions 30 to 35 having an amino acid sequence of SEQ ID NO: 10 with a flexible peptide linker having an amino acid sequence selected from G, SG, GGS, and SEQ ID NOs: 7 to 9; and
(b) amino acid substitutions of (i) R38A, R38E, or R38G; and (ii) F42A or F42K.

In one embodiment, the interleukin-2 polypeptide provided herein comprises: (a) an amino acid substitution at position 8, 9, 15, 16, 32, 76, 79, 81, 84, 88, 92, 95, 127, or 130 as set forth in SEQ ID NO: 1, 2, 3, 4, or 5; and (b) amino acid substitutions at positions 38 and 42 as set forth in SEQ ID NO: 1, 2, 3, 4, or 5.

In another embodiment, the interleukin-2 polypeptide provided herein comprises: (a) an amino acid substitution at position K8, K9, E15, H16, K32, K76, H79, R81, D84, N88, I92, E95, S127, or S130 as set forth in SEQ ID NO: 1, 2, 3, 4, or 5; and (b) amino acid substitutions at positions R38 and F42 as set forth in SEQ ID NO: 1, 2, 3, 4, or 5.

In yet another embodiment, the interleukin-2 polypeptide provided herein comprises: (a) an amino acid substitution of K8D, K8E, K8Q, K9D, K9E, K9Q, E15K, E15Q, H16D, H16E, H16Q, K32D, K32E, K32Q, K76D, K76E, K76Q, H79D, H79E, H79Q, R81D, R81E, R81Q, D84T, N88A, I92A, E95K, E95Q, S127A, S127E, S127F, S127W, S130A, S130E, S130F, or S130W; and (b) amino acid substitutions of (i) R38A, R38E, R38G, or R38N; and (ii) F42A, F42G, F42K, or F42N.

In yet another embodiment, the interleukin-2 polypeptide provided herein comprises: (a) an amino acid substitution of K8D, K8E, K8Q, K9D, K9E, K9Q, E15K, E15Q, H16D, H16E, H16Q, K32D, K32E, K32Q, K76D, K76E, K76Q, H79D, H79E, H79Q, R81D, R81E, R81Q, D84T, N88A, I92A, E95K, E95Q, S127A, S127E, S127F, S127W, S130A, S130E, S130F, or S130W; and (b) amino acid substitutions of (i) R38A, R38E, or R38G; and (ii) F42A, F42G, or F42K.

In still another embodiment, the interleukin-2 polypeptide provided herein comprises: (a) an amino acid substitution of K8E, K9E, E15K, E15Q, H16E, K32E, K76E, H79E, R81E, D84T, N88A, I92A, E95K, E95Q, S127A, or S130A; and (b) amino acid substitutions of (i) R38A, R38E, or R38G; and (ii) F42A or F42K.

In one embodiment, the interleukin-2 polypeptide provided herein comprises: (a) an amino acid substitution at position 8, 9, 16, 32, 76, 79, or 81 as set forth in SEQ ID NO: 1, 2, 3, 4, or 5; and (b) amino acid substitutions at positions 38 and 42 as set forth in SEQ ID NO: 1, 2, 3, 4, or 5.

In another embodiment, the interleukin-2 polypeptide provided herein comprises: (a) an amino acid substitution at position K8, K9, H16, K32, K76, H79, or R81 as set forth in SEQ ID NO: 1, 2, 3, 4, or 5; and (b) amino acid substitutions at positions R38 and F42 as set forth in SEQ ID NO: 1, 2, 3, 4, or 5.

In yet another embodiment, the interleukin-2 polypeptide provided herein comprises: (a) an amino acid substitution of K8D, K8E, K8Q, K9D, K9E, K9Q, H16D, H16E, H16Q, K32D, K32E, K32Q, K76D, K76E, K76Q, H79D, H79E, H79Q, R81D, R81E, or R81Q; and (b) amino acid substitutions of (i) R38A, R38E, R38G, or R38N; and (ii) F42A, F42G, F42K, or F42N.

In yet another embodiment, the interleukin-2 polypeptide provided herein comprises: (a) an amino acid substitution of K8D, K8E, K8Q, K9D, K9E, K9Q, H16D, H16E, H16Q, K32D, K32E, K32Q, K76D, K76E, K76Q, H79D, H79E, H79Q, R81D, R81E, or R81Q; and (b) amino acid substitutions of (i) R38A, R38E, or R38G; and (ii) F42A, F42G, or F42K.

In still another embodiment, the interleukin-2 polypeptide provided herein comprises: (a) an amino acid substitution of K8E, K9E, H16E, K32E, K76E, H79E, or R81E; and (b) amino acid substitutions of (i) R38A, R38E, or R38G; and (ii) F42A or F42K.

In one embodiment, the interleukin-2 polypeptide provided herein comprises: (a) an amino acid substitution at position 16, 32, or 76 as set forth in SEQ ID NO: 1, 2, 3, 4, or 5; and (b) amino acid substitutions at positions 38 and 42 as set forth in SEQ ID NO: 1, 2, 3, 4, or 5.

In another embodiment, the interleukin-2 polypeptide provided herein comprises: (a) an amino acid substitution at position H16, K32, or K76 as set forth in SEQ ID NO: 1, 2, 3, 4, or 5; and (b) amino acid substitutions at positions R38 and F42 as set forth in SEQ ID NO: 1, 2, 3, 4, or 5.

In yet another embodiment, the interleukin-2 polypeptide provided herein comprises: (a) an amino acid substitution of H16D, H16E, H16Q, K32D, K32E, K32Q, K76D, K76E, or K76Q; and (b) amino acid substitutions of (i) R38A, R38E, R38G, or R38N; and (ii) F42A, F42G, F42K, or F42N.

In yet another embodiment, the interleukin-2 polypeptide provided herein comprises: (a) an amino acid substitution of H16D, H16E, H16Q, K32D, K32E, K32Q, K76D, or K76E; and (b) amino acid substitutions of (i) R38A, R38E, or R38G; and (ii) F42A, F42G, or F42K.

In still another embodiment, the interleukin-2 polypeptide provided herein comprises: (a) an amino acid substitution of H16E, K32E, or K76E; and (b) amino acid substitutions of (i) R38A, R38E, or R38G; and (ii) F42A or F42K.

In one embodiment, the interleukin-2 polypeptide provided herein comprises: (a) an amino acid substitution of H16E; and (b) amino acid substitutions of (i) R38A, R38E, or R38G; and (ii) F42A or F42K. In another embodiment, the interleukin-2 polypeptide provided herein comprises: (a) an amino acid substitution of H16E; and (b) amino acid substitutions of (i) R38A, R38E, or R38G; and (ii) F42A. In yet another embodiment, the interleukin-2 polypeptide provided herein comprises amino acid substitutions of H16E, R38A, and F42A. In yet another embodiment, the interleukin-2 polypeptide provided herein comprises amino acid substitutions of H16E, R38E, and F42A. In yet another embodiment, the interleukin-2 polypeptide provided herein comprises amino acid substitutions of H16E, R38G, and F42A. In yet another embodiment, the interleukin-2 polypeptide provided herein comprises: (a) an amino acid substitution of H16E; and (b) amino acid substitutions of (i) R38A, R38E, or R38G; and (ii) F42K. In yet another embodiment, the interleukin-2 polypeptide provided herein comprises amino acid substitutions of H16E, R38A, and F42K. In yet another embodiment, the interleukin-2 polypeptide provided herein comprises amino acid substitutions of H16E, R38E, and F42K. In still another embodiment, the interleukin-2 polypeptide provided herein comprises amino acid substitutions of H16E, R38G, and F42K.

In one embodiment, the interleukin-2 polypeptide provided herein comprises: (a) an amino acid substitution of K32E; and (b) amino acid substitutions of (i) R38A, R38E, or R38G; and (ii) F42A or F42K. In another embodiment, the interleukin-2 polypeptide provided herein comprises: (a) an amino acid substitution of K32E; and (b) amino acid substitutions of (i) R38A, R38E, or R38G; and (ii) F42A. In yet another embodiment, the interleukin-2 polypeptide provided herein comprises amino acid substitutions of K32E, R38A, and F42A. In yet another embodiment, the interleukin-2 polypeptide provided herein comprises amino acid substitutions of K32E, R38E, and F42A. In yet another embodiment, the interleukin-2 polypeptide provided herein comprises amino acid substitutions of K32E, R38G, and F42A. In yet another embodiment, the interleukin-2 polypeptide provided herein comprises: (a) an amino acid substitution of K32E; and (b) amino acid substitutions of (i) R38A, R38E, or R38G; and (ii) F42K. In yet another embodiment, the interleukin-2 polypeptide provided herein comprises amino acid substitutions of K32E, R38A, and F42K. In yet another embodiment, the interleukin-2 polypeptide provided herein comprises amino acid substitutions of K32E, R38E, and F42K. In still another embodiment, the interleukin-2 polypeptide provided herein comprises amino acid substitutions of K32E, R38G, and F42K.

In one embodiment, the interleukin-2 polypeptide provided herein comprises: (a) an amino acid substitution of K76E; and (b) amino acid substitutions of (i) R38A, R38E, or R38G; and (ii) F42A or F42K. In another embodiment, the interleukin-2 polypeptide provided herein comprises: (a) an amino acid substitution of K76E; and (b) amino acid substitutions of (i) R38A, R38E, or R38G; and (ii) F42A. In yet another embodiment, the interleukin-2 polypeptide provided herein comprises amino acid substitutions of R38A, F42A, and K76E. In yet another embodiment, the interleukin-2 polypeptide provided herein comprises amino acid substitutions of R38E, F42A, and K76E. In yet another embodiment, the interleukin-2 polypeptide provided herein comprises amino acid substitutions of R38G, F42A, and K76E. In yet another embodiment, the interleukin-2 polypeptide provided herein comprises: (a) an amino acid substitution of K76E; and (b) amino acid substitutions of (i) R38A, R38E, or R38G; and (ii) F42K. In yet another embodiment, the interleukin-2 polypeptide provided herein comprises amino acid substitutions of R38A, F42K, and K76E. In yet another embodiment, the interleukin-2 polypeptide provided herein comprises amino acid substitutions of R38E, F42K, and K76E. In still another embodiment, the interleukin-2 polypeptide provided herein comprises amino acid substitutions of R38G, F42K, and K76E.

In one embodiment, the interleukin-2 polypeptide provided herein comprises amino acid substitutions of H16E, K32E, R38E, and F42A. In another embodiment, the interleukin-2 polypeptide provided herein comprises amino acid substitutions of H16E, R38E, F42A, and K76E. In yet another embodiment, the interleukin-2 polypeptide provided herein comprises amino acid substitutions of K32E, R38E, F42A, and K76E.

In one embodiment, the interleukin-2 polypeptide provided herein comprises amino acid substitutions of H16E, K32E, R38E, F42A, and K76E. In another embodiment, the interleukin-2 polypeptide provided herein comprises amino acid substitutions of H16E, K32 E, R38E, F42K, and K76E.

In one embodiment, the interleukin-2 polypeptide provided herein comprises an amino acid sequence selected from SEQ ID NOs: 139 to 147 and 150 to 158. In another embodiment, the interleukin-2 polypeptide provided herein comprises an amino acid sequence selected from SEQ ID NOs: 139 to 147. In yet another embodiment, the interleukin-2 polypeptide provided herein comprises an amino acid sequence selected from SEQ ID NOs: 150 to 158.

In one embodiment, the amino acid sequence of the interleukin-2 polypeptide provided herein is one selected from SEQ ID NOs: 139 to 147 and 150 to 158. In another embodiment, the amino acid sequence of the interleukin-2 polypeptide provided herein is one selected from SEQ ID NOs: 139 to 147. In yet another embodiment, the amino acid sequence of the interleukin-2 polypeptide provided herein is one selected from SEQ ID NOs: 150 to 158.

In one embodiment, the interleukin-2 polypeptide provided herein comprises an amino acid sequence selected from SEQ ID NOs: 139 to 141, 143, 145 to 147, 150 to 152, 154, and 156 to 158. In another embodiment, the interleukin-2 polypeptide provided herein comprises an amino acid sequence selected from SEQ ID NOs: 139 to 141, 143, and 145 to 147. In yet another embodiment, the interleukin-2 polypeptide provided herein comprises an amino acid sequence selected from SEQ ID NOs: 150 to 152, 154, and 156 to 158.

In one embodiment, the amino acid sequence of the interleukin-2 polypeptide provided herein is one selected from SEQ ID NOs: 139 to 141, 143, 145 to 147, 150 to 152, 154, and 156 to 158. In another embodiment, the amino acid sequence of the interleukin-2 polypeptide provided herein is one selected from SEQ ID NOs: 139 to 141, 143, and 145 to 147. In yet another embodiment, the amino acid sequence of the interleukin-2 polypeptide provided herein is one selected from SEQ ID NOs: 150 to 152, 154, and 156 to 158.

In one embodiment, the interleukin-2 polypeptide provided herein comprises: (a) an amino acid substitution at position 16, 84, 88, 92, or 95 as set forth in SEQ ID NO: 1, 2, 3, 4, or 5; and (b) amino acid substitutions at positions 38 and 42 as set forth in SEQ ID NO: 1, 2, 3, 4, or 5.

In another embodiment, the interleukin-2 polypeptide provided herein comprises: (a) an amino acid substitution at position H16, D84, N88, I92, or E95 as set forth in SEQ ID NO: 1, 2, 3, 4, or 5; and (b) amino acid substitutions at positions R38 and F42 as set forth in SEQ ID NO: 1, 2, 3, 4, or 5.

In yet another embodiment, the interleukin-2 polypeptide provided herein comprises: (a) an amino acid substitution selected from H16D, H16E, H16Q, D84T, N88A, I92A, E95K, and E95Q; and (b) amino acid substitutions of (i) R38A, R38E, R38G, or R38N; and (ii) F42A, F42G, F42K, or F42N.

In yet another embodiment, the interleukin-2 polypeptide provided herein comprises: (a) an amino acid substitution selected from H16D, H16E, H16Q, D84T, N88A, I92A, E95K, and E95Q; and (b) amino acid substitutions of (i) R38A, R38E, or R38G; and (ii) F42A, F42G, or F42K.

In still another embodiment, the interleukin-2 polypeptide provided herein comprises: (a) an amino acid substitution selected from H16E, D84T, N88A, I92A, E95K, and E95Q; and (b) amino acid substitutions of (i) R38A, R38E, or R38G; and (ii) F42A or F42K.

In one embodiment, the interleukin-2 polypeptide provided herein comprises: (a) an amino acid substitution at position 15 as set forth in SEQ ID NO: 1, 2, 3, 4, or 5; and (b) amino acid substitutions at positions 38 and 42 as set forth in SEQ ID NO: 1, 2, 3, 4, or 5.

In another embodiment, the interleukin-2 polypeptide provided herein comprises: (a) an amino acid substitution at position E15 as set forth in SEQ ID NO: 1, 2, 3, 4, or 5; and (b) amino acid substitutions at positions R38 and F42 as set forth in SEQ ID NO: 1, 2, 3, 4, or 5.

In yet another embodiment, the interleukin-2 polypeptide provided herein comprises: (a) an amino acid substitution of E15K or E15Q; and (b) amino acid substitutions of (i) R38A, R38E, R38G, or R38N; and (ii) F42A, F42G, F42K, or F42N.

In yet another embodiment, the interleukin-2 polypeptide provided herein comprises: (a) an amino acid substitution of E15K or E15Q; and (b) amino acid substitutions of (i) R38A, R38E, or R38G; or (ii) F42A, F42G, or F42K.

In still another embodiment, the interleukin-2 polypeptide provided herein comprises: (a) an amino acid substitution of E15K or E15Q; and (b) amino acid substitutions of (i) R38A, R38E, or R38G; and (ii) F42A or F42K.

In one embodiment, the interleukin-2 polypeptide provided herein comprises: (a) an amino acid substitution at position 127 or 130 as set forth in SEQ ID NO: 1, 2, 3, 4, or 5; and (b) amino acid substitutions at positions 38 and 42 as set forth in SEQ ID NO: 1, 2, 3, 4, or 5.

In another embodiment, the interleukin-2 polypeptide provided herein comprises: (a) an amino acid substitution at position S127 or S130 as set forth in SEQ ID NO: 1, 2, 3, 4, or 5; and (b) amino acid substitutions at positions R38 and F42 as set forth in SEQ ID NO: 1, 2, 3, 4, or 5.

In yet another embodiment, the interleukin-2 polypeptide provided herein comprises: (a) an amino acid substitution selected from S127A, S127E, S127F, S127W, S130A, S130E, S130F, and S130W; and (b) amino acid substitutions of (i) R38A, R38E, R38G, or R38N; and (ii) F42A, F42G, F42K, or F42N.

In yet another embodiment, the interleukin-2 polypeptide provided herein comprises: (a) an amino acid substitution selected from S127A, S127E, S127F, S127W, S130A, S130E, S130F, and S130W; and (b) amino acid substitutions of (i) R38A, R38E, or R38G; and (ii) F42A, F42G, or F42K.

In still another embodiment, the interleukin-2 polypeptide provided herein comprises: (a) an amino acid substitution of S127A or S130A; and (b) amino acid substitutions of (i) R38A, R38E, or R38G; and (ii) F42A or F42K.

In one embodiment, the interleukin-2 polypeptide provided herein comprises: (a) a deletion or replacement of the amino acid residues from positions 30 to 35 as set forth in SEQ ID NO: 1, 2, 3, 4, or 5 with a peptide linker; and (b) amino acid substitutions at positions 38 and 42 as set forth in SEQ ID NO: 1, 2, 3, 4, or 5.

In another embodiment, the interleukin-2 polypeptide provided herein comprises: (a) a deletion or replacement of the amino acid residues from positions N30 to K35 as set forth in SEQ ID NO: 1, 2, 3, 4, or 5 with a peptide linker; and (b) amino acid substitutions at positions R38 and F42 as set forth in SEQ ID NO: 1, 2, 3, 4, or 5.

In yet another embodiment, the interleukin-2 polypeptide provided herein comprises: (a) a deletion or replacement of the amino acid residues from positions 30 to 35 having an amino acid sequence of SEQ ID NO: 10 with a flexible peptide linker having an amino acid sequence selected from G, SG, GGS, and SEQ ID NOs: 7 to 9; and (b) amino acid substitutions of (i) R38A, R38E, R38G, or R38N; and (ii) F42A, F42G, F42K, or F42N.

In yet another embodiment, the interleukin-2 polypeptide provided herein comprises: (a) a deletion or replacement of the amino acid residues from positions 30 to 35 having an amino acid sequence of SEQ ID NO: 10 with a flexible peptide linker having an amino acid sequence selected from G, SG, GGS, and SEQ ID NOs: 7 to 9; and (b) amino acid substitutions of (i) R38A, R38E, or R38G; and (ii) F42A, F42G, or F42K.

In still another embodiment, the interleukin-2 polypeptide provided herein comprises: (a) a deletion or replacement of the amino acid residues from positions 30 to 35 having an amino acid sequence of SEQ ID NO: 10 with a flexible peptide linker having an amino acid sequence selected from G, SG, GGS, and SEQ ID NOs: 7 to 9; and (b) amino acid substitutions of (i) R38A, R38E, or R38G; and (ii) F42A or F42K.

In one embodiment, the interleukin-2 polypeptide provided herein comprises: (a) an amino acid substitution at position 8, 9, 13, 15, 16, 19, 23, 32, 76, 79, 81, 84, 87, 88, 91, 92, 95, 127, or 130 as set forth in SEQ ID NO: 1, 2, 3, 4, or 5; and (b) amino acid substitutions at positions 38 and 42 as set forth in SEQ ID NO: 1, 2, 3, 4, or 5.

In another embodiment, the interleukin-2 polypeptide provided herein comprises: (a) an amino acid substitution at position K8, K9, Q13, E15, H16, L19, M23, K32, K76, H79, R81, D84, S87, N88, V91, I92, E95, S127, or S130 as set forth in SEQ ID NO: 1, 2, 3, 4, or 5; and (b) amino acid substitutions at positions R38 and F42 as set forth in SEQ ID NO: 1, 2, 3, 4, or 5.

In yet another embodiment, the interleukin-2 polypeptide provided herein comprises: (a) an amino acid substitution of K8D, K8E, K8Q, K9D, K9E, K9Q, Q13E, Q13N, E15K, E15Q, E15V, H16D, H16E, H16N, H16Q, L19S, M23K, K32D, K32E, K32Q, K76D, K76E, K76Q, H79D, H79E, H79Q, R81D, R81E, R81Q, D84T, S87D, S87E, N88A, V91I, I92A, I92L, E95K, E95N, E95Q, S127A, S127E, S127F, S127W, S130A, S130E, S130F, or S130W; and (b) amino acid substitutions of (i) R38A, R38E, R38G, or R38N; and (ii) F42A, F42G, F42K, or F42N.

In yet another embodiment, the interleukin-2 polypeptide provided herein comprises: (a) an amino acid substitution of K8D, K8E, K8Q, K9D, K9E, K9Q, Q13E, Q13N, E15K, E15Q, E15V, H16D, H16E, H16N, H16Q, L19S, M23K, K32D, K32E, K32Q, K76D, K76E, K76Q, H79D, H79E, H79Q, R81D, R81E, R81Q, D84T, S87D, S87E, N88A, V91I, I92A, I92L, E95K, E95N, E95Q, S127A, S127E, S127F, S127W, S130A, S130E, S130F, or S130W; and (b) amino acid substitutions of (i) R38A, R38E, or R38G; and (ii) F42A, F42G, or F42K.

In yet another embodiment, the interleukin-2 polypeptide provided herein comprises: (a) an amino acid substitution of K8D, K8E, K8Q, K9D, K9E, K9Q, Q13E, Q13N, E15K, E15Q, E15V, H16D, H16E, H16N, H16Q, L19S, M23K, K32D, K32E, K32Q, K76D, K76E, K76Q, H79D, H79E, H79Q, R81D, R81E, R81Q, D84T, S87D, S87E, N88A, V91I, I92A, I92L, E95K, E95N, E95Q, S127A, S127E, S127F, S127W, S130A, S130E, S130F, or S130W; and (b) amino acid substitutions of (i) R38A, R38E, or R38G; and (ii) F42A or F42K.

In still another embodiment, the interleukin-2 polypeptide provided herein comprises: (a) an amino acid substitution of K8D, K8E, K8Q, K9D, K9E, K9Q, Q13E, Q13N, E15K, E15Q, E15V, H16D, H16E, H16N, H16Q, L19S, M23K, K32D, K32E, K32Q, K76D, K76E, K76Q, H79D, H79E, H79Q, R81D, R81E, R81Q, D84T, S87D, S87E, N88A, V91I, I92A, I92L, E95K, E95N, E95Q, S127A, S127E, S127F, S127W, S130A, S130E, S130F, or S130W; and (b) amino acid substitutions of R38N and F42A.

In one embodiment, the interleukin-2 polypeptide provided herein comprises: (a) an amino acid substitution at position 13, 15, 16, 19, 23, 84, 87, 91, 92, or 95 as set forth in SEQ ID NO: 1, 2, 3, 4, or 5; and (b) amino acid substitution at positions 38 and 42 as set forth in SEQ ID NO: 1, 2, 3, 4, or 5.

In another embodiment, the interleukin-2 polypeptide provided herein comprises: (a) an amino acid substitution at position Q13, E15, H16, L19, M23, D84, S87, V91, I92, or E95 as set forth in SEQ ID NO: 1, 2, 3, 4, or 5; and (b) amino acid substitutions at positions R38 and F42 as set forth in SEQ ID NO: 1, 2, 3, 4, or 5.

In yet another embodiment, the interleukin-2 polypeptide provided herein comprises: (a) an amino acid substitution of Q13E, Q13N, E15V, H16N, L19S, M23K, D84T, S87D, S87E, V91I, I92L, E95N, or E95Q; and (b) amino acid substitutions of (i) R38A, R38E, R38G, or R38N; and (ii) F42A, F42G, F42K, or F42N.

In yet another embodiment, the interleukin-2 polypeptide provided herein comprises: (a) an amino acid substitution of Q13E, Q13N, E15V, H16N, L19S, M23K, D84T, S87D, S87E, V91I, I92L, E95N, or E95Q; and (b) amino acid substitutions of (i) R38A, R38E, or R38G; and (ii) F42A, F42G, or F42K.

In yet another embodiment, the interleukin-2 polypeptide provided herein comprises: (a) an amino acid substitution of Q13E, Q13N, E15V, H16N, L19S, M23K, D84T, S87D, S87E, V91I, I92L, E95N, or E95Q; and (b) amino acid substitutions of (i) R38A, R38E, or R38G; and (ii) F42A or F42K.

In still another embodiment, the interleukin-2 polypeptide provided herein comprises: (a) an amino acid substitution of Q13E, Q13N, E15V, H16N, L19S, M23K, D84T, S87D, S87E, V91I, I92L, E95N, or E95Q; and (b) amino acid substitutions of R38N and F42A.

In one embodiment, the interleukin-2 polypeptide provided herein comprises: (a) an amino acid substitution at position 13, 15, 16, 23, 91, or 95 as set forth in SEQ ID NO: 1, 2, 3, 4, or 5; and (b) amino acid substitutions at positions 38 and 42 as set forth in SEQ ID NO: 1, 2, 3, 4, or 5.

In another embodiment, the interleukin-2 polypeptide provided herein comprises: (a) an amino acid substitution at position Q13, E15, H16, M23, V91, or E95 as set forth in SEQ ID NO: 1, 2, 3, 4, or 5; and (b) amino acid substitutions at positions R38 and F42 as set forth in SEQ ID NO: 1, 2, 3, 4, or 5.

In yet another embodiment, the interleukin-2 polypeptide provided herein comprises: (a) an amino acid substitution of Q13E, E15V, H16N, M23K, V91I, or E95N; and (b) amino acid substitutions of (i) R38A, R38E, R38G, or R38N; and (ii) F42A, F42G, F42K, or F42N.

In yet another embodiment, the interleukin-2 polypeptide provided herein comprises: (a) an amino acid substitution of Q13E, E15V, H16N, M23K, V91I, or E95N; and (b) amino acid substitutions of (i) R38A, R38E, or R38G; and (ii) F42A, F42G, or F42K.

In yet another embodiment, the interleukin-2 polypeptide provided herein comprises: (a) an amino acid substitution of Q13E, E15V, H16N, M23K, V91I, or E95N; and (b) amino acid substitutions of (i) R38A, R38E, or R38G; and (ii) F42A or F42K.

In still another embodiment, the interleukin-2 polypeptide provided herein comprises: (a) an amino acid substitution of Q13E, E15V, H16N, M23K, V91I, or E95N; and (b) amino acid substitutions of R38N and F42A.

In one embodiment, the interleukin-2 polypeptide provided herein is not glycosylated. In another embodiment, the interleukin-2 polypeptide provided herein is not N-glycosylated.

In one embodiment, the interleukin-2 polypeptide provided herein is glycosylated. In another embodiment, the interleukin-2 polypeptide provided herein is N-glycosylated. In yet another embodiment, the interleukin-2 polypeptide provided herein comprises an N-glycosylation site.

In one embodiment, the interleukin-2 polypeptide provided herein comprises an N-glycosylation site having an amino acid sequence of NXT or NXS, wherein each X is independently A, C, D, E, F, G, H, I, K, L, M, N, Q, R, S, T, V, W, or Y.

In one embodiment, X is A, C, D, E, F, G, H, I, K, M, N, Q, R, S, T, V, or Y. In another embodiment, X is A, C, D, G, H, K, M, N, Q, R, S, T, V, W, or Y. In yet another embodiment, X is A, E, F, K, L, M, R, V, W, or Y. In still another embodiment, X is F or M.

In another embodiment, the interleukin-2 polypeptide provided herein comprises an N-glycosylation site having an amino acid sequence of NAT, NAS, NET, NES, NFT, NFS, NKT, NKS, NLT, NLS, NMT, NMS, NRT, NRS, NVT, NVS, NWT, NWS, NYT, or NYS.

In one embodiment, the interleukin-2 polypeptide provided herein comprises an N-glycosylation site having an amino acid sequence of NAT or NAS. In another embodiment, the interleukin-2 polypeptide provided herein comprises an N-glycosylation site having an amino acid sequence of NET or NES. In yet another embodiment, the interleukin-2 polypeptide provided herein comprises an N-glycosylation site having an amino acid sequence of NFT or NFS. In yet another embodiment, the interleukin-2 polypeptide provided herein comprises an N-glycosylation site having an amino acid sequence of NKT or NKS. In yet another embodiment, the interleukin-2 polypeptide provided herein comprises an N-glycosylation site having an amino acid sequence of NLT or NLS. In yet another embodiment, the interleukin-2 polypeptide provided herein comprises an N-glycosylation site having an amino acid sequence of NMT or NMS. In yet another embodiment, the interleukin-2 polypeptide provided herein comprises an N-glycosylation site having an amino acid sequence of NRT or NRS. In yet another embodiment, the interleukin-2 polypeptide provided herein comprises an N-glycosylation site having an amino acid sequence of NVT or NVS. In yet another embodiment, the interleukin-2 polypeptide provided herein comprises an N-glycosylation site having an amino acid sequence of NWT or NWS. In still another embodiment, the interleukin-2 polypeptide provided herein comprises an N-glycosylation site having an amino acid sequence of NYT or NYS.

In yet another embodiment, the interleukin-2 polypeptide provided herein comprises an N-glycosylation site having an amino acid sequence of NAT, NAS, NET, NES, NFT, NFS, NKT, NKS, NLT, NLS, NMT, NMS, NRT, NRS, NVT, NVS, NWT, NWS, NYT, or NYS, each independently starting at position 34, 35, 37, 38, 39, 41, 42, 43, 44, 45, 61, 62, 64, 65, 66, 68, 69, 71, 72, 107, or 109 as set forth in SEQ ID NO: 1, 2, 3, 4, or 5.

In one embodiment, the interleukin-2 polypeptide provided herein comprises an N-glycosylation site having an amino acid sequence of NKT or NKS, each independently starting at position 34 or 42 as set forth in SEQ ID NO: 1, 2, 3, 4, or 5.

In another embodiment, the interleukin-2 polypeptide provided herein comprises an N-glycosylation site having an amino acid sequence of NLT or NLS, each independently starting at position 35, 39, 62, 65, 69, or 71 as set forth in SEQ ID NO: 1, 2, 3, 4, or 5.

In yet another embodiment, the interleukin-2 polypeptide provided herein comprises an N-glycosylation site having an amino acid sequence of NRT or NRS, each independently starting at position 37 as set forth in SEQ ID NO: 1, 2, 3, 4, or 5.

In yet another embodiment, the interleukin-2 polypeptide provided herein comprises an N-glycosylation site having an amino acid sequence of NMT or NMS, each independently starting at position 38 or 45 as set forth in SEQ ID NO: 1, 2, 3, 4, or 5.

In yet another embodiment, the interleukin-2 polypeptide provided herein comprises an N-glycosylation site having an amino acid sequence of NMT or NMS, each independently starting at position 38 as set forth in SEQ ID NO: 1, 2, 3, 4, or 5.

In yet another embodiment, the interleukin-2 polypeptide provided herein comprises an N-glycosylation site having an amino acid sequence of NMT or NMS, each independently starting at position 45 as set forth in SEQ ID NO: 1, 2, 3, 4, or 5.

In yet another embodiment, the interleukin-2 polypeptide provided herein comprises an N-glycosylation site having an amino acid sequence of NFT or NFS, each independently starting at position 41 or 43 as set forth in SEQ ID NO: 1, 2, 3, 4, or 5.

In yet another embodiment, the interleukin-2 polypeptide provided herein comprises an N-glycosylation site having an amino acid sequence of NYT or NYS, each independently starting at position 44 as set forth in SEQ ID NO: 1, 2, 3, 4, or 5.

In yet another embodiment, the interleukin-2 polypeptide provided herein comprises an N-glycosylation site having an amino acid sequence of NET or NES, each independently starting at position 61, 66, or 109 as set forth in SEQ ID NO: 1, 2, 3, 4, or 5.

In yet another embodiment, the interleukin-2 polypeptide provided herein comprises an N-glycosylation site having an amino acid sequence of NAT or NAS, each independently starting at position 64, 72, or 107 as set forth in SEQ ID NO: 1, 2, 3, 4, or 5.

In still another embodiment, the interleukin-2 polypeptide provided herein comprises an N-glycosylation site having an amino acid sequence of NVT or NVS, each independently starting at position 68 as set forth in SEQ ID NO: 1, 2, 3, 4, or 5.

In one embodiment, the interleukin-2 polypeptide provided herein comprises an N-glycosylation site having an amino acid sequence of NA, NE, NK, NM, or NW.

In one embodiment, the interleukin-2 polypeptide provided herein comprises an N-glycosylation site having an amino acid sequence of NA. In another embodiment, the interleukin-2 polypeptide provided herein comprises an N-glycosylation site having an amino acid sequence of NE. In yet another embodiment, the interleukin-2 polypeptide provided herein comprises an N-glycosylation site having an amino acid sequence of NK. In yet another embodiment, the interleukin-2 polypeptide provided herein comprises an N-glycosylation site having an amino acid sequence of NM. In still another embodiment, the interleukin-2 polypeptide provided herein comprises an N-glycosylation site having an amino acid sequence of NW.

In another embodiment, the interleukin-2 polypeptide provided herein comprises an N-glycosylation site having an amino acid sequence of NA, NE, NK, NM, or NW, each independently starting at position 34, 38, 42, 45, 61, 64, 66, 72, 107, or 109 as set forth in SEQ ID NO: 1, 2, 3, 4, or 5.

In one embodiment, the interleukin-2 polypeptide provided herein comprises an N-glycosylation site having an amino acid sequence of NK starting at position 34 or 42 as set forth in SEQ ID NO: 1, 2, 3, 4, or 5. In another embodiment, the interleukin-2 polypeptide provided herein comprises an N-glycosylation site having an amino acid sequence of NM starting at position 38 or 45 as set forth in SEQ ID NO: 1, 2, 3, 4, or 5. In yet another embodiment, the interleukin-2 polypeptide provided herein comprises an N-glycosylation site having an amino acid sequence of NE starting at position 61, 66, or 109 as set forth in SEQ ID NO: 1, 2, 3, 4, or 5. In still another embodiment, the interleukin-2 polypeptide provided herein comprises an N-glycosylation site having an amino acid sequence of NA starting at position 64, 72, or 107 as set forth in SEQ ID NO: 1, 2, 3, 4, or 5.

In yet another embodiment, the interleukin-2 polypeptide provided herein comprises an N-glycosylation site at an interface residue between an interleukin-2 and an IL-2Rα chain.

In one embodiment, the interface residue is K35, T37, R38, T41, F42, K43, F44, Y45, E61, E62, K64, P65, E68, L72, or Y107 as set forth in SEQ ID NO: 1, 2, 3, 4, or 5. In another embodiment, the interface residue is K35 as set forth in SEQ ID NO: 1, 2, 3, 4, or 5. In yet another embodiment, the interface residue is T37 as set forth in SEQ ID NO: 1, 2, 3, 4, or 5. In yet another embodiment, the interface residue is R38 as set forth in SEQ ID NO: 1, 2, 3, 4, or 5. In yet another embodiment, the interface residue is T41 as set forth in SEQ ID NO: 1, 2, 3, 4, or 5. In yet another embodiment, the interface residue is F42 as set forth in SEQ ID NO: 1, 2, 3, 4, or 5. In yet another embodiment, the interface residue is K43 as set forth in SEQ ID NO: 1, 2, 3, 4, or 5. In yet another embodiment, the interface residue is F44 as set forth in SEQ ID NO: 1, 2, 3, 4, or 5. In yet another embodiment, the interface residue is Y45 as set forth in SEQ ID NO: 1, 2, 3, 4, or 5. In yet another embodiment, the interface residue is E61 as set forth in SEQ ID NO: 1, 2, 3, 4, or 5. In yet another embodiment, the interface residue is E62 as set forth in SEQ ID NO: 1, 2, 3, 4, or 5. In yet another embodiment, the interface residue is K64 as set forth in SEQ ID NO: 1, 2, 3, 4, or 5. In yet another embodiment, the interface residue is P65 as set forth in SEQ ID NO: 1, 2, 3, 4, or 5. In yet another embodiment, the interface residue is E68 as set forth in SEQ ID NO: 1, 2, 3, 4, or 5. In still another embodiment, the interface residue as set forth is L72 in SEQ ID NO: 1, 2, 3, 4, or 5. In yet another embodiment, the interface residue is Y107 as set forth in SEQ ID NO: 1, 2, 3, 4, or 5.

In still another embodiment, the interleukin-2 polypeptide provided herein comprises an N-glycosylation site at position K35, T37, R38, T41, F42, K43, F44, Y45, E61, E62, K64, P65, E68, L72, or Y107 as set forth in SEQ ID NO: 1, 2, 3, 4, or 5.

In one embodiment, the interleukin-2 polypeptide provided herein comprises an N-glycosylation site at position K35 as set forth in SEQ ID NO: 1, 2, 3, 4, or 5. In another embodiment, the interleukin-2 polypeptide provided herein comprises an N-glycosylation site at position T37 as set forth in SEQ ID NO: 1, 2, 3, 4, or 5. In yet another embodiment, the interleukin-2 polypeptide provided herein comprises an N-glycosylation site at position R38 as set forth in SEQ ID NO: 1, 2, 3, 4, or 5. In yet another embodiment, the interleukin-2 polypeptide provided herein comprises an N-glycosylation site at position T41 as set forth in SEQ ID NO: 1, 2, 3, 4, or 5. In yet another embodiment, the interleukin-2 polypeptide provided herein comprises an N-glycosylation site at position F42 as set forth in SEQ ID NO: 1, 2, 3, 4, or 5. In yet another embodiment, the interleukin-2 polypeptide provided herein comprises an N-glycosylation site at position K43 as set forth in SEQ ID NO: 1, 2, 3, 4, or 5. In yet another embodiment, the interleukin-2 polypeptide provided herein comprises an N-glycosylation site at position F44 as set forth in SEQ ID NO: 1, 2, 3, 4, or 5. In yet another embodiment, the interleukin-2 polypeptide provided herein comprises an N-glycosylation site at position Y45 as set forth in SEQ ID NO: 1, 2, 3, 4, or 5. In yet another embodiment, the interleukin-2 polypeptide provided herein comprises an N-glycosylation site at position E61 as set forth in SEQ ID NO: 1, 2, 3, 4, or 5. In yet another embodiment, the interleukin-2 polypeptide provided herein comprises an N-glycosylation site at position E62 as set forth in SEQ ID NO: 1, 2, 3, 4, or 5. In yet another embodiment, the interleukin-2 polypeptide provided herein comprises an N-glycosylation site at position K64 as set forth in SEQ ID NO: 1, 2, 3, 4, or 5. In yet another embodiment, the interleukin-2 polypeptide provided herein comprises an N-glycosylation site at position P65 as set forth in SEQ ID NO: 1, 2, 3, 4, or 5. In yet another embodiment, the interleukin-2 polypeptide provided herein comprises an N-glycosylation site at position E68 as set forth in SEQ ID NO: 1, 2, 3, 4, or 5. In yet another embodiment, the interleukin-2 polypeptide provided herein comprises an N-glycosylation site at position L72 as set forth in SEQ ID NO: 1, 2, 3, 4, or 5. In still another embodiment, the interleukin-2 polypeptide provided herein comprises an N-glycosylation site at position Y107 as set forth in SEQ ID NO: 1, 2, 3, 4, or 5.

In certain embodiments, the interleukin-2 polypeptide provided herein comprises an amino acid substitution of K35N, M39N, A73T, A73S, or D109N.

In one embodiment, the interleukin-2 polypeptide provided herein comprises an amino acid substitution of K35N. In another embodiment, the interleukin-2 polypeptide provided herein comprises an amino acid substitution of M39N. In yet another embodiment, the interleukin-2 polypeptide provided herein comprises an amino acid substitution of A73T or A73S. In still another embodiment, the interleukin-2 polypeptide provided herein comprises an amino acid substitution of D109N.

In certain embodiments, the interleukin-2 polypeptide provided herein comprises a two-amino acid substitution combination selected from (i) P34N and L36T or L36S; (ii) K35N and T37S; (iii) T37N and M39T or M39S; (iv) R38N and L40T or L40S; (v) T41N and K43T or K43S; (vi) F42N and F44T or F44S; (vii) K43N and Y45T or Y45S; (viii) F44N and M46T or M46S; (ix) Y45N and P47T or P47S; (x) E61N and L63T or L63S; (xi) E62N and K64T or K64S; (xii) P65N and E67T or E67S; (xiii) L66N and E68T or E68S; (xiv) E68N and L70T or L70S; (xv) V69N and N71T or N71S; (xvi) L72N and Q74T or Q74S; (xvii) Y107N and D109T or D109S; or (xviii) D109N and T111S.

In one embodiment, the interleukin-2 polypeptide provided herein comprises two amino acid substitutions: (i) P34N and (ii) L36T or L36S. In another embodiment, the interleukin-2 polypeptide provided herein comprises two amino acid substitutions: K35N and T37S. In yet another embodiment, the interleukin-2 polypeptide provided herein comprises two amino acid substitutions: (i) T37N and (ii) M39T or M39S. In yet another embodiment, the interleukin-2 polypeptide provided herein comprises two amino acid substitutions: (i) R38N and (ii) L40T or L40S. In yet another embodiment, the interleukin-2 polypeptide provided herein comprises two amino acid substitutions: R38N and L40T. In yet another embodiment, the interleukin-2 polypeptide provided herein comprises two amino acid substitutions: (i) T41N and (ii) K43T or K43S. In yet another embodiment, the interleukin-2 polypeptide provided herein comprises two amino acid substitutions: (i) F42N and (ii) F44T or F44S. In yet another embodiment, the interleukin-2 polypeptide provided herein comprises two amino acid substitutions: (i) K43N and (ii) Y45T or Y45S. In yet another embodiment, the interleukin-2 polypeptide provided herein comprises two amino acid substitutions: (i) F44N and (ii) M46T or M46S. In yet another embodiment, the interleukin-2 polypeptide provided herein comprises two amino acid substitutions: (i) Y45N and (ii) P47T or P47S. In yet another embodiment, the interleukin-2 polypeptide provided herein comprises two amino acid substitutions: (i) E61N and (ii) L63T or L63S. In yet another embodiment, the interleukin-2 polypeptide provided herein comprises two amino acid substitutions: (i) E62N and (ii) K64T or K64S. In yet another embodiment, the interleukin-2 polypeptide provided herein comprises two amino acid substitutions: (i) P65N and (ii) E67T or E67S. In yet another embodiment, the interleukin-2 polypeptide provided herein comprises two amino acid substitutions: (i) L66N and (ii) E68T or E68S. In yet another embodiment, the interleukin-2 polypeptide provided herein comprises two amino acid substitutions: (i) E68N and (ii) L70T or L70S. In yet another embodiment, the interleukin-2 polypeptide provided herein comprises two amino acid substitutions: (i) V69N and (ii) N71T or N71S. In yet another embodiment, the interleukin-2 polypeptide provided herein comprises two amino acid substitutions: (i) L72N and (ii) Q74T or Q74S. In yet another embodiment, the interleukin-2 polypeptide provided herein comprises two amino acid substitutions: (i) Y107N and (ii) D109T or D109S. In still another embodiment, the interleukin-2 polypeptide provided herein comprises two amino acid substitutions: D109N and T111S.

In certain embodiments, the interleukin-2 polypeptide provided herein comprises three amino acid substitutions: (i) R38N, (ii) L40T, and (iii) F42A, Y45A, E61A, or E62A. In certain embodiments, the interleukin-2 polypeptide provided herein comprises three amino acid substitutions: (i) K64N, (ii) P65A, and (iii) L66T or L66S. In certain embodiments, the interleukin-2 polypeptide provided herein comprises four amino acid substitutions: (i) R38N, (ii) L40T, (iii) K43N, and (iv) Y45T or Y45S.

In one embodiment, provided herein is an interleukin-2 polypeptide comprising an amino acid sequence of SEQ ID NO: 1, 2, 3, 4, or 5, wherein the interleukin-2 polypeptide comprises (i) an amino acid substitution selected from K8D, K8E, K8Q, K9D, K9E, K9Q, E15K, E15Q, H16D, H16E, H16Q, K32D, K32E, K32Q, K76D, K76E, K76Q, H79D, H79E, H79Q, R81D, R81E, R81Q, D84T, N88A, I92A, E95K, E95Q, S127A, S127E, S127F, S127W, S130A, S130E, S130F, and S130W; and (ii) an amino acid substitution of R38N.

In another embodiment, provided herein is an interleukin-2 polypeptide comprising an amino acid sequence of SEQ ID NO: 1, 2, 3, 4, or 5, wherein the interleukin-2 polypeptide comprises (i) an amino acid substitution selected from K8D, K8E, K8Q, K9D, K9E, K9Q, H16D, H16E, H16Q, K32D, K32E, K32Q, K76D, K76E, K76Q, H79D, H79E, H79Q, R81D, R81E, and R81Q; and (ii) an amino acid substitution of R38N.

In one embodiment, the interleukin-2 polypeptide provided herein comprises (i) an amino acid substitution of K8D, K8E, or K8Q; and (ii) an amino acid substitution of R38N. In another embodiment, the interleukin-2 polypeptide provided herein comprises amino acid substitutions K8E and R38N. In yet another embodiment, the interleukin-2 polypeptide provided herein comprises (i) an amino acid substitution of K9D, K9E, or K9Q; and (ii) an amino acid substitution of R38N. In yet another embodiment, the interleukin-2 polypeptide provided herein comprises amino acid substitutions K9E and R38N. In yet another embodiment, the interleukin-2 polypeptide provided herein comprises (i) an amino acid substitution of H16D, H16E, or H16Q; and (ii) an amino acid substitution of R38N. In yet another embodiment, the interleukin-2 polypeptide provided herein comprises amino acid substitutions H16E and R38N. In yet another embodiment, the interleukin-2 polypeptide provided herein comprises (i) an amino acid substitution of K32D, K32E, or K32Q; and (ii) an amino acid substitution of R38N. In yet another embodiment, the interleukin-2 polypeptide provided herein comprises amino acid substitutions K32E and R38N. In yet another embodiment, the interleukin-2 polypeptide provided herein comprises (i) an amino acid substitution of K76D, K76E, or K76Q; and (ii) an amino acid substitution of R38N. In yet another embodiment, the interleukin-2 polypeptide provided herein comprises amino acid substitutions R38N and K76E. In yet another embodiment, the interleukin-2 polypeptide provided herein comprises (i) an amino acid substitution of H79D, H79E, or H79Q; and (ii) an amino acid substitution of R38N. In yet another embodiment, the interleukin-2 polypeptide provided herein comprises amino acid substitutions R38N and H79E. In yet another embodiment, the interleukin-2 polypeptide provided herein comprises (i) an amino acid substitution of R81D, R81E, or R81Q; and (ii) an amino acid substitution of R38N. In still another embodiment, the interleukin-2 polypeptide provided herein comprises amino acid substitutions R38N and R81E.

In one embodiment, provided herein is an interleukin-2 polypeptide comprising an amino acid sequence of SEQ ID NO: 1, 2, 3, 4, or 5, wherein the interleukin-2 polypeptide comprises (i) an amino acid substitution of K8D, K8E, K8Q, K9D, K9E, K9Q, Q13E, Q13N, E15K, E15Q, E15V, H16D, H16E, H16N, H16Q, L19S, M23K, K32D, K32E, K32Q, K76D, K76E, K76Q, H79D, H79E, H79Q, R81D, R81E, R81Q, D84T, S87D, S87E, N88A, V91I, I92A, I92L, E95K, E95N, E95Q, S127A, S127E, S127F, S127W, S130A, S130E, S130F, or S130W; and (ii) amino acid substitutions of R38N and L40T.

In another embodiment, provided herein is an interleukin-2 polypeptide comprising an amino acid sequence of SEQ ID NO: 1, 2, 3, 4, or 5, wherein the interleukin-2 polypeptide comprises (i) an amino acid substitution of K8D, K8E, K8Q, K9D, K9E, K9Q, E15K, E15Q, H16D, H16E, H16Q, K32D, K32E, K32Q, K76D, K76E, K76Q, H79D, H79E, H79Q, R81D, R81E, R81Q, D84T, N88A, I92A, E95K, E95Q, S127A, S127E, S127F, S127W, S130A, S130E, S130F, or S130W; and (ii) amino acid substitutions of R38N and L40T.

In yet another embodiment, provided herein is an interleukin-2 polypeptide comprising an amino acid sequence of SEQ ID NO: 1, 2, 3, 4, or 5, wherein the interleukin-2 polypeptide comprises (i) an amino acid substitution of K8D, K8E, K8Q, K9D, K9E, K9Q, Q13E, E15V, H16D, H16E, H16N, H16Q, M23K, K32D, K32E, K32Q, K76D, K76E, K76Q, H79D, H79E, H79Q, R81D, R81E, R81Q, D84T, S87D, S87E, V91I, I92L, E95N, or E95Q; and (ii) amino acid substitutions of R38N and L40T.

In yet another embodiment, provided herein is an interleukin-2 polypeptide comprising an amino acid sequence of SEQ ID NO: 1, 2, 3, 4, or 5, wherein the interleukin-2 polypeptide comprises (i) an amino acid substitution of K8D, K8E, K8Q, K9D, K9E, K9Q, H16D, H16E, H16Q, K32D, K32E, K32Q, K76D, K76E, K76Q, H79D, H79E, H79Q, R81D, R81E, or R81Q; and (ii) amino acid substitutions of R38N and L40T.

In still another embodiment, provided herein is an interleukin-2 polypeptide comprising an amino acid sequence of SEQ ID NO: 1, 2, 3, 4, or 5, wherein the interleukin-2 polypeptide comprises (i) an amino acid substitution of Q13E, E15V, H16N, M23K, V91I, or E95N; and (ii) amino acid substitutions of R38N and L40T.

In one embodiment, the interleukin-2 polypeptide provided herein comprises (i) an amino acid substitution of K8D, K8E, or K8Q; and (ii) amino acid substitutions of R38N and L40T. In another embodiment, the interleukin-2 polypeptide provided herein comprises amino acid substitutions K8E, R38N, and L40T.

In one embodiment, the interleukin-2 polypeptide provided herein comprises (i) an amino acid substitution of K9D, K9E, or K9Q; and (ii) amino acid substitutions of R38N and L40T. In another embodiment, the interleukin-2 polypeptide provided herein comprises amino acid substitutions K9E, R38N, and L40T.

In one embodiment, the interleukin-2 polypeptide provided herein comprises amino acid substitutions of Q13E, R38N, and L40T. In another embodiment, the interleukin-2 polypeptide provided herein comprises amino acid substitutions of E15V, R38N, and L40T.

In one embodiment, the interleukin-2 polypeptide provided herein comprises (i) an amino acid substitution of H16D, H16E, H16N, or H16Q; and (ii) amino acid substitutions of R38N and L40T. In another embodiment, the interleukin-2 polypeptide provided herein comprises (i) an amino acid substitution of H16D, H16E, or H16Q; and (ii) amino acid substitutions of R38N and L40T. In yet another embodiment, the interleukin-2 polypeptide provided herein comprises amino acid substitutions H16E, R38N, and L40T. In still another embodiment, the interleukin-2 polypeptide provided herein comprises amino acid substitutions H16N, R38N, and L40T.

In one embodiment, the interleukin-2 polypeptide provided herein comprises amino acid substitutions of M23K, R38N, and L40T.

In one embodiment, the interleukin-2 polypeptide provided herein comprises (i) an amino acid substitution of K32D, K32E, or K32Q; and (ii) amino acid substitutions of R38N and L40T. In another embodiment, the interleukin-2 polypeptide provided herein comprises amino acid substitutions K32E, R38N, and L40T.

In one embodiment, the interleukin-2 polypeptide provided herein comprises (i) an amino acid substitution of K76D, K76E, or K76Q; and (ii) amino acid substitutions of R38N and L40T. In another embodiment, the interleukin-2 polypeptide provided herein comprises amino acid substitutions R38N, L40T, and K76E.

In one embodiment, the interleukin-2 polypeptide provided herein comprises (i) an amino acid substitution of H79D, H79E, or H79Q; and (ii) amino acid substitutions of R38N and L40T. In another embodiment, the interleukin-2 polypeptide provided herein comprises amino acid substitutions R38N, L40T, and H79E.

In one embodiment, the interleukin-2 polypeptide provided herein comprises (i) an amino acid substitution of R81D, R81E, or R81Q; and (ii) amino acid substitutions of R38N, L40T, and R81D. In another embodiment, the interleukin-2 polypeptide provided herein comprises amino acid substitutions R38N, L40T, and R81E.

In one embodiment, the interleukin-2 polypeptide provided herein comprises amino acid substitutions of R38N, L40T, and V91I.

In one embodiment, the interleukin-2 polypeptide provided herein comprises amino acid substitutions of R38N, L40T, and E95N.

In one embodiment, the interleukin-2 polypeptide provided herein comprises amino acid substitutions of H16E, K32E, R38N, and L40T. In another embodiment, the interleukin-2 polypeptide provided herein comprises amino acid substitutions of H16E, R38N, L40T, and K76E. In yet another embodiment, the interleukin-2 polypeptide provided herein comprises amino acid substitutions of K32E, R38N, L40T, and K76E.

In one embodiment, the interleukin-2 polypeptide provided herein comprises amino acid substitutions of Q13E, R38N, L40T, and F42A. In another embodiment, the interleukin-2 polypeptide provided herein comprises amino acid substitutions of E15V, R38N, L40T, and F42A. In yet another embodiment, the interleukin-2 polypeptide provided herein comprises amino acid substitutions of H16N, R38N, L40T, and F42A. In yet another embodiment, the interleukin-2 polypeptide provided herein comprises amino acid substitutions of M23K, R38N, L40T, and F42A. In yet another embodiment, the interleukin-2 polypeptide provided herein comprises amino acid substitutions of R38N, L40T, F42A, and V91I. In still another embodiment, the interleukin-2 polypeptide provided herein comprises amino acid substitutions of R38N, L40T, F42A, and E95N.

In one embodiment, the interleukin-2 polypeptide provided herein comprises amino acid substitutions of T3A, Q13E, R38N, L40T, and F42A. In another embodiment, the interleukin-2 polypeptide provided herein comprises amino acid substitutions of T3A, E15V, R38N, L40T, and F42A. In yet another embodiment, the interleukin-2 polypeptide provided herein comprises amino acid substitutions of T3A, H16N, R38N, L40T, and F42A. In yet another embodiment, the interleukin-2 polypeptide provided herein comprises amino acid substitutions of T3A, M23K, R38N, L40T, and F42A. In yet another embodiment, the interleukin-2 polypeptide provided herein comprises amino acid substitutions of T3A, R38N, L40T, F42A, and V91I. In still another embodiment, the interleukin-2 polypeptide provided herein comprises amino acid substitutions of T3A, R38N, L40T, F42A, and E95N.

In one embodiment, the interleukin-2 polypeptide provided herein comprises amino acid substitutions of T3A, Q13E, R38N, L40T, F42A, and C125S. In another embodiment, the interleukin-2 polypeptide provided herein comprises amino acid substitutions of T3A, E15V, R38N, L40T, F42A, and C125S. In yet another embodiment, the interleukin-2 polypeptide provided herein comprises amino acid substitutions of T3A, H16N, R38N, L40T, F42A, and C125S. In yet another embodiment, the interleukin-2 polypeptide provided herein comprises amino acid substitutions of T3A, M23K, R38N, L40T, F42A, and C125S. In yet another embodiment, the interleukin-2 polypeptide provided herein comprises amino acid substitutions of T3A, R38N, L40T, aF42A, V91I, and C125S. In still another embodiment, the interleukin-2 polypeptide provided herein comprises amino acid substitutions of T3A, R38N, L40T, aF42A, E95N, and C125S.

In yet another embodiment, provided herein is an interleukin-2 polypeptide comprising an amino acid sequence of SEQ ID NO: 1, 2, 3, 4, or 5, wherein the interleukin-2 polypeptide comprises (i) an amino acid substitution of E15K or E15Q; and (ii) an amino acid substitution of R38N.

In one embodiment, the interleukin-2 polypeptide provided herein comprises amino acid substitutions of E15K and R38N. In another embodiment, the interleukin-2 polypeptide provided herein comprises amino acid substitutions of E15Q and R38N.

In yet another embodiment, provided herein is an interleukin-2 polypeptide comprising an amino acid sequence of SEQ ID NO: 1, 2, 3, 4, or 5, wherein the interleukin-2 polypeptide comprises (i) an amino acid substitution of E15K or E15Q; and (ii) amino acid substitutions of R38N and L40T.

In one embodiment, the interleukin-2 polypeptide provided herein comprises amino acid substitutions of E15K, R38N, and L40T. In another embodiment, the interleukin-2 polypeptide provided herein comprises amino acid substitutions of E15Q, R38N, and L40T.

In yet another embodiment, provided herein is an interleukin-2 polypeptide comprising an amino acid sequence of SEQ ID NO: 1, 2, 3, 4, or 5, wherein the interleukin-2 polypeptide comprises (i) an amino acid substitution selected from H16D, H16E, H16Q, D84T, N88A, I92A, E95K, and E95Q; and (ii) an amino acid substitution of R38N.

In one embodiment, the interleukin-2 polypeptide provided herein comprises (i) an amino acid substitution of H16D, H16E, or H16Q; and (ii) an amino acid substitution of R38N. In another embodiment, the interleukin-2 polypeptide provided herein comprises amino acid substitutions H16E and R38N. In yet another embodiment, the interleukin-2 polypeptide provided herein comprises amino acid substitutions R38N and D84T. In yet another embodiment, the interleukin-2 polypeptide provided herein comprises amino acid substitutions R38N and N84A. In yet another embodiment, the interleukin-2 polypeptide provided herein comprises amino acid substitutions R38N and I92A. In yet another embodiment, the interleukin-2 polypeptide provided herein comprises amino acid substitutions R38N and E95K. In still another embodiment, the interleukin-2 polypeptide provided herein comprises amino acid substitutions R38N and E95Q.

In yet another embodiment, provided herein is an interleukin-2 polypeptide comprising an amino acid sequence of SEQ ID NO: 1, 2, 3, 4, or 5, wherein the interleukin-2 polypeptide comprises (i) an amino acid substitution selected from H16D, H16E, H16Q, D84T, N88A, I92A, E95K, and E95Q; and (ii) amino acid substitutions of R38N and L40T.

In one embodiment, the interleukin-2 polypeptide provided herein comprises (i) an amino acid substitution of H16D, H16E, or H16Q; and (ii) amino acid substitutions of R38N and L40T. In another embodiment, the interleukin-2 polypeptide provided herein comprises amino acid substitutions H16E, R38N, and L40T. In yet another embodiment, the interleukin-2 polypeptide provided herein comprises amino acid substitutions R38N, L40T, and D84T. In yet another embodiment, the interleukin-2 polypeptide provided herein comprises amino acid substitutions R38N, L40T, and N84A. In yet another embodiment, the interleukin-2 polypeptide provided herein comprises amino acid substitutions R38N, L40T, and I92A. In yet another embodiment, the interleukin-2 polypeptide provided herein comprises amino acid substitutions R38N, L40T, and E95K. In still another embodiment, the interleukin-2 polypeptide provided herein comprises amino acid substitutions R38N, L40T, and E95Q.

In yet another embodiment, provided herein is an interleukin-2 polypeptide comprising an amino acid sequence of SEQ ID NO: 1, 2, 3, 4, or 5, wherein the interleukin-2 polypeptide comprises (i) an amino acid substitution selected from S127A, S127E, S127F, S127W, S130A, S130E, S130F, and S130W; and (ii) an amino acid substitution of R38N.

In one embodiment, the interleukin-2 polypeptide provided herein comprises (i) an amino acid substitution of S127A, S127E, S127F, or S127W; and (ii) an amino acid substitution of R38N. In another embodiment, the interleukin-2 polypeptide provided herein comprises amino acid substitutions R38N and S127A. In yet another embodiment, the interleukin-2 polypeptide provided herein comprises (i) an amino acid substitution of S130A, S130E, S130F, or S130W; and (ii) an amino acid substitution of R38N. In still another embodiment, the interleukin-2 polypeptide provided herein comprises amino acid substitutions R38N and S130A.

In still another embodiment, provided herein is an interleukin-2 polypeptide comprising an amino acid sequence of SEQ ID NO: 1, 2, 3, 4, or 5, wherein the interleukin-2 polypeptide comprises (i) an amino acid substitution selected from S127A, S127E, S127F, S127W, S130A, S130E, S130F, and S130W; and (ii) amino acid substitutions of R38N and L40T.

In one embodiment, the interleukin-2 polypeptide provided herein comprises (i) an amino acid substitution of S127A, S127E, S127F, or S127W; and (ii) amino acid substitutions of R38N and L40T. In another embodiment, the interleukin-2 polypeptide provided herein comprises amino acid substitutions R38N, L40T, and S127A. In yet another embodiment, the interleukin-2 polypeptide provided herein comprises (i) an amino acid substitution of S130A, S130E, S130F, or S130W; and (ii) amino acid substitutions of R38N and L40T. In still another embodiment, the interleukin-2 polypeptide provided herein comprises amino acid substitutions R38N, L40T, and S130A.

In one embodiment, provided herein is an interleukin-2 polypeptide comprising an amino acid sequence of SEQ ID NO: 1, 2, 3, 4, or 5, wherein the interleukin-2 polypeptide comprises (i) a deletion of an amino acid sequence of SEQ ID NO: 10 or a replacement of an amino acid sequence of SEQ ID NO: 10 with an amino acid sequence selected from G, SG, GGS, and SEQ ID NOs: 7 to 9; and (ii) an amino acid substitution of R38N.

In certain embodiments, the interleukin-2 polypeptide provided herein comprises (i) a deletion of an amino acid sequence of SEQ ID NO: 10 and (ii) an amino acid substitution of R38N. In certain embodiments, the interleukin-2 polypeptide provided herein comprises a replacement of an amino acid sequence of SEQ ID NO: 10 with an amino acid sequence of G and (ii) an amino acid substitution of R38N. In certain embodiments, the interleukin-2 polypeptide provided herein comprises (i) a replacement of an amino acid sequence of SEQ ID NO: 10 with an amino acid sequence of SG and (ii) an amino acid substitution of R38N. In certain embodiments, the interleukin-2 polypeptide provided herein comprises (i) a replacement of an amino acid sequence of SEQ ID NO: 10 with an amino acid sequence of GGS and (ii) an amino acid substitution of R38N. In certain embodiments, the interleukin-2 polypeptide provided herein comprises (i) a replacement of an amino acid sequence of SEQ ID NO: 10 with an amino acid sequence of SEQ ID NO: 7 and (ii) an amino acid substitution of R38N. In certain embodiments, the interleukin-2 polypeptide provided herein comprises (i) a replacement of an amino acid sequence of SEQ ID NO: 10 with an amino acid sequence of SEQ ID NO: 8 and (ii) an amino acid substitution of R38N. In certain embodiments, the interleukin-2 polypeptide provided herein comprises (i) a replacement of an amino acid sequence of SEQ ID NO: 10 with an amino acid sequence of SEQ ID NO: 9 and (ii) an amino acid substitution of R38N.

In another embodiment, provided herein is an interleukin-2 polypeptide comprising an amino acid sequence of SEQ ID NO: 1, 2, 3, 4, or 5, wherein the interleukin-2 polypeptide comprises (i) a deletion of an amino acid sequence of SEQ ID NO: 10 or a replacement of an amino acid sequence of SEQ ID NO: 10 with an amino acid sequence selected from G, SG, GGS, and SEQ ID NOs: 7 to 9; and (ii) amino acid substitutions of R38N and L40T.

In certain embodiments, the interleukin-2 polypeptide provided herein comprises (i) a deletion of an amino acid sequence of SEQ ID NO: 10 and (ii) amino acid substitutions of R38N and L40T. In certain embodiments, the interleukin-2 polypeptide provided herein comprises a replacement of an amino acid sequence of SEQ ID NO: 10 with an amino acid sequence of G and (ii) amino acid substitutions of R38N and L40T. In certain embodiments, the interleukin-2 polypeptide provided herein comprises (i) a replacement of an amino acid sequence of SEQ ID NO: 10 with an amino acid sequence of SG and (ii) amino acid substitutions of R38N and L40T. In certain embodiments, the interleukin-2 polypeptide provided herein comprises (i) a replacement of an amino acid sequence of SEQ ID NO: 10 with an amino acid sequence of GGS and (ii) amino acid substitutions of R38N and L40T. In certain embodiments, the interleukin-2 polypeptide provided herein comprises (i) a replacement of an amino acid sequence of SEQ ID NO: 10 with an amino acid sequence of SEQ ID NO: 7 and (ii) amino acid substitutions of R38N and L40T. In certain embodiments, the interleukin-2 polypeptide provided herein comprises (i) a replacement of an amino acid sequence of SEQ ID NO: 10 with an amino acid sequence of SEQ ID NO: 8 and (ii) amino acid substitutions of R38N and L40T. In certain embodiments, the interleukin-2 polypeptide provided herein comprises (i) a replacement of an amino acid sequence of SEQ ID NO: 10 with an amino acid sequence of SEQ ID NO: 9 and (ii) amino acid substitutions of R38N and L40T.

In one embodiment, the interleukin-2 polypeptide provided herein is an N-glycosylated polypeptide comprising an amino acid sequence selected from SEQ ID NOs: 14 to 20, 24 to 28, 30, 32 to 34, 98 to 104, 108 to 112, 114, 116 to 136, 189 to 194, and 204 to 209. In another embodiment, the interleukin-2 polypeptide provided herein is an N-glycosylated polypeptide comprising an amino acid sequence selected from SEQ ID NOs: 14 to 20, 24 to 28, 30, 32 to 34, 119 to 127, and 189 to 194. In yet another embodiment, the interleukin-2 polypeptide provided herein is an N-glycosylated polypeptide comprising an amino acid sequence selected from 98 to 104, 118 to 112, 114, 116 to 118, 128 to 136, and 204 to 209.

In one embodiment, the interleukin-2 polypeptide provided herein is an N-glycosylated polypeptide comprising an amino acid sequence selected from SEQ ID NOs: 14 to 20, 24 to 28, 30, 32 to 34, 98 to 104, 108 to 112, 114, 116 to 136, 189 to 194, and 204 to 209. In another embodiment, the interleukin-2 polypeptide provided herein is an N-glycosylated polypeptide comprising an amino acid sequence selected from SEQ ID NOs: 14 to 20, 24 to 28, 30, 32 to 34, 119 to 127, and 189 to 194. In yet another embodiment, the interleukin-2 polypeptide provided herein is an N-glycosylated polypeptide comprising an amino acid sequence selected from 98 to 104, 118 to 112, 114, 116 to 118, 128 to 136, and 204 to 209.

In one embodiment, the interleukin-2 polypeptide provided herein is an N-glycosylated polypeptide comprising an amino acid sequence selected from SEQ ID NOs: 14 to 20, 24 to 28, 30, 32 to 34, 98 to 104, 108 to 112, 114, and 116 to 136. In another embodiment, the interleukin-2 polypeptide provided herein is an N-glycosylated polypeptide comprising an amino acid sequence selected from SEQ ID NOs: 14 to 20, 24 to 28, 30, 32 to 34, and 119 to 127. In yet another embodiment, the interleukin-2 polypeptide provided herein is an N-glycosylated polypeptide comprising an amino acid sequence selected from 98 to 104, 118 to 112, 114, 116 to 118, and 128 to 136.

In one embodiment, the interleukin-2 polypeptide provided herein is an N-glycosylated polypeptide having an amino acid sequence selected from SEQ ID NOs: 14 to 20, 24 to 28, 30, 32 to 34, 98 to 104, 108 to 112, 114, and 116 to 136. In another embodiment, the interleukin-2 polypeptide provided herein is an N-glycosylated polypeptide having an amino acid sequence selected from SEQ ID NOs: 14 to 20, 24 to 28, 30, 32 to 34, and 119 to 127. In yet another embodiment, the interleukin-2 polypeptide provided herein is an N-glycosylated polypeptide having an amino acid sequence selected from 98 to 104, 118 to 112, 114, 116 to 118, and 128 to 136.

In certain embodiments, the interleukin-2 polypeptide provided herein has a reduced binding affinity to an IL-2Rα as compared to a wild-type interleukin-2 described herein. In certain embodiment, the binding affinity of the interleukin-2 polypeptide provided herein to an IL-2Rα is measured by its $K_a$, which is the inverse of its $K_d$.

In certain embodiments, the interleukin-2 polypeptide provided herein has a $K_d$ to the IL-2Rα of no less than about 2 times, no less than about 5 times, no less than about 10 times, no less than about 100 times, or no less than about 1,000 times higher than that of the wild-type interleukin-2 to the IL-2Rα. In one embodiment, the interleukin-2 polypeptide provided herein has a $K_d$ to the IL-2Rα of no less than about 2 times higher than that of the wild-type interleukin-2 to the IL-2Rα. In another embodiment, the interleukin-2 polypeptide provided herein has a $K_d$ to the IL-2Rα of no less than about 5 times higher than that of the wild-type interleukin-2 to the IL-2Rα. In yet another embodiment, the interleukin-2 polypeptide provided herein has a $K_d$ to the IL-2Rα of no less than about 10 times higher than that of the wild-type interleukin-2 to the IL-2Rα. In yet another embodiment, the interleukin-2 polypeptide provided herein has a $K_d$ to the IL-2Rα of no less than about 100 times higher than that of the wild-type interleukin-2 to the IL-2Rα. In still another embodiment, the interleukin-2 polypeptide provided herein has a $K_d$ to the IL-2Rα of no less than about 1,000 times higher than that of the wild-type interleukin-2 to the IL-2Rα.

In another embodiment, the interleukin-2 polypeptide provided herein has a $K_d$ to an IL-2Rα of no less than about 20 nM, no less than about 50 nM, no less than about 100 nM, no less than about 1 μM, no less than about 10 μM, no less than about 100 μM, or no less than about 1 mM. In certain embodiments, the interleukin-2 polypeptide provided herein has a $K_d$ to the IL-2Rα of no less than about 20 nM. In certain embodiments, the interleukin-2 polypeptide provided herein has a $K_d$ to the IL-2Rα of no less than about 50 nM. In certain embodiments, the interleukin-2 polypeptide provided herein has a $K_d$ to the IL-2Rα of no less than about 100 nM. In certain embodiments, the interleukin-2 polypeptide provided herein has a $K_d$ to the IL-2Rα of no less than about 1 μM. In certain embodiments, the interleukin-2 polypeptide provided herein has a $K_d$ to the IL-2Rα of no less than about 10 μM. In certain embodiments, the interleukin-2 polypeptide provided herein has a $K_d$ to the IL-2Rα of no less than about 100 μM. In certain embodiments, the interleukin-2 polypeptide provided herein has a $K_d$ to the IL-2Rα of no less than about 1 mM. In certain embodiments, the interleukin-2 polypeptide provided herein has no measurable binding to the IL-2Rα. In certain embodiments, the interleukin-2 polypeptide provided herein has no detectable binding to the IL-2Rα as measured with a surface plasmon resonance (SPR) method. In certain embodiments, the interleukin-2 polypeptide provided herein has no detectable binding to the IL-2Rα as measured with bio-layer interferometry (BLI).

In yet another embodiment, the interleukin-2 polypeptide provided herein has a selectivity for an IL-2Rβ over an IL-2Rα; wherein the selectivity is no greater than about 1, no greater than about 0.5, no greater than about 0.2, no greater than about 0.1, no greater than about 0.01, or no greater than about 0.001; and wherein the selectivity is measured as a ratio of a $K_d$ of the interleukin-2 polypeptide to the IL-2Rβ over a $K_d$ of the interleukin-2 polypeptide to the IL-2Rα. In certain embodiments, the interleukin-2 polypeptide provided herein has a selectivity of no greater than about 1. In certain embodiments, the interleukin-2 polypeptide provided herein has a selectivity of no greater than about 0.5. In certain embodiments, the interleukin-2 polypeptide provided herein has a selectivity of no greater than about 0.2.

In certain embodiments, the interleukin-2 polypeptide provided herein has a selectivity of no greater than about 0.1. In certain embodiments, the interleukin-2 polypeptide provided herein has a selectivity of no greater than about 0.01. In certain embodiments, the interleukin-2 polypeptide provided herein has a selectivity of no greater than about 0.001.

In yet another embodiment, the interleukin-2 polypeptide provided herein has a selectivity for an IL-2Rβ/γ complex over an IL-2Rα; wherein the selectivity is no greater than about 0.01 or no greater than about 0.001; and wherein the selectivity is measured as a ratio of a $K_d$ of the interleukin-2 polypeptide to the IL-2Rβ/γ complex over a $K_d$ of the interleukin-2 polypeptide to the IL-2Rα. In certain embodiments, the interleukin-2 polypeptide provided herein has a selectivity of no greater than about 0.01. In certain embodiments, the interleukin-2 polypeptide provided herein has a selectivity of no greater than about 0.001. In one embodiment, the dissociation constants of an IL-2 to the IL-2Rα and the IL-2Rβ/γ complex are determined as described in Richert et al., *J. Mol. Biol.* 2004, 339, 1115-1119.

In one embodiment, the IL-2Rα is a human IL-2Rα. In another embodiment, the human IL-2Rα has an amino acid sequence of SEQ ID NO: 35.

In one embodiment, the IL-2Rβ is a human IL-2Rβ. In another embodiment, the human IL-2Rβ has an amino acid sequence of SEQ ID NO: 36.

In one embodiment, the IL-2Rγ is a human IL-2Rγ. In another embodiment, the human IL-2Rγ has an amino acid sequence of SEQ ID NO: 37.

In one embodiment, a $K_d$ of an IL-2 to an IL-2Rα is determined with a surface plasmon resonance (SPR) method. In another embodiment, a $K_d$ of an IL-2 to an IL-2Rα is determined with a BIACORE® assay. In yet another embodiment, a $K_d$ of an IL-2 to an IL-2Rα is determined with bio-layer interferometry (BLI). In still another embodiment, a $K_d$ of an IL-2 to an IL-2Rα is determined with an OCTET® assay.

In one embodiment, a $K_d$ of an IL-2 to an IL-2Rβ is determined with an SPR method. In another embodiment, a $K_d$ of an IL-2 to an IL-2Rβ is determined with a BIACORE® assay. In yet another embodiment, a $K_d$ of an IL-2 to an IL-2Rβ is determined with BLI. In still another embodiment, a $K_d$ of an IL-2 to an IL-2Rβ is determined with an OCTET® assay.

In one embodiment, a $K_d$ of an IL-2 to an IL-2Rβ/γ complex is determined with an SPR method. In another embodiment, a $K_d$ of an IL-2 to an IL-2Rβ/γ complex is determined with a BIACORE® assay. In yet another embodiment, a $K_d$ of an IL-2 to an IL-2Rβ/γ complex is determined with BLI. In still another embodiment, a $K_d$ of an IL-2 to an IL-2Rβ/γ complex is determined with an OCTET® assay.

In one embodiment, a $K_d$ of an IL-2 to an IL-2Rα/β/γ complex is determined with an SPR method. In another embodiment, a $K_d$ of an IL-2 to an IL-2Rα/β/γ complex is determined with a BIACORE® assay. In yet another embodiment, a $K_d$ of an IL-2 to an IL-2Rα/β/γ complex is determined with BLI. In still another embodiment, a $K_d$ of an IL-2 to an IL-2Rα/β/γ complex is determined with an OCTET® assay.

In certain embodiments, the interleukin-2 polypeptide provided herein comprises an amino acid sequence that is no less than about 80%, no less than about 85%, no less than about 90%, no less than about 91%, no less than about 92%, no less than about 93%, no less than about 94%, no less than about 95%, no less than about 96%, no less than about 97%, no less than about 98%, or no less than about 99% identical to the amino acid sequence of SEQ ID NO: 1, 2, 3, 4, or 5.

In certain embodiments, the interleukin-2 polypeptide provided herein is no less than about 80% identical to the amino acid sequence of SEQ ID NO: 1, 2, 3, 4, or 5. In certain embodiments, the interleukin-2 polypeptide provided herein comprises an amino acid sequence that is no less than about 85% identical to the amino acid sequence of SEQ ID NO: 1, 2, 3, 4, or 5. In certain embodiments, the interleukin-2 polypeptide provided herein comprises an amino acid sequence that is no less than about 90% identical to the amino acid sequence of SEQ ID NO: 1, 2, 3, 4, or 5. In certain embodiments, the interleukin-2 polypeptide provided herein comprises an amino acid sequence that is no less than about 91% identical to the amino acid sequence of SEQ ID NO: 1, 2, 3, 4, or 5. In certain embodiments, the interleukin-2 polypeptide provided herein comprises an amino acid sequence that is no less than about 92% identical to the amino acid sequence of SEQ ID NO: 1, 2, 3, 4, or 5. In certain embodiments, the interleukin-2 polypeptide provided herein comprises an amino acid sequence that is no less than about 93% identical to the amino acid sequence of SEQ ID NO: 1, 2, 3, 4, or 5. In certain embodiments, the interleukin-2 polypeptide provided herein comprises an amino acid sequence that is no less than about 94% identical to the amino acid sequence of SEQ ID NO: 1, 2, 3, 4, or 5. In certain embodiments, the interleukin-2 polypeptide provided herein comprises an amino acid sequence that is no less than about 95% identical to the amino acid sequence of SEQ ID NO: 1, 2, 3, 4, or 5. In certain embodiments, the interleukin-2 polypeptide provided herein comprises an amino acid sequence that is no less than about 96% identical to the amino acid sequence of SEQ ID NO: 1, 2, 3, 4, or 5. In certain embodiments, the interleukin-2 polypeptide provided herein comprises an amino acid sequence that is no less than about 97% identical to the amino acid sequence of SEQ ID NO: 1, 2, 3, 4, or 5. In certain embodiments, the interleukin-2 polypeptide provided herein comprises an amino acid sequence that is no less than about 98% identical to the amino acid sequence of SEQ ID NO: 1, 2, 3, 4, or 5. In certain embodiments, the interleukin-2 polypeptide provided herein comprises an amino acid sequence that is no less than about 99% identical to the amino acid sequence of SEQ ID NO: 1, 2, 3, 4, or 5.

In certain embodiments, the interleukin-2 polypeptide provided herein is no less than about 80%, no less than about 85%, no less than about 90%, no less than about 91%, no less than about 92%, no less than about 93%, no less than about 94%, no less than about 95%, no less than about 96%, no less than about 97%, no less than about 98%, or no less than about 99% identical to the amino acid sequence of SEQ ID NO: 1, 2, 3, 4, or 5.

In certain embodiments, the interleukin-2 polypeptide provided herein is no less than about 80% identical to the amino acid sequence of SEQ ID NO: 1, 2, 3, 4, or 5. In certain embodiments, the interleukin-2 polypeptide provided herein is no less than about 85% identical to the amino acid sequence of SEQ ID NO: 1, 2, 3, 4, or 5. In certain embodiments, the interleukin-2 polypeptide provided herein is no less than about 90% identical to the amino acid sequence of SEQ ID NO: 1, 2, 3, 4, or 5. In certain embodiments, the interleukin-2 polypeptide provided herein is no less than about 91% identical to the amino acid sequence of SEQ ID NO: 1, 2, 3, 4, or 5. In certain embodiments, the interleukin-2 polypeptide provided herein is no less than about 92% identical to the amino acid sequence of SEQ ID NO: 1, 2, 3, 4, or 5. In certain embodiments, the interleukin-2 polypeptide provided herein is no less than about 93% identical to the amino acid sequence of SEQ ID NO: 1, 2, 3, 4, or 5. In certain embodiments, the interleukin-2 polypeptide provided herein is no less than about 94% identical to the amino acid sequence of SEQ ID NO: 1, 2, 3, 4, or 5. In certain embodiments, the interleukin-2 polypeptide provided herein is no less than about 95% identical to the amino acid sequence of SEQ ID NO: 1, 2, 3, 4, or 5. In certain embodiments, the interleukin-2 polypeptide provided herein is no less than about 96% identical to the amino acid sequence of SEQ ID NO: 1, 2, 3, 4, or 5. In certain embodiments, the interleukin-2 polypeptide provided herein is no less than about 97% identical to the amino acid sequence of SEQ ID NO: 1, 2, 3, 4, or 5. In certain embodiments, the interleukin-2 polypeptide provided herein is no less than about 98% identical to the amino acid sequence of SEQ ID NO: 1, 2, 3, 4, or 5. In certain embodiments, the interleukin-2 polypeptide provided herein is no less than about 99% identical to the amino acid sequence of SEQ ID NO: 1, 2, 3, 4, or 5.

In one embodiment, the interleukin-2 polypeptide provided herein is an isolated interleukin-2 polypeptide. In another embodiment, the interleukin-2 polypeptide provided herein is a recombinant interleukin-2 polypeptide.

In one embodiment, the interleukin-2 polypeptide provided herein is N-glycosylated. In another embodiment, the interleukin-2 polypeptide provided herein is N-glycosylated at a glycosylation site.

In one embodiment, the interleukin-2 polypeptide provided herein has one glycan. In another embodiment, the interleukin-2 polypeptide provided herein has one glycan attached to the nitrogen in the side chain of an asparagine residue.

In one embodiment, the interleukin-2 polypeptide provided herein has two glycans. In another embodiment, the interleukin-2 polypeptide provided herein has two glycans, of which at least one glycan is attached to the nitrogen in the side chain of an asparagine residue. In yet another embodiment, the interleukin-2 polypeptide provided herein has two glycans, each of which is attached to the nitrogen in the side chain of an asparagine residue.

In one embodiment, the interleukin-2 polypeptide provided herein has three glycans. In one embodiment, the glycan is an N-glycan.

In one embodiment, the N-glycan on the interleukin-2 polypeptide provided herein is oligomannose-type. In another embodiment, the N-glycan on the interleukin-2 polypeptide provided herein is complex-type. In another embodiment, the N-glycan on the interleukin-2 polypeptide provided herein is hybrid-type.

In one embodiment, the N-glycan on the interleukin-2 polypeptide provided herein is biantennary complex-type. In another embodiment, the N-glycan on the interleukin-2 polypeptide provided herein is triantennary complex-type. In yet another embodiment, the N-glycan on the interleukin-2 polypeptide provided herein is tetraantennary complex-type.

In one embodiment, the N-glycan on the interleukin-2 polypeptide provided herein is one of the glycans described in FIG. 1. Szabo et al., *J. Proteome. Res.* 2018, 17, 1559-1574, the disclosure of which is incorporated herein by reference in its entirety.

In one embodiment, the interleukin-2 polypeptide provided herein is produced from a yeast cell, insect cell, mammalian cell, a human cell, or a plant cell. In another embodiment, the interleukin-2 polypeptide provided herein is produced from a yeast cell. In yet another embodiment, the interleukin-2 polypeptide provided herein is produced from an insect cell. In yet another embodiment, the interleukin-2 polypeptide provided herein is produced from a mammalian cell. In yet another embodiment, the interleukin-2 polypeptide provided herein is produced from a CHO cell. In yet another embodiment, the interleukin-2 polypeptide provided herein is produced from a human cell. In still another embodiment, the interleukin-2 polypeptide provided herein is produced from a plant cell.

In certain embodiments, the interleukin-2 polypeptide provided herein further includes one or more additional substitutions, deletions, and/or insertions.

In certain embodiments, the interleukin-2 polypeptide provided herein comprises an amino acid substitution, deletion, and/or insertion that results in an enhanced stability and/or production yield. In certain embodiments, the interleukin-2 polypeptide provided herein comprises an amino acid substitution, deletion, and/or insertion that results in a reduced binding affinity to an IL-2Rα. In certain embodiments, the interleukin-2 polypeptide provided herein comprises an amino acid substitution, deletion, and/or insertion that results in a reduced binding affinity to an IL-2Rβ. In certain embodiments, the interleukin-2 polypeptide provided herein comprises an amino acid substitution, deletion, and/or insertion that results in an enhanced binding affinity to an IL-2Rβ. In certain embodiments, the interleukin-2 polypeptide provided herein comprises an amino acid substitution, deletion, and/or insertion that results in a reduced binding affinity to an IL-2Rγ. In certain embodiments, the interleukin-2 polypeptide provided herein comprises an amino acid substitution, deletion, and/or insertion that results in a reduced binding affinity to an IL-2Rβ/γ complex.

In certain embodiments, the interleukin-2 polypeptide provided herein comprises an amino acid substitution, deletion, and/or insertion that results in (i) an enhanced stability and/or production yield and (ii) a reduced binding affinity to an IL-2Rα. In certain embodiments, the interleukin-2 polypeptide provided herein comprises an amino acid substitution, deletion, and/or insertion that results in (i) an enhanced stability and/or production yield and (ii) a reduced binding affinity to an IL-2Rβ. In certain embodiments, the interleukin-2 polypeptide provided herein comprises an amino acid substitution, deletion, and/or insertion that results in (i) an enhanced stability and/or production yield and (ii) an enhanced binding affinity to an IL-2Rβ. In certain embodiments, the interleukin-2 polypeptide provided herein comprises an amino acid substitution, deletion, and/or insertion that results in (i) an enhanced stability and/or production yield and (ii) a reduced binding affinity to an IL-2Rγ. In certain embodiments, the interleukin-2 polypeptide provided herein comprises an amino acid substitution, deletion, and/or insertion that results in (i) an enhanced stability and/or production yield and (ii) a reduced binding affinity to an IL-2Rβ/γ complex.

In certain embodiments, the interleukin-2 polypeptide provided herein comprises an amino acid substitution, deletion, and/or insertion that results in (i) a reduced binding affinity to an IL-2Rα and (ii) a reduced binding affinity to an IL-2Rβ. In certain embodiments, the interleukin-2 polypeptide provided herein comprises an amino acid substitution, deletion, and/or insertion that results in (i) a reduced binding affinity to an IL-2Rα and (ii) an enhanced binding affinity to an IL-2Rβ. In certain embodiments, the interleukin-2 polypeptide provided herein comprises an amino acid substitution, deletion, and/or insertion that results in (i) a reduced binding affinity to an IL-2Rα and (ii) a reduced binding affinity to an IL-2Rγ. In certain embodiments, the interleukin-2 polypeptide provided herein comprises an amino acid substitution, deletion, and/or insertion that results in (i) a reduced binding affinity to an IL-2Rα and (ii) a reduced binding affinity to an IL-2Rβ/γ complex.

In certain embodiments, the interleukin-2 polypeptide provided herein comprises an amino acid substitution, deletion, and/or insertion that results in (i) an enhanced stability and/or production yield, (ii) a reduced binding affinity to an IL-2Rα, and (iii) a reduced binding affinity to an IL-2Rβ. In certain embodiments, the interleukin-2 polypeptide provided herein comprises an amino acid substitution, deletion, and/or insertion that results in (i) an enhanced stability and/or production yield, (ii) a reduced binding affinity to an IL-2Rα, and (iii) an enhanced binding affinity to an IL-2Rβ. In certain embodiments, the interleukin-2 polypeptide provided herein comprises an amino acid substitution, deletion, and/or insertion that results in (i) an enhanced stability and/or production yield, (ii) a reduced binding affinity to an IL-2Rα, and (iii) a reduced binding affinity to an IL-2Rγ In certain embodiments, the interleukin-2 polypeptide provided herein comprises an amino acid substitution, deletion, and/or insertion that results in (i) an enhanced stability and/or production yield, (ii) a reduced binding affinity to an IL-2Rα, and (iii) a reduced binding affinity to an IL-2Rβ/γ complex.

Interleukin-2 Polypeptide Fusion Proteins

In one embodiment, provided herein is a fusion protein comprising an interleukin-2 polypeptide domain and a half-life-extension domain.

In certain embodiments, the interleukin-2 polypeptide domain comprises an amino acid sequence of an interleukin-2 polypeptide provided herein. In certain embodiments, the amino acid sequence of the interleukin-2 polypeptide domain is an amino acid sequence of an interleukin-2 polypeptide provided herein.

In certain embodiments, the half-life-extension domain extends the half-life of the interleukin-2 polypeptide domain in vivo as compared to the corresponding interleukin-2 polypeptide alone.

In one embodiment, the half-life-extension domain comprises an albumin binding domain, a fragment crystallizable (Fc) domain, a serum albumin, a polyethylene glycol (PEG) group, or a fatty acyl group. In another embodiment, the half-life-extension domain is an albumin binding domain. In yet another embodiment, the half-life-extension domain is an Fc domain. In yet another embodiment, the half-life-extension domain is an Fc domain having a first and second peptide chains. In yet another embodiment, the half-life-extension domain is a serum albumin. In yet another embodiment, the half-life-extension domain comprises a PEG group. In still another embodiment, the half-life-extension domain comprises a fatty acyl group.

In another embodiment, provided herein is a fusion protein comprising an interleukin-2 polypeptide domain and an albumin binding domain.

In one embodiment, the fusion protein provided herein comprises an interleukin-2 polypeptide domain, an albumin binding domain, and optionally a peptide linker; wherein the carboxyl terminus (C-terminus) of the interleukin-2 polypeptide domain is connected to the amino terminus (N-terminus) of the albumin binding domain directly or via the peptide linker; or the N-terminus of the interleukin-2 polypeptide domain is connected to the C-terminus of the albumin binding domain directly or via the peptide linker.

In one embodiment, the fusion protein provided herein comprises one interleukin-2 polypeptide domain and one albumin binding domain; wherein the C-terminus of the interleukin-2 polypeptide domain is connected directly to the N-terminus of the albumin binding domain; or the N-terminus of the interleukin-2 polypeptide domain is connected directly to the C-terminus of the albumin binding domain.

In another embodiment, the fusion protein provided herein comprises one interleukin-2 polypeptide domain, one albumin binding domain, and one peptide linker; wherein the C-terminus of the interleukin-2 polypeptide domain is connected to the N-terminus of the albumin binding domain via the peptide linker; or the N-terminus of the interleukin-2 polypeptide domain is connected to the C-terminus of the albumin binding domain via the peptide linker.

In another embodiment, the fusion protein provided herein comprises first and second interleukin-2 polypeptide domains, one albumin binding domain, and optionally first and second peptide linkers; wherein the C-terminus of the first interleukin-2 polypeptide domain is connected to the N-terminus of the albumin binding domain directly or via the first peptide linker; and the C-terminus of the albumin binding domain is connected to the N-terminus of the second interleukin-2 polypeptide domain directly or via the second peptide linker.

In one embodiment, the fusion protein provided herein comprises first and second interleukin-2 polypeptide domains, and one albumin binding domain; wherein the C-terminus of the first interleukin-2 polypeptide domain is connected directly to the N-terminus of the albumin binding domain; and the C-terminus of the albumin binding domain is connected directly to the N-terminus of the second interleukin-2 polypeptide domain.

In another embodiment, the fusion protein provided herein comprises first and second interleukin-2 polypeptide domains, one albumin binding domain, and first and second peptide linkers; wherein the C-terminus of the first interleukin-2 polypeptide domain is connected to the N-terminus of the albumin binding domain via the first peptide linker; and the C-terminus of the albumin binding domain is connected to the N-terminus of the second interleukin-2 polypeptide domain via the second peptide linker.

In yet another embodiment, the fusion protein provided herein comprises first and second interleukin-2 polypeptide domains, one albumin binding domain, and one peptide linker; wherein the C-terminus of the first interleukin-2 polypeptide domain is connected directly to the N-terminus of the albumin binding domain directly; and the C-terminus of the albumin binding domain is connected to the N-terminus of the second interleukin-2 polypeptide domain via the peptide linker.

In still another embodiment, the fusion protein provided herein comprises first and second interleukin-2 polypeptide domains, one albumin binding domain, and one peptide linker; wherein the C-terminus of the first interleukin-2 polypeptide domain is connected to the N-terminus of the albumin binding domain via the peptide linker; and the C-terminus of the albumin binding domain is connected directly to the N-terminus of the second interleukin-2 polypeptide domain directly.

In one embodiment, the albumin binding domain comprises an amino acid sequence of an antibody that binds to an albumin. In one embodiment, the antibody binds to a human serum albumin (HSA). In another embodiment, the antibody binds to an HSA specifically.

In certain embodiments, the antibody binds to an HSA with a $K_d$ ranging from about 10 pM to about 1,000 nM. In certain embodiments, the antibody binds to an HSA with a $K_d$ ranging from about 1 nM to about 500 nM. In certain embodiments, the antibody binds to an HSA with a $K_d$ ranging from about 1 nM to about 200 nM. In certain embodiments, the antibody binds to an HSA with a $K_d$ ranging from about 1 nM to about 100 nM.

In one embodiment, the antibody comprises (i) complementarity determining region 1 (CDR1) of SEQ ID NO: 38, complementarity determining region 2 (CDR2) of SEQ ID NO: 39, and complementarity determining region 3 (CDR3) of SEQ ID NO: 40; or (ii) CDR1 of SEQ ID NO: 46, CDR2 of SEQ ID NO: 47, and CDR3 of SEQ ID NO: 48. In one embodiment, the antibody comprises CDR1 of SEQ ID NO: 38, CDR2 of SEQ ID NO: 39, and CDR3 of SEQ ID NO: 40. In another embodiment, the antibody comprises CDR1 of SEQ ID NO: 46, CDR2 of SEQ ID NO: 47, and CDR3 of SEQ ID NO: 48. In yet another embodiment, the antibody has an amino acid sequence of SEQ ID NO: 45 or 52.

In certain embodiments, the antibody is a human antibody. In certain embodiments, the antibody is a humanized antibody.

In another embodiment, the antibody is a single domain antibody (sdAb) that binds to an albumin. In certain embodiments, the antibody is an sdAb that binds to an HSA.

In certain embodiments, the sdAb binds to an HSA with a $K_d$ ranging from about 10 pM to about 1,000 nM. In certain embodiments, the sdAb binds to an HSA with a $K_d$ ranging from about 1 nM to about 500 nM. In certain embodiments, the sdAb binds to an HSA with a $K_d$ ranging from about 1 nM to about 200 nM. In certain embodiments, the sdAb binds to an HSA with a $K_d$ ranging from about 1 nM to about 100 nM.

In one embodiment, the sdAb comprises (i) CDR1 of SEQ ID NO: 38, CDR2 of SEQ ID NO: 39, and CDR3 of SEQ ID NO: 40; or (ii) CDR1 of SEQ ID NO: 46, CDR2 of SEQ ID NO: 47, and CDR3 of SEQ ID NO: 48. In one embodiment, the sdAb comprises CDR1 of SEQ ID NO: 38, CDR2 of SEQ ID NO: 39, and CDR3 of SEQ ID NO: 40. In another embodiment, the sdAb comprises CDR1 of SEQ ID NO: 46, CDR2 of SEQ ID NO: 47, and CDR3 of SEQ ID NO: 48.

In one embodiment, the sdAb has the structure of FR1-CDR1-FR2-CDR2-FR3-CDR3-FR4, wherein:
CDR1, CDR2, and CDR3 are:
  (i) CDR1 of SEQ ID NO: 38, CDR2 of SEQ ID NO: 39, and CDR3 of SEQ ID NO: 40; or
  (ii) CDR1 of SEQ ID NO: 46, CDR2 of SEQ ID NO: 47, and CDR3 of SEQ ID NO: 48;
FR1 is an amino acid sequence of SEQ ID NO: 41 or 49;
FR2 is an amino acid sequence of SEQ ID NO: 42 or 50;
FR3 is an amino acid sequence of SEQ ID NO: 43; and
FR4 is an amino acid sequence of SEQ ID NO: 44 or 51.

In another embodiment, the sdAb has the structure of FR1-CDR1-FR2-CDR2-FR3-CDR3-FR4, wherein:
CDR1, CDR2, and CDR3 are:
  (i) CDR1 of SEQ ID NO: 38, CDR2 of SEQ ID NO: 39, and CDR3 of SEQ ID NO: 40; or
  (ii) CDR1 of SEQ ID NO: 46, CDR2 of SEQ ID NO: 47, and CDR3 of SEQ ID NO: 48;
FR1 is an amino acid sequence of SEQ ID NO: 41;
FR2 is an amino acid sequence of SEQ ID NO: 42;
FR3 is an amino acid sequence of SEQ ID NO: 43; and
FR4 is an amino acid sequence of SEQ ID NO: 44.

In yet another embodiment, the sdAb has the structure of FR1-CDR1-FR2-CDR2-FR3-CDR3-FR4, wherein:
CDR1, CDR2, and CDR3 are:
  (i) CDR1 of SEQ ID NO: 38, CDR2 of SEQ ID NO: 39, and CDR3 of SEQ ID NO: 40; or
  (ii) CDR1 of SEQ ID NO: 46, CDR2 of SEQ ID NO: 47, and CDR3 of SEQ ID NO: 48;
FR1 is an amino acid sequence of SEQ ID NO: 49;
FR2 is an amino acid sequence of SEQ ID NO: 50;
FR3 is an amino acid sequence of SEQ ID NO: 43; and
FR3 is an amino acid sequence of SEQ ID NO: 51.

In yet another embodiment, the sdAb has an amino acid sequence of SEQ ID NO: 45 or 52.

In certain embodiments, the sdAb is a human antibody. In certain embodiments, the sdAb is a humanized antibody.

In yet another embodiment, the antibody is a $V_HH$ single domain antibody that binds to an albumin. In certain embodiments, the antibody is $V_HH$ single domain antibody that binds to an HSA.

In certain embodiments, the $V_HH$ single domain antibody binds to an HSA with a $K_d$ ranging from about 10 pM to about 1,000 nM. In certain embodiments, the $V_HH$ single domain antibody binds to an HSA with a $K_d$ ranging from about 1 nM to about 500 nM. In certain embodiments, the $V_HH$ single domain antibody binds to an HSA with a $K_d$ ranging from about 1 nM to about 200 nM. In certain embodiments, the $V_HH$ single domain antibody binds to an HSA with a $K_d$ ranging from about 1 nM to about 100 nM.

In one embodiment, the $V_HH$ single domain antibody comprises (i) heavy chain CDR1 of SEQ ID NO: 38, heavy chain CDR2 of SEQ ID NO: 39, and heavy chain CDR3 of SEQ ID NO: 40; or (ii) heavy chain CDR1 of SEQ ID NO: 46, heavy chain CDR2 of SEQ ID NO: 47, and heavy chain CDR3 of SEQ ID NO: 48. In one embodiment, the $V_HH$ single domain antibody comprises heavy chain CDR1 of SEQ ID NO: 38, heavy chain CDR2 of SEQ ID NO: 39, and heavy chain CDR3 of SEQ ID NO: 40. In another embodiment, the $V_HH$ single domain antibody comprises heavy chain CDR1 of SEQ ID NO: 46, heavy chain CDR2 of SEQ ID NO: 47, and heavy chain CDR3 of SEQ ID NO: 48.

In one embodiment, the $V_HH$ single domain antibody has the structure of FR1-CDR1-FR2-CDR2-FR3-CDR3-FR4, wherein:
CDR1, CDR2, and CDR3 are:
  (i) CDR1 of SEQ ID NO: 38, CDR2 of SEQ ID NO: 39, and CDR3 of SEQ ID NO: 40; or
  (ii) CDR1 of SEQ ID NO: 46, CDR2 of SEQ ID NO: 47, and CDR3 of SEQ ID NO: 48;
FR1 is an amino acid sequence of SEQ ID NO: 41 or 49;
FR2 is an amino acid sequence of SEQ ID NO: 42 or 50;
FR3 is an amino acid sequence of SEQ ID NO: 43; and
FR4 is an amino acid sequence of SEQ ID NO: 44 or 51.

In another embodiment, the $V_HH$ single domain antibody has the structure of FR1-CDR1-FR2-CDR2-FR3-CDR3-FR4, wherein:
CDR1, CDR2, and CDR3 are:
  (i) CDR1 of SEQ ID NO: 38, CDR2 of SEQ ID NO: 39, and CDR3 of SEQ ID NO: 40; or
  (ii) CDR1 of SEQ ID NO: 46, CDR2 of SEQ ID NO: 47, and CDR3 of SEQ ID NO: 48;
FR1 is an amino acid sequence of SEQ ID NO: 41;
FR2 is an amino acid sequence of SEQ ID NO: 42;
FR3 is an amino acid sequence of SEQ ID NO: 43; and
FR4 is an amino acid sequence of SEQ ID NO: 44.

In yet another embodiment, the $V_HH$ single domain antibody has the structure of FR1-CDR1-FR2-CDR2-FR3-CDR3-FR4, wherein:
CDR1, CDR2, and CDR3 are:
  (i) CDR1 of SEQ ID NO: 38, CDR2 of SEQ ID NO: 39, and CDR3 of SEQ ID NO: 40; or
  (ii) CDR1 of SEQ ID NO: 46, CDR2 of SEQ ID NO: 47, and CDR3 of SEQ ID NO: 48;

FR1 is an amino acid sequence of SEQ ID NO: 49;
FR2 is an amino acid sequence of SEQ ID NO: 50;
FR3 is an amino acid sequence of SEQ ID NO: 43; and
FR4 is an amino acid sequence of SEQ ID NO: 51.

In yet another embodiment, the $V_HH$ single domain antibody has an amino acid sequence of SEQ ID NO: 45 or 52.

In certain embodiments, the $V_HH$ single domain antibody is a human antibody. In certain embodiments, the $V_HH$ single domain antibody is a humanized antibody.

In one embodiment, the peptide linker has an amino acid sequence of GSG or one of SEQ ID NOs: 61 to 92. In another embodiment, the peptide linker is a GSG linker having an amino acid sequence of GSG or SEQ ID NO: 61, 62, or 63. In yet another embodiment, the peptide linker is a G3S linker having an amino acid sequence of SEQ ID NO: 64, 65, 66, or 67. In yet another embodiment, the peptide linker is a G4S linker having an amino acid sequence of SEQ ID NO: 68, 69, 70, or 71. In yet another embodiment, the peptide linker is an SGSG linker having an amino acid sequence of SEQ ID NO: 72, 73, 74, or 75. In yet another embodiment, the peptide linker is an SG3S linker having an amino acid sequence of SEQ ID NO: 76, 77, 78, or 79. In yet another embodiment, the peptide linker is an SG4S linker having an amino acid sequence of SEQ ID NO: 80, 81, 82, or 83. In yet another embodiment, the peptide linker is an EAAAK linker having an amino acid sequence of SEQ ID NO: 84, 85, 86, or 87. In yet another embodiment, the peptide linker is a PAPAP linker having an amino acid sequence of SEQ ID NO: 88, 89, 90, or 91. In still another embodiment, the peptide linker is a linker having an amino acid sequence of SEQ ID NO: 92.

In one embodiment, the fusion protein provided herein comprises one interleukin-2 polypeptide domain having an amino acid sequence of any one of SEQ ID NOs: 11 to 34, 119 to 127, 137 to 147, 159 to 165, 172 to 176, and 189 to 203; one albumin binding domain comprising an amino acid sequence of a $V_HH$ single domain antibody having an amino acid sequence of SEQ ID NO: 45 or 52; and a peptide linker having an amino acid sequence of GSG or one of SEQ ID NOs: 61 to 92. In one embodiment, the C-terminus of the interleukin-2 polypeptide domain is connected to the albumin binding domain via the peptide linker.

In another embodiment, the fusion protein provided herein comprises one interleukin-2 polypeptide domain having an amino acid sequence of any one of SEQ ID NOs: 11 to 34 and 119 to 127; one albumin binding domain comprising an amino acid sequence of a $V_HH$ single domain antibody having an amino acid sequence of SEQ ID NO: 45 or 52; and a peptide linker having an amino acid sequence of GSG or one of SEQ ID NOs: 61 to 92. In one embodiment, the C-terminus of the interleukin-2 polypeptide domain is connected to the albumin binding domain via the peptide linker.

In another embodiment, the fusion protein provided herein comprises one interleukin-2 polypeptide domain having an amino acid sequence of any one of SEQ ID NOs: 137 to 147; one albumin binding domain comprising an amino acid sequence of a $V_HH$ single domain antibody having an amino acid sequence of SEQ ID NO: 45 or 52; and a peptide linker having an amino acid sequence of GSG or one of SEQ ID NOs: 61 to 92. In one embodiment, the C-terminus of the interleukin-2 polypeptide domain is connected to the albumin binding domain via the peptide linker.

In yet another embodiment, the fusion protein provided herein comprises one interleukin-2 polypeptide domain having an amino acid sequence of any one of SEQ ID NOs: 159 to 165 and 172 to 176; one albumin binding domain comprising an amino acid sequence of a $V_HH$ single domain antibody having an amino acid sequence of SEQ ID NO: 45 or 52; and a peptide linker having an amino acid sequence of GSG or one of SEQ ID NOs: 61 to 92. In one embodiment, the C-terminus of the interleukin-2 polypeptide domain is connected to the albumin binding domain via the peptide linker.

In yet another embodiment, the fusion protein provided herein comprises one interleukin-2 polypeptide domain having an amino acid sequence of any one of SEQ ID NOs: 189 to 203; one albumin binding domain comprising an amino acid sequence of a $V_HH$ single domain antibody having an amino acid sequence of SEQ ID NO: 45 or 52; and a peptide linker having an amino acid sequence of GSG or one of SEQ ID NOs: 61 to 92. In one embodiment, the C-terminus of the interleukin-2 polypeptide domain is connected to the albumin binding domain via the peptide linker.

In yet another embodiment, the fusion protein provided herein comprises one interleukin-2 polypeptide domain having an amino acid sequence of any one of SEQ ID NOs: 189 to 194; one albumin binding domain comprising an amino acid sequence of a $V_HH$ single domain antibody having an amino acid sequence of SEQ ID NO: 45 or 52; and a peptide linker having an amino acid sequence of GSG or one of SEQ ID NOs: 61 to 92. In one embodiment, the C-terminus of the interleukin-2 polypeptide domain is connected to the albumin binding domain via the peptide linker.

In still another embodiment, the fusion protein provided herein comprises one interleukin-2 polypeptide domain having an amino acid sequence of any one of SEQ ID NOs: 195 to 203; one albumin binding domain comprising an amino acid sequence of a $V_HH$ single domain antibody having an amino acid sequence of SEQ ID NO: 45 or 52; and a peptide linker having an amino acid sequence of GSG or one of SEQ ID NOs: 61 to 92. In one embodiment, the C-terminus of the interleukin-2 polypeptide domain is connected to the albumin binding domain via the peptide linker.

In one embodiment, the fusion protein provided herein comprises an amino acid selected from SEQ ID NOs: 95 to 118, 128 to 136, and 148 to 158, 177 to 188, and 204 to 218. In another embodiment, the amino acid sequence of the fusion protein provided herein is one selected from SEQ ID NOs: 95 to 118, 128 to 136, and 148 to 158, 177 to 188, and 204 to 218.

In another embodiment, the fusion protein provided herein comprises an amino acid selected from SEQ ID NOs: 95 to 118, 128 to 136, and 148 to 158. In another embodiment, the amino acid sequence of the fusion protein provided herein is one selected from SEQ ID NOs: 95 to 118, 128 to 136, and 148 to 158.

In yet another embodiment, the fusion protein provided herein comprises an amino acid selected from SEQ ID NOs: 177 to 188. In another embodiment, the amino acid sequence of the fusion protein provided herein is one selected from SEQ ID NOs: 177 to 188.

In still another embodiment, the fusion protein provided herein comprises an amino acid selected from SEQ ID NOs: 204 to 218. In another embodiment, the amino acid sequence of the fusion protein provided herein is one selected from SEQ ID NOs: 204 to 218.

In yet another embodiment, provided herein is a fusion protein comprising an interleukin-2 polypeptide domain and a fragment crystalizable (Fc) domain.

In one embodiment, the fusion protein provided herein comprises one interleukin-2 polypeptide domain, one Fc domain having first and second peptide chains, and optionally one peptide linker; wherein the C-terminus of the interleukin-2 polypeptide domain is connected to the N-terminus of the first peptide chain of the Fc domain directly or via the peptide linker; or the N-terminus of the interleukin-2 polypeptide domain is connected to the C-terminus of the first peptide chain of the Fc domain directly or via the peptide linker.

In one embodiment, the fusion protein provided herein comprises one interleukin-2 polypeptide domain and one Fc domain having first and second peptide chains; wherein the C-terminus of the interleukin-2 polypeptide domain is connected directly to the first peptide chain of the N-terminus of the Fc domain; or the N-terminus of the interleukin-2 polypeptide domain is connected directly to the first peptide chain of the C-terminus of the Fc domain.

In another embodiment, the fusion protein provided herein comprises one interleukin-2 polypeptide domain, one Fc domain having first and second peptide chains, and one peptide linker; wherein the C-terminus of the interleukin-2 polypeptide domain is connected to the N-terminus of the first peptide chain of the Fc domain via the peptide linker; or the N-terminus of the interleukin-2 polypeptide domain is connected to the C-terminus of the first peptide chain of the Fc domain via the peptide linker.

In another embodiment, the fusion protein provided herein comprises first and second interleukin-2 polypeptide domains, one Fc domain having first and second peptide chains, and optionally first and second peptide linkers; wherein the C-terminus of the first interleukin-2 polypeptide domain is connected to the N-terminus of the first peptide chain of the Fc domain directly or via the first peptide linker; and the N-terminus of the second interleukin-2 polypeptide domain is connected to the C-terminus of the second peptide chain of the Fc domain directly or via the second peptide linker.

In one embodiment, the fusion protein provided herein comprises first and second interleukin-2 polypeptide domains, and one Fc domain having first and second peptide chains; wherein the C-terminus of the first interleukin-2 polypeptide domain is connected directly to the N-terminus of the first peptide chain of the Fc domain; and the N-terminus of the second interleukin-2 polypeptide domain is connected directly to the C-terminus of the second peptide chain of the Fc domain.

In another embodiment, the fusion protein provided herein comprises first and second interleukin-2 polypeptide domains, one Fc domain having first and second peptide chains, and first and second peptide linkers; wherein the C-terminus of the first interleukin-2 polypeptide domain is connected to the N-terminus of the first peptide chain of the Fc domain via the first peptide linker; and the N-terminus of the second interleukin-2 polypeptide domain is connected to the C-terminus of the second peptide chain of the Fc domain via the second peptide linker.

In yet another embodiment, the fusion protein provided herein comprises first and second interleukin-2 polypeptide domains, one Fc domain having first and second peptide chains, and one peptide linker; wherein the C-terminus of the first interleukin-2 polypeptide domain is connected directly to the N-terminus of the first peptide chain of the Fc domain; and the N-terminus of the second interleukin-2 polypeptide domain is connected to the C-terminus of the second peptide chain of the Fc domain via the peptide linker.

In still another embodiment, the fusion protein provided herein comprises first and second interleukin-2 polypeptide domains, one Fc domain having first and second peptide chains, and one peptide linker; wherein the C-terminus of the first interleukin-2 polypeptide domain is connected to the N-terminus of the first peptide chain of the Fc domain via the peptide linker; and the N-terminus of the second interleukin-2 polypeptide domain is connected directly to the C-terminus of the second peptide chain of the Fc domain.

In one embodiment, the Fc domain is a hIgG1 Fc domain or a mutein thereof, or a fragment thereof. In another embodiment, the Fc domain is a hIgG1 Fc chain 1 or a mutein thereof, or a fragment thereof. In yet another embodiment, the Fc domain is a hIgG1 Fc chain 2 or a mutein thereof, or a fragment thereof. In yet another embodiment, the Fc domain is a hIgG2 Fc domain or a mutein thereof, or a fragment thereof. In still another embodiment, the Fc domain is a hIgG4 Fc domain or a mutein thereof, or a fragment thereof.

In one embodiment, the Fc domain comprises the amino acid sequence of SEQ ID NO: 53, 54, 55, 56, 57, 58, 59, or 60. In yet another embodiment, the Fc domain comprises the amino acid sequence of SEQ ID NO: 53. In another embodiment, the Fc domain comprises the amino acid sequence of SEQ ID NO: 54. In yet another embodiment, the Fc domain comprises the amino acid sequence of SEQ ID NO: 55. In yet another embodiment, the Fc domain comprises the amino acid sequence of SEQ ID NO: 56. In yet another embodiment, the Fc domain comprises the amino acid sequence of SEQ ID NO: 57. In yet another embodiment, the Fc domain comprises the amino acid sequence of SEQ ID NO: 58. In yet another embodiment, the Fc domain comprises the amino acid sequence of SEQ ID NO: 59. In still another embodiment, the Fc domain comprises the amino acid sequence of SEQ ID NO: 60.

In one embodiment, the Fc domain comprises a pair of chains in a knobs-in-holes configuration. Thus, in one embodiment, the Fc domain comprises amino acid sequences of SEQ ID NO: 55 and 56 or 57 and 58 as a pair of chains in a knobs-in-holes configuration. In another embodiment, the Fc domain comprises amino acid sequences of SEQ ID NO: 55 and 56 as a pair of chains in a knobs-in-holes configuration. In yet another embodiment, the Fc domain comprises amino acid sequences of SEQ ID NO: 57 and 58 as a pair of chains in a knobs-in-holes configuration.

In one embodiment, the peptide linker has an amino acid sequence of GSG or one of SEQ ID NOs: 61 to 92. In another embodiment, the peptide linker is a GSG linker having an amino acid sequence of GSG or SEQ ID NO: 61, 62, or 63. In yet another embodiment, the peptide linker is a G3S linker having an amino acid sequence of SEQ ID NO: 64, 65, 66, or 67. In yet another embodiment, the peptide linker is a G4S linker having an amino acid sequence of SEQ ID NO: 68, 69, 70, or 71. In yet another embodiment, the peptide linker is an SGSG linker having an amino acid sequence of SEQ ID NO: 72, 73, 74, or 75. In yet another embodiment, the peptide linker is an SG3S linker having an amino acid sequence of SEQ ID NO: 76, 77, 78, or 79. In yet another embodiment, the peptide linker is an SG4S linker having an amino acid sequence of SEQ ID NO: 80, 81, 82, or 83. In yet another embodiment, the peptide linker is an EAAAK linker having an amino acid sequence of SEQ ID NO: 84, 85, 86, or 87. In yet another embodiment, the peptide linker is a PAPAP linker having an amino acid sequence of SEQ ID NO: 88, 89, 90, or 91. In still another embodiment, the peptide linker is a linker having an amino acid sequence of SEQ ID NO: 92.

In one embodiment, the fusion protein provided herein is an isolated fusion protein. In another embodiment, the fusion protein provided herein is a recombinant fusion protein.

In one embodiment, the fusion protein provided herein is glycosylated. In another embodiment, the fusion protein provided herein is N-glycosylated. In yet another embodiment, the fusion protein provided herein is N-glycosylated at a glycosylation site.

In one embodiment, the fusion protein provided herein has one glycan. In another embodiment, the fusion protein provided herein has one glycan attached to the nitrogen in the side chain of an asparagine residue.

In one embodiment, the fusion protein provided herein has two glycans. In another embodiment, the fusion protein provided herein has two glycans, of which at least one glycan is attached to the nitrogen in the side chain of an asparagine residue. In yet another embodiment, the fusion protein provided herein has two glycans, each of which is attached to the nitrogen in the side chain of an asparagine residue.

In one embodiment, the fusion protein provided herein has three glycans. In one embodiment, the glycan is an N-glycan.

In one embodiment, the N-glycan on the fusion protein provided herein is oligomannose-type. In another embodiment, the N-glycan on the fusion protein provided herein is complex-type. In another embodiment, the N-glycan on the fusion protein provided herein is hybrid-type.

In one embodiment, the N-glycan on the fusion protein provided herein is biantennary complex-type. In another embodiment, the N-glycan on the fusion protein provided herein is triantennary complex-type. In yet another embodiment, the N-glycan on the fusion protein provided herein is tetraantennary complex-type.

In one embodiment, the N-glycan on the fusion protein provided herein is one of the glycans described in FIG. 1. Szabo et al., *J. Proteome. Res.* 2018, 17, 1559-1574, the disclosure of which is incorporated herein by reference in its entirety.

In one embodiment, the fusion protein provided herein is produced from a yeast cell, insect cell, mammalian cell, a human cell, or a plant cell. In another embodiment, the fusion protein provided herein is produced from a yeast cell. In yet another embodiment, the fusion protein provided herein is produced from an insect cell. In yet another embodiment, the fusion protein provided herein is produced from a mammalian cell. In yet another embodiment, the fusion protein provided herein is produced from a CHO cell. In yet another embodiment, the fusion protein provided herein is produced from a human cell. In still another embodiment, the fusion protein provided herein is produced from a plant cell.

In certain embodiments, the fusion protein provided herein further includes one or more additional substitutions, deletions, and/or insertions.

Pharmaceutical Compositions

In one embodiment, provided herein is a pharmaceutical composition comprising an interleukin-2 polypeptide provided herein and a pharmaceutically acceptable excipient. In another embodiment, provided herein is a pharmaceutical composition comprising a fusion protein provided herein and a pharmaceutically acceptable excipient.

In one embodiment, the pharmaceutical composition is formulated as single dosage form.

In one embodiment, the pharmaceutical composition provided herein is a solid formulation. In another embodiment, the pharmaceutical composition provided herein is a lyophilized solid formulation. In yet another embodiment, the pharmaceutical composition provided herein is a solution. In still another embodiment, the pharmaceutical composition provided herein is an aqueous solution.

In one embodiment, the pharmaceutical composition provided herein is formulated in a dosage form for parenteral administration. In another embodiment, the pharmaceutical composition provided herein is formulated in a dosage form for intravenous administration. In yet another embodiment, the pharmaceutical composition provided herein is formulated in a dosage form for intramuscular administration. In yet another embodiment, the pharmaceutical composition provided herein is formulated in a dosage form for subcutaneous administration. In still another embodiment, the pharmaceutical composition provided herein is formulated in a dosage form for intratumoral administration.

In one embodiment, the pharmaceutical composition provided herein comprises an interleukin-2 polypeptide provided herein, mannitol, sodium dodecyl sulfate, monobasic sodium phosphate, dibasic sodium phosphate, and water. In another embodiment, the pharmaceutical composition provided herein comprises a fusion protein provided herein, mannitol, sodium dodecyl sulfate, monobasic sodium phosphate, dibasic sodium phosphate, and water.

In one embodiment, the pharmaceutical composition provided herein has a pH ranging from about 7.2 to about 7.8. In another embodiment, the pharmaceutical composition provided herein has a pH of about 7.5.

Methods of Use

In one embodiment, provided herein is a method for treating, preventing, or ameliorating a proliferative disease in a subject, comprising administering to the subject a therapeutically effective amount of an interleukin-2 polypeptide provided herein.

In another embodiment, provided herein is a method for treating, preventing, or ameliorating a proliferative disease in a subject, comprising administering to the subject a therapeutically effective amount of a fusion protein provided herein.

In one embodiment, the proliferative disease is cancer. In another embodiment, the proliferative disease is metastatic cancer. In yet another embodiment, the proliferative disease is renal cell carcinoma (RCC) or melanoma. In yet another embodiment, the proliferative disease is metastatic renal cell carcinoma (RCC) or metastatic melanoma.

In one embodiment, provided herein is a method of activating an immune effector cell, comprising contacting the cell with an effective amount of an interleukin-2 polypeptide provided herein.

In certain embodiments, the therapeutically effective amount of the interleukin-2 polypeptide is ranging from about 0.001 to 100 mg per kg subject body weight per day (mg/kg per day), from about 0.01 to about 75 mg/kg per day, from about 0.1 to about 50 mg/kg per day, from about 0.5 to about 25 mg/kg per day, or from about 1 to about 20 mg/kg per day, which can be administered in single or multiple doses. Within this range, the dosage can be ranging from about 0.005 to about 0.05, from about 0.05 to about 0.5, from about 0.5 to about 5.0, from about 1 to about 15, from about 1 to about 20, or from about 1 to about 50 mg/kg per day.

In certain embodiments, the therapeutically effective amount of the fusion protein is ranging from about 0.001 to 100 mg per kg subject body weight per day (mg/kg per day), from about 0.01 to about 75 mg/kg per day, from about 0.1 to about 50 mg/kg per day, from about 0.5 to about 25 mg/kg per day, or from about 1 to about 20 mg/kg per day, which can be administered in single or multiple doses. Within this range, the dosage can be ranging from about 0.005 to about 0.05, from about 0.05 to about 0.5, from about 0.5 to about 5.0, from about 1 to about 15, from about 1 to about 20, or from about 1 to about 50 mg/kg per day.

In certain embodiments, the subject is a mammal. In certain embodiments, the subject is a human.

The disclosure will be further understood by the following non-limiting examples.

EXAMPLES

Example 1

Cloning, Expression, and Purification of Anti-HSA-IL-2 Polypeptide Fusion Proteins The protein sequence of the human IL-2 was obtained from UniProt (P60568, 21-153 aa). The deoxyoligonucleotide sequence of the human IL-2 was codon optimized for CHO cell expression.

For a fusion protein comprising an anti-HSA and an interleukin-2 polypeptide, the C-terminus of the interleukin-2 polypeptide was fused to the N-terminus of the anti-HSA VHH antibody with a peptide linker. The deoxyoligonucleotide sequences encoding the anti-HSA $V_HH$ antibody, the interleukin-2 polypeptide, and the peptide linker were seamlessly assembled together by homology assembly cloning with a commercially available kit. The oligonucleotide of the fusion protein was inserted into UCOE® expression vector for CHO cell expression.

To determine the expression level of an interleukin-2 polypeptide as a part of an anti-HSA-IL-2 polypeptide fusion protein, a plasmid encoding the fusion protein was transiently transfected into EXPICHO™ cells. After 6 days of expression, EXPICHO™ cell culture (20 mL) was harvested for the fusion protein. The expression level of the fusion protein was determined by measuring either the total secreted fusion protein in 20 mL of EXPICHO™ culture medium using BLI (Octet) with a protein A biosensor or the total fusion protein from 20 mL of EXPICHO™ culture medium after purification using protein A affinity chromatography (e.g., AMSPHERE™ A3). The expression levels of different interleukin-2 polypeptides are summarized in Table 1 below, each expressed as a ratio of the expression level of the fusion protein over the expression level of wild type IL-2 fusion protein A1; where A represents a value no less than 6, B represents a value less than 6 but no less than 2, C represents a value less than 2 but no less than 1, and D represents a value less than 1.

TABLE 1

| Fusion Protein (SEQ ID NO) | IL-2 Polypeptide | Total Secreted Protein | Total Purified Protein |
|---|---|---|---|
| A1 (93) | hIL-2 mutein (C125S) (SEQ ID NO: 2) | 1 | 1 |
| A2 (94) | hIL-2 mutein (R38N, L40T, C125S) (SEQ ID NO: 6) | D | B |
| A3 (95) | hIL-2 mutein (H16E, C125S) (SEQ ID NO: 11) | B | B |
| A4 (96) | hIL-2 mutein (K32E, C125S) (SEQ ID NO: 12) | B | A |
| A5 (97) | hIL-2 mutein (K76E, C125S) (SEQ ID NO: 13) | B | B |
| A6 (98) | hIL-2 mutein (K8E, R38N, L40T, C125S) (SEQ ID NO: 14) | C | |
| A7 (99) | hIL-2 mutein (K9E, R38N, L40T, C125S) (SEQ ID NO: 15) | C | |
| A8 (100) | hIL-2 mutein (H16E, R38N, L40T, C125S) (SEQ ID NO: 16) | C | B |
| A9 (101) | hIL-2 mutein (K32E, R38N, L40T, C125S) (SEQ ID NO: 17) | C | B |
| A10 (102) | hIL-2 mutein (R38N, L40T, K76E, C125S) (SEQ ID NO: 18) | C | A |
| A11 (103) | hIL-2 mutein (R38N, L40T, H79E, C125S) (SEQ ID NO: 19) | C | B |
| A12 (104) | hIL-2 mutein (R38N, L40T, R81E, C125S) (SEQ ID NO: 20) | C | B |
| A13 (105) | hIL-2 mutein (H16E, K32E, C125S) (SEQ ID NO: 21) | B | |
| A14 (106) | hIL-2 mutein (H16E, K76E, C125S) (SEQ ID NO: 22) | B | |
| A15 (107) | hIL-2 mutein (K32E, K76E, C125S) (SEQ ID NO: 23) | B | |
| A16 (108) | hIL-2 mutein (H16E, R38N, L40T, K76E, C125S) (SEQ ID NO: 24) | B | |
| A17 (109) | hIL-2 mutein (K32E, R38N, L40T, K76E, C125S) (SEQ ID NO: 25) | B | |
| A18 (110) | hIL-2 mutein (N30_K35del, R38N, L40T, C125S) (SEQ ID NO: 26) | B | B |
| A19 (111) | hIL-2 mutein (N30_K35delinsG, R38N, L40T, C125S) (SEQ ID NO: 27) | B | A |
| A20 (112) | hIL-2 mutein (N30_K35delinsSG, R38N, L40T, C125S) (SEQ ID NO: 28) | B | A |
| A21 (113) | hIL-2 mutein (N30_K35delinsGGS, C125S) (SEQ ID NO: 29) | C | B |
| A22 (114) | hIL-2 mutein (N30_K35delinsGGS, R38N, L40T, C125S) (SEQ ID NO: 30) | B | A |

TABLE 1-continued

| Fusion Protein (SEQ ID NO) | IL-2 Polypeptide | Total Secreted Protein | Total Purified Protein |
|---|---|---|---|
| A23 (115) | hIL-2 mutein (N30_K35delinsGGSG, C125S) (SEQ ID NO: 31) | C | |
| A24 (116) | hIL-2 mutein (N30_K35delinsGGSG, R38N, L40T, C125S) (SEQ ID NO: 32) | C | A |
| A25 (117) | hIL-2 mutein (N30_K35delinsGGSGG, R38N, L40T, C125S) (SEQ ID NO: 33) | C | A |
| A26 (118) | hIL-2 mutein (N30_K35delinsGGGSGG, R38N, L40T, C125S) (SEQ ID NO: 34) | D | A |
| A36 (148) | IL2 mutein (K32E, R38A, C125S) (SEQ ID NO: 137) | B | A |
| A37 (149) | IL2 mutein (K32E, F42A, C125S) (SEQ ID NO: 138) | B | A |
| A38 (150) | IL2 mutein (K32E, R38A, F42A, C125S) (SEQ ID NO: 139) | B | A |
| A39 (151) | IL2 mutein (K32E, R38E, F42A, C125S) (SEQ ID NO: 140) | B | A |
| A40 (152) | IL2 mutein (K32E, R38G, F42A, C125S) (SEQ ID NO: 141) | C | A |
| A41 (153) | IL2 mutein (K32E, R38A, F42G, C125S) (SEQ ID NO: 142) | D | D |
| A42 (154) | IL2 mutein (K32E, R38E, F42G, C125S) (SEQ ID NO: 143) | C | A |
| A43 (155) | IL2 mutein (K32E, R38G, F42G, C125S) (SEQ ID NO: 144) | D | C |
| A44 (156) | IL2 mutein (K32E, R38A, F42K, C125S) (SEQ ID NO: 145) | B | A |
| A45 (157) | IL2 mutein (K32E, R38E, F42K, C125S) (SEQ ID NO: 146) | B | A |
| A46 (158) | IL2 mutein (K32E, R38G, F42K, C125S) (SEQ ID NO: 147) | B | A |
| A47 (177) | hIL-2 mutein (K32E, K35C, L72C, C125S) (SEQ ID NO: 159) | | A |
| A48 (178) | hIL-2 mutein (K32E, R38C, L72C, C125S) (SEQ ID NO: 160) | | B |
| A49 (179) | hIL-2 mutein (K32E, F42C, V69C, C125S) (SEQ ID NO: 161) | | A |
| A50 (180) | hIL-2 mutein (K32E, Y45C, E62C, C125S) (SEQ ID NO: 162) | | B |
| A51 (181) | hIL-2 mutein (K32E, F42C, L72C, C125S) (SEQ ID NO: 163) | | D |
| A54 (184) | IL-2-IL-15 chimera 1 (SEQ ID NO: 172) | | B |
| A55 (185) | IL-2-IL-15 chimera 2 (SEQ ID NO: 173) | | A |
| A56 (186) | IL-2-IL-15 chimera 3 (SEQ ID NO: 174) | | A |
| A57 (187) | IL-2-IL-15 chimera 4 (SEQ ID NO: 175) | | B |
| A58 (188) | IL-2-IL-15 chimera 5 (SEQ ID NO: 176) | | D |
| A59 (204) | hIL-2 mutein (T3A, Q8E, R38N, L40T, F42A, C125S) (SEQ ID NO: 189) | | C |
| A60 (205) | hIL-2 mutein (T3A, E15V, R38N, L40T, F42A, C125S) (SEQ ID NO: 190) | | D |
| A61 (206) | hIL-2 mutein (T3A, H16N, R38N, L40T, F42A, C125S) (SEQ ID NO: 191) | | B |
| A62 (207) | hIL-2 mutein (T3A, M23K, R38N, L40T, F42A, C125S) (SEQ ID NO: 192) | | C |
| A63 (208) | hIL-2 mutein (T3A, R38N, L40T, F42A, V91I, C125S) (SEQ ID NO: 193) | | C |
| A64 (209) | hIL-2 mutein (T3A, R38N, L40T, F42A, E95N, C125S) (SEQ ID NO: 194) | | D |
| A65 (210) | hIL-2 mutein (Q13N, K32E, F42C, V69C, C125S) (SEQ ID NO: 195) | | A |
| A66 (211) | hIL-2 mutein (L19S, K32E, F42C, V69C, C125S) (SEQ ID NO: 196) | | A |
| A67 (212) | hIL-2 mutein (K32E, F42C, V69C, D84T, C125S) (SEQ ID NO: 197) | | A |
| A68 (213) | hIL-2 mutein (K32E, F42C, V69C, S87E, C125S) (SEQ ID NO: 198) | | A |
| A69 (214) | hIL-2 mutein (K32E, F42C, V69C, S87D, C125S) (SEQ ID NO: 199) | | A |
| A70 (215) | hIL-2 mutein (K32E, F42C, V69C, V91I, I92L, C125S) (SEQ ID NO: 200) | | A |
| A71 (216) | hIL-2 mutein (K32E, F42C, V69C, I92L, C125S) (SEQ ID NO: 201) | | A |

TABLE 1-continued

| Fusion Protein (SEQ ID NO) | IL-2 Polypeptide | Total Secreted Protein | Total Purified Protein |
|---|---|---|---|
| A72 (217) (SEQ ID NO: 202) | hIL-2 mutein (K32E, F42C, V69C, E95N, C125S) | | A |
| A73 (218) (SEQ ID NO: 203) | hIL-2 mutein (K32E, F42C, V69C, E95Q, C125S) | | A |

Example 2

CD25 Binding of Anti-HSA-IL-2 Polypeptide Fusion Proteins

OCTET® RED96 was used to characterize the interactions of a wild-type hIL-2 and hIL-2 muteins with a human IL-2Rα (CD25). Briefly, an IL-2Rα-Fc fusion protein was loaded onto an anti-human IgG Fc capture (AHC) biosensor. The biosensor was then dipped into a solution containing a wild-type hIL-2 (WT IL-2) or an IL-2 mutein at various concentrations. Primary experimental data was analyzed with global fitting to determine a binding affinity ($K_d$). The results are summarized in Table 2.

TABLE 2

| Fusion Protein | IL-2 Polypeptide | $K_d$ (nM) |
|---|---|---|
| A1 (SEQ ID NO: 93) | hIL-2 mutein (C125S) (SEQ ID NO: 2) | 21 |
| A2 (SEQ ID NO: 94) | hIL-2 mutein (R38N, L40T, C125S) (SEQ ID NO: 6) | NB[a] |
| A36 (SEQ ID NO: 148) | IL2 mutein (K32E, R38A, C125S) (SEQ ID NO: 137) | 50 |
| A37 (SEQ ID NO: 149) | IL2 mutein (K32E, F42A, C125S) (SEQ ID NO: 138) | NB |
| A38 (SEQ ID NO: 150) | IL2 mutein (K32E, R38A, F42A, C125S) (SEQ ID NO: 139) | NB |
| A39 (SEQ ID NO: 151) | IL2 mutein (K32E, R38E, F42A, C125S) (SEQ ID NO: 140) | NB |
| A40 (SEQ ID NO: 152) | IL2 mutein (K32E, R38G, F42A, C125S) (SEQ ID NO: 141) | NB |
| A41 (SEQ ID NO: 153) | IL2 mutein (K32E, R38A, F42G, C125S) (SEQ ID NO: 142) | WB[b] |
| A42 (SEQ ID NO: 154) | IL2 mutein (K32E, R38E, F42G, C125S) (SEQ ID NO: 143) | NB |
| A43 (SEQ ID NO: 155) | IL2 mutein (K32E, R38G, F42G, C125S) (SEQ ID NO: 144) | WB |
| A44 (SEQ ID NO: 156) | IL2 mutein (K32E, R38A, F42K, C125S) (SEQ ID NO: 145) | NB |
| A45 (SEQ ID NO: 157) | IL2 mutein (K32E, R38E, F42K, C125S) (SEQ ID NO: 146) | NB |
| A46 (SEQ ID NO: 158) | IL2 mutein (K32E, R38G, F42K, C125S) (SEQ ID NO: 147) | NB |
| A47 (SEQ ID NO: 177) | hIL-2 mutein (K32E, K35C, L72C, C125S) (SEQ ID NO: 159) | >15 |
| A48 (SEQ ID NO: 178) | hIL-2 mutein (K32E, R38C, L72C, C125S) (SEQ ID NO: 160) | NB |
| A49 (SEQ ID NO: 179) | hIL-2 mutein (K32E, F42C, V69C, C125S) (SEQ ID NO: 161) | NB |
| A50 (SEQID NO: 180) | hIL-2 mutein (K32E, Y45C, E62C, C125S) (SEQ ID NO: 162) | NB |
| A52 (SEQID NO: 182) | hIL-2 mutein (F42C, V69C, C125S) (SEQ ID NO: 164) | NB |
| A53 (SEQID NO: 183) | hIL-2 mutein (F42C, V69C, K76E, C125S) (SEQ ID NO: 165) | NB |
| A54 (SEQID NO: 184) | IL-2-IL-15 chimera 1 (SEQ ID NO: 172) | NB |
| A55 (SEQID NO: 185) | IL-2-IL-15 chimera 2 (SEQ ID NO: 173) | NB |
| A56 (SEQID NO: 186) | IL-2-IL-15 chimera 3 (SEQ ID NO: 174) | NB |

[a]NB: no binding detected
[b]WB: weak binding detected

Example 3

CD122 Binding of Anti-HSA-IL-2 Polypeptide Fusion Proteins

OCTET® RED96 was used to characterize the interactions of a human CD122-Fc (AbroBio) with a wild-type hIL-2 and hIL-2 muteins. Briefly, an anti-human Fc sensor (AHC) loaded with the human CD122 was dip into 400 nM of an hIL-2 polypeptide. The binding signaling of fusion protein A1 was normalized to 1. The results are summarized in Table 3.

TABLE 3

| Fusion Protein | IL-2 Polypeptide | CD122 Binding Response |
|---|---|---|
| A1 (SEQ ID NO: 93) | hIL-2 mutein (C125S) (SEQ ID NO: 2) | 1 |
| A2 (SEQ ID NO: 94) | hIL-2 mutein (R38N, L40T, C125S) (SEQ ID NO: 6) | 0.68 |
| A49 (SEQ ID NO: 179) | hIL-2 mutein (K32E, F42C, V69C, C125S) (SEQ ID NO: 161) | 1.04 |
| A59 (SEQ ID NO: 204) | hIL-2 mutein (T3A, Q6E, R38N, L40T, F42A, C125S) (SEQ ID NO: 189) | 0.55 |
| A60 (SEQ ID NO: 205) | hIL-2 mutein (T3A, E15V, R38N, L40T, F42A, C125S) (SEQ ID NO: 190) | 0.14 |
| A61 (SEQ ID NO: 206) | hIL-2 mutein (T3A, H16N, R38N, L40T, F42A, C125S) (SEQ ID NO: 191) | 0.17 |
| A62 (SEQ ID NO: 207) | hIL-2 mutein (T3A, M23K, R38N, L40T, F42A, C125S) (SEQ ID NO: 192) | 0.29 |
| A63 (SEQ ID NO: 208) | hIL-2 mutein (T3A, R38N, L40T, F42A, V91I, C125S) (SEQ ID NO: 193) | 0.35 |
| A64 (SEQ ID NO: 209) | hIL-2 mutein (T3A, R38N, L40T, F42A, E95N, C125S) (SEQ ID NO: 194) | 0.22 |
| A65 (SEQ ID NO: 210) | hIL-2 mutein (Q13N, K32E, F42C, V69C, C125S) (SEQ ID NO: 195) | 0.5 |
| A66 (SEQ ID NO: 211) | hIL-2 mutein (L19S, K32E, F42C, V69C, C125S) (SEQ ID NO: 196) | 0.65 |
| A67 (SEQ ID NO: 212) | hIL-2 mutein (K32E, F42C, V69C, D84T, C125S) (SEQ ID NO: 197) | 0.3 |
| A68 (SEQ ID NO: 213) | hIL-2 mutein (K32E, F42C, V69C, S87E, C125S) (SEQ ID NO: 198) | 1.72 |
| A69 (SEQ ID NO: 214) | hIL-2 mutein (K32E, F42C, V69C, S87D, C125S) (SEQ ID NO: 199) | 1.93 |
| A70 (SEQ ID NO: 215) | hIL-2 mutein (K32E, F42C, V69C, V91I, I92L, C125S) (SEQ ID NO: 200) | 1.31 |
| A71 (SEQ ID NO: 216) | hIL-2 mutein (K32E, F42C, V69C, I92L, C125S) (SEQ ID NO: 201) | 1.44 |
| A72 (SEQ ID NO: 217) | hIL-2 mutein (K32E, F42C, V69C, E95N, C125S) (SEQ ID NO: 202) | 0.39 |
| A73 (SEQ ID NO: 218) | hIL-2 mutein (K32E, F42C, V69C, E95Q, C125S) (SEQ ID NO: 203) | 0.38 |

Example 4

Effect of Anti-HSA-IL-2 Polypeptide Fusion Proteins on STAT5 Signal Activation In vitro potency of an interleukin-2 polypeptide as a part of an anti-HSA-IL-2 polypeptide fusion protein was measured by quantifying phosphorylation of STAT5 in preactivated CD3 T-cells, which express IL-2Rα, β, and γ chains. CD3 T-cells were isolated from human buffy coat using ROSETTESEP™ T cells isolation kit. Activated CD3 T-cells were prepared by incubating the CD3 T-cells in RPMI-1640 medium containing 10% fetal bovine serum with a CD3/CD28 T-cell activation mix and expanded with an IL-2 for 10 days, which were then frozen in liquid nitrogen for future use. Before the day of assay, the activated CD3 T cells were thawed and grown overnight in a RPMI medium containing 10% FBS. The activated cells (150,000) were stimulated with an anti-HSA-IL-2 polypeptide fusion protein for 20 min at 37° C., 5% $CO_2$ in Hanks Balanced Salt Solution containing 10 mM HEPES. Phospho-STAT5 was measured using a phospho-STAT5 (Tyr694) homogeneous time resolved fluorescence (HTRF) assay. The signal ratio of 665 nm/620 nm was multiplied by 1,000, plotted, and fit using a dose response curve to calculate an $EC_{50}$. The results are summarized in Table 4 below, where A represents a value no greater than 0.1 nM, B represents a value greater than 0.1 nM but no greater than 1 nM, C represents a value greater than 1 nM but no greater than 10 nM, D represents a value greater than 10 nM but no greater than 100 nM; and E represents a value greater than 100 nM but no greater than 1,000 nM. In the assay, fusion protein A1 was used as a control and determined to have an $EC_{50}$ of 0.06 nM; and fusion protein A37 was determined to have an $EC_{50}$ of 0.92 nM.

TABLE 4

| Fusion Protein | IL-2 Polypeptide | EC$_{50}$ (nM) |
|---|---|---|
| A1 (SEQ ID NO: 93) | hIL-2 mutein (C125S) (SEQ ID NO: 2) | A |
| A2 (SEQ ID NO: 94) | hIL-2 mutein (R38N, L40T, C125S) (SEQ ID NO: 6) | C |
| A8 (SEQ ID NO: 100) | hIL-2 mutein (H16E, R38N, L40T, C125S) (SEQ ID NO: 16) | D |
| A9 (SEQ ID NO: 101) | hIL-2 mutein (K32E, R38N, L40T, C125S) (SEQ ID NO: 17) | C |
| A10 (SEQ ID NO: 102) | hIL-2 mutein (R38N, L40T, K76E, C125S) (SEQ ID NO: 18) | C |
| A27 (SEQ ID NO: 128) | hIL-2 mutein (E15K, R38N, L40T, C125S) (SEQ ID NO: 119) | D |
| A28 (SEQ ID NO: 129) | hIL-2 mutein (E15Q, R38N, L40T, C125S) (SEQ ID NO: 120) | C |
| A29 (SEQ ID NO: 130) | hIL-2 mutein (R38N, L40T, D84T, C125S) (SEQ ID NO: 121) | E |
| A30 (SEQ ID NO: 131) | hIL-2 mutein (R38N, L40T, N88A, C125S) (SEQ ID NO: 122) | E |
| A31 (SEQ ID NO: 132) | hIL-2 mutein (R38N, L40T, I92A, C125S) (SEQ ID NO: 123) | E |
| A32 (SEQ ID NO: 133) | hIL-2 mutein (R38N, L40T, E95K, C125S) (SEQ ID NO: 124) | D |
| A33 (SEQ ID NO: 134) | hIL-2 mutein (R38N, L40T, E95Q, C125S) (SEQ ID NO: 125) | E |
| A34 (SEQ ID NO: 135) | hIL-2 mutein (R38N, L40T, C125S, S127A) (SEQ ID NO: 126) | C |
| A35 (SEQ ID NO: 136) | hIL-2 mutein (R38N, L40T, C125S, S130A) (SEQ ID NO: 127) | C |
| A36 (SEQ ID NO: 148) | IL2 mutein (K32E, R38A, C125S) (SEQ ID NO: 137) | B |
| A37 (SEQ ID NO: 149) | IL2 mutein (K32E, F42A, C125S) (SEQ ID NO: 138) | C |
| A38 (SEQ ID NO: 150) | IL2 mutein (K32E, R38A, F42A, C125S) (SEQ ID NO: 139) | C |
| A39 (SEQ ID NO: 151) | IL2 mutein (K32E, R38E, F42A, C125S) (SEQ ID NO: 140) | C |
| A44 (SEQ ID NO: 156) | IL2 mutein (K32E, R38A, F42K, C125S) (SEQ ID NO: 145) | D |
| A45 (SEQ ID NO: 157) | IL2 mutein (K32E, R38E, F42K, C125S) (SEQ ID NO: 146) | D |
| A46 (SEQ ID NO: 158) | IL2 mutein (K32E, R38G, F42K, C125S) (SEQ ID NO: 147) | D |
| A49 (SEQ ID NO: 179) | hIL-2 mutein (K32E, F42C, V69C, C125S) (SEQ ID NO: 161) | C |
| A55 (SEQ ID NO: 185) | IL-2-IL-15 chimera 2 (SEQ ID NO: 173) | C |
| A65 (SEQ ID NO: 210) | hIL-2 mutein (Q13N, K32E, F42C, V69C, C125S) (SEQ ID NO: 195) | D |
| A66 (SEQ ID NO: 211) | hIL-2 mutein (L19S, K32E, F42C, V69C, C125S) (SEQ ID NO: 196) | E |
| A67 (SEQ ID NO: 212) | hIL-2 mutein (K32E, F42C, V69C, D84T, C125S) (SEQ ID NO: 197) | D |
| A68 (SEQ ID NO: 213) | hIL-2 mutein (K32E, F42C, V69C, S87E, C125S) (SEQ ID NO: 198) | B |
| A69 (SEQ ID NO: 214) | hIL-2 mutein (K32E, F42C, V69C, S87D, C125S) (SEQ ID NO: 199) | B |
| A70 (SEQ ID NO: 215) | hIL-2 mutein (K32E, F42C, V69C, V91I, I92L, C125S) (SEQ ID NO: 200) | D |
| A71 (SEQ ID NO: 216) | hIL-2 mutein (K32E, F42C, V69C, I92L, C125S) (SEQ ID NO: 201) | B |
| A72 (SEQ ID NO: 217) | hIL-2 mutein (K32E, F42C, V69C, E95N, C125S) (SEQ ID NO: 202) | D |
| A73 (SEQ ID NO: 218) | hIL-2 mutein (K32E, F42C, V69C, E95Q, C125S) (SEQ ID NO: 203) | D |

Example 5

In Vitro Cytotoxic Effect of Anti-HSA-IL-2 Polypeptide Fusion Proteins on NCI-N87 Cells The in vitro potency of an interleukin-2 polypeptide as a part of an anti-HSA-IL-2 polypeptide fusion protein was determined by quantifying improvement in N87 (stomach cancer) cell killing by CD3/CD28 stimulated CD3+ T-cell. NCI-N87 cancer cells were maintained in RPMI-1640 containing 10% fetal bovine serum and penicillin/streptomycin. On Day 0, 10,000 NCI-N87 cells/well were plated in the culture medium in a 96-well flat bottom plate. On Day 1, 30,000 CD3+ T-cells/well and 1:300 diluted anti-CD3/anti-CD28 antibody complex were added to the cancer cells together with the anti-HSA-IL-2 polypeptide fusion protein. The plates were incubated for 48 h at 37° C. and 5% CO$_2$. The cells were then fixed with 4% paraformaldehyde and nuclei stained with SYTOX™ Orange. The number of remaining cancer cells was calculated by counting the number of cancer cell nuclei remaining in each well using a CYTATION™ 1 Cell Imaging Multi-Mode Reader. Lower cell counts indicated better CD3+ T-cell mediated cell killing. The $IC_{50}$ values determined are summarized in Table 5 below.

TABLE 5

| Fusion Protein | IL-2 Polypeptide | $IC_{50}$ (nM) |
| --- | --- | --- |
| A2 (SEQ ID NO: 94) | hIL-2 mutein (R38N, L40T, C125S) (SEQ ID NO: 6) | 0.9 |
| A8 (SEQ ID NO: 100) | hIL-2 mutein (H16E, R38N, L40T, C125S) | 29 |
| A9 (SEQ ID NO: 101) | hIL-2 mutein (K32E, R38N, L40T, C125S) | 2.0 |
| A10 (SEQ ID NO: 102) | hIL-2 mutein (R38N, L40T, K76E, C125S) | 3.3 |

Example 6

Glycan Analysis

The glycan profile of an interleukin-2 polypeptide is analyzed using an ADVANCEBIO® GLY-X™ N-glycan prep with INSTANTPC™ kit. The interleukin-2 polypeptide is denatured and N-glycans are released by an N-glycanase at 50° C. The released N-glycans are labeled by an INSTANTPC™ dye and then cleaned up with a Gly-X™. The labeled glycans are analyzed on an HPLC system equipped with an ACQUITY UPLC Glycan BEH Amide column (130 Å, 1.7 μm, 2.1 mm×150 mm) connected to a Shimadzu Nexera-i LC-2040C 3D MT coupled with a RF-20A fluorescence detector. The N-glycans are identified by comparing them with the INSTANTPC™ labeled glycan standard libraries from Agilent Technologies.

Example 7

Protein Thermal Stability Determination

To evaluate the stability of an IL-2 polypeptide, a purified IL-2 fusion protein comprising the IL-2 polypeptide was buffer exchanged into a sodium phosphate buffer at 25 mM (pH 6.0). The IL-2 fusion protein solution was then gradually heated from 40 to 80° C. and the real-time protein size distribution of the IL-2 fusion protein was determined by dynamic light scattering (DLS) using DYNAPRO® PLATE READER™ III. As the temperature increased, the IL-2 fusion protein unfolded under the influence of heat and led to massive aggregation. The minimum temperature required to induce aggregation of the IL-2 fusion protein was determined as aggregation onset temperature ($T_{Agg}$). Higher $T_{Agg}$ correlates to higher stability for the IL-2 fusion protein. The results are shown in FIG. 1, which demonstrates that fusion protein A49 with an IL-2 having an additional disulfide bond has a $T_{Agg}$ that is significantly higher than fusion proteins A1 (wild type-IL-2) and A2 (glycosylated IL-2).

Sequences described herein are provided in the sequence table below.

SEQUENCE TABLE

| SEQ ID NO: | Description | Amino Acid Sequence |
| --- | --- | --- |
| 1 | hIL-2 | APTSSSTKKTQLQLEHLLLDLQMILNGINNYKNPK LTRMLTFKFYMPKKATELKHLQCLEEELKPLEEVL NLAQSKNFHLRPRDLISNINVIVLELKGSETTFMCE YADETATIVEFLNRWITFCQSIISTLT |
| 2 | hIL-2 (C125S) | APTSSSTKKTQLQLEHLLLDLQMILNGINNYKNPK LTRMLTFKFYMPKKATELKHLQCLEEELKPLEEVL NLAQSKNFHLRPRDLISNINVIVLELKGSETTFMCE YADETATIVEFLNRWITFSQSIISTLT |
| 3 | hIL-2 (C125A) | APTSSSTKKTQLQLEHLLLDLQMILNGINNYKNPK LTRMLTFKFYMPKKATELKHLQCLEEELKPLEEVL NLAQSKNFHLRPRDLISNINVIVLELKGSETTFMCE YADETATIVEFLNRWITFAQSIISTLT |
| 4 | hIL-2 (T3A, C125S) | APASSSTKKTQLQLEHLLLDLQMILNGINNYKNPK LTRMLTFKFYMPKKATELKHLQCLEEELKPLEEVL NLAQSKNFHLRPRDLISNINVIVLELKGSETTFMCE YADETATIVEFLNRWITFSQSIISTLT |
| 5 | hIL-2 (T3A, C125A) | APASSSTKKTQLQLEHLLLDLQMILNGINNYKNPK LTRMLTFKFYMPKKATELKHLQCLEEELKPLEEVL NLAQSKNFHLRPRDLISNINVIVLELKGSETTFMCE YADETATIVEFLNRWITFAQSIISTLT |

SEQUENCE TABLE

| SEQ ID NO: | Description | Amino Acid Sequence |
|---|---|---|
| 6 | hIL-2 mutein (R38N, L40T, C125S) | APTSSSTKKTQLQLEHLLLDLQMILNGINNYKNPK LTNMTTFKFYMPKKATELKHLQCLEEELKPLEEV LNLAQSKNFHLRPRDLISNINVIVLELKGSETTFMC EYADETATIVEFLNRWITFSQSIISTLT |
| 7 | Flexible linker | GGSG |
| 8 | Flexible linker | GGSGG |
| 9 | Flexible linker | GGGSGG |
| 10 | hIL-2 fragment (N30 to K35) | NYKNPK |
| 11 | hIL-2 mutein (H16E, C125S) | APTSSSTKKTQLQLEELLLDLQMILNGINNYKNPK LTRMLTFKFYMPKKATELKHLQCLEEELKPLEEVL NLAQSKNFHLRPRDLISNINVIVLELKGSETTFMCE YADETATIVEFLNRWITFSQSIISTLT |
| 12 | hIL-2 mutein (K32E, C125S) | APTSSSTKKTQLQLEHLLLDLQMILNGINNYENPK LTRMLTFKFYMPKKATELKHLQCLEEELKPLEEVL NLAQSKNFHLRPRDLISNINVIVLELKGSETTFMCE YADETATIVEFLNRWITFSQSIISTLT |
| 13 | hIL-2 mutein (K76E, C125S) | APTSSSTKKTQLQLEHLLLDLQMILNGINNYKNPK LTRMLTFKFYMPKKATELKHLQCLEEELKPLEEVL NLAQSENFHLRPRDLISNINVIVLELKGSETTFMCE YADETATIVEFLNRWITFSQSIISTLT |
| 14 | hIL-2 mutein (K8E, R38N, L40T, C125S) | APTSSSTEKTQLQLEHLLLDLQMILNGINNYKNPK LTNMTTFKFYMPKKATELKHLQCLEEELKPLEEV LNLAQSKNFHLRPRDLISNINVIVLELKGSETTFMC EYADETATIVEFLNRWITFSQSIISTLT |
| 15 | hIL-2 mutein (K9E, R38N, L40T, C125S) | APTSSSTKETQLQLEHLLLDLQMILNGINNYKNPK LTNMTTFKFYMPKKATELKHLQCLEEELKPLEEV LNLAQSKNFHLRPRDLISNINVIVLELKGSETTFMC EYADETATIVEFLNRWITFSQSIISTLT |
| 16 | hIL-2 mutein (H16E, R38N, L40T, C125S) | APTSSSTKKTQLQLEELLLDLQMILNGINNYKNPK LTNMTTFKFYMPKKATELKHLQCLEEELKPLEEV LNLAQSKNFHLRPRDLISNINVIVLELKGSETTFMC EYADETATIVEFLNRWITFSQSIISTLT |
| 17 | hIL-2 mutein (K32E, R38N, L40T, C125S) | APTSSSTKKTQLQLEHLLLDLQMILNGINNYENPK LTNMTTFKFYMPKKATELKHLQCLEEELKPLEEV LNLAQSKNFHLRPRDLISNINVIVLELKGSETTFMC EYADETATIVEFLNRWITFSQSIISTLT |
| 18 | hIL-2 mutein (R38N, L40T, K76E, C125S) | APTSSSTKKTQLQLEHLLLDLQMILNGINNYKNPK LTNMTTFKFYMPKKATELKHLQCLEEELKPLEEV LNLAQSENFHLRPRDLISNINVIVLELKGSETTFMC EYADETATIVEFLNRWITFSQSIISTLT |
| 19 | hIL-2 mutein (R38N, L40T, H79E, C125S) | APTSSSTKKTQLQLEHLLLDLQMILNGINNYKNPK LTNMTTFKFYMPKKATELKHLQCLEEELKPLEEV LNLAQSKNFELRPRDLISNINVIVLELKGSETTFMC EYADETATIVEFLNRWITFSQSIISTLT |
| 20 | hIL-2 mutein (R38N, L40T, R81E, C125S) | APTSSSTKKTQLQLEHLLLDLQMILNGINNYKNPK LTNMTTFKFYMPKKATELKHLQCLEEELKPLEEV LNLAQSKNFHLEPRDLISNINVIVLELKGSETTFMC FYATIFTATIVFFTNRWITFVISTISTIT |
| 21 | hIL-2 mutein (H16E, K32E, C125S) | APTSSSTKKTQLQLEELLLDLQMILNGINNYENPK LTRMLTFKFYMPKKATELKHLQCLEEELKPLEEVL NLAQSKNFHLRPRDLISNINVIVLELKGSETTFMCE YADETATIVEFLNRWITFSQSIISTLT |
| 22 | hIL-2 mutein (H16E, K76E, C125S) | APTSSSTKKTQLQLEELLLDLQMILNGINNYKNPK LTRMLTFKFYMPKKATELKHLQCLEEELKPLEEVL NLAQSENFHLRPRDLISNINVIVLELKGSETTFMCE YADETATIVEFLNRWITFSQSIISTLT |

SEQUENCE TABLE

| SEQ ID NO: | Description | Amino Acid Sequence |
|---|---|---|
| 23 | hIL-2 mutein (K32E, K76E, C125S) | APTSSSTKKTQLQLEHLLLDLQMILNGINNYENPK LTRMLTFKFYMPKKATELKHLQCLEEELKPLEEVL NLAQSENFHLRPRDLISNINVIVLELKGSETTFMCE YADETATIVEFLNRWITFSQSIISTLT |
| 24 | hIL-2 mutein (H16E, R38N, L40T, K76E, C125S) | APTSSSTKKTQLQLEELLLDLQMILNGINNYKNPK LTNMTTFKFYMPKKATELKHLQCLEEELKPLEEV LNLAQSENFHLRPRDLISNINVIVLELKGSETTFMC EYADETATIVEFLNRWITFSQSIISTLT |
| 25 | hIL-2 mutein (K32E, R38N, L40T, K76E, C125S) | APTSSSTKKTQLQLEHLLLDLQMILNGINNYENPK LTNMTTFKFYMPKKATELKHLQCLEEELKPLEEV LNLAQSENFHLRPRDLISNINVIVLELKGSETTFMC EYADETATIVEFLNRWITFSQSIISTLT |
| 26 | hIL-2 mutein (N30_K35del, R38N, L40T, C125S) | APTSSSTKKTQLQLEHLLLDLQMILNGINLTNMTT FKFYMPKKATELKHLQCLEEELKPLEEVLNLAQS KNFHLRPRDLISNINVIVLELKGSETTFMCEYADET ATIVEFLNRWITFSQSIISTLT |
| 27 | hIL-2 mutein (N30_K35delinsG, R38N, L40T, C125S) | APTSSSTKKTQLQLEHLLLDLQMILNGINGLTNMT TFKFYMPKKATELKHLQCLEEELKPLEEVLNLAQS KNFHLRPRDLISNINVIVLELKGSETTFMCEYADET ATIVEFLNRWITFSQSIISTLT |
| 28 | hIL-2 mutein (N30_K35delinsSG, R38N, L40T, C125S) | APTSSSTKKTQLQLEHLLLDLQMILNGINSGLTNM TTFKFYMPKKATELKHLQCLEEELKPLEEVLNLAQ SKNFHLRPRDLISNINVIVLELKGSETTFMCEYADE TATIVEFLNRWITFSQSIISTLT |
| 29 | hIL-2 mutein (N30_K35delinsGGS, C125S) | APTSSSTKKTQLQLEHLLLDLQMILNGINGGSLTR MLTFKFYMPKKATELKHLQCLEEELKPLEEVLNL AQSKNFHLRPRDLISNINVIVLELKGSETTFMCEYA DETATIVEFLNRWITFSQSIISTLT |
| 30 | hIL-2 mutein (N30_K35delinsGGS, R38N, L40T, C125S) | APTSSSTKKTQLQLEHLLLDLQMILNGINGGSLTN MTTFKFYMPKKATELKHLQCLEEELKPLEEVLNL AQSKNFHLRPRDLISNINVIVLELKGSETTFMCEYA DETATIVEFLNRWITFSQSIISTLT |
| 31 | hIL-2 mutein (N30_K35delinsGGSG, C125S) | APTSSSTKKTQLQLEHLLLDLQMILNGINGGSGLT RMLTFKFYMPKKATELKHLQCLEEELKPLEEVLN LAQSKNFHLRPRDLISNINVIVLELKGSETTFMCEY ADETATIVEFLNRWITFSQSIISTLT |
| 32 | hIL-2 mutein (N30_K35delinsGGSG R38N, L40T, C125S) | APTSSSTKKTQLQLEHLLLDLQMILNGINGGSGLT NMTTFKFYMPKKATELKHLQCLEEELKPLEEVLN LAQSKNFHLRPRDLISNINVIVLELKGSETTFMCEY ADETATIVEFLNRWITFSQSIISTLT |
| 33 | hIL-2 mutein (N30_K35delinsGGSGG R38N, L40T, C125S) | APTSSSTKKTQLQLEHLLLDLQMILNGINGGSGGL TNMTTFKFYMPKKATELKHLQCLEEELKPLEEVL NLAQSKNFHLRPRDLISNINVIVLELKGSETTFMCE YADETATIVEFLNRWITFSQSIISTLT |
| 34 | hIL-2 mutein (N30_K35delinsGGGSGG R38N, L40T, C125S) | APTSSSTKKTQLQLEHLLLDLQMILNGINGGGSGG LTNMTTFKFYMPKKATELKHLQCLEEELKPLEEV LNLAQSKNFHLRPRDLISNINVIVLELKGSETTFMC EYADETATIVEFLNRWITFSQSIISTLT |
| 35 | hIL-2Rα | ELCDDDPPEIPHATFKAMAYKEGTMLNCECKRGF RRIKSGSLYMLCTGNSSHSSWDNQCQCTSSATRNT TKQVTPQPEEQKERKTTEMQSPMQPVDQASLPGH CREPPPWENEATERIYHFVVGQMVYYQCVQGYR ALHRGPAESVCKMTHGKTRWTQPQLICTGEMETS QFPGEEKPQASPEGRPESETSCLVTTTDFQIQTEMA ATMETSIFTTEYQ |
| 36 | hIL-2Rβ | AVNGTSQFTCFYNSRANISCVWSQDGALQDTSCQ VHAWPDRRRWNQTCELLPVSQASWACNLILGAP DSQKLTTVDIVTLRVLCREGVRWRVMAIQDFKPF |

SEQUENCE TABLE

| SEQ ID NO: | Description | Amino Acid Sequence |
|---|---|---|
| | | ENLRLMAPISLQVVHVETHRCNISWEISQASHYFE RHLEFEARTLSPGHTWEEAPLLTLKQKQEWICLET LTPDTQYEFQVRVKPLQGEFTTWSPWSQPLAFRT KPAALGKD |
| 37 | hIL-2Rγ | LNTTILTPNGNEDTTADFFLTTMPTDSLSVSTLPLP EVQCFVFNVEYMNCTWNSSSEPQPTNLTLHYWY KNSDNDKVQKCSHYLFSEEITSGCQLQKKEIHLYQ TFVVQLQDPREPRRQATQMLKLQNLVIPWAPENL TLHKLSESQLELNWNNRFLNHCLEHLVQYRTDW DHSWTEQSVDYRHKFSLPSVDGQKRYTFRVRSRF NPLCGSAQHWSEWSHPIHWGSNTSKENPFLFALE A |
| 38 | Anti-HSA-1 CDR1 | GSTWSINT |
| 39 | Anti-HSA-1 CDR2 | ISSGGST |
| 40 | Anti-HSA-1 CDR3 | YAQSTWYPPS |
| 41 | Anti-HSA-1 FR1 | EVQLVESGGGLVQPGGSLRLSCAAS |
| 42 | Anti-HSA-1 FR2 | LAWYRQAPGKQRDLVAR |
| 43 | Anti-HSA-1 FR3 | YYADSVKGRFTISRDNSKNTLYLQMNSLRAEDTA VYYC |
| 44 | Anti-HSA-1 FR4 | WGQGTLVTVSS |
| 45 | Anti-HSA-1 | EVQLVESGGGLVQPGGSLRLSCAASGSTWSINTLA WYRQAPGKQRDLVARISSGGSTYYADSVKGRFTI SRDNSKNTLYLQMNSLRAEDTAVYYCYAQSTWY PPSWGQGTLVTVSS |
| 46 | Anti-HSA-2 CDR1 | GFAFRGFG |
| 47 | Anti-HSA-2 CDR2 | INNGGSDT |
| 48 | Anti-HSA-2 CDR3 | AIGGPGASP |
| 49 | Anti-HSA-2 FR1 | QVQLVESGGGVVQPGGSLRLSCAAS |
| 50 | Anti-HSA-2 FR2 | MSWVRQAPGKGLEWVSS |
| 51 | Anti-HSA-2 FR4 | SGQGTQVTVSS |
| 52 | Anti-HSA-2 | QVQLVESGGGVVQPGGSLRLSCAASGFAFRGFGM SWVRQAPGKGLEWVSSINNGGSDTYYADSVKGR FTISRDNSKNTLYLQMNSLRAEDTAVYYCAIGGPG ASPSGQGTQVTVSS |
| 53 | hIgG1 Fc | DKTHTCPPCPAPELLGGPSVFLFPPKPKDTLMISRT PEVTCVVVDVSHEDPEVKFNWYVDGVEVHNAKT KPREEQYNSTYRVVSVLTVLHQDWLNGKEYKCK VSNKALPAPIEKTISKAKGQPREPQVYTLPPSREEM TKNQVSLTCLVKGFYPSDIAVEWESNGQPENNYK TTPPVLDSDGSFFLYSKLTVDKSRWQQGNVFSCSV MHEALHNHYTQKSLSLSPGK |
| 54 | hIgG1 Fc mutein (N297A) | DKTHTCPPCPAPELLGGPSVFLFPPKPKDTLMISRT PEVTCVVVDVSHEDPEVKFNWYVDGVEVHNAKT KPREEQYASTYRVVSVLTVLHQDWLNGKEYKCK VSNKALPAPIEKTISKAKGQPREPQVYTLPPSREEM TKNQVSLTCLVKGFYPSDIAVEWESNGQPENNYK TTPPVLDSDGSFFLYSKLTVDKSRWQQGNVFSCSV MHEALHNHYTQKSLSLSPGK |
| 55 | hIgG1 Fc mutein (S354C, T366W) | DKTHTCPPCPAPELLGGPSVFLFPPKPKDTLMISRT PEVTCVVVDVSHEDPEVKFNWYVDGVEVHNAKT KPREEQYNSTYRVVSVLTVLHQDWLNGKEYKCK VSNKALPAPIEKTISKAKGQPREPQVYTLPPCREE MTKNQVSLWCLVKGFYPSDIAVEWESNGQPENN YKTTPPVLDSDGSFFLYSKLTVDKSRWQQGNVFS CSVMHEALHNHYTQKSLSLSPGK |

-continued

| SEQ ID NO: | Description | Amino Acid Sequence |
|---|---|---|
| 56 | hIgG1 Fc mutein (Y349C, T366S, L368A, Y407V) | DKTHTCPPCPAPELLGGPSVFLFPPKPKDTLMISRT PEVTCVVVDVSHEDPEVKFNWYVDGVEVHNAKT KPREEQYNSTYRVVSVLTVLHQDWLNGKEYKCK VSNKALPAPIEKTISKAKGQPREPQVCTLPPSREEM TKNQVSLSCAVKGFYPSDIAVEWESNGQPENNYK TTPPVLDSDGSFFLVSKLTVDKSRWQQGNVFSCSV MHEALHNHYTQKSLSLSPGK |
| 57 | hIgG1 Fc mutein (S354C, T366W, N297A) | DKTHTCPPCPAPELLGGPSVFLFPPKPKDTLMISRT PEVTCVVVDVSHEDPEVKFNWYVDGVEVHNAKT KPREEQYASTYRVVSVLTVLHQDWLNGKEYKCK VSNKALPAPIEKTISKAKGQPREPQVYTLPPCREE MTKNQVSLWCLVKGFYPSDIAVEWESNGQPENN YKTTPPVLDSDGSFFLYSKLTVDKSRWQQGNVFS CSVMHEALHNHYTQKSLSLSPGK |
| 58 | hIgG1 Fc mutein (Y349C, T366S, L368A, Y407V, N297A) | DKTHTCPPCPAPELLGGPSVFLFPPKPKDTLMISRT PEVTCVVVDVSHEDPEVKFNWYVDGVEVHNAKT KPREEQYASTYRVVSVLTVLHQDWLNGKEYKCK VSNKALPAPIEKTISKAKGQPREPQVCTLPPSREEM TKNQVSLSCAVKGFYPSDIAVEWESNGQPENNYK TTPPVLDSDGSFFLVSKLTVDKSRWQQGNVFSCSV MHEALHNHYTQKSLSLSPGK |
| 59 | hIgG2 Fc | ERKCCVECPPCPAPPVAGPSVFLFPPKPKDTLMISR TPEVTCVVVDVSHEDPEVQFNWYVDGVEVHNAK TKPREEQFNSTFRVVSVLTVVHQDWLNGKEYKCK VSNKGLPAPIEKTISKTKGQPREPQVYTLPPSREEM TKNQVSLTCLVKGFYPSDIAVEWESNGQPENNYK TTPPMLDSDGSFFLYSKLTVDKSRWQQGNVFSCS VMHEALHNHYTQKSLSLSPGK |
| 60 | hIgG4 Fc | ESKYGPPCPPCPAPEFLGGPSVFLFPPKPKDTLMIS RTPEVTCVVVDVSQEDPEVQFNWYVDGVEVHNA KTKPREEQFNSTYRVVSVLTVLHQDWLNGKEYKC KVSNKGLPSSIEKTISKAKGQPREPQVYTLPPSQEE MTKNQVSLTCLVKGFYPSDIAVEWESNGQPENNY KTTPPVLDSDGSFFLYSRLTVDKSRWQEGNVFSCS VMHEALHNHYTQKSLSLSLGK |
| 61 | (GSG)$_2$ Linker | GSGGSG |
| 62 | (GSG)$_3$ Linker | GSGGSGGSG |
| 63 | (GSG)$_4$ Linker | GSGGSGGSGGSG |
| 64 | G3S Linker | GGGS |
| 65 | (G3S)$_2$ Linker | GGGSGGGS |
| 66 | (G3S)$_3$ Linker | GGGSGGGSGGGS |
| 67 | (G3S)$_4$ Linker | GGGSGGGSGGGSGGGS |
| 68 | G4S Linker | GGGGS |
| 69 | (G4S)$_2$ Linker | GGGGSGGGGS |
| 70 | (G4S)$_3$ Linker | GGGGSGGGGSGGGGS |
| 71 | (G4S)$_4$ Linker | GGGGSGGGGSGGGGSGGGGS |
| 72 | SGSG Linker | SGSG |
| 73 | S(GSG)$_2$ Linker | SGSGGSG |
| 74 | S(GSG)$_3$ Linker | SGSGGSGGSG |
| 75 | S(GSG)$_4$ Linker | SGSGGSGGSGGSG |
| 76 | SG3S Linker | SGGGS |
| 77 | S(G3S)$_2$ Linker | SGGGSGGGS |
| 78 | S(G3S)$_3$ Linker | SGGGSGGGSGGGS |

SEQUENCE TABLE

| SEQ ID NO: | Description | Amino Acid Sequence |
|---|---|---|
| 79 | S(G3S)$_4$ Linker | SGGGSGGGSGGGSGGGS |
| 80 | SG4S Linker | SGGGGS |
| 81 | S(G4S)$_2$ Linker | SGGGGSGGGGS |
| 82 | S(G4S)$_3$ Linker | SGGGGSGGGGSGGGGS |
| 83 | S(G4S)$_4$ Linker | SGGGGSGGGGSGGGGSGGGGS |
| 84 | EAAAK Linker | EAAAK |
| 85 | (EAAAK)$_2$ Linker | EAAAKEAAAK |
| 86 | (EAAAK)$_3$ Linker | EAAAKEAAAKEAAAK |
| 87 | (EAAAK)$_4$ Linker | EAAAKEAAAKEAAAKEAAAK |
| 88 | PAPAP Linker | PAPAP |
| 89 | (PAPAP)$_2$ Linker | PAPAPPAPAP |
| 90 | (PAPAP)$_3$ Linker | PAPAPPAPAPPAPAP |
| 91 | (PAPAP)$_4$ Linker | PAPAPPAPAPPAPAPPAPAP |
| 92 | VLVH Linker | IKRTVAAP |
| 93 | hIL-2-anti-HSA A1 | APTSSSTKKTQLQLEHLLLDLQMILNGINNYKNPK LTRMLTFKFYMPKKATELKHLQCLEEELKPLEEVL NLAQSKNFHLRPRDLISNINVIVLELKGSETTFMCE YADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 94 | hIL-2-anti-HSA A2 | APTSSSTKKTQLQLEHLLLDLQMILNGINNYKNPK LTNMTTFKFYMPKKATELKHLQCLEEELKPLEEV LNLAQSKNFHLRPRDLISNINVIVLELKGSETTFMC EYADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 95 | hIL-2-anti-HSA A3 | APTSSSTKKTQLQLEELLLDLQMILNGINNYKNPK LTRMLTFKFYMPKKATELKHLQCLEEELKPLEEVL NLAQSKNFHLRPRDLISNINVIVLELKGSETTFMCE YADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 96 | hIL-2-anti-HSA A4 | APTSSSTKKTQLQLEHLLLDLQMILNGINNYENPK LTRMLTFKFYMPKKATELKHLQCLEEELKPLEEVL NLAQSKNFHLRPRDLISNINVIVLELKGSETTFMCE YADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 97 | hIL-2-anti-HSA A5 | APTSSSTKKTQLQLEHLLLDLQMILNGINNYKNPK LTRMLTFKFYMPKKATELKHLQCLEEELKPLEEVL NLAQSENFHLRPRDLISNINVIVLELKGSETTFMCE YADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |

SEQUENCE TABLE

| SEQ ID NO: | Description | Amino Acid Sequence |
|---|---|---|
| 98 | hIL-2-anti-HSA A6 | APTSSSTEKTQLQLEHLLLDLQMILNGINNYKNPK<br>LTNMTTFKFYMPKKATELKHLQCLEEELKPLEEV<br>LNLAQSKNFHLRPRDLISNINVIVLELKGSETTFMC<br>EYADETATIVEFLNRWITFSQSIISTLTGSGGSGGSG<br>GSGEVQLVESGGGLVQPGGSLRLSCAASGSTWSIN<br>TLAWYRQAPGKQRDLVARISSGGSTYYADSVKGR<br>FTISRDNSKNTLYLQMNSLRAEDTAVYYCYAQST<br>WYPPSWGQGTLVTVSS |
| 99 | hIL-2-anti-HSA A7 | APTSSSTKETQLQLEHLLLDLQMILNGINNYKNPK<br>LTNMTTFKFYMPKKATELKHLQCLEEELKPLEEV<br>LNLAQSKNFHLRPRDLISNINVIVLELKGSETTFMC<br>EYADETATIVEFLNRWITFSQSIISTLTGSGGSGGSG<br>GSGEVQLVESGGGLVQPGGSLRLSCAASGSTWSIN<br>TLAWYRQAPGKQRDLVARISSGGSTYYADSVKGR<br>FTISRDNSKNTLYLQMNSLRAEDTAVYYCYAQST<br>WYPPSWGQGTLVTVSS |
| 100 | hIL-2-anti-HSA A8 | APTSSSTKKTQLQLEELLLDLQMILNGINNYKNPK<br>LTNMTTFKFYMPKKATELKHLQCLEEELKPLEEV<br>LNLAQSKNFHLRPRDLISNINVIVLELKGSETTFMC<br>EYADETATIVEFLNRWITFSQSIISTLTGSGGSGGSG<br>GSGEVQLVESGGGLVQPGGSLRLSCAASGSTWSIN<br>TLAWYRQAPGKQRDLVARISSGGSTYYADSVKGR<br>FTISRDNSKNTLYLQMNSLRAEDTAVYYCYAQST<br>WYPPSWGQGTLVTVSS |
| 101 | hIL-2-anti-HSA A9 | APTSSSTKKTQLQLEHLLLDLQMILNGINNYENPK<br>LTNMTTFKFYMPKKATELKHLQCLEEELKPLEEV<br>LNLAQSKNFHLRPRDLISNINVIVLELKGSETTFMC<br>EYADETATIVEFLNRWITFSQSIISTLTGSGGSGGSG<br>GSGEVQLVESGGGLVQPGGSLRLSCAASGSTWSIN<br>TLAWYRQAPGKQRDLVARISSGGSTYYADSVKGR<br>FTISRDNSKNTLYLQMNSLRAEDTAVYYCYAQST<br>WYPPSWGQGTLVTVSS |
| 102 | hIL-2-anti-HSA A10 | APTSSSTKKTQLQLEHLLLDLQMILNGINNYKNPK<br>LTNMTTFKFYMPKKATELKHLQCLEEELKPLEEV<br>LNLAQSENFHLRPRDLISNINVIVLELKGSETTFMC<br>EYADETATIVEFLNRWITFSQSIISTLTGSGGSGGSG<br>GSGEVQLVESGGGLVQPGGSLRLSCAASGSTWSIN<br>TLAWYRQAPGKQRDLVARISSGGSTYYADSVKGR<br>FTISRDNSKNTLYLQMNSLRAEDTAVYYCYAQST<br>WYPPSWGQGTLVTVSS |
| 103 | hIL-2-anti-HSA A11 | APTSSSTKKTQLQLEHLLLDLQMILNGINNYKNPK<br>LTNMTTFKFYMPKKATELKHLQCLEEELKPLEEV<br>LNLAQSKNFELRPRDLISNINVIVLELKGSETTFMC<br>EYADETATIVEFLNRWITFSQSIISTLTGSGGSGGSG<br>GSGEVQLVESGGGLVQPGGSLRLSCAASGSTWSIN<br>TLAWYRQAPGKQRDLVARISSGGSTYYADSVKGR<br>FTISRDNSKNTLYLQMNSLRAEDTAVYYCYAQST<br>WYPPSWGQGTLVTVSS |
| 104 | hIL-2-anti-HSA A12 | APTSSSTKKTQLQLEHLLLDLQMILNGINNYKNPK<br>LTNMTTFKFYMPKKATELKHLQCLEEELKPLEEV<br>LNLAQSKNFHLEPRDLISNINVIVLELKGSETTFMC<br>EYADETATIVEFLNRWITFSQSIISTLTGSGGSGGSG<br>GSGEVQLVESGGGLVQPGGSLRLSCAASGSTWSIN<br>TLAWYRQAPGKQRDLVARISSGGSTYYADSVKGR<br>FTISRDNSKNTLYLQMNSLRAEDTAVYYCYAQST<br>WYPPSWGQGTLVTVSS |
| 105 | hIL-2-anti-HSA A13 | APTSSSTKKTQLQLEELLLDLQMILNGINNYENPK<br>LTRMLTFKFYMPKKATELKHLQCLEEELKPLEEVL<br>NLAQSKNFHLRPRDLISNINVIVLELKGSETTFMCE<br>YADETATIVEFLNRWITFSQSIISTLTGSGGSGGSG<br>GSGEVQLVESGGGLVQPGGSLRLSCAASGSTWSIN<br>TLAWYRQAPGKQRDLVARISSGGSTYYADSVKGR<br>FTISRDNSKNTLYLQMNSLRAEDTAVYYCYAQST<br>WYPPSWGQGTLVTVSS |
| 106 | hIL-2-anti-HSA A14 | APTSSSTKKTQLQLEELLLDLQMILNGINNYKNPK<br>LTRMLTFKFYMPKKATELKHLQCLEEELKPLEEVL |

SEQUENCE TABLE

| SEQ ID NO: | Description | Amino Acid Sequence |
|---|---|---|
| | | NLAQSENFHLRPRDLISNINVIVLELKGSETTFMCE<br>YADETATIVEFLNRWITFSQSIISTLTGSGGSGGSG<br>GSGEVQLVESGGGLVQPGGSLRLSCAASGSTWSIN<br>TLAWYRQAPGKQRDLVARISSGGSTYYADSVKGR<br>FTISRDNSKNTLYLQMNSLRAEDTAVYYCYAQST<br>WYPPSWGQGTLVTVSS |
| 107 | hIL-2-anti-HSA A15 | APTSSSTKKTQLQLEHLLLDLQMILNGINNYENPK<br>LTRMLTFKFYMPKKATELKHLQCLEEELKPLEEVL<br>NLAQSENFHLRPRDLISNINVIVLELKGSETTFMCE<br>YADETATIVEFLNRWITFSQSIISTLTGSGGSGGSG<br>GSGEVQLVESGGGLVQPGGSLRLSCAASGSTWSIN<br>TLAWYRQAPGKQRDLVARISSGGSTYYADSVKGR<br>FTISRDNSKNTLYLQMNSLRAEDTAVYYCYAQST<br>WYPPSWGQGTLVTVSS |
| 108 | hIL-2-anti-HSA A16 | APTSSSTKKTQLQLEELLLDLQMILNGINNYKNPK<br>LTNMTTFKFYMPKKATELKHLQCLEEELKPLEEV<br>LNLAQSENFHLRPRDLISNINVIVLELKGSETTFMC<br>EYADETATIVEFLNRWITFSQSIISTLTGSGGSGGSG<br>GSGEVQLVESGGGLVQPGGSLRLSCAASGSTWSIN<br>TLAWYRQAPGKQRDLVARISSGGSTYYADSVKGR<br>FTISRDNSKNTLYLQMNSLRAEDTAVYYCYAQST<br>WYPPSWGQGTLVTVSS |
| 109 | hIL-2-anti-HSA A17 | APTSSSTKKTQLQLEHLLLDLQMILNGINNYENPK<br>LTNMTTFKFYMPKKATELKHLQCLEEELKPLEEV<br>LNLAQSENFHLRPRDLISNINVIVLELKGSETTFMC<br>EYADETATIVEFLNRWITFSQSIISTLTGSGGSGGSG<br>GSGEVQLVESGGGLVQPGGSLRLSCAASGSTWSIN<br>TLAWYRQAPGKQRDLVARISSGGSTYYADSVKGR<br>FTISRDNSKNTLYLQMNSLRAEDTAVYYCYAQST<br>WYPPSWGQGTLVTVSS |
| 110 | hIL-2-anti-HSA A18 | APTSSSTKKTQLQLEHLLLDLQMILNGINLTNMTT<br>FKFYMPKKATELKHLQCLEEELKPLEEVLNLAQS<br>KNFHLRPRDLISNINVIVLELKGSETTFMCEYADET<br>ATIVEFLNRWITFSQSIISTLTGSGGSGGSGGSGEVQ<br>LVESGGGLVQPGGSLRLSCAASGSTWSINTLAWY<br>RQAPGKQRDLVARISSGGSTYYADSVKGRFTISRD<br>NSKNTLYLQMNSLRAEDTAVYYCYAQSTWYPPS<br>WGQGTLVTVSS |
| 111 | hIL-2-anti-HSA A19 | APTSSSTKKTQLQLEHLLLDLQMILNGINGLTNMT<br>TFKFYMPKKATELKHLQCLEEELKPLEEVLNLAQS<br>KNFHLRPRDLISNINVIVLELKGSETTFMCEYADET<br>ATIVEFLNRWITFSQSIISTLTGSGGSGGSGGSGEVQ<br>LVESGGGLVQPGGSLRLSCAASGSTWSINTLAWY<br>RQAPGKQRDLVARISSGGSTYYADSVKGRFTISRD<br>NSKNTLYLQMNSLRAEDTAVYYCYAQSTWYPPS<br>WGQGTLVTVSS |
| 112 | hIL-2-anti-HSA A20 | APTSSSTKKTQLQLEHLLLDLQMILNGINSGLTNM<br>TTFKFYMPKKATELKHLQCLEEELKPLEEVLNLAQ<br>SKNFHLRPRDLISNINVIVLELKGSETTFMCEYADE<br>TATIVEFLNRWITFSQSIISTLTGSGGSGGSGGSGEV<br>QLVESGGGLVQPGGSLRLSCAASGSTWSINTLAW<br>YRQAPGKQRDLVARISSGGSTYYADSVKGRFTISR<br>DNSKNTLYLQMNSLRAEDTAVYYCYAQSTWYPP<br>SWGQGTLVTVSS |
| 113 | hIL-2-anti-HSA A21 | APTSSSTKKTQLQLEHLLLDLQMILNGINGGSLTR<br>MLTFKFYMPKKATELKHLQCLEEELKPLEEVLNL<br>AQSKNFHLRPRDLISNINVIVLELKGSETTFMCEYA<br>DETATIVEFLNRWITFSQSIISTLTGSGGSGGSGGSG<br>EVQLVESGGGLVQPGGSLRLSCAASGSTWSINTLA<br>WYRQAPGKQRDLVARISSGGSTYYADSVKGRFTI<br>SRDNSKNTLYLQMNSLRAEDTAVYYCYAQSTWY<br>PPSWGQGTLVTVSS |
| 114 | hIL-2-anti-HSA A22 | APTSSSTKKTQLQLEHLLLDLQMILNGINGGSLTN<br>MTTFKFYMPKKATELKHLQCLEEELKPLEEVLNL<br>AQSKNFHLRPRDLISNINVIVLELKGSETTFMCEYA<br>DETATIVEFLNRWITFSQSIISTLTGSGGSGGSGGSG<br>EVQLVESGGGLVQPGGSLRLSCAASGSTWSINTLA |

SEQUENCE TABLE

| SEQ ID NO: | Description | Amino Acid Sequence |
|---|---|---|
| | | WYRQAPGKQRDLVARISSGGSTYYADSVKGRFTI<br>SRDNSKNTLYLQMNSLRAEDTAVYYCYAQSTWY<br>PPSWGQGTLVTVSS |
| 115 | hIL-2-anti-HSA A23 | APTSSSTKKTQLQLEHLLLDLQMILNGINGGSGLT<br>RMLTFKFYMPKKATELKHLQCLEEELKPLEEVLN<br>LAQSKNFHLRPRDLISNINVIVLELKGSETTFMCEY<br>ADETATIVEFLNRWITFSQSIISTLTGSGGSGGSGGS<br>GEVQLVESGGGLVQPGGSLRLSCAASGSTWSINTL<br>AWYRQAPGKQRDLVARISSGGSTYYADSVKGRFT<br>ISRDNSKNTLYLQMNSLRAEDTAVYYCYAQSTWY<br>PPSWGQGTLVTVSS |
| 116 | hIL-2-anti-HSA A24 | APTSSSTKKTQLQLEHLLLDLQMILNGINGGSGLT<br>NMTTFKFYMPKKATELKHLQCLEEELKPLEEVLN<br>LAQSKNFHLRPRDLISNINVIVLELKGSETTFMCEY<br>ADETATIVEFLNRWITFSQSIISTLTGSGGSGGSGGS<br>GEVQLVESGGGLVQPGGSLRLSCAASGSTWSINTL<br>AWYRQAPGKQRDLVARISSGGSTYYADSVKGRFT<br>ISRDNSKNTLYLQMNSLRAEDTAVYYCYAQSTWY<br>PPSWGQGTLVTVSS |
| 117 | hIL-2-anti-HSA A25 | APTSSSTKKTQLQLEHLLLDLQMILNGINGGSGGL<br>TNMTTFKFYMPKKATELKHLQCLEEELKPLEEVL<br>NLAQSKNFHLRPRDLISNINVIVLELKGSETTFMCE<br>YADETATIVEFLNRWITFSQSIISTLTGSGGSGGSG<br>GSGEVQLVESGGGLVQPGGSLRLSCAASGSTWSIN<br>TLAWYRQAPGKQRDLVARISSGGSTYYADSVKGR<br>FTISRDNSKNTLYLQMNSLRAEDTAVYYCYAQST<br>WYPPSWGQGTLVTVSS |
| 118 | hIL-2-anti-HSA A26 | APTSSSTKKTQLQLEHLLLDLQMILNGINGGGSGG<br>LTNMTTFKFYMPKKATELKHLQCLEEELKPLEEV<br>LNLAQSKNFHLRPRDLISNINVIVLELKGSETTFMC<br>EYADETATIVEFLNRWITFSQSIISTLTGSGGSGGSG<br>GSGEVQLVESGGGLVQPGGSLRLSCAASGSTWSIN<br>TLAWYRQAPGKQRDLVARISSGGSTYYADSVKGR<br>FTISRDNSKNTLYLQMNSLRAEDTAVYYCYAQST<br>WYPPSWGQGTLVTVSS |
| 119 | hIL-2 mutein<br>(E15K, R38N, L40T, C125S) | APTSSSTKKTQLQLKHLLLDLQMILNGINNYKNPK<br>LTNMTTFKFYMPKKATELKHLQCLEEELKPLEEV<br>LNLAQSKNFHLRPRDLISNINVIVLELKGSETTFMC<br>EYADETATIVEFLNRWITFSQSIISTLT |
| 120 | hIL-2 mutein<br>(E15Q, R38N, L40T, C125S) | APTSSSTKKTQLQLQHLLLDLQMILNGINNYKNPK<br>LTNMTTFKFYMPKKATELKHLQCLEEELKPLEEV<br>LNLAQSKNFHLRPRDLISNINVIVLELKGSETTFMC<br>EYADETATIVEFLNRWITFSQSIISTLT |
| 121 | hIL-2 mutein<br>(R38N, L40T, D84T, C125S) | APTSSSTKKTQLQLEHLLLDLQMILNGINNYKNPK<br>LTNMTTFKFYMPKKATELKHLQCLEEELKPLEEV<br>LNLAQSKNFHLRPRTLISNINVIVLELKGSETTFMC<br>EYADETATIVEFLNRWITFSQSIISTLT |
| 122 | hIL-2 mutein<br>(R38N, L40T, N88A, C125S) | APTSSSTKKTQLQLEHLLLDLQMILNGINNYKNPK<br>LTNMTTFKFYMPKKATELKHLQCLEEELKPLEEV<br>LNLAQSKNFHLRPRDLISAINVIVLELKGSETTFMC<br>EYADETATIVEFLNRWITFSQSIISTLT |
| 123 | hIL-2 mutein<br>(R38N, L40T, I92A, C125S) | APTSSSTKKTQLQLEHLLLDLQMILNGINNYKNPK<br>LTNMTTFKFYMPKKATELKHLQCLEEELKPLEEV<br>LNLAQSKNFHLRPRDLISNINVAVLELKGSETTFM<br>CEYADETATIVEFLNRWITFSQSIISTLT |
| 124 | hIL-2 mutein<br>(R38N, L40T, E95K, C125A) | APTSSSTKKTQLQLEHLLLDLQMILNGINNYKNPK<br>LTNMTTFKFYMPKKATELKHLQCLEEELKPLEEV<br>LNLAQSKNFHLRPRDLISNINVIVLKLKGSETTFMC<br>EYADETATIVEFLNRWITFSQSIISTLT |
| 125 | hIL-2 mutein<br>(R38N, L40T, E95Q, C125S) | APTSSSTKKTQLQLEHLLLDLQMILNGINNYKNPK<br>LTNMTTFKFYMPKKATELKHLQCLEEELKPLEEV<br>LNLAQSKNFHLRPRDLISNINVIVLQLKGSETTFMC<br>EYADETATIVEFLNRWITFSQSIISTLT |

-continued

| SEQ ID NO: | Description | Amino Acid Sequence |
|---|---|---|
| 126 | hIL-2 mutein (R38N, L40T, C125S, S127A) | APTSSSTKKTQLQLEHLLLDLQMILNGINNYKNPK LTNMTTFKFYMPKKATELKHLQCLEEELKPLEEV LNLAQSKNFHLRPRDLISNINVIVLELKGSETTFMC EYADETATIVEFLNRWITFSQAIISTLT |
| 127 | hIL-2 mutein (R38N, L40T, C125S, S130A) | APTSSSTKKTQLQLEHLLLDLQMILNGINNYKNPK LTNMTTFKFYMPKKATELKHLQCLEEELKPLEEV LNLAQSKNFHLRPRDLISNINVIVLELKGSETTFMC EYADETATIVEFLNRWITFSQSIIATLT |
| 128 | hIL-2-anti-HSA A27 | APTSSSTKKTQLQLKHLLLDLQMILNGINNYKNPK LTNMTTFKFYMPKKATELKHLQCLEEELKPLEEV LNLAQSKNFHLRPRDLISNINVIVLELKGSETTFMC EYADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 129 | hIL-2-anti-HSA A28 | APTSSSTKKTQLQLQHLLLDLQMILNGINNYKNPK LTNMTTFKFYMPKKATELKHLQCLEEELKPLEEV LNLAQSKNFHLRPRDLISNINVIVLELKGSETTFMC EYADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 130 | hIL-2-anti-HSA A29 | APTSSSTKKTQLQLEHLLLDLQMILNGINNYKNPK LTNMTTFKFYMPKKATELKHLQCLEEELKPLEEV LNLAQSKNFHLRPRTLISNINVIVLELKGSETTFMC EYADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 131 | hIL-2-anti-HSA A30 | APTSSSTKKTQLQLEHLLLDLQMILNGINNYKNPK LTNMTTFKFYMPKKATELKHLQCLEEELKPLEEV LNLAQSKNFHLRPRDLISAINVIVLELKGSETTFMC EYADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 132 | hIL-2-anti-HSA A31 | APTSSSTKKTQLQLEHLLLDLQMILNGINNYKNPK LTNMTTFKFYMPKKATELKHLQCLEEELKPLEEV LNLAQSKNFHLRPRDLISNINVAVLELKGSETTFM CEYADETATIVEFLNRWITFSQSIISTLTGSGGSGGS GGSGEVQLVESGGGLVQPGGSLRLSCAASGSTWSI NTLAWYRQAPGKQRDLVARISSGGSTYYADSVKG RFTISRDNSKNTLYLQMNSLRAEDTAVYYCYAQS TWYPPSWGQGTLVTVSS |
| 133 | hIL-2-anti-HSA A32 | APTSSSTKKTQLQLEHLLLDLQMILNGINNYKNPK LTNMTTFKFYMPKKATELKHLQCLEEELKPLEEV LNLAQSKNFHLRPRDLISNINVIVLKLKGSETTFMC EYADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 134 | hIL-2-anti-HSA A33 | APTSSSTKKTQLQLEHLLLDLQMILNGINNYKNPK LTNMTTFKFYMPKKATELKHLQCLEEELKPLEEV LNLAQSKNFHLRPRDLISNINVIVLQLKGSETTFMC EYADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 135 | hIL-2-anti-HSA A34 | APTSSSTKKTQLQLEHLLLDLQMILNGINNYKNPK LTNMTTFKFYMPKKATELKHLQCLEEELKPLEEV |

| SEQUENCE TABLE | | |
|---|---|---|
| SEQ ID NO: | Description | Amino Acid Sequence |
| | | LNLAQSKNFHLRPRDLISNINVIVLELKGSETTFMC EYADETATIVEFLNRWITFSQAIISTLTGSGGSGGS GGSGEVQLVESGGGLVQPGGSLRLSCAASGSTWSI NTLAWYRQAPGKQRDLVARISSGGSTYYADSVKG RFTISRDNSKNTLYLQMNSLRAEDTAVYYCYAQS TWYPPSWGQGTLVTVSS |
| 136 | hIL-2-anti-HSA A35 | APTSSSTKKTQLQLEHLLLDLQMILNGINNYKNPK LTNMTTFKFYMPKKATELKHLQCLEEELKPLEEV LNLAQSKNFHLRPRDLISNINVIVLELKGSETTFMC EYADETATIVEFLNRWITFSQSIIATLTGSGGSGGS GGSGEVQLVESGGGLVQPGGSLRLSCAASGSTWSI NTLAWYRQAPGKQRDLVARISSGGSTYYADSVKG RFTISRDNSKNTLYLQMNSLRAEDTAVYYCYAQS TWYPPSWGQGTLVTVSS |
| 137 | hIL-2 mutein (K32E, R38A, C125S) | APTSSSTKKTQLQLEHLLLDLQMILNGINNYENPK LTAMLTFKFYMPKKATELKHLQCLEEELKPLEEV LNLAQSKNFHLRPRDLISNINVIVLELKGSETTFMC EYADETATIVEFLNRWITFSQSIISTLT |
| 138 | hIL-2 mutein (K32E, F42A, C125S) | APTSSSTKKTQLQLEHLLLDLQMILNGINNYENPK LTRMLTAKFYMPKKATELKHLQCLEEELKPLEEV LNLAQSKNFHLRPRDLISNINVIVLELKGSETTFMC EYADETATIVEFLNRWITFSQSIISTLT |
| 139 | hIL-2 mutein (K32E, R38A, F42A, C125S) | APTSSSTKKTQLQLEHLLLDLQMILNGINNYENPK LTAMLTAKFYMPKKATELKHLQCLEEELKPLEEV LNLAQSKNFHLRPRDLISNINVIVLELKGSETTFMC EYADETATIVEFLNRWITFSQSIISTLT |
| 140 | hIL-2 mutein (K32E, R38E, F42A, C125S) | APTSSSTKKTQLQLEHLLLDLQMILNGINNYENPK LTEMLTAKFYMPKKATELKHLQCLEEELKPLEEV LNLAQSKNFHLRPRDLISNINVIVLELKGSETTFMC EYADETATIVEFLNRWITFSQSIISTLT |
| 141 | hIL-2 mutein (K32E, R38G, F42A, C125S) | APTSSSTKKTQLQLEHLLLDLQMILNGINNYENPK LTGMLTAKFYMPKKATELKHLQCLEEELKPLEEV LNLAQSKNFHLRPRDLISNINVIVLELKGSETTFMC EYADETATIVEFLNRWITFSQSIISTLT |
| 142 | hIL-2 mutein (K32E, R38A, F42G, C125S) | APTSSSTKKTQLQLEHLLLDLQMILNGINNYENPK LTAMLTGKFYMPKKATELKHLQCLEEELKPLEEV LNLAQSKNFHLRPRDLISNINVIVLELKGSETTFMC EYADETATIVEFLNRWITFSQSIISTLT |
| 143 | hIL-2 mutein (K32E, R38E, F42G, C125S) | APTSSSTKKTQLQLEHLLLDLQMILNGINNYENPK LTEMLTGKFYMPKKATELKHLQCLEEELKPLEEV LNLAQSKNFHLRPRDLISNINVIVLELKGSETTFMC EYADETATIVEFLNRWITFSQSIISTLT |
| 144 | hIL-2 mutein (K32E, R38G, F42G, C125S) | APTSSSTKKTQLQLEHLLLDLQMILNGINNYENPK LTGMLTGKFYMPKKATELKHLQCLEEELKPLEEV LNLAQSKNFHLRPRDLISNINVIVLELKGSETTFMC EYADETATIVEFLNRWITFSQSIISTLT |
| 145 | hIL-2 mutein (K32E, R38A, F42K, C125S) | APTSSSTKKTQLQLEHLLLDLQMILNGINNYENPK LTAMLTKKFYMPKKATELKHLQCLEEELKPLEEV LNLAQSKNFHLRPRDLISNINVIVLELKGSETTFMC EYADETATIVEFLNRWITFSQSIISTLT |
| 146 | hIL-2 mutein (K32E, R38E, F42K, C125S) | APTSSSTKKTQLQLEHLLLDLQMILNGINNYENPK LTEMLTKKFYMPKKATELKHLQCLEEELKPLEEV LNLAQSKNFHLRPRDLISNINVIVLELKGSETTFMC EYADETATIVEFLNRWITFSQSIISTLT |
| 147 | hIL-2 mutein (K32E, R38G, F42K, C125S) | APTSSSTKKTQLQLEHLLLDLQMILNGINNYENPK LTGMLTKKFYMPKKATELKHLQCLEEELKPLEEV LNLAQSKNFHLRPRDLISNINVIVLELKGSETTFMC EYADETATIVEFLNRWITFSQSIISTLT |
| 148 | hIL-2-anti-HSA A36 | APTSSSTKKTQLQLEHLLLDLQMILNGINNYENPK LTAMLTFKFYMPKKATELKHLQCLEEELKPLEEV LNLAQSKNFHLRPRDLISNINVIVLELKGSETTFMC EYADETATIVEFLNRWITFSQSIISTLTGSGGSGGSG |

-continued

| SEQ ID NO: | Description | Amino Acid Sequence |
|---|---|---|
| | | GSGEVQLVESGGGLVQPGGSLRLSCAASGSTWSIN<br>TLAWYRQAPGKQRDLVARISSGGSTYYADSVKGR<br>FTISRDNSKNTLYLQMNSLRAEDTAVYYCYAQST<br>WYPPSWGQGTLVTVSS |
| 149 | hIL-2-anti-HSA A37 | APTSSSTKKTQLQLEHLLLDLQMILNGINNYENPK<br>LTRMLTAKFYMPKKATELKHLQCLEEELKPLEEV<br>LNLAQSKNFHLRPRDLISNINVIVLELKGSETTFMC<br>EYADETATIVEFLNRWITFSQSIISTLTGSGGSGGSG<br>GSGEVQLVESGGGLVQPGGSLRLSCAASGSTWSIN<br>TLAWYRQAPGKQRDLVARISSGGSTYYADSVKGR<br>FTISRDNSKNTLYLQMNSLRAEDTAVYYCYAQST<br>WYPPSWGQGTLVTVSS |
| 150 | hIL-2-anti-HSA A38 | APTSSSTKKTQLQLEHLLLDLQMILNGINNYENPK<br>LTAMLTAKFYMPKKATELKHLQCLEEELKPLEEV<br>LNLAQSKNFHLRPRDLISNINVIVLELKGSETTFMC<br>EYADETATIVEFLNRWITFSQSIISTLTGSGGSGGSG<br>GSGEVQLVESGGGLVQPGGSLRLSCAASGSTWSIN<br>TLAWYRQAPGKQRDLVARISSGGSTYYADSVKGR<br>FTISRDNSKNTLYLQMNSLRAEDTAVYYCYAQST<br>WYPPSWGQGTLVTVSS |
| 151 | hIL-2-anti-HSA A39 | APTSSSTKKTQLQLEHLLLDLQMILNGINNYENPK<br>LTEMLTAKFYMPKKATELKHLQCLEEELKPLEEV<br>LNLAQSKNFHLRPRDLISNINVIVLELKGSETTFMC<br>EYADETATIVEFLNRWITFSQSIISTLTGSGGSGGSG<br>GSGEVQLVESGGGLVQPGGSLRLSCAASGSTWSIN<br>TLAWYRQAPGKQRDLVARISSGGSTYYADSVKGR<br>FTISRDNSKNTLYLQMNSLRAEDTAVYYCYAQST<br>WYPPSWGQGTLVTVSS |
| 152 | hIL-2-anti-HSA A40 | APTSSSTKKTQLQLEHLLLDLQMILNGINNYENPK<br>LTGMLTAKFYMPKKATELKHLQCLEEELKPLEEV<br>LNLAQSKNFHLRPRDLISNINVIVLELKGSETTFMC<br>EYADETATIVEFLNRWITFSQSIISTLTGSGGSGGSG<br>GSGEVQLVESGGGLVQPGGSLRLSCAASGSTWSIN<br>TLAWYRQAPGKQRDLVARISSGGSTYYADSVKGR<br>FTISRDNSKNTLYLQMNSLRAEDTAVYYCYAQST<br>WYPPSWGQGTLVTVSS |
| 153 | hIL-2-anti-HSA A41 | APTSSSTKKTQLQLEHLLLDLQMILNGINNYENPK<br>LTAMLTGKFYMPKKATELKHLQCLEEELKPLEEV<br>LNLAQSKNFHLRPRDLISNINVIVLELKGSETTFMC<br>EYADETATIVEFLNRWITFSQSIISTLTGSGGSGGSG<br>GSGEVQLVESGGGLVQPGGSLRLSCAASGSTWSIN<br>TLAWYRQAPGKQRDLVARISSGGSTYYADSVKGR<br>FTISRDNSKNTLYLQMNSLRAEDTAVYYCYAQST<br>WYPPSWGQGTLVTVSS |
| 154 | hIL-2-anti-HSA A42 | APTSSSTKKTQLQLEHLLLDLQMILNGINNYENPK<br>LTEMLTGKFYMPKKATELKHLQCLEEELKPLEEV<br>LNLAQSKNFHLRPRDLISNINVIVLELKGSETTFMC<br>EYADETATIVEFLNRWITFSQSIISTLTGSGGSGGSG<br>GSGEVQLVESGGGLVQPGGSLRLSCAASGSTWSIN<br>TLAWYRQAPGKQRDLVARISSGGSTYYADSVKGR<br>FTISRDNSKNTLYLQMNSLRAEDTAVYYCYAQST<br>WYPPSWGQGTLVTVSS |
| 155 | hIL-2-anti-HSA A43 | APTSSSTKKTQLQLEHLLLDLQMILNGINNYENPK<br>LTGMLTGKFYMPKKATELKHLQCLEEELKPLEEV<br>LNLAQSKNFHLRPRDLISNINVIVLELKGSETTFMC<br>EYADETATIVEFLNRWITFSQSIISTLTGSGGSGGSG<br>GSGEVQLVESGGGLVQPGGSLRLSCAASGSTWSIN<br>TLAWYRQAPGKQRDLVARISSGGSTYYADSVKGR<br>FTISRDNSKNTLYLQMNSLRAEDTAVYYCYAQST<br>WYPPSWGQGTLVTVSS |
| 156 | hIL-2-anti-HSA A44 | APTSSSTKKTQLQLEHLLLDLQMILNGINNYENPK<br>LTAMLTKKFYMPKKATELKHLQCLEEELKPLEEV<br>LNLAQSKNFHLRPRDLISNINVIVLELKGSETTFMC<br>EYADETATIVEFLNRWITFSQSIISTLTGSGGSGGSG<br>GSGEVQLVESGGGLVQPGGSLRLSCAASGSTWSIN |

| SEQUENCE TABLE | | |
|---|---|---|
| SEQ ID NO: | Description | Amino Acid Sequence |
| | | TLAWYRQAPGKQRDLVARISSGGSTYYADSVKGR FTISRDNSKNTLYLQMNSLRAEDTAVYYCYAQST WYPPSWGQGTLVTVSS |
| 157 | hIL-2-anti-HSA A45 | APTSSSTKKTQLQLEHLLLDLQMILNGINNYENPK LTEMLTKKFYMPKKATELKHLQCLEEELKPLEEV LNLAQSKNFHLRPRDLISNINVIVLELKGSETTFMC EYADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 158 | hIL-2-anti-HSA A46 | APTSSSTKKTQLQLEHLLLDLQMILNGINNYENPK LTGMLTKKFYMPKKATELKHLQCLEEELKPLEEV LNLAQSKNFHLRPRDLISNINVIVLELKGSETTFMC EYADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 159 | hIL-2 mutein (K32E, K35C, L72C, C125S) | APTSSSTKKTQLQLEHLLLDLQMILNGINNYENPC LTRMLTFKFYMPKKATELKHLQCLEEELKPLEEVL NCAQSKNFHLRPRDLISNINVIVLELKGSETTFMCE YADETATIVEFLNRWITFSQSIISTLT |
| 160 | hIL-2 mutein (K32E, R38C, L72C, C125S) | APTSSSTKKTQLQLEHLLLDLQMILNGINNYENPK LTCMLTFKFYMPKKATELKHLQCLEEELKPLEEVL NCAQSKNFHLRPRDLISNINVIVLELKGSETTFMCE YADETATIVEFLNRWITFSQSIISTLT |
| 161 | hIL-2 mutein (K32E, F42C, V69C, C125S) | APTSSSTKKTQLQLEHLLLDLQMILNGINNYENPK LTRMLTCKFYMPKKATELKHLQCLEEELKPLEEC LNLAQSKNFHLRPRDLISNINVIVLELKGSETTFMC EYADETATIVEFLNRWITFSQSIISTLT |
| 162 | hIL-2 mutein (K32E, Y45C, E62C, C125S) | APTSSSTKKTQLQLEHLLLDLQMILNGINNYENPK LTRMLTFKFCMPKKATELKHLQCLEECLKPLEEVL NLAQSKNFHLRPRDLISNINVIVLELKGSETTFMCE YADETATIVEFLNRWITFSQSIISTLT |
| 163 | hIL-2 mutein (K32E, F42C, L72C, C125S) | APTSSSTKKTQLQLEHLLLDLQMILNGINNYENPK LTRMLTCKFYMPKKATELKHLQCLEEELKPLEEV LNCAQSKNFHLRPRDLISNINVIVLELKGSETTFMC EYADETATIVEFLNRWITFSQSIISTLT |
| 164 | hIL-2 mutein (F42C, V69C, C125S) | APTSSSTKKTQLQLEHLLLDLQMILNGINNYKNPK LTRMLTCKFYMPKKATELKHLQCLEEELKPLEEC LNLAQSKNFHLRPRDLISNINVIVLELKGSETTFMC EYADETATIVEFLNRWITFSQSIISTLT |
| 165 | hIL-2 mutein (F42C, V69C, K76E, C125S) | APTSSSTKKTQLQLEHLLLDLQMILNGINNYKNPK LTRMLTCKFYMPKKATELKHLQCLEEELKPLEEC LNLAQSENFHLRPRDLISNINVIVLELKGSETTFMC EYADETATIVEFLNRWITFSQSIISTLT |
| 166 | IL-15 hinge fragment-containing peptide 1 | NNYENPKLTDATLYMPKKA |
| 167 | IL-15 hinge fragment-containing peptide 2 | QSMEIDATTFKFYMPKKA |
| 168 | IL-15 hinge fragment-containing peptide 3 | QSMEIDATKFYMPKKA |
| 169 | IL-15 hinge fragment-containing peptide 4 | QSMEIDATLFYMPKKA |
| 170 | IL-15 hinge fragment-containing peptide 5 | QSMEIDATLYTESDV |
| 171 | hIL-2 fragment (N29 to A50) | NNYKNPKLTRMLTFKFYMPKKA |

-continued

| SEQ ID NO: | Description | Amino Acid Sequence |
|---|---|---|
| 172 | IL-2-IL-15 chimera 1 | APTSSSTKKTQLQLEHLLLDLQMILNGINNYENPK LTDATLYMPKKATELKHLQCLEEELKPLEEVLNL AQSKNFHLRPRDLISNINVIVLELKGSETTFMCEYA DETATIVEFLNRWITFSQSIISTLT |
| 173 | IL-2-IL-15 chimera 2 | APTSSSTKKTQLQLEHLLLDLQMILNGIQSMEIDAT TFKFYMPKKATELKHLQCLEEELKPLEEVLNLAQS KNFHLRPRDLISNINVIVLELKGSETTFMCEYADET ATIVEFLNRWITFSQSIISTLT |
| 174 | IL-2-IL-15 chimera 3 | APTSSSTKKTQLQLEHLLLDLQMILNGIQSMEIDAT KFYMPKKATELKHLQCLEEELKPLEEVLNLAQSK NFHLRPRDLISNINVIVLELKGSETTFMCEYADETA TIVEFLNRWITFSQSIISTLT |
| 175 | IL-2-IL-15 chimera 4 | APTSSSTKKTQLQLEHLLLDLQMILNGIQSMEIDAT LFYMPKKATELKHLQCLEEELKPLEEVLNLAQSK NFHLRPRDLISNINVIVLELKGSETTFMCEYADETA TIVEFLNRWITFSQSIISTLT |
| 176 | IL-2-IL-15 chimera 5 | APTSSSTKKTQLQLEHLLLDLQMILNGIQSMEIDAT LYTESDVTELKHLQCLEEELKPLEEVLNLAQSKNF HLRPRDLISNINVIVLELKGSETTFMCEYADETATI VEFLNRWITFSQSIISTLT |
| 177 | hIL-2-anti-HSA A47 | APTSSSTKKTQLQLEHLLLDLQMILNGINNYENPC LTRMLTFKFYMPKKATELKHLQCLEEELKPLEEVL NCAQSKNFHLRPRDLISNINVIVLELKGSETTFMCE YADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 178 | hIL-2-anti-HSA A48 | APTSSSTKKTQLQLEHLLLDLQMILNGINNYENPK LTCMLTFKFYMPKKATELKHLQCLEEELKPLEEVL NCAQSKNFHLRPRDLISNINVIVLELKGSETTFMCE YADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 179 | hIL-2-anti-HSA A49 | APTSSSTKKTQLQLEHLLLDLQMILNGINNYENPK LTRMLTCKFYMPKKATELKHLQCLEEELKPLEEC LNLAQSKNFHLRPRDLISNINVIVLELKGSETTFMC EYADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 180 | hIL-2-anti-HSA A50 | APTSSSTKKTQLQLEHLLLDLQMILNGINNYENPK LTRMLTFKFCMPKKATELKHLQCLEECLKPLEEVL NLAQSKNFHLRPRDLISNINVIVLELKGSETTFMCE YADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 181 | hIL-2-anti-HSA A51 | APTSSSTKKTQLQLEHLLLDLQMILNGINNYENPK LTRMLTCKFYMPKKATELKHLQCLEEELKPLEEV LNCAQSKNFHLRPRDLISNINVIVLELKGSETTFMC EYADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 182 | hIL-2-anti-HSA A52 | APTSSSTKKTQLQLEHLLLDLQMILNGINNYKNPK LTRMLTCKFYMPKKATELKHLQCLEEELKPLEEC LNLAQSKNFHLRPRDLISNINVIVLELKGSETTFMC EYADETATIVEFLNRWITFSQSIISTLTGSGGSGGSG GSGEVQLVESGGGLVQPGGSLRLSCAASGSTWSIN |

SEQUENCE TABLE

| SEQ ID NO: | Description | Amino Acid Sequence |
|---|---|---|
| | | TLAWYRQAPGKQRDLVARISSGGSTYYADSVKGR FTISRDNSKNTLYLQMNSLRAEDTAVYYCYAQST WYPPSWGQGTLVTVSS |
| 183 | hIL-2-anti-HSA A53 | APTSSSTKKTQLQLEHLLLDLQMILNGINNYKNPK LTRMLTCKFYMPKKATELKHLQCLEEELKPLEEC LNLAQSENFHLRPRDLISNINVIVLELKGSETTFMC EYADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 184 | hIL-2-anti-HSA A54 | APTSSSTKKTQLQLEHLLLDLQMILNGINNYENPK LTDATLYMPKKATELKHLQCLEEELKPLEEVLNL AQSKNFHLRPRDLISNINVIVLELKGSETTFMCEYA DETATIVEFLNRWITFSQSIISTLTGSGGSGGSGGSG EVQLVESGGGLVQPGGSLRLSCAASGSTWSINTLA WYRQAPGKQRDLVARISSGGSTYYADSVKGRFTI SRDNSKNTLYLQMNSLRAEDTAVYYCYAQSTWY PPSWGQGTLVTVSS |
| 185 | hIL-2-anti-HSA A55 | APTSSSTKKTQLQLEHLLLDLQMILNGIQSMEIDAT TFKFYMPKKATELKHLQCLEEELKPLEEVLNLAQS KNFHLRPRDLISNINVIVLELKGSETTFMCEYADET ATIVEFLNRWITFSQSIISTLTGSGGSGGSGGSGEVQ LVESGGGLVQPGGSLRLSCAASGSTWSINTLAWY RQAPGKQRDLVARISSGGSTYYADSVKGRFTISRD NSKNTLYLQMNSLRAEDTAVYYCYAQSTWYPPS WGQGTLVTVSS |
| 186 | hIL-2-anti-HSA A56 | APTSSSTKKTQLQLEHLLLDLQMILNGIQSMEIDAT KFYMPKKATELKHLQCLEEELKPLEEVLNLAQSK NFHLRPRDLISNINVIVLELKGSETTFMCEYADETA TIVEFLNRWITFSQSIISTLTGSGGSGGSGGSEVQL VESGGGLVQPGGSLRLSCAASGSTWSINTLAWYR QAPGKQRDLVARISSGGSTYYADSVKGRFTISRDN SKNTLYLQMNSLRAEDTAVYYCYAQSTWYPPSW GQGTLVTVSS |
| 187 | hIL-2-anti-HSA A57 | APTSSSTKKTQLQLEHLLLDLQMILNGIQSMEIDAT LFYMPKKATELKHLQCLEEELKPLEEVLNLAQSK NFHLRPRDLISNINVIVLELKGSETTFMCEYADETA TIVEFLNRWITFSQSIISTLTGSGGSGGSGGSEVQL VESGGGLVQPGGSLRLSCAASGSTWSINTLAWYR QAPGKQRDLVARISSGGSTYYADSVKGRFTISRDN SKNTLYLQMNSLRAEDTAVYYCYAQSTWYPPSW GQGTLVTVSS |
| 188 | hIL-2-anti-HSA A58 | APTSSSTKKTQLQLEHLLLDLQMILNGIQSMEIDAT LYTESDVTELKHLQCLEEELKPLEEVLNLAQSKNF HLRPRDLISNINVIVLELKGSETTFMCEYADETATI VEFLNRWITFSQSIISTLTGSGGSGGSGGSEVQLV ESGGGLVQPGGSLRLSCAASGSTWSINTLAWYRQ APGKQRDLVARISSGGSTYYADSVKGRFTISRDNS KNTLYLQMNSLRAEDTAVYYCYAQSTWYPPSWG QGTLVTVSS |
| 189 | hIL-2 mutein (T3A, Q13E, R38N, L40T, F42A, C125S) | APASSSTKKTQLELEHLLLDLQMILNGINNYKNPK LTNMTTAKFYMPKKATELKHLQCLEEELKPLEEV LNLAQSKNFHLRPRDLISNINVIVLELKGSETTFMC EYADETATIVEFLNRWITFSQSIISTLT |
| 190 | hIL-2 mutein (T3A, E15V, R38N, L40T, F42A, C125S) | APASSSTKKTQLQLVHLLLDLQMILNGINNYKNPK LTNMTTAKFYMPKKATELKHLQCLEEELKPLEEV LNLAQSKNFHLRPRDLISNINVIVLELKGSETTFMC EYADETATIVEFLNRWITFSQSIISTLT |
| 191 | hIL-2 mutein (T3A, H16N, R38N, L40T, F42A, C125S) | APASSSTKKTQLQLENLLLDLQMILNGINNYKNPK LTNMTTAKFYMPKKATELKHLQCLEEELKPLEEV LNLAQSKNFHLRPRDLISNINVIVLELKGSETTFMC EYADETATIVEFLNRWITFSQSIISTLT |
| 192 | hIL-2 mutein (T3A, M23K, R38N, L40T, | APASSSTKKTQLQLEHLLLDLQKILNGINNYKNPK LTNMTTAKFYMPKKATELKHLQCLEEELKPLEEV |

| SEQ ID NO: | Description | Amino Acid Sequence |
|---|---|---|
|  | F42A, C125S) | LNLAQSKNFHLRPRDLISNINIVIVLELKGSETTFMC EYADETATIVEFLNRWITFSQSIISTLT |
| 193 | hIL-2 mutein (T3A, R38N, L40T, F42A, V91I, C125S) | APASSSTKKTQLQLEHLLLDLQMILNGINNYKNPK LTNMTTAKFYMPKKATELKHLQCLEEELKPLEEV LNLAQSKNFHLRPRDLISNINIIVLELKGSETTFMCE YADETATIVEFLNRWITFSQSIISTLT |
| 194 | hIL-2 mutein (T3A, R38N, L40T, F42A, E95N, C125S) | APASSSTKKTQLQLEHLLLDLQMILNGINNYKNPK LTNMTTAKFYMPKKATELKHLQCLEEELKPLEEV LNLAQSKNFHLRPRDLISNINVIVLNLKGSETTFMC EYADETATIVEFLNRWITFSQSIISTLT |
| 195 | hIL-2 mutein (Q13N, K32E, F42C, V69C, C125S) | APTSSSTKKTQLNLEHLLLDLQMILNGINNYENPK LTRMLTCKFYMPKKATELKHLQCLEEELKPLEEC LNLAQSKNFHLRPRDLISNINVIVLELKGSETTFMC EYADETATIVEFLNRWITFSQSIISTLT |
| 196 | hIL-2 mutein (L19S, K32E, F42C, V69C, C125S) | APTSSSTKKTQLQLEHLLSDLQMILNGINNYENPK LTRMLTCKFYMPKKATELKHLQCLEEELKPLEEC LNLAQSKNFHLRPRDLISNINVIVLELKGSETTFMC EYADETATIVEFLNRWITFSQSIISTLT |
| 197 | hIL-2 mutein (K32E, F42C, V69C, D84T, C125S) | APTSSSTKKTQLQLEHLLLDLQMILNGINNYENPK LTRMLTCKFYMPKKATELKHLQCLEEELKPLEEC LNLAQSKNFHLRPRTLISNINVIVLELKGSETTFMC EYADETATIVEFLNRWITFSQSIISTLT |
| 198 | hIL-2 mutein (K32E, F42C, V69C, S87E, C125S) | APTSSSTKKTQLQLEHLLLDLQMILNGINNYENPK LTRMLTCKFYMPKKATELKHLQCLEEELKPLEEC LNLAQSKNFHLRPRDLIENINVIVLELKGSETTFMC EYADETATIVEFLNRWITFSQSIISTLT |
| 199 | hIL-2 mutein (K32E, F42C, V69C, S87D, C125S) | APTSSSTKKTQLQLEHLLLDLQMILNGINNYENPK LTRMLTCKFYMPKKATELKHLQCLEEELKPLEEC LNLAQSKNFHLRPRDLIDNINVIVLELKGSETTFMC EYADETATIVEFLNRWITFSQSIISTLT |
| 200 | hIL-2 mutein (K32E, F42C, V69C, V91I, I92L, C125S) | APTSSSTKKTQLQLEHLLLDLQMILNGINNYENPK LTRMLTCKFYMPKKATELKHLQCLEEELKPLEEC LNLAQSKNFHLRPRDLISNINILVLELKGSETTFMC EYADETATIVEFLNRWITFSQSIISTLT |
| 201 | hIL-2 mutein (K32E, F42C, V69C, I92L, C125S) | APTSSSTKKTQLQLEHLLLDLQMILNGINNYENPK LTRMLTCKFYMPKKATELKHLQCLEEELKPLEEC LNLAQSKNFHLRPRDLISNINVLVLELKGSETTFM CEYADETATIVEFLNRWITFSQSIISTLT |
| 202 | hIL-2 mutein (K32E, F42C, V69C, E95N, C125S) | APTSSSTKKTQLQLEHLLLDLQMILNGINNYENPK LTRMLTCKFYMPKKATELKHLQCLEEELKPLEEC LNLAQSKNFHLRPRDLISNINVIVLNLKGSETTFMC EYADETATIVEFLNRWITFSQSIISTLT |
| 203 | hIL-2 mutein (K32E, F42C, V69C, E95Q, C125S) | APTSSSTKKTQLQLEHLLLDLQMILNGINNYENPK LTRMLTCKFYMPKKATELKHLQCLEEELKPLEEC LNLAQSKNFHLRPRDLISNINVIVLQLKGSETTFMC EYADETATIVEFLNRWITFSQSIISTLT |
| 204 | hIL-2-anti-HSA A59 | APASSSTKKTQLELEHLLLDLQMILNGINNYKNPK LTNMTTAKFYMPKKATELKHLQCLEEELKPLEEV LNLAQSKNFHLRPRDLISNINVIVLELKGSETTFMC EYADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 205 | hIL-2-anti-HSA A60 | APASSSTKKTQLQLVHLLLDLQMILNGINNYKNPK LTNMTTAKFYMPKKATELKHLQCLEEELKPLEEV LNLAQSKNFHLRPRDLISNINVIVLELKGSETTFMC EYADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |

-continued

SEQUENCE TABLE

| SEQ ID NO: | Description | Amino Acid Sequence |
|---|---|---|
| 206 | hIL-2-anti-HSA A61 | APASSSTKKTQLQLENLLLDLQMILNGINNYKNPK LTNMTTAKFYMPKKATELKHLQCLEEELKPLEEV LNLAQSKNFHLRPRDLISNINVIVLELKGSETTFMC EYADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 207 | hIL-2-anti-HSA A62 | APASSSTKKTQLQLEHLLLDLQKILNGINNYKNPK LTNMTTAKFYMPKKATELKHLQCLEEELKPLEEV LNLAQSKNFHLRPRDLISNINVIVLELKGSETTFMC EYADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 208 | hIL-2-anti-HSA A63 | APASSSTKKTQLQLEHLLLDLQMILNGINNYKNPK LTNMTTAKFYMPKKATELKHLQCLEEELKPLEEV LNLAQSKNFHLRPRDLISNINIIVLELKGSETTFMCE YADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 209 | hIL-2-anti-HSA A64 | APASSSTKKTQLQLEHLLLDLQMILNGINNYKNPK LTNMTTAKFYMPKKATELKHLQCLEEELKPLEEV LNLAQSKNFHLRPRDLISNINVIVLNLKGSETTFMC EYADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 210 | hIL-2-anti-HSA A65 | APTSSSTKKTQLNLEHLLLDLQMILNGINNYENPK LTRMLTCKFYMPKKATELKHLQCLEEELKPLEEC LNLAQSKNFHLRPRDLISNINVIVLELKGSETTFMC EYADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 211 | hIL-2-anti-HSA A66 | APTSSSTKKTQLQLEHLLSDLQMILNGINNYENPK LTRMLTCKFYMPKKATELKHLQCLEEELKPLEEC LNLAQSKNFHLRPRDLISNINVIVLELKGSETTFMC EYADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 212 | hIL-2-anti-HSA A67 | APTSSSTKKTQLQLEHLLLDLQMILNGINNYENPK LTRMLTCKFYMPKKATELKHLQCLEEELKPLEEC LNLAQSKNFHLRPRTLISNINVIVLELKGSETTFMC EYADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 213 | hIL-2-anti-HSA A68 | APTSSSTKKTQLQLEHLLLDLQMILNGINNYENPK LTRMLTCKFYMPKKATELKHLQCLEEELKPLEEC LNLAQSKNFHLRPRDLIENINVIVLELKGSETTFMC EYADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 214 | hIL-2-anti-HSA A69 | APTSSSTKKTQLQLEHLLLDLQMILNGINNYENPK LTRMLTCKFYMPKKATELKHLQCLEEELKPLEEC |

| SEQUENCE TABLE | | |
|---|---|---|
| SEQ ID NO: | Description | Amino Acid Sequence |
| | | LNLAQSKNFHLRPRDLIDNINVIVLELKGSETTFMC EYADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 215 | hIL-2-anti-HSA A70 | APTSSSTKKTQLQLEHLLLDLQMILNGINNYENPK LTRMLTCKFYMPKKATELKHLQCLEEELKPLEEC LNLAQSKNFHLRPRDLISNINILVLELKGSETTFMC EYADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 216 | hIL-2-anti-HSA A71 | APTSSSTKKTQLQLEHLLLDLQMILNGINNYENPK LTRMLTCKFYMPKKATELKHLQCLEEELKPLEEC LNLAQSKNFHLRPRDLISNINVLVLELKGSETTFM CEYADETATIVEFLNRWITFSQSIISTLTGSGGSGGS GGSGEVQLVESGGGLVQPGGSLRLSCAASGSTWSI NTLAWYRQAPGKQRDLVARISSGGSTYYADSVKG RFTISRDNSKNTLYLQMNSLRAEDTAVYYCYAQS TWYPPSWGQGTLVTVSS |
| 217 | hIL-2-anti-HSA A72 | APTSSSTKKTQLQLEHLLLDLQMILNGINNYENPK LTRMLTCKFYMPKKATELKHLQCLEEELKPLEEC LNLAQSKNFHLRPRDLISNINVIVLNLKGSETTFMC EYADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 218 | hIL-2-anti-HSA A73 | APTSSSTKKTQLQLEHLLLDLQMILNGINNYENPK LTRMLTCKFYMPKKATELKHLQCLEEELKPLEEC LNLAQSKNFHLRPRDLISNINVIVLQLKGSETTFMC EYADETATIVEFLNRWITFSQSIISTLTGSGGSGGSG GSGEVQLVESGGGLVQPGGSLRLSCAASGSTWSIN TLAWYRQAPGKQRDLVARISSGGSTYYADSVKGR FTISRDNSKNTLYLQMNSLRAEDTAVYYCYAQST WYPPSWGQGTLVTVSS |
| 219 | IL-15 hinge fragment-containing peptide 6 | NNYHNPKLTDATLYMPKKA |
| 220 | IL-15 hinge fragment-containing peptide 7 | QSMHIDATTFKFYMPKKA |
| 221 | IL-15 hinge fragment-containing peptide 8 | QSMHIDATKFYMPKKA |
| 222 | IL-15 hinge fragment-containing peptide 9 | QSMHIDATLFYMPKKA |
| 223 | IL-15 hinge fragment-containing peptide 10 | QSMHIDATLYTESDV |
| 224 | IL-2-IL-15 chimera 6 | APTSSSTKKTQLQLEHLLLDLQMILNGIQSMHIDA TTFKFYMPKKATELKHLQCLEEELKPLEEVLNLAQ SKNFHLRPRDLISNINVIVLELKGSETTFMCEYADE TATIVEFLNRWITFSQSIISTLT |
| 225 | IL-2-IL-15 chimera 7 | APTSSSTKKTQLQLKHLLLDLQMILNGIQSMEIDA TTFKFYMPKKATELKHLQCLEEELKPLEEVLNLAQ SKNFHLRPRDLISNINVIVLELKGSETTFMCEYADE TATIVEFLNRWITFSQSIISTLT |
| 226 | IL-2-IL-15 chimera 8 | APTSSSTKKTQLQLEHLLLDLQMILNGIQSMEIDAT TFKFYMPKKATELKHLQCLEEELKPLEEVLNLAQS KNFHLRPRDLIENINVIVLELKGSETTFMCEYADET ATIVEFLNRWITFSQSIISTLT |
| 227 | IL-2-IL-15 chimera 9 | APTSSSTKKTQLQLEHLLLDLQMILNGIQSMEIDAT TFKFYMPKKATELKHLQCLEEELKPLEEVLNLAQS |

SEQUENCE TABLE

| SEQ ID NO: | Description | Amino Acid Sequence |
|---|---|---|
| | | KNFHLRPRDLIDNINVIVLELKGSETTFMCEYADET ATIVEFLNRWITFSQSIISTLT |
| 228 | IL-2-IL-15 chimera 10 | APTSSSTKKTQLQLKHLLLDLQMILNGIQSMEIDA TTFKFYMPKKATELKHLQCLEEELKPLEEVLNLAQ SKNFHLRPRDLIENINVIVLELKGSETTFMCEYADE TATIVEFLNRWITFSQSIISTLT |
| 229 | IL-2-IL-15 chimera 11 | APTSSSTKKTQLQLKHLLLDLQMILNGIQSMEIDA TTFKFYMPKKATELKHLQCLEEELKPLEEVLNLAQ SKNFHLRPRDLIDNINVIVLELKGSETTFMCEYADE TATIVEFLNRWITFSQSIISTLT |
| 230 | IL-2-IL-15 chimera 12 | APTSSSTKKTQLQLKHLLLDLQMILNGIQSMHIDA TTFKFYMPKKATELKHLQCLEEELKPLEEVLNLAQ SKNFHLRPRDLISNINVIVLELKGSETTFMCEYADE TATIVEFLNRWITFSQSIISTLT |
| 231 | IL-2-IL-15 chimera 13 | APTSSSTKKTQLQLEHLLLDLQMILNGIQSMHIDA TTFKFYMPKKATELKHLQCLEEELKPLEEVLNLAQ SKNFHLRPRDLIENINVIVLELKGSETTFMCEYADE TATIVEFLNRWITFSQSIISTLT |
| 232 | IL-2-IL-15 chimera 14 | APTSSSTKKTQLQLEHLLLDLQMILNGIQSMHIDA TTFKFYMPKKATELKHLQCLEEELKPLEEVLNLAQ SKNFHLRPRDLIDNINVIVLELKGSETTFMCEYADE TATIVEFLNRWITFSQSIISTLT |
| 233 | IL-2-IL-15 chimera 15 | APTSSSTKKTQLQLKHLLLDLQMILNGIQSMHIDA TTFKFYMPKKATELKHLQCLEEELKPLEEVLNLAQ SKNFHLRPRDLIENINVIVLELKGSETTFMCEYADE TATIVEFLNRWITFSQSIISTLT |
| 234 | IL-2-IL-15 chimera 16 | APTSSSTKKTQLQLKHLLLDLQMILNGIQSMHIDA TTFKFYMPKKATELKHLQCLEEELKPLEEVLNLAQ SKNFHLRPRDLIDNINVIVLELKGSETTFMCEYADE TATIVEFLNRWITFSQSIISTLT |

The examples set forth above are provided to give those of ordinary skill in the art with a complete disclosure and description of how to make and use the claimed embodiments and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. An interleukin-2 polypeptide comprising an amino acid sequence of SEQ ID NO: 1, 2, 3, 4, or 5, wherein the interleukin-2 polypeptide comprises a replacement of the amino acid residues from positions 29 to 50 as set forth in SEQ ID NO: 1, 2, 3, 4, or 5 with a peptide comprising the amino acid sequence of an IL-15 hinge or a fragment thereof.

2. The interleukin-2 polypeptide of claim 1, wherein the interleukin-2 polypeptide further comprises an amino acid substitution at position 8, 9, 13, 15, 16, 19, 23, 76, 79, 81, 84, 87, 88, 91, 92, 95, 127, or 130 as set forth in SEQ ID NO: 1, 2, 3, 4, or 5.

3. The interleukin-2 polypeptide of claim 1, wherein the interleukin-2 polypeptide further comprises an amino acid substitution at position 15 as set forth in SEQ ID NO: 1, 2, 3, 4, or 5.

4. The interleukin-2 polypeptide of claim 1, wherein the interleukin-2 polypeptide further comprises an amino acid substitution of E15K.

5. The interleukin-2 polypeptide of claim 1, wherein the interleukin-2 polypeptide further comprises an amino acid substitution at position 16 as set forth in SEQ ID NO: 1, 2, 3, 4, or 5.

6. The interleukin-2 polypeptide of claim 1, wherein the interleukin-2 polypeptide further comprises an amino acid substitution of H16D, H16E, H16N, or H16Q.

7. A fusion protein comprising (i) an interleukin-2 polypeptide domain having an amino acid sequence of the interleukin-2 polypeptide of claim 1 and (ii) a half-life-extension domain.

8. A pharmaceutical composition comprising the interleukin-2 polypeptide of claim 1 and a pharmaceutically acceptable excipient.

9. A method of treating one or more symptoms of treating, preventing, or ameliorating one or more symptoms of a proliferative disease in a subject, comprising administering to the subject a therapeutically effective amount of the interleukin-2 polypeptide of claim 1.

10. A method of activating an immune effector cell, comprising contacting the cell with an effective amount of the IL-2 polypeptide of any one of the interleukin-2 polypeptides of claim 1.

11. The interleukin-2 polypeptide of claim 1, wherein the interleukin-2 polypeptide further comprises an amino acid substitution at position 15, 16, or 130 as set forth in SEQ ID NO: 1, 2, 3, 4, or 5.

12. The interleukin-2 polypeptide of claim 1, wherein the interleukin-2 polypeptide further comprises an amino acid substitution of E15K, E15Q, E15V, H16D, H16E, H16N, H16Q, S130A, S130E, S130F, or S130W.

13. The interleukin-2 polypeptide of claim 1, wherein the interleukin-2 polypeptide further comprises an amino acid substitution of E15K or E15Q.

14. The interleukin-2 polypeptide of claim 1, wherein the interleukin-2 polypeptide further comprises an amino acid substitution at position 130 as set forth in SEQ ID NO: 1, 2, 3, 4, or 5.

15. The interleukin-2 polypeptide of claim 1, wherein the interleukin-2 polypeptide further comprises an amino acid substitution of S130A, S130E, S130F, or S130W.

16. The interleukin-2 polypeptide of claim 1, wherein the interleukin-2 polypeptide comprises a replacement of an amino acid sequence of SEQ ID NO: 171 with an amino acid sequence of one of SEQ ID NOs: 166 to 170 and 219 to 223.

17. The interleukin-2 polypeptide of claim 1, wherein the interleukin-2 polypeptide comprises a replacement of an amino acid sequence of SEQ ID NO: 171 with an amino acid sequence of SEQ ID NO: 166.

18. The interleukin-2 polypeptide of claim 1, wherein the interleukin-2 polypeptide comprises a replacement of an amino acid sequence of SEQ ID NO: 171 with an amino acid sequence of SEQ ID NO: 167.

19. The interleukin-2 polypeptide of claim 1, wherein the interleukin-2 polypeptide comprises a replacement of an amino acid sequence of SEQ ID NO: 171 with an amino acid sequence of SEQ ID NO: 168.

20. The interleukin-2 polypeptide of claim 1, wherein the interleukin-2 polypeptide comprises a replacement of an amino acid sequence of SEQ ID NO: 171 with an amino acid sequence of SEQ ID NO: 169.

21. The interleukin-2 polypeptide of claim 1, wherein the interleukin-2 polypeptide comprises a replacement of an amino acid sequence of SEQ ID NO: 171 with an amino acid sequence of SEQ ID NO: 170.

22. The interleukin-2 polypeptide of claim 1, wherein the interleukin-2 polypeptide comprises a replacement of an amino acid sequence of SEQ ID NO: 171 with an amino acid sequence of SEQ ID NO: 219.

23. The interleukin-2 polypeptide of claim 1, wherein the interleukin-2 polypeptide comprises a replacement of an amino acid sequence of SEQ ID NO: 171 with an amino acid sequence of SEQ ID NO: 220.

24. The interleukin-2 polypeptide of claim 1, wherein the interleukin-2 polypeptide comprises a replacement of an amino acid sequence of SEQ ID NO: 171 with an amino acid sequence of SEQ ID NO: 221.

25. The interleukin-2 polypeptide of claim 1, wherein the interleukin-2 polypeptide comprises a replacement of an amino acid sequence of SEQ ID NO: 171 with an amino acid sequence of SEQ ID NO: 222.

26. The interleukin-2 polypeptide of claim 1, wherein the interleukin-2 polypeptide comprises a replacement of an amino acid sequence of SEQ ID NO: 171 with an amino acid sequence of SEQ ID NO: 223.

27. The interleukin-2 polypeptide of claim 1, comprising an amino acid sequence selected from SEQ ID NOs: 172 to 176, 184 to 188, and 224 to 234.

28. The interleukin-2 polypeptide of claim 1, comprising an amino acid sequence selected from SEQ ID NOs: 172 to 176 and 224 to 234.

* * * * *